US010822601B2

(12) United States Patent
Yaver et al.

(10) Patent No.: US 10,822,601 B2

(45) Date of Patent: Nov. 3, 2020

(54) METHODS FOR PRODUCING MULTIPLE RECOMBINANT POLYPEPTIDES IN A FILAMENTOUS FUNGAL HOST CELL

(71) Applicant: Novozymes, Inc., Davis, CA (US)

(72) Inventors: Debbie Yaver, Davis, CA (US); Qiming Jin, Sacramento, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 16/394,951

(22) Filed: Apr. 25, 2019

(65) Prior Publication Data

US 2019/0249161 A1 Aug. 15, 2019

Related U.S. Application Data

(62) Division of application No. 15/280,706, filed on Sep. 29, 2016, now Pat. No. 10,301,610, which is a division of application No. 14/238,691, filed as application No. PCT/US2012/052143 on Aug. 23, 2012, now Pat. No. 9,493,790.

(60) Provisional application No. 61/526,809, filed on Aug. 24, 2011.

(51) Int. Cl.

| | |
|---|---|
| ***C12N 9/42*** | (2006.01) |
| ***C12N 15/80*** | (2006.01) |
| ***C12N 9/24*** | (2006.01) |
| ***C12N 15/87*** | (2006.01) |

(52) U.S. Cl.

CPC ......... *C12N 9/2437* (2013.01); *C12N 9/2402* (2013.01); *C12N 15/80* (2013.01); *C12N 15/87* (2013.01); *C12Y 302/0115* (2013.01); *C12Y 302/01091* (2013.01)

(58) Field of Classification Search

None

See application file for complete search history.

(56) References Cited

U.S. PATENT DOCUMENTS

| | | | | |
|---|---|---|---|---|
| 5,958,727 | A | 9/1999 | Brody et al. | |
| 6,323,002 | B1 | 11/2001 | Brody et al. | |
| 6,590,078 | B2 | 7/2003 | Ward et al. | |
| 7,163,804 | B1 | 1/2007 | Royer et al. | |
| 8,415,119 | B2 | 4/2013 | Hansen et al. | |
| 8,686,218 | B2 | 4/2014 | Romaine et al. | |
| 9,387,175 | B2 | 7/2016 | Abe et al. | |
| 9,404,101 | B2 | 8/2016 | Moyer | |
| 9,493,790 | B2 | 11/2016 | Yaver et al. | |
| 10,006,016 | B2 | 6/2018 | Yaver et al. | |
| 10,023,872 | B2 | 7/2018 | Merino et al. | |
| 10,144,920 | B2 * | 12/2018 | Wogulis | C12N 19/14 |
| 10,190,109 | B2 * | 1/2019 | Moyer | C12N 15/80 |
| 10,221,406 | B2 * | 3/2019 | Borch | C12N 9/2437 |
| 10,260,072 | B2 * | 4/2019 | Jessen | C12N 15/81 |
| 10,301,610 | B2 * | 5/2019 | Yaver | C12N 15/80 |
| 10,385,352 | B2 * | 8/2019 | Jin | C12N 15/902 |
| 2003/0092131 | A1 | 5/2003 | Ward et al. | |
| 2008/0299613 | A1 | 12/2008 | Merino et al. | |
| 2011/0003333 | A1 | 1/2011 | Hansen et al. | |
| 2011/0223671 | A1 | 9/2011 | Yoder et al. | |
| 2013/0109055 | A1 | 5/2013 | Ryding et al. | |
| 2014/0206086 | A1 | 7/2014 | Moyer | |
| 2014/0212977 | A1 * | 7/2014 | Yaver | C12N 15/80 435/477 |
| 2014/0303036 | A1 | 10/2014 | Roubos et al. | |
| 2014/0314859 | A1 | 10/2014 | Abe et al. | |
| 2017/0015986 | A1 * | 1/2017 | Yaver | C12Y 302/0115 |
| 2017/0204441 | A1 | 7/2017 | Shasky et al. | |
| 2017/0260520 | A1 | 9/2017 | Matsui et al. | |
| 2018/0037897 | A1 | 2/2018 | Jin et al. | |
| 2018/0237759 | A1 | 8/2018 | Merino et al. | |
| 2018/0312849 | A1 | 11/2018 | Merino et al. | |
| 2019/0249161 | A1 * | 8/2019 | Yaver | C12N 9/2402 |
| 2019/0330644 | A1 * | 10/2019 | Jin | C12N 15/79 |
| 2020/0063166 | A1 * | 2/2020 | Van Peij | C12N 15/80 |
| 2020/0071693 | A1 * | 3/2020 | Sunspiral | C12N 15/11 |
| 2020/0123535 | A1 * | 4/2020 | Sunspiral | C12N 15/11 |

FOREIGN PATENT DOCUMENTS

| | | | |
|---|---|---|---|
| CN | 101970651 | | 2/2011 |
| EP | 0225078 | A2 | 11/1986 |
| EP | 2 371 963 | A1 | 3/2010 |
| EP | 2 840 139 | A1 | 8/2013 |
| WO | 1992006209 | A1 | 4/1992 |
| WO | 1994/03072 | A1 | 2/1994 |
| WO | 1998011203 | A1 | 3/1998 |
| WO | 1998031821 | A2 | 7/1998 |
| WO | 1999051756 | A2 | 10/1999 |
| WO | 1999060136 | A1 | 11/1999 |
| WO | 2007136865 | A2 | 11/2007 |

(Continued)

OTHER PUBLICATIONS

Suominen et al, 1993, Mol and Gene Gen 241(5-6), 523-530.
Sirkka et al, 1995, Cur Opi in Biote 6(5), 534-537.
Sakai et al, 2008, J of Bios and Bioeng 106(5), 466-472.
Karhunen et al, 1993, Mol and Gen Gen 241(5-6), 515-522.
Hansen et al, 2011, App and Envi Micro 77(9), 3044-3051.
De Vries et al, 2004, Appl Environ Microbiol 70(7), 3954-3959.
Devchand et al, 1991, J Biotechnol 17, 3-1.

(Continued)

*Primary Examiner* — Nita M. Minnifield

(74) *Attorney, Agent, or Firm* — Eric J. Fetcher

(57) ABSTRACT

The present invention relates to methods for constructing a filamentous fungal strain for production of multiple recombinant polypeptides having biological activity. The present invention also relates to methods for producing multiple recombinant polypeptides having biological activity in a filamentous fungal strain. The present invention also relates to filamentous fungal strains expressing multiple recombinant polypeptides having biological activity.

24 Claims, 16 Drawing Sheets

Specification includes a Sequence Listing.

(56) References Cited

FOREIGN PATENT DOCUMENTS

| | | | |
|---|---|---|---|
| WO | 2008009728 | A1 | 1/2008 |
| WO | 2008073914 | A2 | 6/2008 |
| WO | 2008151043 | A1 | 12/2008 |
| WO | 2008151079 | A2 | 12/2008 |
| WO | 2010039889 | A2 | 4/2010 |
| WO | 2011120952 | A1 | 10/2011 |
| WO | 2013111754 | A1 | 8/2013 |
| WO | 2014145768 | A2 | 9/2014 |

OTHER PUBLICATIONS

Gerngross et al, 2004, Nature Biotechnol 22(11), 1409-1414.
Granado et al, 1997, Mol Gen Genet 256, 28-36.
Hondel et al, 1991, NY Academic Press, 396-428.
Kues et al, Coprinus cinereus, 1-5.
Lubertozzi et al, 2009, Biotechnol Adv 27, 53-75.
Menzella et al, 2007, Curr Opin Microbiol 10(3), 238-245.
Nykanen et al, 1997, Appl Environ Microbiol 63(12), 4929-4937.
Nyyssonen et al, 1995, ACS Symp 108-122.
Paloheimo et al, 2007, Appl Environ Microbiol 73(10), 3215-3224.
Punt et al, 2002, Trends Biotechnol 20(5), 200-206.
Read et al, 2007, Appl Environ Microbiol 73(16), 5088-5096.
Suominen et al, 1993, Mol and Gen Genet 241(5-6), 523-530.
Timberlake et al, 1989, Sci 244, 1313-1317.
Upshall et al, 1990, Mol Indus Mycol 31-44.
Wang et al, 2005, Biotechnol Adv 23, 115-129.
Yoder et al, 2004, Adv Fungal Bitoechnol Indus, 201-219.
Gouka et al, 1999, Nature Biotechnol 17, 598-601.
Kimura et al, 1993, J Bacteriol 175, 4427-4435.
Sharma et al, 2006, Biotechnol Appl Biochem 43, 181-186.
Bowie et al, 1990, Science 247(4948), 1306-1310.
Burgess et al, 1990, JBC 111, 2129-2138.
Greenspan et al, 1999, Nature Biotechnol 7, 936-937.
Kumar et al, 1990, PNAS USA 87(4), 1337-1341.

* cited by examiner

METHODS FOR PRODUCING MULTIPLE RECOMBINANT POLYPEPTIDES IN A FILAMENTOUS FUNGAL HOST CELL

CROSS-REFERENCE TO RELATED APPLICATIONS

This application is a divisional application of U.S. patent application Ser. No. 15/280,706 file Sep. 29, 2016, now U.S. Pat. No. 10,301,610, which a divisional application of U.S. patent application Ser. No. 14/238,691 filed Mar. 24, 2014, now U.S. Pat. No. 9,493,790, which is a 35 U.S.C. § 371 national application of PCT/US2012/052143 filed Aug. 23, 2012, which claims priority or the benefit under 35 U.S.C. § 119 of U.S. Provisional Application No. 61/526,809 filed on Aug. 24, 2011, the contents of which are fully incorporated herein by reference

REFERENCE TO A SEQUENCE LISTING

This application contains a Sequence Listing in computer readable form, which is incorporated herein by reference.

BACKGROUND OF THE INVENTION

Field of the Invention

The present invention relates to methods for producing multiple recombinant polypeptides in a filamentous fungal host cell.

Description of the Related Art

Recombinant production of a polypeptide in a filamentous fungal host cell may provide for a more desirable vehicle for producing the polypeptide in commercially relevant quantities. The recombinant production of a polypeptide is generally accomplished by constructing an expression cassette in which the DNA coding for the polypeptide is placed under the expression control of a promoter from a regulated gene. The expression cassette is introduced into the host cell, usually by plasmid-mediated transformation. Production of the polypeptide is then achieved by culturing the transformed host cell under inducing conditions necessary for the proper functioning of the promoter contained on the expression cassette.

Filamentous fungal cells may be transformed with a vector by a process involving protoplast formation, transformation of the protoplasts, and regeneration of the cell wall in a manner known per se. Transformation of a filamentous fungal host cell with two or more vectors, alone or together (co-transformation) is very inefficient and limited by the availability of useful selectable markers.

There is a need in the art for methods of constructing filamentous fungal strains capable of expressing multiple recombinant polypeptides by targeting tandem expression constructs to one or more (e.g., several) specific genomic loci to achieve desired expression levels of all interested polypeptides.

The present invention provides improved methods for producing multiple recombinant polypeptides in a filamentous fungal host cell.

SUMMARY OF THE INVENTION

The present invention relates to methods for constructing a filamentous fungal strain for production of multiple recombinant polypeptides having biological activity, comprising:

(a) replacing an endogenous first gene by targeted integration by introducing into the filamentous fungal strain a first tandem construct comprising (i) a homologous 5' region of the first gene, a homologous flanking region thereof, or a combination thereof, (ii) one or more (e.g., several) first selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the first gene, a homologous flanking region thereof, or a combination thereof;

(b) replacing an endogenous second gene by targeted integration by introducing into the filamentous fungal strain a second tandem construct comprising (i) a homologous 5' region of the second gene, a homologous flanking region thereof, or a combination thereof, (ii) one or more (e.g., several) second selectable markers, (iii) a third polynucleotide encoding a third polypeptide having biological activity operably linked to a third promoter and a third terminator, (iv) a fourth polynucleotide encoding a fourth polypeptide having biological activity operably linked to a fourth promoter and a fourth terminator, and (v) a homologous 3' region of the second gene, a homologous flanking region thereof, or a combination thereof; or (c) a combination of (a) and (b).

The present invention also relates to filamentous fungal strains, comprising:

(a) an endogenous first gene replaced by targeted integration by introducing into the filamentous fungal strain a first tandem construct comprising (i) a homologous 5' region of the first gene, a homologous flanking region thereof, or a combination thereof, (ii) one or more (e.g., several) first selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the first gene, a homologous flanking region thereof, or a combination thereof;

(b) an endogenous second gene replaced by targeted integration by introducing into the filamentous fungal strain a second tandem construct comprising (i) a homologous 5' region of the second gene, a homologous flanking region thereof, or a combination thereof, (ii) one or more (e.g., several) second selectable markers, (iii) a third polynucleotide encoding a third polypeptide having biological activity operably linked to a third promoter and a third terminator, (iv) a fourth polynucleotide encoding a fourth polypeptide having biological activity operably linked to a fourth promoter and a fourth terminator, and (v) a homologous 3' region of the second gene, a homologous flanking region thereof, or a combination thereof; or (c) a combination of (a) and (b).

The present invention also relates to methods for producing multiple recombinant polypeptides having biological activity in a filamentous fungal strain, comprising:

(A) cultivating a filamentous fungal host cell under conditions conducive for production of the polypeptides, wherein the filamentous fungal host cell comprises (a) an endogenous first gene replaced by targeted integration with a first tandem construct comprising (i) a homologous 5' region of the first gene, a homologous flanking region thereof, or a combination thereof, (ii) one or more (e.g., several) first selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the first gene, a homologous flanking region thereof, or a combination thereof; (b) an endogenous second gene replaced by targeted integration with a second tandem construct comprising (i) a homologous 5' region of the second gene, a homologous flanking region thereof, or a combination thereof, (ii) one or more (e.g., several) second selectable markers, (iii) a third polynucleotide encoding a third polypeptide having biological activity operably linked to a third promoter and a third terminator, (iv) a fourth polynucleotide encoding a fourth polypeptide having biological activity operably linked to a fourth promoter and a fourth terminator, and (v) a homologous 3' region of the second gene, a homologous flanking region thereof, or a combination thereof; or (c) a combination of (a) and (b); and optionally (B) recovering the multiple recombinant polypeptides.

The present invention also relates to tandem constructs comprising (i) a homologous 5' region of a gene, a homologous flanking region thereof, or a combination thereof, (ii) one or more (e.g., several) selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the gene, a homologous flanking region thereof, or a combination thereof.

The present invention also relates to methods for constructing a filamentous fungal strain for production of multiple recombinant polypeptides having biological activity, comprising:

(a) inserting into an endogenous first locus by targeted integration a first tandem construct comprising (i) a homologous 5' region of the first locus, a homologous flanking region thereof, or a combination thereof, (ii) one or more first selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the first locus, a homologous flanking region thereof, or a combination thereof;

(b) inserting into an endogenous second locus by targeted integration a second tandem construct comprising (i) a homologous 5' region of the second locus, a homologous flanking region thereof, or a combination thereof, (ii) one or more second selectable markers, (iii) a third polynucleotide encoding a third polypeptide having biological activity operably linked to a third promoter and a third terminator, (iv) a fourth polynucleotide encoding a fourth polypeptide having biological activity operably linked to a fourth promoter and a fourth terminator, and (v) a homologous 3' region of the second locus, a homologous flanking region thereof, or a combination thereof; or (c) a combination of (a) and (b).

The present invention also relates to filamentous fungal strains, comprising: (a) an endogenous first locus modified by insertion by targeted integration with a first tandem construct comprising (i) a homologous 5' region of the first locus, a homologous flanking region thereof, or a combination thereof, (ii) one or more first selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the first locus, a homologous flanking region thereof, or a combination thereof; (b) an endogenous second locus modified by insertion by targeted integration with a second tandem construct comprising (i) a homologous 5' region of the second locus, a homologous flanking region thereof, or a combination thereof, (ii) one or more second selectable markers, (iii) a third polynucleotide encoding a third polypeptide having biological activity operably linked to a third promoter and a third terminator, (iv) a fourth polynucleotide encoding a fourth polypeptide having biological activity operably linked to a fourth promoter and a fourth terminator, and (v) a homologous 3' region of the second locus, a homologous flanking region thereof, or a combination thereof; or (c) a combination of (a) and (b).

The present invention also relates to methods for producing multiple recombinant polypeptides having biological activity in a filamentous fungal strain, comprising:

(A) cultivating a filamentous fungal host cell under conditions conducive for production of the polypeptides, wherein the filamentous fungal host cell comprises (a) an endogenous first locus modified by insertion by targeted integration with a first tandem construct comprising (i) a homologous 5' region of the first locus, a homologous flanking region thereof, or a combination thereof, (ii) one or more first selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the first locus, a homologous flanking region thereof, or a combination thereof; (b) an endogenous second locus modified by insertion by targeted integration with a second tandem construct comprising (i) a homologous 5' region of the second locus, a homologous flanking region thereof, or a combination thereof, (ii) one or more second selectable markers, (iii) a third polynucleotide encoding a third polypeptide having biological activity operably linked to a third promoter and a third terminator, (iv) a fourth polynucleotide encoding a fourth polypeptide having biological activity operably linked to a fourth promoter and a fourth terminator, and (v) a homologous 3' region of the second locus, a homologous flanking region thereof, or a combination thereof; or (c) a combination of (a) and (b); and (B) recovering the multiple recombinant polypeptides.

The present invention also relates to tandem constructs comprising (i) a homologous 5' region of a locus, a homologous flanking region thereof, or a combination thereof, (ii) one or more selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the locus, a homologous flanking region thereof, or a combination thereof.

DEFINITIONS

Figure 1:
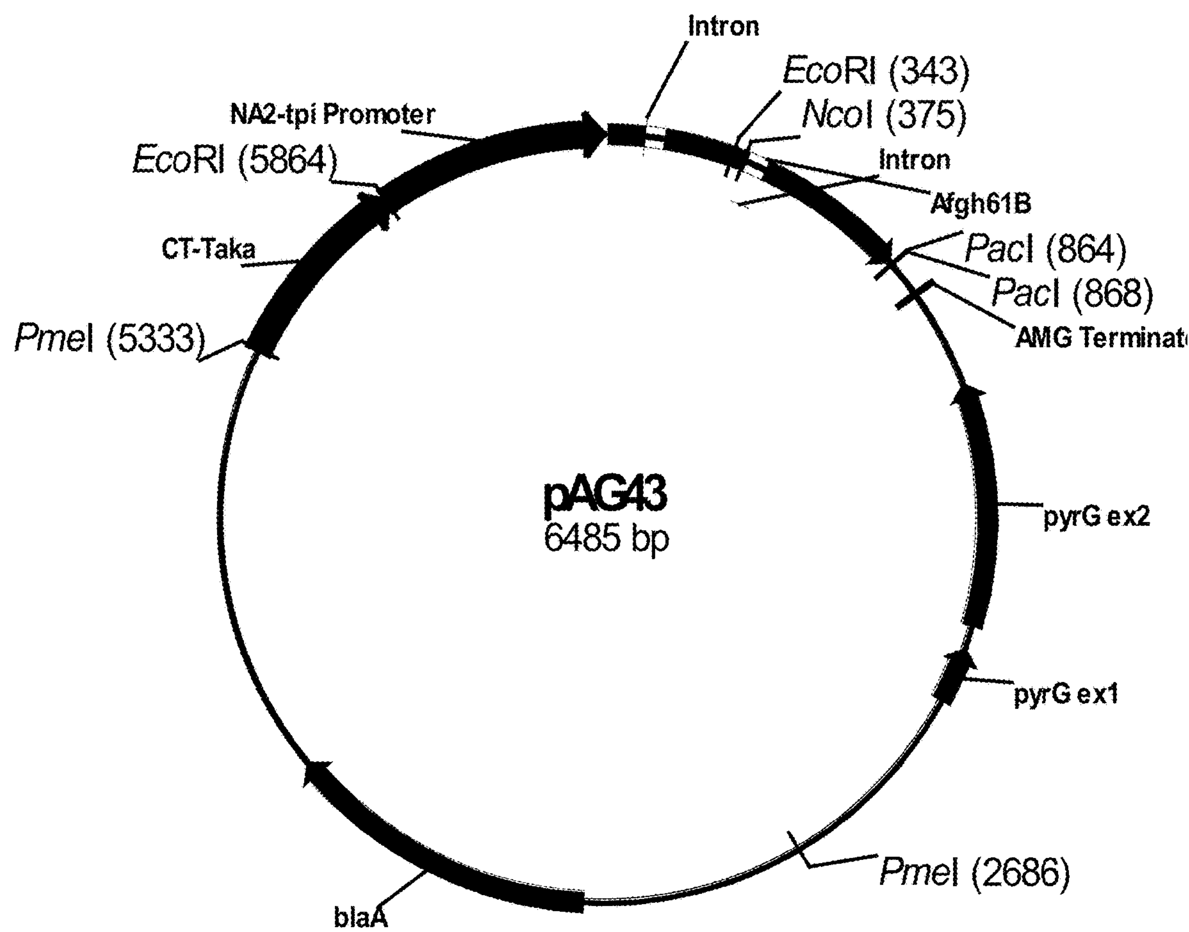
FIG. 1 shows a restriction map of plasmid pAG43.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more (e.g., several) alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 μmole of glucuronic or 4-O-methylglucuronic acid per minute at pH 5, 40° C.

Aspartic protease: The term "aspartic protease" means a protease that uses an aspartate residue(s) for catalyzing the hydrolysis of peptide bonds in peptides and proteins. Aspartic proteases are a family of protease enzymes that use an aspartate residue for catalytic hydrolysis of their peptide substrates. In general, they have two highly-conserved aspartates in the active site and are optimally active at acidic pH (Szecsi, 1992, *Scand. J. Clin. Lab. In vest.* Suppl. 210: 5-22). For purposes of the present invention, aspartic protease activity is determined according to the procedure described by Aikawa et al., 2001, *J. Biochem.* 129: 791-794.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, J. Basic Microbiol. 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 μmole of p-nitrophenolate anion produced per minute at 40° C., pH 5 from 1 mM p-nitrophenyl-beta-D-xyloside as substrate in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters,* 149: 152-156; van Tilbeurgh and Claeyssens, 1985, *FEBS Letters,* 187: 283-288; and Tomme et al., 1988, *Eur. J. Biochem.* 170: 575-581. In the present invention, the Tomme et al. method can be used to determine cellobiohydrolase activity.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is *arundo*. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is *miscanthus*. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is *eucalyptus*. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a polypeptide. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Ectopic integration: The term "ectopic integration" means the insertion of a nucleic acid into the genome of a micro-organism at a non-targeted site or at a site other than its usual chromosomal locus, i.e., random integration.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, Biochem. J. 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C. Flanking: The term "flanking" means DNA sequences extending on either side of a specific DNA sequence, locus, or gene. The flanking DNA is immediately adjacent to another DNA sequence, locus, or gene that is to be integrated into the genome of a filamentous fungal cell.

Fragment: The term "fragment" means a polypeptide having one or more (e.g., several) amino acids absent from the amino and/or carboxyl terminus of a mature polypeptide main; wherein the fragment has enzyme activity. In one aspect, a fragment contains at least 85%, e.g., at least 90% or at least 95% of the amino acid residues of the mature polypeptide of an enzyme.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. *Current Opinion In Microbiology,* 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Homologous 3' or 5' region: The term "homologous 3' region" means a fragment of DNA that is identical in sequence or has a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to a region in the genome and when combined with a homologous 5' region can target integration of a piece of DNA to a specific site in the genome by homologous recombination. The term "homologous 5' region" means a fragment of DNA that is identical in sequence to a region in the genome and when combined with a homologous 3' region can target integration of a piece of DNA to a specific site in the genome by homologous recombination. The homologous 5' and 3' regions must be linked in the genome which means they are on the same chromosome and within at least 200 kb of one another.

Homologous flanking region: The term "homologous flanking region" means a fragment of DNA that is identical or has a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to a region in the genome and is located immediately upstream or downstream of a specific site in the genome into which extracellular DNA is targeted for integration.

Homologous repeat: The term "homologous repeat" means a fragment of DNA that is repeated at least twice in the recombinant DNA introduced into a host cell and which can facilitate the loss of the DNA, i.e., selectable marker that is inserted between two homologous repeats, by homologous recombination. A homologous repeat is also known as a direct repeat.

Host cell: The term "host cell" means any cell type that is susceptible to transformation, transfection, transduction, or the like with a nucleic acid construct or expression vector comprising a polynucleotide encoding a polypeptide. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide of a *T. reesei* cellobiohydrolase I is amino acids 18 to 514 of SEQ ID NO: 2 based on the SignalP program (Nielsen et al., 1997, *Protein Engineering* 10: 1-6) that predicts amino acids 1 to 17 of SEQ ID NO: 2 are a signal peptide. In another aspect, the mature polypeptide of a *T. reesei* cellobiohydrolase II is amino acids 19 to 471 of SEQ ID NO: 4 based on the SignalP program that predicts amino acids 1 to 18 of SEQ ID NO: 4 are a signal peptide. In another aspect, the mature polypeptide of a *T. reesei* endoglucanase I is amino acids 23 to 459 of SEQ ID NO: 6 based on the SignalP program that predicts amino acids 1 to 22 of SEQ ID NO: 6 are a signal peptide. In another aspect, the mature polypeptide of a *T. reesei* endoglucanase II is amino acids 22 to 418 of SEQ ID NO: 8 based on the SignalP program that predicts amino acids 1 to 21 of SEQ ID NO: 8 are a signal peptide. In another aspect, the mature polypeptide of a *T. reesei* beta-glucosidase is amino acids 20 to 744 of SEQ ID NO: 10 based on the SignalP program that predicts amino acids 1 to 19 of SEQ ID NO: 10 are a signal peptide. In another aspect, the mature polypeptide of a *T. reesei* xylanase I is amino acids 20 to 229 of SEQ ID NO: 12 based on the SignalP program that predicts amino acids 1 to 19 of SEQ ID NO: 12 are a signal peptide. In another aspect, the mature polypeptide of a *T. reesei* xylanase II is amino acids 20 to 223 of SEQ ID NO: 14 based on the SignalP program that predicts amino acids 1 to 19 of SEQ ID NO: 14 are a signal peptide. In another aspect, the mature polypeptide of a *T. reesei* xylanase III is amino acids 17 to 347 of SEQ ID NO: 16 based on the SignalP program that predicts amino acids 1 to 16 of SEQ ID NO: 16 are a signal peptide. In another aspect, the mature polypeptide of a *T. reesei* beta-xylosidase is amino acids 21 to 797 of SEQ ID NO: 18 based on the SignalP program that predicts amino acids 1 to 20 of SEQ ID NO: 18 are a signal peptide. In another aspect, the mature polypeptide of a *T. reesei* swollenin is amino acids 19 to 493 of SEQ ID NO: 20 based on the SignalP program that predicts amino acids 1 to 18 of SEQ ID NO: 20 are a signal peptide. In another aspect, the mature polypeptide of a *T. reesei* subtilisin-like serine protease is amino acids 20 to 882 of SEQ ID NO: 22 based on the SignalP program that predicts amino acids 1 to 19 of SEQ ID NO: 22 are a signal peptide. In another aspect, the mature polypeptide of a *T. reesei* aspartic protease is amino acids 21 to 407 of SEQ ID NO: 24 based on the SignalP program that predicts amino acids 1 to 20 of SEQ ID NO: 24 are a signal peptide. In another aspect, the mature polypeptide of a *T. reesei* trypsin-like serine protease is amino acids 20 to 259 of SEQ ID NO: 26 based on the SignalP program that predicts amino acids 1 to 19 of SEQ ID NO: 26 are a signal peptide. In another aspect, the mature polypeptide of another *T. reesei* subtilisin-like serine protease is amino acids 16 to 540 of SEQ ID NO: 28 based on the SignalP program that predicts amino acids 1 to 15 of SEQ ID NO: 28 are a signal peptide. In another aspect, the mature polypeptide of another *T. reesei* aspartic protease is amino acids 18 to 395 of SEQ ID NO: 30 based on the SignalP program that predicts amino acids 1 to 17 of SEQ ID NO: 30 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having enzyme activity. In one aspect, the mature polypeptide coding sequence of a *T. reesei* cellobiohydrolase I is nucleotides 52 to 1545 of SEQ ID NO: 1 or the cDNA sequence thereof based on the SignalP program that predicts nucleotides 1 to 51 of SEQ ID NO: 1 encode a signal peptide. In another aspect, the mature polypeptide coding sequence of a *T. reesei* cellobiohydrolase II is nucleotides 55 to 1608 of SEQ ID NO: 3 or the cDNA sequence thereof based on the SignalP program that predicts nucleotides 1 to 54 of SEQ ID NO: 3 encode a signal peptide. In another aspect, the mature polypeptide coding sequence of a *T. reesei* endoglucanase I is nucleotides 67 to 1374 of SEQ ID NO: 5 or the cDNA sequence thereof based on the SignalP program that predicts nucleotides 1 to 66 of SEQ ID NO: 5 encode a signal peptide. In another aspect, the mature polypeptide coding sequence of a *T. reesei* endoglucanase II is nucleotides 64 to 1254 of SEQ ID NO: 7 or the cDNA sequence thereof based on the SignalP program that predicts nucleotides 1 to 63 of SEQ ID NO: 7 encode a signal peptide. In another aspect, the mature polypeptide coding sequence of a *T. reesei* beta-glucosidase is nucleotides 58 to 2612 of SEQ ID NO: 9 or the cDNA sequence thereof based on the SignalP program that predicts nucleotides 1 to 57 of SEQ ID NO: 9 encode a signal peptide. In another aspect, the mature polypeptide coding sequence of a *T. reesei* xylanase I is nucleotides 58 to 749 of SEQ ID NO: 11 or the cDNA sequence thereof based on the SignalP program that predicts nucleotides 1 to 57 of SEQ ID NO: 11 encode a signal peptide. In another aspect, the mature polypeptide coding sequence of a *T. reesei* xylanase II is nucleotides 58 to 778 of SEQ ID NO: 13 or the cDNA sequence thereof based on the SignalP program that predicts nucleotides 1 to 57 of SEQ ID NO: 13 encode a signal peptide. In another aspect, the mature polypeptide coding sequence of a *T. reesei* xylanase III is nucleotides 49 to 1349 of SEQ ID NO: 15 or the cDNA sequence thereof based on the SignalP program that predicts nucleotides 1 to 48 of SEQ ID NO: 15 encode a signal peptide. In another aspect, the mature polypeptide coding sequence of a *T. reesei* beta-xylosidase is nucleotides 61 to 2391 of SEQ ID NO: 17 or the cDNA sequence thereof based on the SignalP program that predicts nucleotides 1 to 60 of SEQ ID NO: 17 encode a signal peptide. In another aspect, the mature polypeptide coding sequence of a *T. reesei* swollenin is nucleotides 55 to 2776 of SEQ ID NO: 19 or the cDNA sequence thereof based on the SignalP program that predicts nucleotides 1 to 54 of SEQ ID NO: 19 encode a signal peptide. In another aspect, the mature polypeptide coding sequence of a *T. reesei* subtilisin-like serine protease is nucleotides 58 to 2774 of SEQ ID NO: 21 based on the SignalP program that predicts nucleotides 1 to 57 of SEQ ID NO: 21 encode a signal peptide. In another aspect, the mature polypeptide coding sequence of a *T. reesei* aspartic protease is nucleotides 61 to 1299 of SEQ ID NO: 23 based on the SignalP program that predicts nucleotides 1 to 60 of SEQ ID NO: 23 encode a signal peptide. In another aspect, the mature polypeptide coding sequence of a *T. reesei* trypsin-like protease is nucleotides 58 to 930 of SEQ ID NO: 25 based on the SignalP program that predicts nucleotides 1 to 57 of SEQ ID NO: 25 encode a signal peptide. In another aspect, the mature polypeptide coding sequence of another *T. reesei* subtilisin-like serine protease is nucleotides 46 to 1681 of SEQ ID NO: 27 based on the SignalP program that predicts nucleotides 1 to 45 of SEQ ID NO: 27 encode a signal peptide. In another aspect, the mature polypeptide coding sequence of another *T. reesei* aspartic protease is nucleotides 52 to 1339 of SEQ ID NO: 29 based on the SignalP program that predicts nucleotides 1 to 51 of SEQ ID NO: 29 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more (e.g., several) control sequences.

Operably linked: The term "operably linked" means a configuration in which a control sequence is placed at an appropriate position relative to the coding sequence of a polynucleotide such that the control sequence directs expression of the coding sequence.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Pretreated corn stover: The term "PCS" or "Pretreated Corn Stover" means a cellulosic material derived from corn stover by treatment with heat and dilute sulfuric acid, alkaline pretreatment, or neutral pretreatment.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment–Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having enzyme activity. In one aspect, a subsequence contains at least 85%, e.g., at least 90% or at least 95% of the nucleotides of the mature polypeptide coding sequence of an enzyme.

Subtilisin-like serine protease: The term "subtilisin-like serine protease" means a protease with a substrate specificity similar to subtilisin that uses a serine residue for catalyzing the hydrolysis of peptide bonds in peptides and proteins. Subtilisin-like proteases (subtilases) are serine proteases characterized by a catalytic triad of the three amino acids aspartate, histidine, and serine. The arrangement of these catalytic residues is shared with the prototypical subtilisin from *Bacillus licheniformis* (Siezen and Leunissen, 1997, *Protein Science* 6: 501-523). Subtilisin-like serine protease activity can be determined using a synthetic substrate, N-succinyl-L-Ala-L-Ala-L-Pro-L-Phe-p-nitroanilide (AAPF) (Bachem AG, Bubendorf, Switzerland) in 100 mM NaCl-100 mM MOPS pH 7.0 at 50° C. for 3 hours and then the absorbance at 405 nm is measured.

Targeted integration: The term "targeted integration" means the stable integration of extracellular DNA at a defined genomic locus.

Transformant: The term "transformant" means a cell which has taken up extracellular DNA (foreign, artificial or modified) and expresses the gene(s) contained therein.

Transformation: The term "transformation" means the introduction of extracellular DNA into a cell, i.e., the genetic alteration of a cell resulting from the direct uptake, incorporation and expression of exogenous genetic material (exogenous DNA) from its surroundings and taken up through the cell membrane(s).

Transformation efficiency: The term "transformation efficiency" means the efficiency by which cells can take up the extracellular DNA and express the gene(s) contained therein, which is calculated by dividing the number of positive transformants expressing the gene(s) by the amount of DNA used during a transformation procedure.

Trypsin-like serine protease: The term "trypsin-like serine protease" means a protease with a substrate specificity similar to trypsin that uses a serine residue for catalyzing the hydrolysis of peptide bonds in peptides and proteins. For purposes of the present invention, trypsin-like serine protease activity is determined according to the procedure described by Dienes et al., 2007, *Enzyme and Microbial Technology* 40: 1087-1094.

Variant: The term "variant" means a polypeptide having enzyme activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune*, *FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

DETAILED DESCRIPTION OF THE INVENTION

The present invention relates to methods for constructing a filamentous fungal strain for production of multiple recombinant polypeptides having biological activity, comprising: (a) replacing an endogenous first gene by targeted integration by introducing into the filamentous fungal strain a first tandem construct comprising (i) a homologous 5' region of the first gene, a homologous flanking region thereof, or a combination thereof, (ii) one or more (e.g., several) first selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the first gene, a homologous flanking region thereof, or a combination thereof; (b) replacing an endogenous second gene by targeted integration by introducing into the filamentous fungal strain a second tandem construct comprising (i) a homologous 5' region of the second gene, a homologous flanking region thereof, or a combination thereof, (ii) one or more (e.g., several) second selectable markers, (iii) a third polynucleotide encoding a third polypeptide having biological activity operably linked to a third promoter and a third terminator, (iv) a fourth polynucleotide encoding a fourth polypeptide having biological activity operably linked to a fourth promoter and a fourth terminator, and (v) a homologous 3' region of the second gene, a homologous flanking region thereof, or a combination thereof; or (c) a combination of (a) and (b).

The present invention also relates to tandem constructs comprising (i) a homologous 5' region of a gene, a homologous flanking region thereof, or a combination thereof, (ii) one or more (e.g., several) selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the gene, a homologous flanking region thereof, or a combination thereof.

The present invention also relates to methods for constructing a filamentous fungal strain for production of multiple recombinant polypeptides having biological activity, comprising: (a) inserting into an endogenous first locus by targeted integration by introducing into the filamentous fungal strain a first tandem construct comprising (i) a homologous 5' region of the first locus, a homologous flanking region thereof, or a combination thereof, (ii) one or more first selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the first locus, a homologous flanking region thereof, or a combination thereof; (b) inserting into an endogenous second locus by targeted integration by introducing into the filamentous fungal strain a second tandem construct comprising (i) a homologous 5' region of the second locus, a homologous flanking region thereof, or a combination thereof, (ii) one or more second selectable markers, (iii) a third polynucleotide encoding a third polypeptide having biological activity operably linked to a third promoter and a third terminator, (iv) a fourth polynucleotide encoding a fourth polypeptide having biological activity operably linked to a fourth promoter and a fourth terminator, and (v) a homologous 3' region of the second locus, a homologous flanking region thereof, or a combination thereof; or (c) a combination of (a) and (b).

The present invention also relates to tandem constructs comprising (i) a homologous 5' region of a locus, a homologous flanking region thereof, or a combination thereof, (ii) one or more first selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the locus, a homologous flanking region thereof, or a combination thereof.

In the methods of the present invention, each of the tandem constructs integrates by double homologous recombination into a targeted site in the chromosome of the filamentous fungal strain. In one aspect, the homologous 5' region of the first gene or first locus, the homologous flanking region thereof, or the combination thereof is at least 50 bp, e.g., at least 100 bp, at least 200 bp, at least 400 bp, at least 800 bp, at least 1000 bp, at least 1500 bp, or at least 2000 bp. In another aspect, the homologous 3' region of the first gene or first locus, the homologous flanking region thereof, or the combination thereof is at least 50 bp, e.g., at least 100 bp, at least 200 bp, at least 400 bp, at least 800 bp, at least 1000 bp, at least 1500 bp, or at least 2000 bp. In another aspect, the homologous 5' region of the second gene or second locus, the homologous flanking region thereof, or the combination thereof is at least 50 bp, e.g., at least 100 bp, at least 200 bp, at least 400 bp, at least 800 bp, at least 1000 bp, at least 1500 bp, or at least 2000 bp. In another aspect, the homologous 3' region of the second gene or second locus, the homologous flanking region thereof, or the combination thereof is at least 50 bp, e.g., at least 100 bp, at least 200 bp, at least 400 bp, at least 800 bp, at least 1000 bp, at least 1500 bp, or at least 2000 bp.

The methods of the present invention may further comprise replacing one or more (e.g., several) additional endogenous genes each by targeted integration with a corresponding tandem construct for each gene comprising (i) a homologous 5' region of the gene, a homologous flanking region thereof, or a combination thereof, (ii) one or more (e.g., several) selectable markers, (iii) a polynucleotide encoding a polypeptide having biological activity operably linked to a promoter, (iv) another polynucleotide encoding another polypeptide having biological activity operably linked to another promoter, and (v) a homologous 3' region of the gene, a homologous flanking region thereof, or a combination thereof.

The methods of the present invention may further comprise inserting into one or more (e.g., several) additional endogenous loci each by targeted integration a corresponding tandem construct for each locus comprising (i) a homologous 5' region of the locus, a homologous flanking region thereof, or a combination thereof, (ii) one or more selectable markers, (iii) a polynucleotide encoding a polypeptide having biological activity operably linked to a promoter and a terminator, (iv) another polynucleotide encoding another polypeptide having biological activity operably linked to another promoter and another terminator, and (v) a homologous 3' region of the locus, a homologous flanking region thereof, or a combination thereof.

In the methods of the present invention, the filamentous fungal host cell may be further transformed with a tandem construct comprising (i) one or more (e.g., several) selectable markers, (ii) a fifth polynucleotide encoding a fifth polypeptide having biological activity operably linked to a fifth promoter and a fifth terminator, and (iii) a sixth polynucleotide encoding a sixth polypeptide having biological activity operably linked to a sixth promoter and a sixth terminator, wherein the tandem construct integrates by ectopic integration.

The present invention provides several advantages including improved methods for producing multiple recombinant polypeptides in a filamentous fungal host; methods allowing easy replacement and/or deletion of one or more recombinant polypeptides introduced into the filamentous fungal host (if one or more recombinant polypeptides are introduced at a single locus, one of more recombinant polypeptides can be replaced and or/deleted in a single step, instead of multiple steps); and method allowing easy modification (i.e., introducing a variant/mutant gene) of existing one or more recombinant poly peptides in a filamentous fungal strain (if one or more recombinant polypeptides were introduced at a single locus, one or more variant/mutant of those recombinant polypeptides can be easily modified in a single step, instead of multiple steps). An additional advantage of a constructed filamentous fungal strain of the present invention is the possibility of mutagenizing the strain and selecting for yield improved mutants. A tandem construct of such a mutant can then be replaced with a new tandem construct expressing new multiple recombinant polypeptides thereby taking advantage of the improved yield productivity of the mutant as a host cell.

Endogenous Genes

In the methods of the present invention, any gene endogenous to a filamentous fungal strain may be replaced or may be a locus. The gene may be native or foreign to the filamentous fungal strain. The term "endogenous gene" or variations thereof, e.g., "endogenous first gene" or "endogenous second gene", will be understood to encompass one or more (e.g., several) genes. Where more than one gene is replaced, the genes are preferably contiguous. Such multiple genes may be, for example, a metabolic pathway or portion thereof.

The endogenous gene may encode a polypeptide selected from the group consisting of an antibody, an antigen, an antimicrobial peptide, an enzyme, a growth factor, a hormone, an immunodilator, a neurotransmitter, a receptor, a reporter protein, a structural protein, or a transcription factor.

In one aspect, the enzyme is selected from the group consisting of an oxidoreductase, a transferase, a hydrolase, a lyase, an isomerase, and a ligase. In another aspect, the enzyme is selected from the group consisting of an acetylmannan esterase, acetyxylan esterase, aminopeptidase, alpha-amylase, alpha-galactosidase, alpha-glucosidase, alpha-1,6-transglucosidase, arabinanase, arabinofuranosidase, beta-galactosidase, beta-glucosidase, beta-xylosidase, carbohydrase, carboxypeptidase, catalase, cellobiohydrolase, cellulase, chitinase, coumaric acid esterase, cyclodextrin glycosyltransferase, cutinase, cyclodextrin glycosyltransferase, deoxyribonuclease, endoglucanase, esterase, feruloyl esterase, GH61 polypeptide having cellulolytic enhancing activity, glucocerebrosidase, glucose oxidase, glucuronidase, glucuronoyl esterase, haloperoxidase, hemicellulase, invertase, isomerase, laccase, ligase, lipase, mannanase, mannosidase, mutanase, oxidase, pectinolytic enzyme, peroxidase, phospholipase, phytase, phenoloxidase, polyphenoloxidase, proteolytic enzyme, ribonuclease, transglutaminase, urokinase, and xylanase.

In another aspect, one or more (e.g., several) endogenous protease genes are inactivated. In another aspect, the one or more (e.g., several) endogenous protease genes are subtilisin-like serine protease, aspartic protease, and trypsin-like serine protease genes as described in WO 2011/075677, which is incorporated herein by reference in its entirety.

In another aspect, the enzyme is a subtilisin-like serine protease. In another aspect, the enzyme is an aspartic protease. In another aspect, the enzyme is a trypsin-like serine protease.

In another aspect, the enzyme is an endoglucanase. In another aspect, the enzyme is a cellobiohydrolase. In another aspect, the enzyme is a beta-glucosidase. In another aspect, the enzyme is a GH61 polypeptide having cellulolytic enhancing activity. In another aspect, the enzyme is a xylanase. In another aspect, the enzyme is a beta-xylosidase. In another aspect, the enzyme is a swollenin. In another aspect, the enzyme is an acetyxylan esterase. In another aspect, the enzyme is a feruloyl esterase. In another aspect, the enzyme is an arabinofuranosidase. In another aspect, the enzyme is a glucuronidase. In another aspect, the enzyme is an acetylmannan esterase. In another aspect, the enzyme is an arabinanase. In another aspect, the enzyme is a coumaric acid esterase. In another aspect, the enzyme is a galactosidase. In another aspect, the enzyme is a glucuronoyl esterase. In another aspect, the enzyme is a mannanase. In another aspect, the enzyme is a mannosidase.

In another aspect, the endogenous gene may be a cellobiohydrolase I gene. In another aspect, the cellobiohydrolase I gene encodes a cellobiohydrolase I selected from the group consisting of: (i) a cellobiohydrolase I comprising the mature polypeptide of SEQ ID NO: 2; (ii) a cellobiohydrolase I comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 2; (iii) a cellobiohydrolase I encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 1; and (iv) a cellobiohydrolase I encoded by a polynucleotide that hybridizes under at least high stringency conditions, e.g., very high stringency conditions, with the mature polypeptide coding sequence of SEQ ID NO: 1 or the full-length complement thereof.

In another aspect, the endogenous gene may be a cellobiohydrolase II gene. In another aspect, the cellobiohydrolase II gene encodes a cellobiohydrolase II selected from the group consisting of: (i) a cellobiohydrolase II comprising the mature polypeptide of SEQ ID NO: 4; (ii) a cellobiohydrolase II comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 4; (iii) a cellobiohydrolase II encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 3; and (iv) a cellobiohydrolase II encoded by a polynucleotide that hybridizes under at least high stringency conditions, e.g., very high stringency conditions, with the mature polypeptide coding sequence of SEQ ID NO: 3 or the full-length complement thereof.

In another aspect, the endogenous gene may be an endoglucanase I gene. In another aspect, the endoglucanase I gene encodes an endoglucanase I selected from the group consisting of: (i) an endoglucanase I comprising the mature polypeptide of SEQ ID NO: 6; (ii) an endoglucanase I comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 6; (iii) an endoglucanase I encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 5; and (iv) an endoglucanase I encoded by a polynucleotide that hybridizes under at least high stringency conditions, e.g., very high stringency conditions, with the mature polypeptide coding sequence of SEQ ID NO: 5 or the full-length complement thereof.

In another aspect, the endogenous gene may be an endoglucanase II gene. In another aspect, the endoglucanase II gene encodes an endoglucanase II selected from the group consisting of: (i) an endoglucanase II comprising the mature polypeptide of SEQ ID NO: 8; (ii) an endoglucanase II comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 8; (iii) an endoglucanase II encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 7; and (iv) an endoglucanase II encoded by a polynucleotide that hybridizes under at least high stringency conditions, e.g., very high stringency conditions, with the mature polypeptide coding sequence of SEQ ID NO: 7 or the full-length complement thereof.

In another aspect, the endogenous gene may be a beta-glucosidase gene. In another aspect, the beta-glucosidase gene encodes a beta-glucosidase selected from the group consisting of: (i) a beta-glucosidase comprising the mature polypeptide of SEQ ID NO: 10; (ii) a beta-glucosidase II comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 10; (iii) a beta-glucosidase encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 9; and (iv) a beta-glucosidase encoded by a polynucleotide that hybridizes under at least high stringency conditions, e.g., very high stringency conditions, with the mature polypeptide coding sequence of SEQ ID NO: 9 or the full-length complement thereof.

In another aspect, the endogenous gene may be a xylanase I gene. In another aspect, the xylanase I gene encodes a xylanase I selected from the group consisting of: (i) a xylanase I comprising the mature polypeptide of SEQ ID NO: 12; (ii) a xylanase I comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 12; (iii) a xylanase I encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 11; and (iv) a xylanase I encoded by a polynucleotide that hybridizes under at least high stringency conditions, e.g., very high stringency conditions, with the mature polypeptide coding sequence of SEQ ID NO: 11 or the full-length complement thereof.

In another aspect, the endogenous gene may be a xylanase II gene. In another aspect, the xylanase II gene encodes a xylanase II selected from the group consisting of: (i) an xylanase II comprising the mature polypeptide of SEQ ID NO: 14; (ii) a xylanase II comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 14; (iii) a xylanase II encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 13; and (iv) a xylanase II encoded by a polynucleotide that hybridizes under at least high stringency conditions, e.g., very high stringency conditions, with the mature polypeptide coding sequence of SEQ ID NO: 13 or the full-length complement thereof.

In another aspect, the endogenous gene may be a xylanase III gene. In another aspect, the xylanase III gene encodes a xylanase III selected from the group consisting of: (i) an xylanase III comprising the mature polypeptide of SEQ ID NO: 16; (ii) a xylanase III comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 16; (iii) a xylanase III encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 15; and (iv) a xylanase III encoded by a polynucleotide that hybridizes under at least high stringency conditions, e.g., very high stringency conditions, with the mature polypeptide coding sequence of SEQ ID NO: 15 or the full-length complement thereof.

In another aspect, the endogenous gene may be a beta-xylosidase gene. In another aspect, the beta-xylosidase gene encodes a beta-xylosidase selected from the group consisting of: (i) a beta-xylosidase comprising the mature polypeptide of SEQ ID NO: 18; (ii) a beta-xylosidase comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 18; (iii) a beta-xylosidase encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 17; and (iv) a beta-xylosidase encoded by a polynucleotide that hybridizes under at least high stringency conditions, e.g., very high stringency conditions, with the mature polypeptide coding sequence of SEQ ID NO: 17 or the full-length complement thereof.

In another aspect, the endogenous gene may be a swollenin gene. In another aspect, the swollenin gene encodes a swollenin selected from the group consisting of: (i) a swollenin comprising the mature polypeptide of SEQ ID NO: 20; (ii) a swollenin comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 20; (iii) a swollenin encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 19; and (iv) a swollenin encoded by a polynucleotide that hybridizes under at least high stringency conditions, e.g., very high stringency conditions, with the mature polypeptide coding sequence of SEQ ID NO: 19 or the full-length complement thereof.

In another aspect, the endogenous gene may be a subtilisin-like serine protease gene. In another aspect, the subtilisin-like serine protease gene encodes a subtilisin-like serine protease selected from the group consisting of: (i) a subtilisin-like serine protease comprising the mature polypeptide of SEQ ID NO: 22; (ii) a subtilisin-like serine protease comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 22; (iii) a subtilisin-like serine protease encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 21; and (iv) a subtilisin-like serine protease encoded by a polynucleotide that hybridizes under at least high stringency conditions, e.g., very high stringency conditions, with the mature polypeptide coding sequence of SEQ ID NO: 21 or the full-length complement thereof.

In another aspect, the endogenous gene may be an aspartic protease gene. In another aspect, the aspartic protease gene encodes an aspartic protease selected from the group consisting of: (i) an aspartic protease comprising the mature polypeptide of SEQ ID NO: 24; (ii) an aspartic protease comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 24; (iii) an aspartic protease encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 23; and (iv) an aspartic protease encoded by a polynucleotide that hybridizes under at least high stringency conditions, e.g., very high stringency conditions, with the mature polypeptide coding sequence of SEQ ID NO: 23 or the full-length complement thereof.

In another aspect, the endogenous gene may be a trypsin-like serine protease gene. In another aspect, the trypsin-like serine protease gene encodes a trypsin-like serine protease selected from the group consisting of: (i) a trypsin-like serine protease comprising the mature polypeptide of SEQ ID NO: 26; (ii) a trypsin-like serine protease comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 26; (iii) a trypsin-like serine protease encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 25; and (iv) a trypsin-like serine protease encoded by a polynucleotide that hybridizes under at least high stringency conditions, e.g., very high stringency conditions, with the mature polypeptide coding sequence of SEQ ID NO: 25 or the full-length complement thereof.

In another aspect, the endogenous gene may be a subtilisin-like serine protease gene. In another aspect, the subtilisin-like serine protease gene encodes a subtilisin-like serine protease selected from the group consisting of: (i) a subtilisin-like serine protease comprising the mature polypeptide of SEQ ID NO: 28; (ii) a subtilisin-like serine protease comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 28; (iii) a subtilisin-like serine protease encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 27; and (iv) a subtilisin-like serine protease encoded by a polynucleotide that hybridizes under at least high stringency conditions, e.g., very high stringency conditions, with the mature polypeptide coding sequence of SEQ ID NO: 27 or the full-length complement thereof.

In another aspect, the endogenous gene may be an aspartic protease gene. In another aspect, the aspartic protease gene encodes an aspartic protease selected from the group consisting of: (i) an aspartic protease comprising the mature polypeptide of SEQ ID NO: 30; (ii) an aspartic protease comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 30; (iii) an aspartic protease encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 29; and (iv) an aspartic protease encoded by a polynucleotide that hybridizes under at least high stringency conditions, e.g., very high stringency conditions, with the mature polypeptide coding sequence of SEQ ID NO: 29 or the full-length complement thereof.

Tandem Constructs

The present invention also relates to tandem constructs comprising (i) a homologous 5' region of a gene, a homologous flanking region thereof, or a combination thereof, (ii) one or more (e.g., several) selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the gene, a homologous flanking region thereof, or a combination thereof.

The present invention also relates to tandem constructs comprising (i) a homologous 5' region of a locus, a homologous flanking region thereof, or a combination thereof, (ii) one or more first selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the locus, a homologous flanking region thereof, or a combination thereof.

The tandem constructs can be constructed by operably linking one or more (e.g., several) control sequences to each polynucleotide of the construct that direct the expression of the coding sequence in a filamentous fungal host cell under conditions compatible with the control sequences. Manipulation of each polynucleotide prior to insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

In one aspect, the promoters are different promoters. In another aspect, two or more (e.g., several) of the promoters are the same promoter.

Examples of suitable promoters for directing transcription of the constructs in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147, which is incorporated herein in its entirety.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

In one aspect, the terminators are different terminators. In another aspect, two or more (e.g., several) of the terminators are the same terminator.

Preferred terminators for filamentous fungal host cells are obtained from the genes for *Aspergillus nidulans* anthranilate synthase, *Aspergillus nidulans* acetamidase (amdS), *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

The control sequence may also be a leader, a nontranslated region of an mRNA that is important for translation by the host cell. The leader is operably linked to the 5'-terminus of the polynucleotide encoding the polypeptide. Any leader that is functional in a host cell may be used.

Preferred leaders for filamentous fungal host cells are obtained from the genes for *Aspergillus oryzae* TAKA amylase and *Aspergillus nidulans* triose phosphate isomerase.

The control sequence may also be a polyadenylation sequence, a sequence operably linked to the 3'-terminus of the polynucleotide and, when transcribed, is recognized by a host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus nigerglucoamylase, Aspergillus niger* alpha-glucosidase *Aspergillus oryzae* TAKA amylase, *Fusarium oxysporum* trypsin-like protease, *Trichoderma reesei* cellobiohydrolase I, *Trichoderma reesei* cellobiohydrolase II, and *Trichoderma reesei* endoglucanase V.

The control sequence may also be a signal peptide coding region that encodes a signal peptide linked to the N-terminus of a polypeptide and directs the polypeptide into a cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, *Rhizomucor miehei* aspartic proteinase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, and *Trichoderma reesei* endoglucanase V.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Myceliophthora thermophila* laccase (WO 95/33836) and *Rhizomucor miehei* aspartic proteinase.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of a host cell. Examples of regulatory sequences are those that cause expression of the gene to be turned on or off in response to a chemical or physical stimulus, including the presence of a regulatory compound. Regulatory sequences in filamentous fungi include the *Aspergillus niger* glucoamylase promoter, *Aspergillus oryzae* TAKA alpha-amylase promoter, *Aspergillus oryzae* glucoamylase promoter, *Trichoderma reesei* cellobiohydrolase I promoter, and *Trichoderma reesei* cellobiohydrolase II promoter. Other examples of regulatory sequences are those that allow for gene amplification. In these cases, the polynucleotide encoding the polypeptide would be operably linked to the regulatory sequence.

The tandem constructs of the present invention preferably contain one or more (e.g., several) selectable markers that permit easy selection of transformed cells. A selectable marker is a gene the product of which provides for biocide or viral resistance, resistance to heavy metals, prototrophy to auxotrophs, and the like. Examples of selectable markers for use in a filamentous fungal host cell include, but are not limited to, adeA (phosphoribosylaminoimidazole-succinocarboxamide synthase), adeB (phosphoribosylamino-imidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes. Examples of bacterial selectable markers are markers that confer antibiotic resistance such as ampicillin, chloramphenicol, kanamycin, neomycin, spectinomycin, or tetracycline resistance.

The one or more (e.g., several) selectable markers may be a dual selectable marker system as described in WO 2010/039889 A2, which is incorporated herein by reference in its entirety. In one aspect, the one or more selectable markers is a hph-tk dual selectable marker system.

In each tandem construct of the present invention, the one or more (e.g., several) selectable markers are different markers, unless a selectable marker is reused as described herein.

One or more (e.g., several) of the selectable markers may be reused for replacing one or more (e.g., several) additional endogenous genes or for inserting into one or more additional endogenous loci each by targeted integration with a corresponding tandem construct for each gene or locus. The one or more tandem constructs may further comprise a first homologous repeat flanking 5' of the one or more selectable markers and a second homologous repeat flanking 3' of the one or more selectable markers, wherein the first homologous repeat and the second homologous repeat undergo homologous recombination to excise the one or more selectable markers. Upon the excision of the one or more selectable markers, the one or more selectable markers can be reused for replacing the one or more additional endogenous genes or for inserting into the one or more additional endogenous loci each by targeted integration with the corresponding tandem construct for each gene or locus.

In one aspect, the first and second homologous repeats are identical. In another aspect, the first and second homologous repeats have a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to each other. In another aspect, the first and second homologous repeats are each at least 50 bp, e.g., at least 100 bp, at least 200 bp, at least 400 bp, at least 800 bp, at least 1000 bp, at least 1500 bp, or at least 2000 bp. The fragment containing one repeat may be longer than the fragment containing the other repeat.

The tandem constructs of the present invention may further comprise one or more (e.g., several) additional polynucleotides encoding other polypeptides having biological activity. For example, a tandem construct may contain one additional polynucleotide, two additional polynucleotides, three additional polynucleotides, etc.

Polypeptides Having Biological Activity

The polypeptides may be any polypeptides having a biological activity of interest. The term "polypeptide" is not meant herein to refer to a specific length of the encoded product and, therefore, encompasses peptides, oligopeptides, and proteins. The term "polypeptide" also encompasses two or more (e.g., several) polypeptides combined to form the encoded product. The polypeptides also include fusion polypeptides, which comprise a combination of partial or complete polypeptide sequences obtained from at least two different polypeptides wherein one or more (e.g., several) may be heterologous to the filamentous fungal host strain. The polypeptides may further include naturally occurring allelic and engineered variations of the below-mentioned polypeptides and hybrid polypeptides.

In one aspect, the polypeptides are selected from the group consisting of an antibody, an antigen, an antimicrobial peptide, an enzyme, a growth factor, a hormone, an immunodilator, a neurotransmitter, a receptor, a reporter protein, a structural protein, or a transcription factor.

In another aspect, the enzyme is selected from the group consisting of an oxidoreductase, a transferase, a hydrolase, a lyase, an isomerase, and a ligase. In another aspect, the enzyme is selected from the group consisting of an acetylmannan esterase, acetyxylan esterase, aminopeptidase, alpha-amylase, alpha-galactosidase, alpha-glucosidase, alpha-1,6-transglucosidase, arabinanase, arabinofuranosidase, beta-galactosidase, beta-glucosidase, beta-xylosidase, carbohydrase, carboxypeptidase, catalase, cellobiohydrolase, cellulase, chitinase, coumaric acid esterase, cyclodextrin glycosyltransferase, cutinase, deoxyribonuclease, endoglucanase, esterase, feruloyl esterase, GH61 polypeptide having cellulolytic enhancing activity, glucocerebrosidase, glucose oxidase, glucuronidase, glucuronoyl esterase, haloperoxidase, hemicellulase, invertase, isomerase, laccase, ligase, lipase, mannanase, mannosidase, mutanase, oxidase, pectinolytic enzyme, peroxidase, phospholipase, phytase, phenoloxidase, polyphenoloxidase, proteolytic enzyme, ribonuclease, transglutaminase, urokinase, and xylanase.

In another aspect, the polypeptides are selected from the group consisting of an albumin, a collagen, a tropoelastin, an elastin, and a gelatin.

In another aspect, the polypeptides having biological activity may be different polypeptides. In another aspect, two or more (e.g., several) of the polypeptides having biological activity are the same polypeptide.

In another aspect, the polypeptides comprise one or more enzymes selected from the group consisting of a cellulase, a cip1 protein, a GH61 polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is one or more enzymes selected from the group consisting of an endoglucanase, a cellobiohydrolase, and a beta-glucosidase. In another aspect, the hemicellulase is one or more enzymes selected from the group consisting of a xylanase, an acetylxylan esterase, a feruloyl esterase, an arabinofuranosidase, a xylosidase, and a glucuronidase.

In another aspect, one of the polypeptides is a cellulase. In another aspect, one of the polypeptides is an endoglucanase. In another aspect, one of the polypeptides is a cellobiohydrolase. In another aspect, one of the polypeptides is a beta-glucosidase. In another aspect, one of the polypeptides is a GH61 polypeptide having cellulolytic enhancing activity. In another aspect, one of the polypeptides is a swollenin protein. In another aspect, one of the polypeptides is a cip1 protein. In another aspect, one of the polypeptides is an esterase, In another aspect, one of the polypeptides is an expansin. In another aspect, one of the polypeptides is a laccase. In another aspect, one of the polypeptides is a ligninolytic enzyme.

In another aspect, one of the polypeptides is a pectinase, In another aspect, one of the polypeptides is a peroxidase. In another aspect, one of the polypeptides is a protease. In another aspect, one of the polypeptides is a swollenin.

In another aspect, one of the polypeptides is a hemicellulase. In another aspect, one of the polypeptides is a xylanase. In another aspect, one of the polypeptides is a beta-xylosidase. In another aspect, one of the polypeptides is an acetyxylan esterase. In another aspect, one of the polypeptides is a feruloyl esterase. In another aspect, one of the polypeptides is an arabinofuranosidase. In another aspect, one of the polypeptides is a glucuronidase. In another aspect, one of the polypeptides is an acetylmannan esterase. In another aspect, one of the polypeptides is an arabinanase. In another aspect, one of the polypeptides is a coumaric acid esterase. In another aspect, one of the polypeptides is a galactosidase. In another aspect, one of the polypeptides is a glucuronoyl esterase. In another aspect, one of the polypeptides is a mannanase. In another aspect, one of the polypeptides is a mannosidase.

Examples of endoglucanases as the polypeptides having biological activity include, but are not limited to, a *Trichoderma reesei* endoglucanase I (Penttila et al., 1986, *Gene* 45: 253-263, *Trichoderma reesei* Cel7B endoglucanase I (GENBANK™ accession no. M15665), *Trichoderma reesei* endoglucanase II (Saloheimo, et al., 1988, Gene 63:11-22), *Trichoderma reesei* Cel5A endoglucanase II (GENBANK™ accession no. M19373), *Trichoderma reesei* endoglucanase III (Okada et al., 1988, *Appl. Environ. Microbiol.* 64: 555-563, GENBANK™ accession no. AB003694), *Trichoderma reesei* endoglucanase V (Saloheimo et al., 1994, *Molecular Microbiology* 13: 219-228, GENBANK™ accession no. Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Erwinia carotovara* endoglucanase (Saarilahti et al., 1990, *Gene* 90: 9-14), *Fusarium oxysporum* endoglucanase (GENBANK™ accession no. L29381), *Humicola grisea* var. *thermoidea* endoglucanase (GENBANK™ accession no. AB003107), *Melanocarpus albomyces* endoglucanase (GENBANK™ accession no. MAL515703), *Neurospora crassa* endoglucanase (GENBANK™ accession no. XM_324477), *Humicola insolens* endoglucanase V, *Myceliophthora thermophila* CBS 117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris* NRRL 8126 CEL7C endoglucanase, *Thielavia terrestris* NRRL 8126 CEL7E endoglucanase, *Thielavia terrestris* NRRL 8126 CEL7F endoglucanase, *Cladorrhinum foecundissimum* ATCC 62373 CEL7A endoglucanase, and *Trichoderma reesei* strain No. VTT-D-80133 endoglucanase (GENBANK™ accession no. M15665).

Examples of cellobiohydrolases as the polypeptides having biological activity include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of beta-glucosidases as the polypeptides having biological activity include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 2002/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may also be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637).

Examples of other endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 5,457,046, 5,648,263, and 5,686,593.

Examples of GH61 polypeptides having cellulolytic enhancing activity as the polypeptides having biological activity include, but are not limited to, GH61 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290), *Myceliophthora thermophila* (WO 2009/085935, WO 2009/085859, WO 2009/085864, WO 2009/085868), *Aspergillus fumigatus* (WO 2010/138754), GH61 polypeptides from *Penicillium pinophilum* (WO 2011/005867), *Thermoascus* sp. (WO 2011/039319), *Penicillium* sp. (WO 2011/041397), and *Thermoascus crustaceous* (WO 2011/041504).

Examples of xylanases as the polypeptides having biological activity include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thielavia terrestris* NRRL 8126 (WO 2009/079210), and *Trichophaea saccata* GH10 (WO 2011/057083).

Examples of beta-xylosidases as the polypeptides having biological activity include, but are not limited to, beta-xylosidases from *Neurospora crassa* (SwissProt accession number Q7SOW4), *Trichoderma reesei* (UniProtKB/TrEMBL accession number Q92458), and *Talaromyces emersonii* (SwissProt accession number Q8X212).

Examples of acetylxylan esterases as the polypeptides having biological activity include, but are not limited to, acetylxylan esterases from *Aspergillus aculeatus* (WO 2010/108918), *Chaetomium globosum* (Uniprot accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt accession number q7s259), *Phaeosphaeria nodorum* (Uniprot accession number Q0UHJ1), and *Thielavia terrestris* NRRL 8126 (WO 2009/042846).

Examples of feruloyl esterases (ferulic acid esterases) as the polypeptides having biological activity include, but are not limited to, feruloyl esterases form *Humicola insolens* DSM 1800 (WO 2009/076122), *Neosartorya fischeri* (UniProt Accession number A1D9T4), *Neurospora crassa* (UniProt accession number Q9HGR3), *Penicillium aurantiogriseum* (WO 2009/127729), and *Thielavia terrestris* (WO 2010/053838 and WO 2010/065448).

Examples of arabinofuranosidases as the polypeptides having biological activity include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases as the polypeptides having biological activity include, but are not limited to, alpha-glucuronidases from *Aspergillus clavatus* (UniProt accession number alcc12), *Aspergillus fumigatus* (SwissProt accession number Q4WW45), *Aspergillus niger* (Uniprot accession number Q96WX9), *Aspergillus terreus* (SwissProt accession number Q0CJP9), *Humicola insolens* (WO 2010/014706), *Penicillium aurantiogriseum* (WO 2009/068565), *Talaromyces emersonii* (UniProt accession number Q8X211), and *Trichoderma reesei* (Uniprot accession number Q99024).

The accession numbers are incorporated herein by reference in their entirety.

Expression Vectors

The present invention also relates to expression vectors comprising a tandem construct of the present invention. A tandem construct may be inserted into a vector or the various components of a tandem construct may be joined together to produce a recombinant expression vector. The vector may include one or more (e.g., several) convenient restriction sites to allow for insertion of polynucleotides at such sites. In creating the expression vector, the coding sequences are located in the vector so that the coding sequences are operably linked with the appropriate control sequences for expression.

The recombinant expression vector may be any vector (e.g., a plasmid or virus) that can be conveniently subjected to recombinant DNA procedures and can bring about expression of the polynucleotides. The choice of the vector will typically depend on the compatibility of the vector with the host cell into which the vector is to be introduced. The vector may be a linear or closed circular plasmid.

The vector preferably contains one or more (e.g., several) selectable markers that permit easy selection of transformed cells. Examples of selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes. Examples of bacterial selectable markers are markers that confer antibiotic resistance such as ampicillin, chloramphenicol, kanamycin, neomycin, spectinomycin, or tetracycline resistance.

The procedures used to ligate the elements described above to construct the recombinant expression vectors are well known to one skilled in the art (see, e.g., Sambrook et al., 1989, supra).

Filamentous Fungal Host Cells

The present invention also relates to filamentous fungal strains, comprising: (a) an endogenous first gene replaced by targeted integration with a first tandem construct comprising (i) a homologous 5' region of the first gene, a homologous flanking region thereof, or a combination thereof, (ii) one or more (e.g., several) first selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the first gene, a homologous flanking region thereof, or a combination thereof; (b) an endogenous second gene replaced by targeted integration with a second tandem construct comprising (i) a homologous 5' region of the second gene, a homologous flanking region thereof, or a combination thereof, (ii) one or more (e.g., several) second selectable markers, (iii) a third polynucleotide encoding a third polypeptide having biological activity operably linked to a third promoter and a third terminator, (iv) a fourth polynucleotide encoding a fourth polypeptide having biological activity operably linked to a fourth promoter and a fourth terminator, and (v) a homologous 3' region of the second gene, a homologous flanking region thereof, or a combination thereof; or (c) a combination of (a) and (b).

The present invention also relates to filamentous fungal strains, comprising: (a) an endogenous first locus modified by insertion by targeted integration with a first tandem construct comprising (i) a homologous 5' region of the first locus, a homologous flanking region thereof, or a combination thereof, (ii) one or more first selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the first locus, a homologous flanking region thereof, or a combination thereof; (b) an endogenous second locus modified by insertion by targeted integration with a second tandem construct comprising (i) a homologous 5' region of the second locus, a homologous flanking region thereof, or a combination thereof, (ii) one or more second selectable markers, (iii) a third polynucleotide encoding a third polypeptide having biological activity operably linked to a third promoter and a third terminator, (iv) a fourth polynucleotide encoding a fourth polypeptide having biological activity operably linked to a fourth promoter and a fourth terminator, and (v) a homologous 3' region of the second locus, a homologous flanking region thereof, or a combination thereof; or (c) a combination of (a) and (b).

The term “host cell” encompasses any progeny of a parent cell that is not identical to the parent cell due to mutations that occur during replication. The choice of a host cell will to a large extent depend upon the gene encoding the polypeptide and its source.

The host cell may be any filamentous fungal cell useful in the recombinant production of polypeptides. “Filamentous fungi” include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium suiphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

In one aspect, the filamentous fungal host cell is *Aspergillus oryzae*. In another aspect, the filamentous fungal host cell is *Aspergillus niger*. In another aspect, the filamentous fungal host cell is *Fusarium venenatum*. In another aspect, the filamentous fungal host cell is *Trichoderma reesei*. In another aspect, the filamentous fungal host cell is *Trichoderma longibrachiatum.*

In another aspect, the filamentous fungal host cell is *Trichoderma reesei* RutC30. In another aspect, the filamentous fungal host cell is *Trichoderma reesei* TV10. In another aspect, the filamentous fungal host cell is a mutant of *Trichoderma reesei* RutC30. In another aspect, the filamentous fungal host cell is a mutant of *Trichoderma reesei* TV10. In another aspect, the filamentous fungal host cell is a morphological mutant of *Trichoderma reesei*. See, for example, WO 97/26330, which is incorporated herein by reference in its entirety.

In another aspect, the filamentous fungal host cell is a *Trichoderma* strain comprising one or more (several) genes selected from the group consisting of a first subtilisin-like serine protease gene, a first aspartic protease gene, a trypsin-like serine protease gene, a second subtilisin-like serine protease gene, and a second aspartic protease gene, wherein the one or more (several) genes are modified rendering the mutant strain deficient in the production of one or more (several) enzymes selected from the group consisting of a first subtilisin-like serine protease, a first aspartic protease, a trypsin-like serine protease, a second subtilisin-like serine protease, and a second aspartic protease, respectively, compared to the parent *Trichoderma* strain when cultivated under identical conditions, as described in WO 2011/075677, which is incorporated herein by reference in its entirety.

Filamentous fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 1996/00787.

Methods of Production

The present invention also relates to methods for producing multiple recombinant polypeptides having biological activity in a filamentous fungal strain, comprising:

(A) cultivating a filamentous fungal host cell under conditions conducive for production of the polypeptides, wherein the filamentous fungal host cell comprises (a) an endogenous first gene replaced by targeted integration with a first tandem construct comprising (i) a homologous 5' region of the first gene, a homologous flanking region thereof, or a combination thereof, (ii) one or more (e.g., several) first selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the first gene, a homologous flanking region thereof, or a combination thereof; (b) an endogenous second gene replaced by targeted integration with a second tandem construct comprising (i) a homologous 5' region of the second gene, a homologous flanking region thereof, or a combination thereof, (ii) one or more (e.g., several) second selectable markers, (iii) a third polynucleotide encoding a third polypeptide having biological activity operably linked to a third promoter and a third terminator, (iv) a fourth polynucleotide encoding a fourth polypeptide having biological activity operably linked to a fourth promoter and a fourth terminator, and (v) a homologous 3' region of the second gene, a homologous flanking region thereof, or a combination thereof; or (c) a combination of (a) and (b); and optionally (B) Recovering the Multiple Recombinant Polypeptides.

The present invention also relates to methods for producing multiple recombinant polypeptides having biological activity in a filamentous fungal strain, comprising:

(A) cultivating a filamentous fungal host cell under conditions conducive for production of the polypeptides, wherein the filamentous fungal host cell comprises (a) an endogenous first locus modified by insertion by targeted integration with a first tandem construct comprising (i) a homologous 5' region of the first locus, a homologous flanking region thereof, or a combination thereof, (ii) one or more first selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the first locus, a homologous flanking region thereof, or a combination thereof; (b) an endogenous second locus modified by insertion by targeted integration with a second tandem construct comprising (i) a homologous 5' region of the second locus, a homologous flanking region thereof, or a combination thereof, (ii) one or more second selectable markers, (iii) a third polynucleotide encoding a third polypeptide having biological activity operably linked to a third promoter and a third terminator, (iv) a fourth polynucleotide encoding a fourth polypeptide having biological activity operably linked to a fourth promoter and a fourth terminator, and (v) a homologous 3' region of the second locus, a homologous flanking region thereof, or a combination thereof; or (c) a combination of (a) and (b); and optionally (B) Recovering the Multiple Recombinant Polypeptides.

The filamentous fungal host cells are cultivated in a nutrient medium suitable for production of the polypeptides using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptides to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptides are secreted into the nutrient medium, the polypeptides can be recovered directly from the medium. If the polypeptides are not secreted, they can be recovered from cell lysates.

The polypeptides may be detected using methods known in the art that are specific for the polypeptides. These detection methods include, but are not limited to, use of specific antibodies, formation of an enzyme product, or disappearance of an enzyme substrate. For example, enzyme assays may be used to determine the activity of the polypeptides.

The polypeptides may be recovered using methods known in the art. For example, the polypeptides may be recovered from the nutrient medium by conventional procedures including, but not limited to, collection, centrifugation, filtration, extraction, spray-drying, evaporation, or precipitation. In one aspect, the whole fermentation broth is recovered.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

The present invention is further described by the following examples that should not be construed as limiting the scope of the invention.

EXAMPLES

Strains

*Trichoderma reesei* strain 981-O-8 (D4) is a mutagenized strain of *Trichoderma reesei* RutC30 (ATCC 56765; Montenecourt and Eveleigh, 1979, *Adv. Chem. Ser.* 181: 289-301).

*Trichoderma reesei* strain AgJg115-104-7B1 (PCT/US2010/061105, WO 2011/075677) is a ku70-derivative of *T. reesei* strain 981-O-8 (D4).

Media and Buffer Solutions

LB plates were composed of 10 g of tryptone, 5 g of yeast extract, 5 g of NaCl, 15 g of Bacto agar, and deionized water to 1 liter.

2XYT plus ampicillin plates were composed of 16 g of tryptone, 10 g of yeast extract, 5 g of sodium chloride, 15 g of Bacto agar, and deionized water to 1 liter. One ml of a 100 mg/ml solution of ampicillin was added after the autoclaved medium was cooled to 55° C.

SOC medium was composed of 20 g of Bacto-tryptone, 5 g of Bacto yeast extract, 0.5 g of NaCl, 2.5 ml of 1 M KCl, and deionized water to 1 liter. The pH was adjusted to 7.0 with 10 N NaOH before autoclaving. Then 20 ml of sterile 1 M glucose was added immediately before use.

COVE salt solution was composed of 26 g of KCl, 26 g of $MgSO_4.7H_2O$, 76 g of $KH_2PO_4$, 50 ml of COVE trace metals solution, and deionized water to 1 liter.

COVE trace metals solution was composed of 0.04 g of $NaB_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, 10 g of $ZnSO_4.7H_2O$, and deionized water to 1 liter.

COVE plates were composed of 342.3 g of sucrose, 20 ml of COVE salt solution, 10 ml of 1 M acetamide, 10 ml of 1.5 M CsCl, 25 g of Noble agar (Difco), and deionized water to 1 liter.

COVE2 plates were composed of 30 g of sucrose, 20 ml of COVE salt solution, 10 ml of 1 M acetamide, 25 g of Noble agar (Difco), and deionized water to 1 liter.

*Trichoderma* trace metals solution was composed of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, 336 g of citric acid, and deionized water to 1 liter.

CIM medium was composed of 20 g of cellulose, 10 g of corn steep solids, 1.45 g of $(NH_4)_2SO_4$, 2.08 g of $KH_2PO_4$, 0.28 g of $CaCl_2$, 0.42 g of $MgSO_4.7H_2O$, 0.42 ml of *Trichoderma* trace metals solution, 1-2 drops of antifoam, and deionized water to 1 liter; pH adjusted to 6.0.

YP medium was composed of 10 g of yeast extract, 20 g of Bacto peptone, and deionized water to 1 liter.

YPG medium was composed of 4 g of yeast extract, 1 g of $K_2HPO_4$, 0.5 g of $MgSO_4$, 15.0 g of glucose, and deionized water to 1 liter (pH 6.0).

PEG buffer was composed of 500 g of polyethylene glycol 4000 (PEG 4000), 10 mM $CaCl_2$, 10 mM Tris-HCl pH 7.5, and deionized water to 1 liter; filter sterilized.

PDA plates were composed of 39 g of Potato Dextrose Agar (Difco) and deionized water to 1 liter.

PDA overlay medium was composed of 39 g of Potato Dextrose Agar (Difco), 2.44 g of uridine, and deionized water to 1 liter. The autoclaved medium was melted in a microwave and then cooled to 55° C. before use.

STC was composed of 1 M sorbitol, 10 mM mM $CaCl_2$, and 10 mM Tris-HCl, pH 7.5; filter sterilized.

TE buffer was composed of 1 M Tris pH 8.0 and 0.5 M EDTA pH 8.0

Denaturing Solution was composed of 0.5 M NaOH and 1.5 M NaCl.

Neutralization Solution was composed of 1 M Tris pH 8.0 and 1.5 M NaCl.

20×SSC was composed of 175.3 g of NaCl, 88.2 g of sodium citrate, and deionized water to 1 liter.

TrMM-G medium was composed of 20 ml of COVE salt solution, 6 g of $(NH_4)_2SO_4$, 0.6 g of $CaCl_2$, 25 g of Nobel agar (Difco), 20 g of glucose, and deionized water to 1 liter.

NZY+ medium was composed of 5 g of NaCl, 3 g of $MgSO_4.7H_2O$, 5 g of yeast extract, 10 g of NZ amine, 1.2 g of $MgCl_2$, 4 g of glucose, and deionized water to 1 liter.

Example 1: Cloning of an *Aspergillus fumigatus* GH61B Polypeptide Gene

A tblastn search (Altschul et al., 1997, *Nucleic Acids Res.* 25: 3389-3402) of the *Aspergillus fumigatus* partial genome sequence (The Institute for Genomic Research, Rockville, Md., USA) was performed using as query several known GH61 polypeptides including the *Thermoascus aurantiacus* GH61A polypeptide (GeneSeqP Accession Number AEC05922). Several genes were identified as putative Family GH61 homologs based upon a high degree of similarity to the query sequences at the amino acid level. One genomic region of approximately 850 bp with greater than 70% sequence identity to the *Thermoascus aurantiacus* GH61A polypeptide sequence at the amino acid level was chosen for further study.

*A. fumigatus* NN051616 was grown and harvested as described in U.S. Pat. No. 7,244,605. Frozen mycelia were ground, by mortar and pestle, to a fine powder and genomic DNA was isolated using a DNEASY® Plant Maxi Kit (QIAGEN Inc., Valencia, Calif., USA) according to manufacturer's instructions.

Two synthetic oligonucleotide primers shown below were designed to PCR amplify the *A. fumigatus* GH61B polypeptide coding sequence from the genomic DNA. An IN-FUSION® Cloning Kit (Clontech Laboratories, Inc., Mountain View, Calif., USA) was used to clone the fragment directly into the expression vector pAlLo2 (WO 2004/099228), without the need for restriction digestion and ligation.

```
Forward primer:
                                    (SEQ ID NO: 31)
5'-ACTGGATTTACCATGACTTTGTCCAAGATCACTTCCA-3'

Reverse primer:
                                    (SEQ ID NO: 32)
5'-TCACCTCTAGTTAATTAAGCGTTGAACAGTGCAGGACCAG-3'
```

Bold letters represent coding sequence. The remaining sequences are homologous to the insertion sites of pAlLo2.

Fifty picomoles of each of the primers above were used in a PCR reaction composed of 204 ng of *A. fumigatus* genomic DNA, 1×Pfx Amplification Buffer (Invitrogen, Carlsbad, Calif., USA), 1.5 μl of a 10 mM blend of dATP, dTTP, dGTP, and dCTP, 2.5 units of PLATINUM® Pfx DNA Polymerase (Invitrogen Corp., Carlsbad, Calif., USA), and 1 μl of 50 mM $MgSO_4$ in a final volume of 50 μl. The amplification was performed using an EPPENDORF® MASTERCYCLER® 5333 epgradient S (Eppendorf Scientific, Inc., Westbury, N.Y., USA) programmed for 1 cycle at 94° C. for 3 minutes; and 30 cycles each at 94° C. for 30 seconds, 56° C. for 30 seconds, and 72° C. for 1 minutes. The heat block was then held at 72° C. for 15 minutes followed by a 4° C. soak cycle. The reaction products were isolated by 1.0% agarose gel electrophoresis using 40 mM Tris base, 20 mM sodium acetate, 1 mM disodium EDTA (TAE) buffer where an approximately 850 bp product band was excised from the gel and purified using a MINELUTE® Gel Extraction Kit (QIAGEN Inc., Valencia, Calif., USA) according to the manufacturer's instructions.

The 850 bp fragment was then cloned into pAlLo2 using an IN-FUSION® Cloning Kit. Plasmid pAlLo2 was digested with Nco I and Pac I. The plasmid fragment was purified by gel electrophoresis as above and a QIAQUICK® Gel Purification Kit (QIAGEN Inc., Valencia, Calif., USA). The gene fragment and the digested vector were combined together in a reaction described below resulting in the expression plasmid pAG43 (FIG. 1) in which transcription of the *A. fumigatus* GH61B polypeptide coding sequence was under the control of the NA2-tpi promoter. The NA2-tpi promoter is a modified promoter from the *Aspergillus niger* neutral alpha-amylase gene in which the untranslated leader has been replaced by an untranslated leader from the *Aspergillus nidulans* triose phosphate isomerase gene. The recombination reaction (20 μl) was composed of 1× IN-FUSION® Reaction Buffer (Clontech Laboratories, Inc., Mountain View, Calif., USA), 1×BSA (Clontech Laboratories, Inc., Mountain View, Calif., USA), 1 μl of IN-FUSION® Enzyme (diluted 1:10) (Clontech Laboratories, Inc., Mountain View, Calif., USA), 166 ng of pAlLo2 digested with Nco I and Pac I, and 110 ng of the *A. fumigatus* GH61B polypeptide purified PCR product. The reaction was incubated at 37° C. for 15 minutes followed by 15 minutes at 50° C. The reaction was diluted with 40 μl of 10 mM Tris-0.1 M EDTA buffer and 2.5 μl of the diluted reaction was used to transform *E. coli* XL10 SOLOPACK® Gold Competent Cells (Stratagene, La Jolla, Calif., USA) according to the manufacturer's instructions. An *E. coli* transformant containing pAG43 (GH61B polypeptide coding sequence) was identified by restriction enzyme digestion and plasmid DNA was prepared using a BIOROBOT® 9600 (QIAGEN Inc., Valencia, Calif., USA).

DNA sequencing of the 862 bp PCR fragment was performed with an Applied Biosystems Model 377 XL Automated DNA Sequencer (Applied Biosystems, Carlsbad, Calif., USA) using dye-terminator chemistry (Giesecke et al., 1992, *Journal of Virology Methods* 38: 47-60) and primer walking strategy. The following vector specific primers were used for sequencing:

```
pAllo2 5 Seq:
                                    (SEQ ID NO: 33)
5'-TGTCCCTTGTCGATGCG 3'

pAllo2 3 Seq:
                                    (SEQ ID NO: 34)
5'-CACATGACTTGGCTTCC 3'
```

Nucleotide sequence data were scrutinized for quality and all sequences were compared to each other with assistance of PHRED/PHRAP software (University of Washington, Seattle, Wash., USA).

A gene model for the *A. fumigatus* sequence was constructed based on similarity of the encoded protein to the *Thermoascus aurantiacus* GH61A protein (GeneSeqP Accession Number AEC05922). The nucleotide sequence and deduced amino acid sequence of the *A. fumigatus* GH61B polypeptide coding sequence are shown in SEQ ID NO: 35 and SEQ ID NO: 36, respectively. The genomic fragment encodes a polypeptide of 250 amino acids, interrupted by 2 introns of 53 and 56 bp. The % G+C content of the coding sequence and the mature coding sequence are 53.9% and 57%, respectively. Using the SignalP software program (Nielsen et al., 1997, *Protein Engineering* 10: 1-6), a signal peptide of 21 residues was predicted. The predicted mature protein contains 221 amino acids with a predicted molecular mass of 23.39 kDa.

Example 2: Construction of pSMai214 for Expression of the *Aspergillus fumigatus GH*61B Polypeptide The *Aspergillus fumigatus* GH61B polypeptide coding sequence was amplified from plasmid pAG43 (Example 1) using the gene-specific forward and reverse primers shown below. The region in italics represents vector homology to the site of insertion for an IN-FUSION® reaction.

```
Forward primer:
                                    (SEQ ID NO: 37)
5'-GGACTGCGCACCATGACTTTGTCCAAGATCACTTCCA-3'

Reverse primer:
                                    (SEQ ID NO: 38)
5'-GCCACGGAGCTTAATTAATTAAGCGTTGAACAGTGCAG-3'
```

Fifty picomoles of each of the primers above were used in a PCR reaction composed of 10 ng of pAG43 DNA, 1×Pfx Amplification Buffer, 1.5 μl of a 10 mM blend of dATP, dTTP, dGTP, and dCTP, 2.5 units of PLATINUM® Pfx DNA Polymerase, and 1 μl of 50 mM $MgSO_4$ in a final volume of 50 μl. The amplification was performed using an EPPENDORF® MASTERCYCLER® 5333 epgradient S programmed for 1 cycle at 98° C. for 3 minutes; and 30 cycles each at 98° C. for 30 seconds, 56° C. for 30 seconds, and 72° C. for 1 minute. The heat block was then held at 72° C. for 15 minutes. The PCR products were separated by 1% agarose gel electrophoresis using TAE buffer where an approximately 0.9 kb fragment was excised from the gel and extracted using a MINELUTE® Gel Extraction Kit according to the manufacturer's protocol.

Plasmid pMJ09 (WO 2005/047499) was digested with Nco I and Pac I, isolated by 1.0% agarose gel electrophoresis in 1 mM disodium EDTA-50 mM Tris base-50 mM boric acid (TBE) buffer, excised from the gel, and extracted using a QIAQUICK® Gel Extraction Kit (QIAGEN Inc., Valencia, Calif., USA) according to the manufacturer's instructions.

Figure 2:
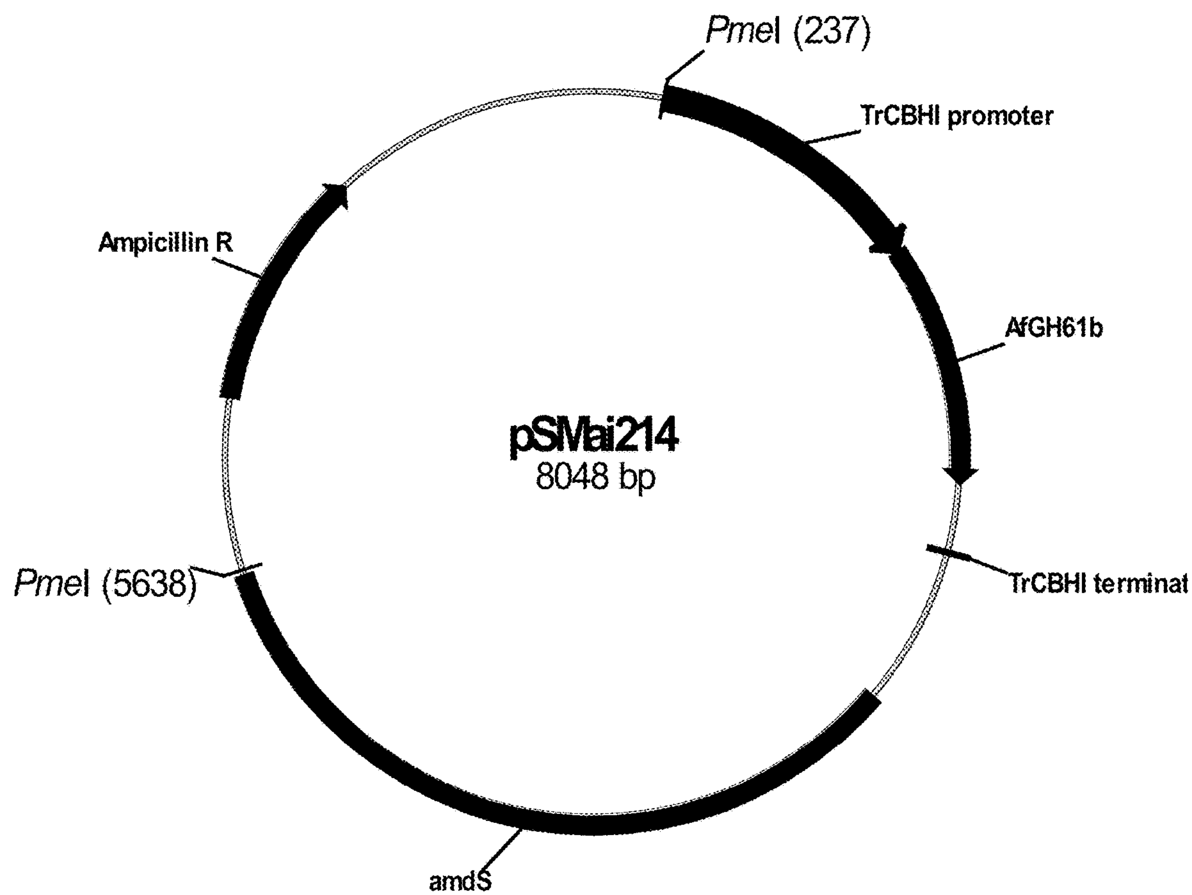
FIG. 2 shows a restriction map of plasmid pSMai214.

The 0.9 kb PCR product was inserted into the gel-purified Nco I/Pac I digested pMJ09 using an IN-FUSION® PCR Cloning Kit according to the manufacturer's protocol. The IN-FUSION® reaction was composed of 1×IN-FUSION® Reaction Buffer, 100 ng of the gel-purified Nco I/Pac I digested pMJ09, 37 ng of the 0.9 kb PCR product, 2 μl of 500 μg/ml BSA, and 1 μl of IN-FUSION® Enzyme in a 20 μl reaction volume. The reaction was incubated for 15 minutes at 37° C. and 15 minutes at 50° C. After the incubation period 30 μl of TE buffer were added to the reaction. A 2.5 μl aliquot was used to transform SOLOPACK® Gold Supercompetent Cells (Agilent Technologies, Inc., Cedar Creek, Tex., USA) according to the manufacturer's protocol. Transformants were screened by sequencing and one clone containing the insert with no PCR errors was identified and designated pSMai214 (FIG. 2). Plasmid pSMai214 can be digested with Pme I to generate an approximately 5.4 kb fragment for *T. reesei* transformation. The 5.4 kb fragment contains the expression cassette composed of the *T. reesei* Cel7A cellobiohydrolase I gene promoter, *A. fumigatus* GH61B polypeptide coding sequence, *T. reesei* Cel7A cellobiohydrolase I gene terminator, and *Aspergillus nidulans* acetamidase (amdS) gene.

Example 3: Construction of a Tandem Construct pDM287 for Expression of Both *Aspergillus fumigatus* CEL3A Beta-Glucosidase and *Aspergillus fumigatus* GH61B Polypeptide An *A. fumigatus* GH61B polypeptide expression cassette was amplified from plasmid pSMai214 using the gene-specific forward and reverse primers shown below. The region in italics represents vector homology to the site of insertion for an IN-FUSION® reaction.

```
Forward primer:
                                    (SEQ ID NO: 39)
5'-CGCGGTAGTGGCGCGGTCGACCGAATGTAGGATTGTT-3'

Reverse primer:
                                    (SEQ ID NO: 40)
5'-TTACCAATTGGCGCGCCACTACCGCGTTCGAGAAGA-3'
```

Fifty picomoles of each of the primers above were used in a PCR reaction composed of 25 ng of pSMai214 DNA, 1× PHUSION™ High-Fidelity Hot Start DNA Polymerase Buffer (Finnzymes Oy, Espoo, Finland), 1 μl of a 10 mM blend of dATP, dTTP, dGTP, and dCTP, and 1 unit of PHUSION™ High-Fidelity Hot Start DNA Polymerase (Finnzymes Oy, Espoo, Finland) in a final volume of 50 μl. The amplification was performed using an EPPENDORF® MASTERCYCLER® 5333 epgradient S programmed for 1 cycle at 98° C. for 30 seconds; 35 cycles each at 98° C. for 10 seconds, 60° C. for 30 seconds, and 72° C. for 1 minute 30 seconds; and 1 cycle at 72° C. for 10 minutes. PCR products were separated by 0.8% agarose gel electrophoresis using TAE buffer where an approximately 2.3 kb fragment was excised from the gel and extracted using a NUCLEOSPIN® Extract II Kit (Macherey-Nagel, Inc., Bethlehem, Pa., USA) according to the manufacturer's protocol.

Figure 3:
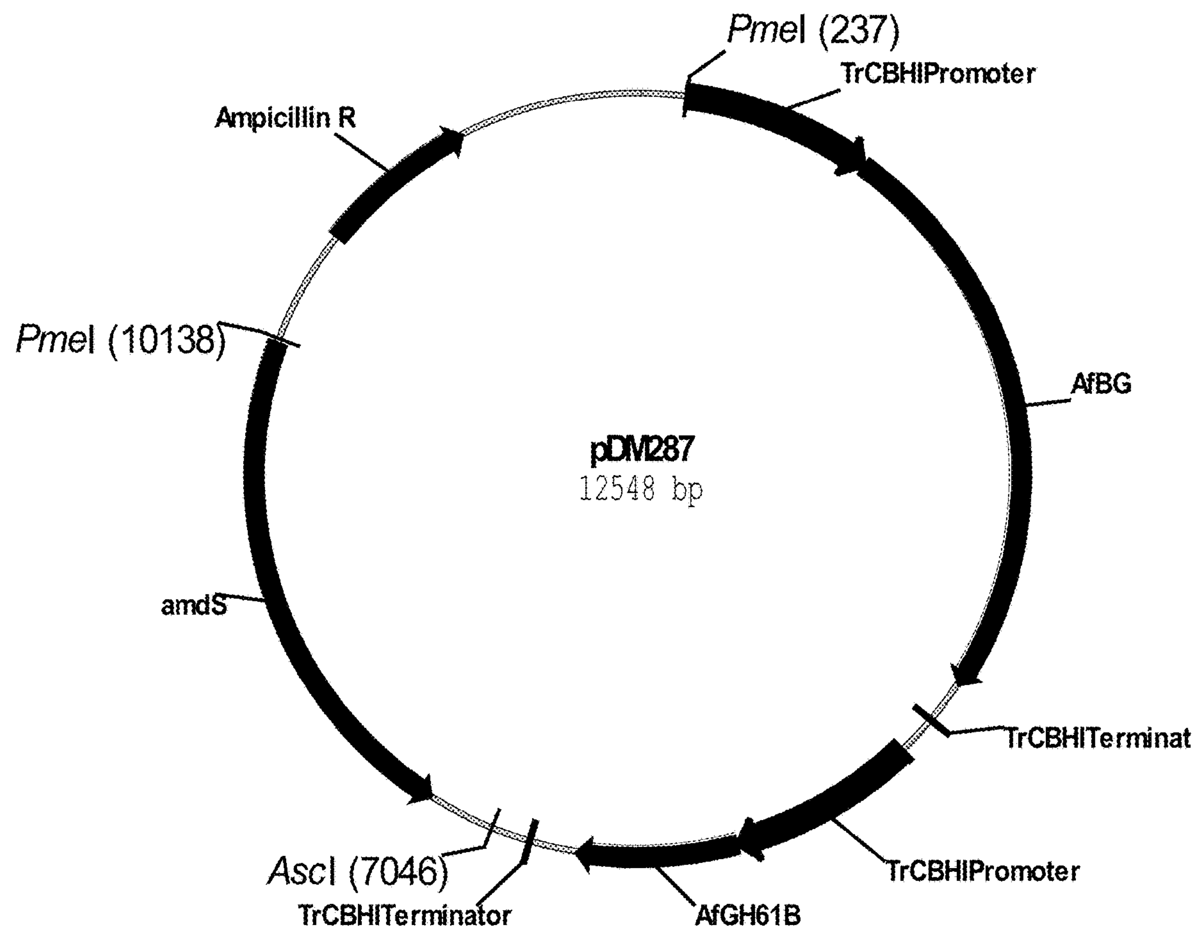
FIG. 3 shows a restriction map of plasmid pDM287.

The approximately 2.3 kb PCR product was inserted into Asc I-digested pEJG107 (WO 2005/047499) using an IN-FUSION® Advantage PCR Cloning Kit (Clontech Laboratories, Inc., Mountain View, Calif., USA) according to the manufacturer's protocol. Plasmid pEJG107 comprises an *Aspergillus fumigatus* CEL3A beta-glucosidase encoding sequence (SEQ ID NO: 53 [DNA sequence] and SEQ ID NO: 54 [deduced amino acid sequence]). The IN-FUSION® reaction was composed of 1×IN-FUSION® Reaction Buffer, 125 ng of the Asc !-digested pEJG107, 90 ng of the 2.33 kb PCR product, and 1 μl of IN-FUSION® Enzyme in a 10 μl reaction volume. The reaction was incubated for 15 minutes at 37° C. followed by 15 minutes at 50° C. After the incubation period 40 μl of TE were added to the reaction. A 2 μl aliquot was used to transform ONE SHOT® TOP10 competent cells (Invitrogen, Carlsbad, Calif., USA) according to the manufacturer's protocol. The *E. coli* transformation reactions were spread onto 2XYT plus ampicillin plates. The transformants were screened by sequencing and one clone containing the insert with no PCR errors was identified and designated pDM287 (FIG. 3). Plasmid pDM287 can be digested with Pme I to generate an approximately 9.9 kb fragment for *T. reesei* transformation. The 9.9 kb fragment contains two expression cassettes composed of (1) the *T. reesei* Cel7A cellobiohydrolase I gene promoter, *A. fumigatus* CEL3A beta-glucosidase coding sequence, and *T. reesei* Cel7A cellobiohydrolase I gene terminator; and (2) the *T. reesei* Cel7A cellobiohydrolase I gene promoter, *A. fumigatus* GH61B polypeptide coding sequence, and *T. reesei* Cel7A cellobiohydrolase I gene terminator. The 9.9 kb fragment also contains the *Aspergillus nidulans* acetamidase (amdS) gene.

Example 4: *Trichoderma reesei* Protoplast Generation and Transformation

Protoplast preparation and transformation were performed using a modified protocol by Penttila et al., 1987, *Gene* 61: 155-164. Briefly, *Trichoderma reesei* strain 981-O-8 (D4) was cultivated in 25 ml of YP medium supplemented with 2% (w/v) glucose and 10 mM uridine at 27° C. for 17 hours with gentle agitation at 90 rpm. Mycelia were collected by filtration using a Vacuum Driven Disposable Filtration System (Millipore, Bedford, Mass., USA) and washed twice with deionized water and twice with 1.2 M sorbitol. Protoplasts were generated by suspending the washed mycelia in 20 ml of 1.2 M sorbitol containing 15 mg of GLUCANEX® 200 G (Novozymes A/S, Bagsvaerd, Denmark) per ml and 0.36 units of chitinase (Sigma Chemical Co., St. Louis, Mo., USA) per ml for 15-25 minutes at 34° C. with gentle shaking at 90 rpm. Protoplasts were collected by centrifuging for 7 minutes at 400×g and washed twice with cold 1.2 M sorbitol. The protoplasts were counted using a haemocytometer and resuspended to a final concentration of $1\times10^8$ protoplasts/ml in STC. Excess protoplasts were stored in a Cryo 1° C. Freezing Container (Nalgene, Rochester, N.Y., USA) at −80° C.

Approximately 100 μg of transforming plasmid (pSMai214, pDM287, or pEJG107) were digested with Pme I. The digestion reaction was purified by 0.8% agarose gel electrophoresis using TAE buffer. A DNA band containing the expression cassette of pSMai214, pDM287, or pEJG107, and the *Aspergillus nidulans* acetamidase (amdS) gene, was excised from the gel and extracted using a NUCLEOSPIN® Extract II Kit according to the manufacturer's suggested protocol.

The resulting purified DNA [1 μg of the 9.9 kb Pme I digested pDM287 (tandem transformation) or 1 μg of the 7.6 kb Pme I digested pEJG107 plus 1 μg of the 5.4 kb Pme I digested pSMai214 (co-transformation)] was added to 100 μl of the protoplast solution and mixed gently. PEG buffer (250 μl) was added, and the reaction was mixed and incubated at 34° C. for 30 minutes. STC (3 ml) was then added, and the reaction was mixed and then spread onto COVE plates for amdS selection. The plates were incubated at 28° C. for 6-11 days.

Example 5: Evaluation of *Trichoderma reesei* Transformants Expressing *Aspergillus fumigatus* CEL3A Beta-Glucosidase and *Aspergillus fumigatus* GH 61B Polypeptide

*Trichoderma reesei* transformants (Example 4) were transferred from COVE transformation plates to COVE2 plates supplemented with 10 mM uridine using an inoculation loop and incubated 5-7 days at 28° C. Spores were collected with an inoculating loop and transferred to 25 ml of CIM medium in a 125 ml plastic shake flask. The shake flask cultures were incubated for 5 days at 28° C., 200 rpm. A 1 ml aliquot of each culture was centrifuged at 13,400×g in a microcentrifuge and culture supernatant was recovered. Five μl of each culture supernatant were analyzed by SDS-PAGE using a CRITERION® 8-16% Tris-HCl Gel (Bio-Rad Laboratories, Hercules, Calif., USA) according to the manufacturer's instructions. The resulting gel was stained with BIO-SAFE™ Coomassie (Bio-Rad Laboratories, Hercules, Calif., USA). SDS-PAGE profiles of 45 transformants of pDM287 (tandem construct) and 45 transformants of pEJG107+pSMai214 (co-transformation) showed that the transformants produced major protein bands of approximately 130 kDa corresponding to the *A. fumigatus* CEL3A beta-glucosidase and approximately 24 kDa corresponding to the *A. fumigatus* GH61B polypeptide. A negative control sample, consisting of untransformed *T. reesei* strain 981-O-8 (D4) culture supernatant, showed no prominent bands at approximately 130 kDa and approximately 24 kDa.

The results shown below demonstrated that transformation with the tandem construct pDM287 yielded more positive transformants for *A. fumigatus* beta-glucosidase and *A. fumigatus* GH61B polypeptide production than co-transformation with pEJG107 and pSMai214.

| Transforming DNA | Number of transformants positive for *A. fumigatus* beta-glucosidase and *A. fumigatus* GH61B polypeptide production by SDS-PAGE |
|---|---|
| pDM287 (tandem construct) | 33 of 45 (73%) |
| pEJG107 + pSMai214 (co-transformation) | 13 of 45 (29%) |

Example 6: Beta-Glucosidase Assay of *Trichoderma reesei* Transformants Expressing *Aspergillus fumigatus* CEL3A Beta-Glucosidase and *Aspergillus fumigatus* GH61B Polypeptide The culture supernatants of Example 5 were assayed for beta-glucosidase activity using a BIOMEK® 3000, a BIOMEK® NX, and an ORCA® robotic arm (Beckman Coulter, Inc, Fullerton, Calif., USA). Culture supernatants were diluted appropriately in 0.1 M succinate, 0.01% TRITON® X-100 (4-(1,1,3,3-tetramethylbutyl)phenyl-polyethylene glycol) buffer pH 5.0 (sample buffer) followed by a series of dilutions from 0-fold to ⅓-fold to ⅑-fold of the diluted sample. A total of 20 μl of each dilution was transferred to a 96-well flat bottom plate. Two hundred microliters of a p-nitrophenyl-beta-D-glucopyranoside substrate solution (1 mg of p-nitrophenyl-beta-D-glucopyranoside per ml of 0.1 M succinate pH 5.0) were added to each well and then incubated at ambient temperature for 45 minutes. Upon completion of the incubation period 50 μl of quenching buffer (1 M Tris buffer pH 9) were added to each well. An endpoint was measured at an optical density of 405 nm for the 96-well plate.

Figure 4:
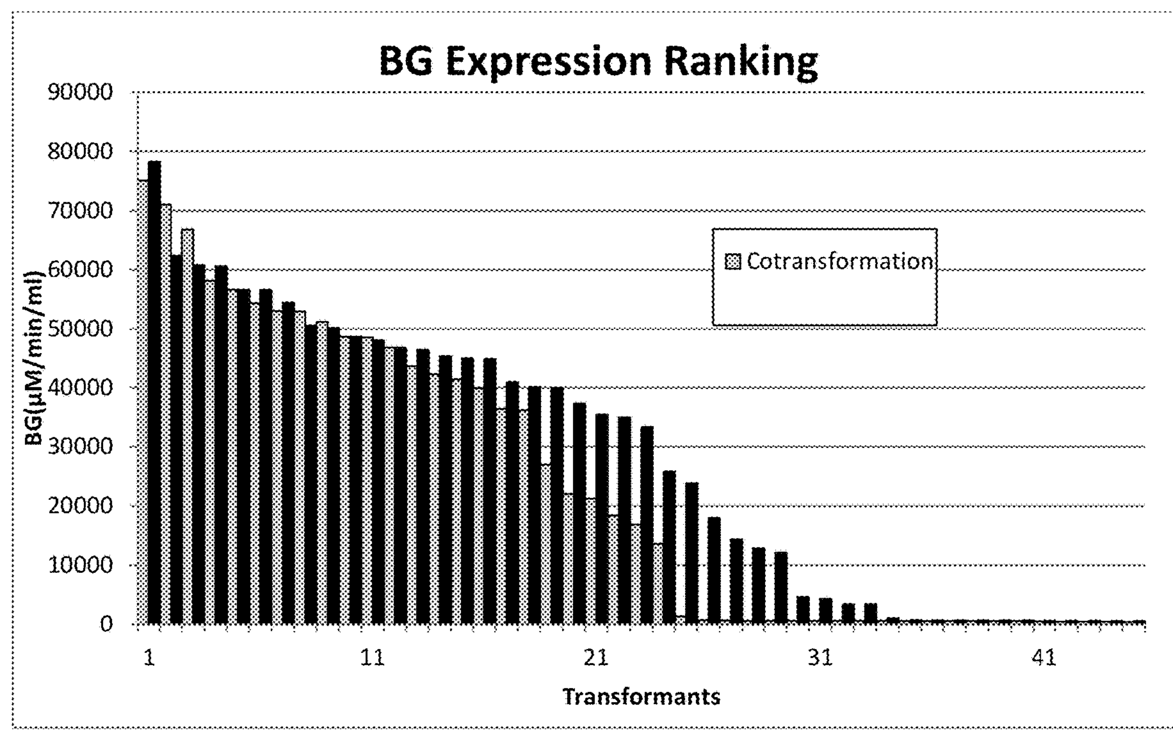
FIG. 4 shows a comparison of positive transformants for beta-glucosidase activity: between 45 transformants of pDM287 and 45 transformants of pEJG107+pSMai214.

The results shown in FIG. 4 confirmed the SDS-PAGE results of Example 5 that transformation with the tandem construct pDM287 yielded more positive transformants for *A. fumigatus* beta-glucosidase and *A. fumigatus* GH61B polypeptide production than co-transformation with pEJG107 and pSMai214.

Example 7: Construction of pDM286 Expressing a *Penicillium* sp. GH61A Polypeptide The *Penicillium* sp. (*emersonii*) GH61A polypeptide coding sequence (SEQ ID NO: 43 [DNA sequence] and SEQ ID NO: 44 [deduced amino acid sequence]) was amplified from plasmid pGH61D23Y4 (WO 2011/041397) using the gene-specific forward and reverse primers shown below. The region in italics represents vector homology to the site of insertion for an IN-FUSION® reaction.

```
Forward primer:
                                    (SEQ ID NO: 45)
5'-CGGACTGCGCACCATGCTGTCTTCGACGACTCGCAC-3'

Reverse primer:
                                    (SEQ ID NO: 46)
5'-TCGCCACGGAGCTTATCGACTTCTTCTAGAACGTC-3'
```

The amplification reaction was composed of 30 ng of pGH61D23Y4 DNA, 50 μmoles of each of the primers listed above, 1 μl of a 10 mM blend of dATP, dTTP, dGTP, and dCTP, 1× PHUSION™ High-Fidelity Hot Start DNA Polymerase Buffer, and 1 unit of PHUSION™ High-Fidelity Hot Start DNA Polymerase in a final volume of 50 μl. The amplification reaction was incubated in an EPPENDORF® MASTERCYCLER® 5333 epgradient S programmed for 1 cycle at 98° C. for 30 seconds; 35 cycles each at 98° C. for 10 seconds, 60° C. for 30 seconds, and 72° C. for 30 seconds; and 1 cycle at 72° C. for 10 minutes. The PCR products were separated by 1% agarose gel electrophoresis using TAE buffer where an approximately 0.9 kb fragment was excised from the gel and extracted using a QIAQUICK® Gel Extraction Kit according to the manufacturer's protocol.

Plasmid pMJ09 (WO 2005/047499) was digested with Nco I and Pac I, isolated by 1.0% agarose gel electrophoresis using TBE buffer, excised from the gel, and extracted using a QIAQUICK® Gel Extraction Kit according to the manufacturer's instructions.

Figure 5:
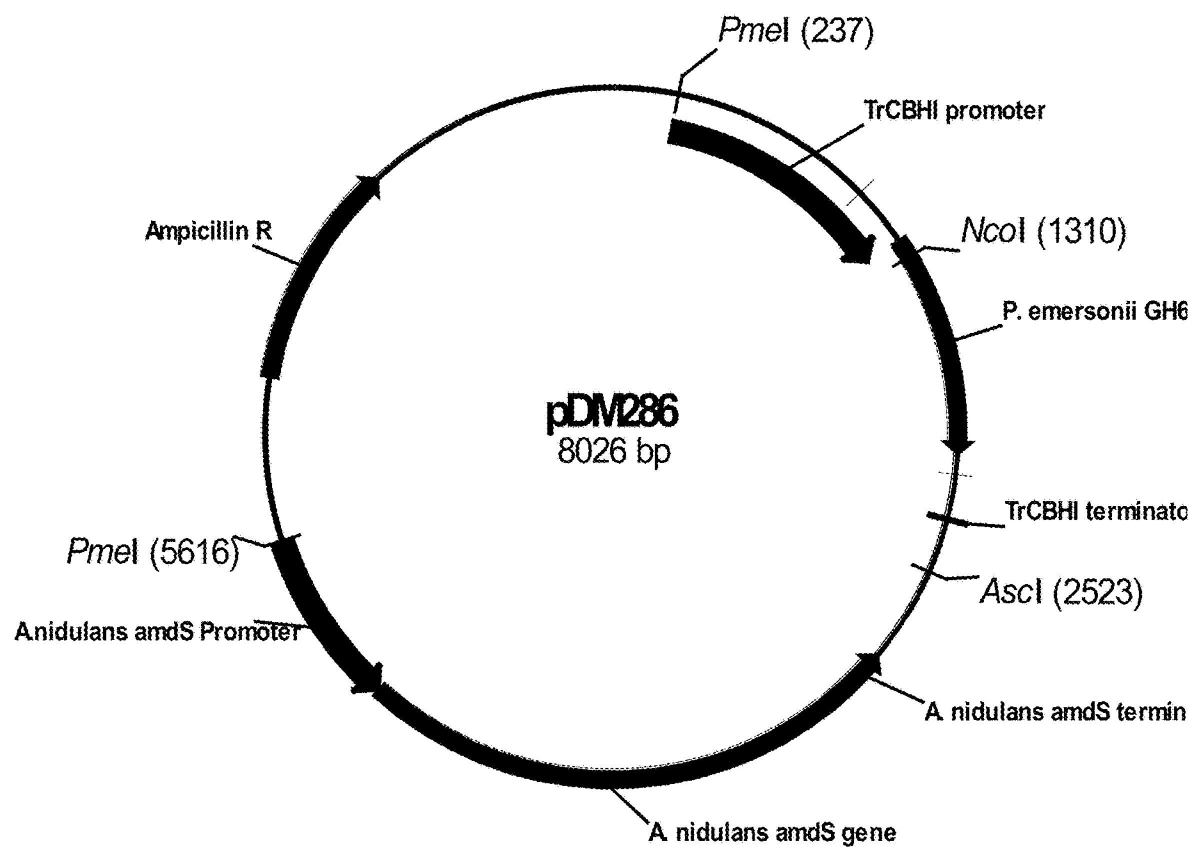
FIG. 5 shows a restriction map of plasmid pDM286.

The 0.9 kb PCR product was inserted into the gel-purified Nco I/Pac I digested pMJ09 using an IN-FUSION™ Advantage PCR Cloning Kit according to the manufacturer's protocol. The IN-FUSION™ reaction was composed of 1× IN-FUSION™ Reaction Buffer, 180 ng of the gel-purified Nco I/Pac I digested pMJ09, 108 ng of the 0.9 kb PCR product, and 1 μl of IN-FUSION™ Enzyme in a 10 μl reaction volume. The reaction was incubated for 15 minutes at 37° C. followed by 15 minutes at 50° C. After the incubation period 40 μl of TE were added to the reaction. A 2 μl aliquot was used to transform ONE SHOT® TOP10 competent cells according to the manufacturer's protocol. The *E. coli* transformation reactions were spread onto 2XYT plus ampicillin plates. The transformants were screened by sequencing and one clone containing the insert with no PCR errors was identified and designated pDM286 (FIG. 5). Plasmid pDM286 can be digested with Pme I to generate an approximately 5.4 kb fragment for *T. reesei* transformation. The 5.4 kb fragment contains the expression cassette composed of the *T. reesei* Cel7A cellobiohydrolase I gene promoter, *P. emersonii* GH61A polypeptide coding sequence, and *T. reesei* Cel7A cellobiohydrolase I gene terminator. The 5.4 kb fragment also contains the *Aspergillus nidulans* acetamidase (amdS) gene.

Example 8: Construction of a Tandem Construct pDM290 for Expression of Both *Penicillium emersonii* GH61A Polypeptide and *Aspergillus fumigatus* CEL3A Beta-Glucosidase An *Aspergillus fumigatus* CEL3A beta-glucosidase expression cassette was amplified from plasmid pEJG107 using the gene-specific forward and reverse primers shown below. The region in italics represents vector homology to the site of insertion for an IN-FUSION® reaction.

```
Forward primer:
                                    (SEQ ID NO: 47)
5'-CGCGGTAGTGGCGCGGTCGACCGAATGTAGGATTGTT-3'

Reverse primer:
                                    (SEQ ID NO: 48)
5'-TTACCAATTGGCGCGCCACTACCGCGTTCGAGAAGA-3'
```

Fifty picomoles of each of the primers above were used in a PCR reaction composed of 25 ng of pEJG107 DNA, 1× PHUSION™ High-Fidelity Hot Start DNA Polymerase Buffer, 1 μl of a 10 mM blend of dATP, dTTP, dGTP, and dCTP, and 1 unit of PHUSION™ High-Fidelity Hot Start DNA Polymerase in a final volume of 50 μl. The amplification was performed in an EPPENDORF® MASTERCYCLER® 5333 epgradient S programmed for 1 cycle at 98° C. for 30 seconds; 35 cycles each at 98° C. for 10 seconds, 60° C. for 30 seconds, and 72° C. for 2 minutes 30 seconds; and 1 cycle at 72° C. for 10 minutes.

PCR products were separated by 0.8% agarose gel electrophoresis using TAE buffer where an approximately 4.5 kb fragment was excised from the gel and extracted using a NUCLEOSPIN® Extract II Kit according to the manufacturer's protocol.

Figure 6:
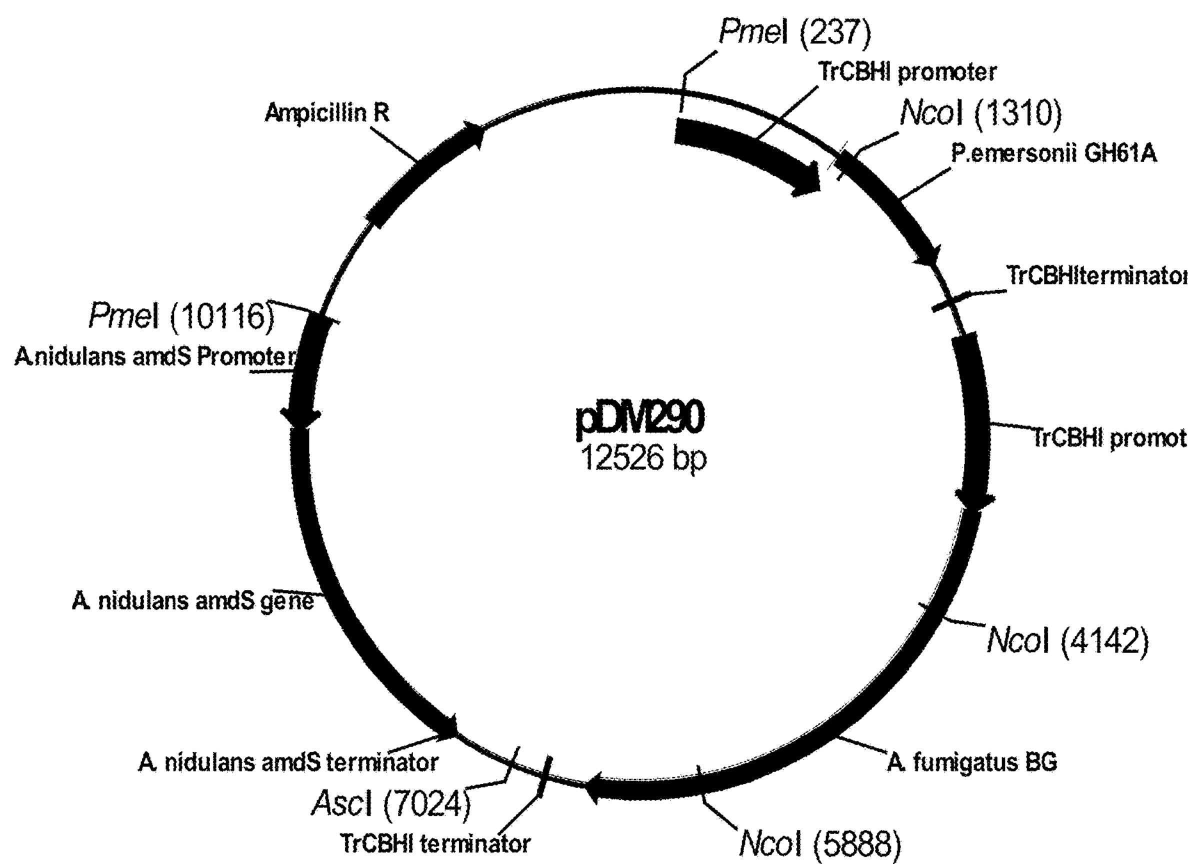
FIG. 6 shows a restriction map of plasmid pDM290.

The 4.5 kb PCR product was inserted into Asc I-digested pDM286 using an IN-FUSION™ Advantage PCR Cloning Kit according to the manufacturer's protocol. The IN-FUSION™ reaction was composed of 1× IN-FUSION™ Reaction Buffer, 125 ng of Asc I-digested pDM286, 100 ng of the 4.5 kb PCR product, and 1 μl of IN-FUSION™ Enzyme in a 10 μl reaction volume. The reaction was incubated for 15 minutes at 37° C. followed by 15 minutes at 50° C. After the incubation period 40 μl of TE were added to the reaction. A 2 μl aliquot was used to transform ONE SHOT® TOP10 competent cells according to the manufacturer's protocol. The *E. coli* transformation reactions were spread onto 2XYT plus ampicillin plates. Transformants were screened by sequencing and one clone containing the insert with no PCR errors was identified and designated pDM290 (FIG. 6). Plasmid pDM290 can be digested with Pme I to generate an approximately 9.9 kb fragment for *T. reesei* transformation. The 9.9 kb fragment contains two expression cassettes: (1) the *T. reesei* Cel7A cellobiohydrolase I gene promoter, *P. emersonii* GH61A polypeptide coding sequence, and *T. reesei* Cel7A cellobiohydrolase I gene terminator; and (2) the *T. reesei* Cel7A cellobiohydrolase I gene promoter, *A. fumigatus* CEL3A beta-glucosidase coding sequence, and *T. reesei* Cel7A cellobiohydrolase I gene terminator. The 9.9 kb fragment also contains the *Aspergillus nidulans* acetamidase (amdS) gene.

Example 9: Construction of an Empty *T. reesei* cbhII Replacement Construct pJfyS142

To generate a construct to replace the *Trichoderma reesei* cbhII gene (SEQ ID NO: 3 [DNA sequence] and SEQ ID NO: 4 [deduced amino acid sequence]) with the *Aspergillus fumigatus* cbhII coding sequence (SEQ ID NO: 49 [DNA sequence] and SEQ ID NO: 50 [deduced amino acid sequence]), the *T. reesei* cbhII promoter was first amplified from *T. reesei* RutC30 genomic DNA using the gene-specific forward and reverse primers shown below. The region in italics represents vector homology to the site of insertion for an IN-FUSION® reaction.

```
Forward primer:
                                        (SEQ ID NO: 51)
5'-acgaattgtttaaacgtcgacCCAAGTATCCAGAGGTGTATGGAAAT

ATCAGAT-3'

Reverse primer:
                                        (SEQ ID NO: 52)
5'-cgcgtagatctgcggccatGGTGCAATACACAGAGGGTGATCTT-3'
```

*Trichoderma reesei* RutC30 was grown in 50 ml of YP medium supplemented with 2% glucose (w/v) in a 250 ml baffled shake flask at 28° C. for 2 days with agitation at 200 rpm. Mycelia were harvested by filtration using MIRACLOTH® (Calbiochem, La Jolla, Calif., USA), washed twice in deionized water, and frozen under liquid nitrogen. Frozen mycelia were ground, by mortar and pestle, to a fine powder, and genomic DNA was isolated using a DNEASY® Plant Maxi Kit with the lytic incubation extended to 2 hours.

The amplification reaction was composed of 20 ng of *T. reesei* RutC30 genomic DNA, 200 μM dNTP's, 0.4 μM primers, 1× HERCULASE® Reaction Buffer (Stratagene, La Jolla, Calif., USA), and 1.875 units of HERCULASE® Hot Start High-Fidelity DNA Polymerase (Stratagene, La Jolla, Calif., USA) in a final volume of 50 μl. The amplification reaction was incubated in an EPPENDORF® MASTERCYCLER® 5333 epgradient S programmed for 1 cycle at 95° C. for 2 minutes; 25 cycles each at 95° C. for 30 seconds, 55° C. for 30 seconds, and 72° C. for 1 minute 30 seconds; and 1 cycle at 72° C. for 7 minutes. The PCR products were separated by 1% agarose gel electrophoresis using TAE buffer where a 1.6 kb fragment was excised from the gel and extracted using a MINELUTE® Gel Extraction Kit.

The 1.6 kb PCR product was inserted into Nco I/Sal I-digested pSMai155 (WO 05/074647) using an IN-FUSION® Advantage PCR Cloning Kit according to the manufacturer's protocol. The IN-FUSION® reaction was composed of 1× IN-FUSION® Reaction Buffer, 125 ng of the Nco I/Sal I-digested pSMai155, 100 ng of the 1.6 kb PCR product, and 1 μl of IN-FUSION® Enzyme in a 10 μl reaction volume. The reaction was incubated for 15 minutes at 37° C. and 15 minutes at 50° C. After the incubation period 40 μl of TE were added to the reaction. A 2 μl aliquot was used to transform ONE SHOT® TOP10 competent cells according to the manufacturer's protocol. The *E. coli* transformation reactions were spread onto 2XYT plus ampicillin plates. The resulting transformants were screened by restriction analysis with Pci I and positive clones sequenced to ensure the absence of PCR errors. One clone containing the insert with no PCR errors was identified and designated pJfyS142-A. Plasmid pJfyS142-A was used for insertion of the *T. reesei* cbhII terminator.

The cbhII terminator was amplified from *T. reesei* RutC30 genomic DNA using the gene-specific forward and reverse primers shown below. The region in italics represents vector homology to the site of insertion for an IN-FUSION® reaction.

```
Forward primer:
                                        (SEQ ID NO: 53)
5'-atctacgcgtactagttaattaaGGCTTTCGTGACCGGGCTTCAAAC

A-3'

Reverse primer:
                                        (SEQ ID NO: 54)
5'-gcggccgttactagtggatccACTCGGAGTTGTTATACGCTACTCG-

3'
```

The amplification reaction was composed of 150 ng of *T. reesei* RutC30 genomic DNA, 200 μM dNTP's, 0.4 μM primers, 1× HERCULASE® Reaction Buffer, and 1.875 units of HERCULASE® Hot Start High-Fidelity DNA Polymerase in a final volume of 50 μl. The amplification reaction was incubated in an EPPENDORF® MASTERCYCLER® 5333 epgradient S programmed for 1 cycle at 95° C. for 2 minutes; 25 cycles each at 95° C. for 30 seconds, 54° C. for 30 seconds, and 72° C. for 50 seconds; and 1 cycle at 72° C. for 7 minutes. The PCR products were separated by 1% agarose gel electrophoresis using TAE buffer where a 0.3 kb fragment was excised from the gel and extracted using a MINELUTE® Gel Extraction Kit.

The 0.3 kb PCR product was inserted into Pac I/Bam HI-digested pJfyS142-A using an IN-FUSION® Advantage PCR Cloning Kit according to the manufacturer's protocol. The IN-FUSION® reaction was composed of 1× IN-FUSION® Reaction Buffer, 150 ng of the PacI/Bam HI-digested pJfyS142-A, 50 ng of the 0.3 kb PCR product, and 1 μl of IN-FUSION® Enzyme in a 10 μl reaction volume. The reaction was incubated for 15 minutes at 37° C. and 15 minutes at 50° C. After the incubation period 40 μl of TE were added to the reaction. A 2 μl aliquot was used to transform ONE SHOT® TOP10 competent cells according to the manufacturer's protocol. The cells were heat shocked at 42° C. for 30 seconds and 250 μl of SOC medium were added. The tubes were incubated at 37° C., 200 rpm for 1 hour and 250 μl were plated onto 150 mm diameter 2XYT plus ampicillin plates and incubated at 37° C. overnight. The transformants were screened by sequence analysis to identify positive clones and to ensure the absence of PCR errors. One clone containing the insert with no PCR errors was identified and designated pJfyS142-B. Plasmid pJfyS142-B was used for insertion of the Herpes simplex tk gene.

The Herpes simplex tk gene was liberated from pJfyS1579-8-6 (WO 2010/039840) by digesting the plasmid with Bgl II and Bam HI. The digestion was submitted to 1% agarose gel electrophoresis using TAE buffer where a 2.3 kb band was excised from the gel and extracted using a MINELUTE® Gel Extraction Kit. The tk cassette was inserted into Bam HI-digested, calf Intestine phoshatase-dephosphorylated pJfyS142-B using a QUICK LIGATION™ Kit according to the manufacturer's protocol. The ligation reaction was composed of 50 ng of the Bam HI-digested, calf Intestine phoshatase-dephosphorylated pJfyS142-B, 50 ng of the 2.3 kb tk gene insert, 1× QUICK LIGATION™ Buffer, and 5 units of QUICK LIGASE™ in a 20 μl ligation volume. The reaction was incubated at room temperature for 5 minutes and 2 μl of the reaction was used to transform ONE SHOT® TOP10 competent cells according to the manufacturer's protocol. The cells were heat shocked at 42° C. for 30 seconds and 250 μl of SOC medium were added. The tubes were incubated at 37° C., 200 rpm for 1 hour and 250 μl were plated onto 150 mm diameter 2XYT plus ampicillin plates and incubated at 37° C. overnight. The resulting transformants were screened by restriction digestion analysis with Xma I and Bam HI to determine the presence and orientation of the insert and a clone containing the insert was identified and designated pJfyS142-C. Plasmid pJfyS142-C was used for insertion of the *T. reesei* 3' cbhII gene flanking sequence.

The 3' cbhII gene flanking sequence was amplified from *T. reesei* RutC30 genomic DNA using the forward and reverse primers shown below. The region in italics represents vector homology to the site of insertion for an IN-FUSION® reaction.

Forward primer:
(SEQ ID NO: 55)
5'-*atccatcacactggcggccgc*GCTTCAAACAATGATGTGCGATGGT-3'

Reverse primer:
(SEQ ID NO: 56)
5'-*gatgcatgctcgagcggccgc*CTACCTTGGCAGCCCTACGAGAGAG-3'

Figure 7:
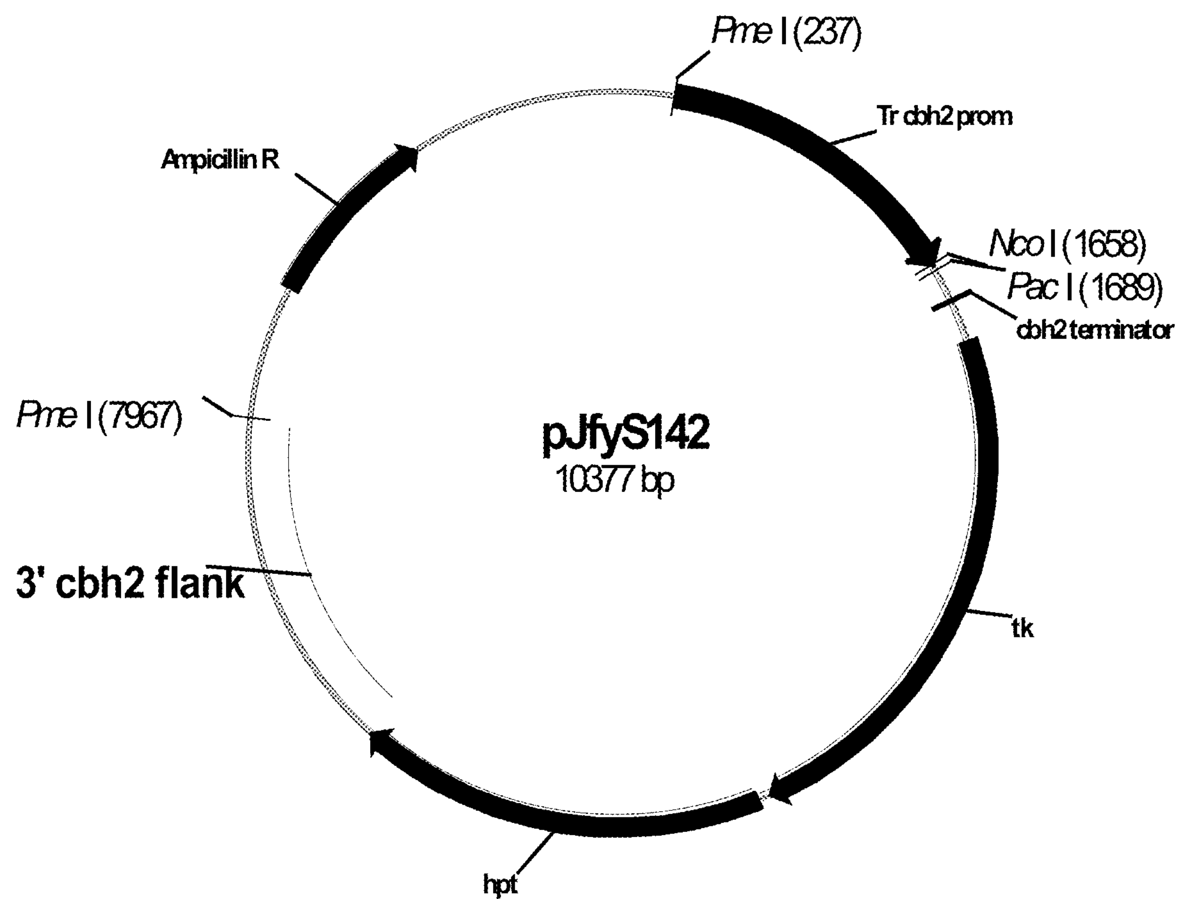
FIG. 7 shows a restriction map of plasmid pJfyS142.

The amplification reaction was composed of 150 ng of *T. reesei* RutC30 genomic DNA, 200 μM dNTP's, 0.4 μM primers, 1× HERCULASE® Reaction Buffer, and 1.875 units of HERCULASE® Hot Start High-Fidelity DNA Polymerase in a final volume of 50 μl. The amplification reaction was incubated in an EPPENDORF® MASTERCYCLER® 5333 epgradient S programmed for 1 cycle at 95° C. for 2 minutes; 30 cycles each at 95° C. for 30 seconds, 56° C. for 30 seconds, and 72° C. for 1 minute 50 seconds; and 1 cycle at 72° C. for 7 minutes. The PCR reaction was subjected to 1% agarose gel electrophoresis using TAE buffer where a 1.5 kb band was excised from the gel and extracted using a MINELUTE® Gel Extraction Kit. The 3' cbhII gene flanking sequence was inserted into Not I-linearized pJfyS142-C using an IN-FUSION® Advantage PCR Cloning Kit according to the manufacturer's protocol. The IN-FUSION® reaction was composed of 1× IN-FUSION® Reaction Buffer, 150 ng of Not I-linearized pJfyS142-C, 80 ng of the 1.5 kb PCR product, and 1 μl of IN-FUSION® Enzyme in a 10 μl reaction volume. The reaction was incubated for 15 minutes at 37° C. and 15 minutes at 50° C. After the incubation period 40 μl of TE were added to the reaction. A 2 μl aliquot was used to transform ONE SHOT® TOP10 competent cells according to the manufacturer's protocol. The cells were heat shocked at 42° C. for 30 seconds and 250 μl of SOC medium were added. The tubes were incubated at 37° C., 200 rpm for 1 hour and 250 μl were plated onto 150 mm diameter 2XYT plus ampicillin plates and incubated at 37° C. overnight. The resulting transformants were screened by restriction digestion analysis with Bgl II and positive clones were sequenced to ensure the absence of PCR errors. One clone containing the insert with no PCR errors was identified and designated pJfyS142 (FIG. 7). Plasmid pJfyS142 was used for insertion of the *A. fumigatus* cbhII coding sequence.

Example 10: Construction of a *Trichoderma reesei* cbhII-*Aspergillus fumigatus* cbhII Replacement Construct pJfyS144

The *Aspergillus fumigatus* cbhII coding sequence was amplified from pAlLo33 (WO 2011/057140) using the forward and reverse primers shown below. The region in italics represents vector homology to the site of insertion for an IN-FUSION® reaction.

Forward primer:
(SEQ ID NO: 57)
5'-*ctctgtgtattgcacc*ATGAAGCACCTTGCATCTTCCATCG-3'

Reverse primer:
(SEQ ID NO: 58)
5'-*ccggtcacgaaagcc*TTAATTAAAAGGACGGGTTAGCGTT-3'

The amplification reaction was composed of 20 ng of pAlLo33, 200 μm dNTP's, 0.4 μM primers, 1 mM HERCULASE® Reaction Buffer, and 1.875 units of HERCULASE® Hot Start High-Fidelity DNA Polymerase in a final volume of 50 μl. The amplification reaction was incubated in an EPPENDORF® MASTERCYCLER® 5333 epgradient S programmed for 1 cycle at 95° C. for 2 minutes; 30 cycles each at 95° C. for 30 seconds, 55° C. for 30 seconds, and 72° C. for 2 minutes; and 1 cycle at 72° C. for 7 minutes.

Figure 8:
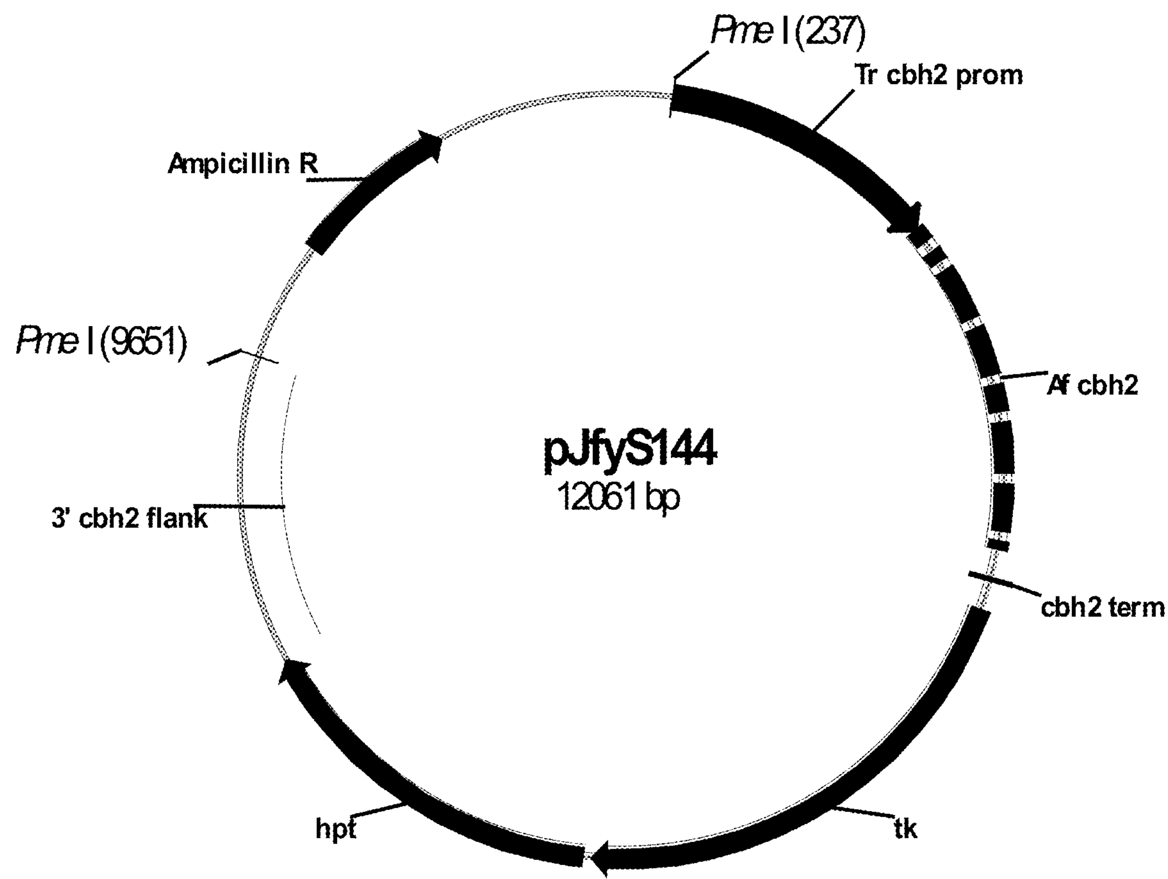
FIG. 8 shows a restriction map of plasmid pJfyS144.

The PCR reaction was subjected to 1% agarose gel electrophoresis using TAE buffer where a 1.7 kb band was excised from the gel and extracted using a MINELUTE® Gel Extraction Kit. The 1.7 kb PCR product was inserted into Nco I/Pac I-digested pJfyS142 (Example 9) using an IN-FUSION® Advantage PCR Cloning Kit according to the manufacturer's protocol. The IN-FUSION® reaction was composed of 1× IN-FUSION® Reaction Buffer, 120 ng of the Nco I/Pac I-digested pJfyS142, 70 ng of the 1.7 kb PCR product, and 1 μl of IN-FUSION® Enzyme in a 10 μl reaction volume. The reaction was incubated for 15 minutes at 37° C. and 15 minutes at 50° C. After the incubation period 40 μl of TE were added to the reaction. A 2 μl aliquot was used to transform ONE SHOT® TOP10 competent cells according to the manufacturer's protocol. The cells were heat shocked at 42° C. for 30 seconds and 250 μl of SOC medium were added. The tubes were incubated at 37° C., 200 rpm for 1 hour and 250 μl were plated onto 150 mm diameter 2XYT plus ampicillin plates and incubated at 37° C. overnight. The resulting transformants were sequenced to ensure the absence of PCR errors and determine the presence of the insert. One clone with error-free sequence was identified and designated pJfyS144 (FIG. 8).

Example 11: Construction of a *Trichoderma reesei* cbhI-*Aspergillus fumigatus* cbhI Replacement Construct pJfyS139

The *Aspergillus fumigatus* cellobiohydrolase I (cbhI) coding sequence (SEQ ID NO: 59 [DNA sequence] and SEQ ID NO: 60 [deduced amino acid sequence]) was amplified from pEJG93 (WO 2011/057140) using the gene-specific forward and reverse primers shown below. The region in italics represents vector homology to the site of insertion for an IN-FUSION® reaction and the underlined portion is an introduced Pac I site.

Forward primer:
(SEQ ID NO: 61)
5'-*cgcggactgcgcacc*ATGCTGGCCTCCACCTTCTCCTACC-3'

Reverse primer:
(SEQ ID NO: 62)
5'-ctttcgccacggag*cttaattaa*CTACAGGCACTGAGAGTAATAATCA-3'

The amplification reaction was composed of 20 ng of pEJG93, 200 μM dNTP's, 0.4 μM primers, 1× HERCULASE® Reaction Buffer, and 1.875 units of HERCULASE® Hot Start High-Fidelity DNA Polymerase in a final volume of 50 μl. The amplification reaction was incubated in an EPPENDORF® MASTERCYCLER® 5333 epgradient S programmed for 1 cycle at 95° C. for 2 minutes; 30 cycles each at 95° C. for 30 seconds, 55° C. for 30 seconds, and 72° C. for 1 minute; and 1 cycle at 72° C. for 7 minutes. The PCR products were separated by 1% agarose gel electrophoresis using TAE buffer where a 1.6 kb fragment was excised from the gel and extracted using a MINELUTE® Gel Extraction Kit according to the manufacturer's protocol.

The 1.6 kb PCR product was inserted into Nco I/Pac I-digested pSMai155 (WO 05/074647) using an IN-FUSION® Advantage PCR Cloning Kit according to the manufacturer's protocol. The IN-FUSION® reaction was composed of 1× IN-FUSION® Reaction Buffer, 125 ng of Nco I/Pac I-digested pSMai155, 100 ng of the 1.6 kb PCR product, and 1 μl of IN-FUSION® Enzyme in a 10 μl reaction volume. The reaction was incubated for 15 minutes at 37° C. followed by 15 minutes at 50° C. After the incubation period 40 μl of TE buffer were added to the reaction. A 2 μl aliquot was used to transform ONE SHOT® TOP10 competent cells according to the manufacturer's protocol. The *E. coli* transformation reactions were spread onto 2XYT plus ampicillin plates. The resulting transformants were screened by sequencing and one clone containing the insert with no PCR errors was identified and designated pJfyS139-A. Plasmid pJfyS139-A was used for insertion of the Herpes simplex virus thymidine kinase (tk) gene.

The Herpes simplex virus tk coding sequence (SEQ ID NO: 63 [DNA sequence] and SEQ ID NO: 64 [deduced amino acid sequence]) was liberated from pJfyS1579-8-6 (WO 2010/039840) by digesting the plasmid with Bgl II and Bam HI. The digestion was subjected to 1% agarose gel electrophoresis using TAE buffer where a 2.3 kb band was excised from the gel and extracted using a MINELUTE® Gel Extraction Kit. The tk gene cassette was inserted into Bam HI-digested, calf intestine phosphatase-treated pJfyS139-A using a QUICK LIGATION™ Kit according to the manufacturer's protocol. The ligation reaction was composed of 50 ng of the Bam HI-digested, calf intestine phosphatase-treated pJfyS139-A, 50 ng of the 2.3 kb tk gene insert, 1× QUICK LIGATION™ Buffer, and 5 units of QUICK LIGASE™ in a final volume of 20 μl. The reaction was incubated at room temperature for 5 minutes and 2 μl of the reaction were used to transform ONE SHOT® TOP10 competent cells according to the manufacturer's protocol. The cells were heat shocked at 42° C. for 30 seconds and 250 μl of SOC medium were added. The tubes were incubated at 37° C., 200 rpm for 1 hour and 250 μl were plated onto 150 mm diameter 2XYT plus ampicillin plates and incubated at 37° C. overnight. The resulting transformants were screened by restriction digestion analysis with Xma I to determine the presence and orientation of the insert and a clone containing the insert was identified and designated pJfyS139-B. Plasmid pJfyS139-B was used for insertion of a *T. reesei* 3' cbhI gene flanking sequence.

The 3' cbhI gene flanking sequence was amplified from *T. reesei* RutC30 genomic DNA (Example 9) using the forward and reverse primers below. The underlined portion represents an introduced Not I site for cloning.

```
Forward Primer:
                                        (SEQ ID NO: 65)
5'-ttagactgcggccgcGTGGCGAAAGCCTGACGCACCGGTAGAT-3'

Reverse Primer:
                                        (SEQ ID NO: 66)
5'-agtagttagcggccgcACGGCACGGTTAAGCAGGGTCTTGC-3'
```

The amplification reaction was composed of 150 ng of *T. reesei* RutC30 genomic DNA, 200 μM dNTP's, 0.4 μM primers, 1× HERCULASE® Reaction Buffer, and 1.875 units of HERCULASE® Hot Start High-Fidelity DNA Polymerase in a final volume of 50 μl. The amplification reaction was incubated in an EPPENDORF® MASTERCYCLER® 5333 epgradient S programmed for 1 cycle at 95° C. for 2 minutes; 30 cycles each at 95° C. for 30 seconds, 60° C. for 30 seconds, and 72° C. for 1 minute 30 seconds; and 1 cycle at 72° C. for 7 minutes.

Figure 9:
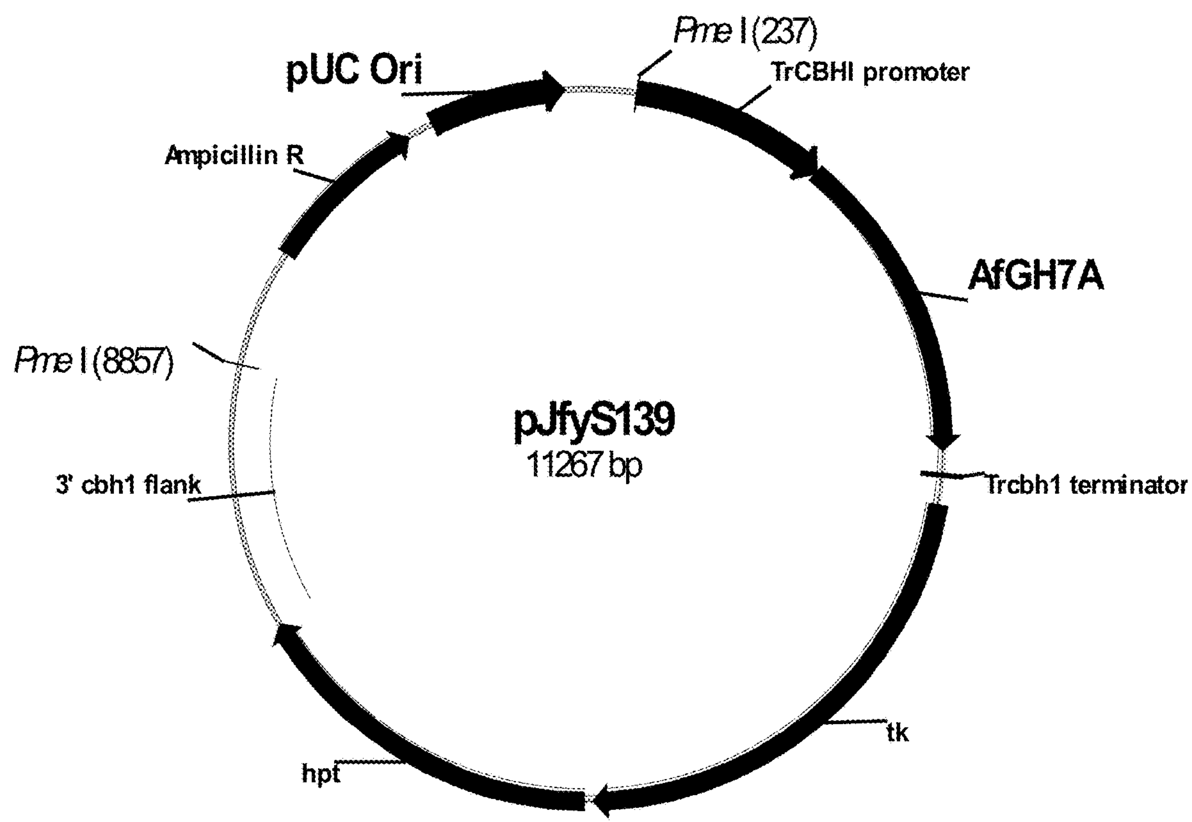
FIG. 9 shows a restriction map of plasmid pJfyS139.

The PCR reaction was subjected to a MINELUTE® Nucleotide Removal Kit (QIAGEN Inc., Valencia, Calif., USA) according to the manufacturer's protocol. The resulting PCR mixture was digested with Not I and the digested PCR products were separated by 1% agarose gel electrophoresis using TAE buffer. A 1.3 kb fragment containing the 3' cbhI gene flanking sequence was excised from the gel and extracted using a MINELUTE® Gel Extraction Kit. The 1.3 kb fragment was inserted into Not I-linearized, calf intestine phosphatase-treated pJfyS139-B using a QUICK LIGATION™ Kit. The QUICK LIGATION™ reaction was composed of 100 ng of the Not I-linearized, calf intestine phosphatase-treated pJfyS139-B, 20 ng of the 1.3 kb fragment, 1× QUICK LIGATION™ Buffer, and 5 units of QUICK LIGASE™ in a final volume of 20 μl. The reaction was incubated at room temperature for 5 minutes and 2 μl of the reaction was used to transform ONE SHOT® TOP10 competent cells according to the manufacturer's protocol. The cells were heat shocked at 42° C. for 30 seconds and 250 μl of SOC medium were added. The tubes were incubated at 37° C., 200 rpm for 1 hour and 250 μl were plated onto 150 mm diameter 2XYT plus ampicillin plates and incubated at 37° C. overnight. The resulting transformants were screened by restriction digestion analysis with Xma I to determine the presence and orientation of the insert and positive clones were sequenced. A clone containing the 3' cbhI gene flanking sequence with no PCR errors was designated pJfyS139 (FIG. 9).

Example 12: Construction of an *Aspergillus fumigatus* cbhI-*Aspergillus fumigatus* cbhII Tandem Expression Vector for Replacement of the *Trichoderma reesei* cbhI Gene A tandem replacement vector, pQM21, was constructed for replacing the native *T. reesei* cbhI gene in *Trichoderma reesei* with a tandem expression cassette for expressing two recombinant proteins. Plasmid pQM21 contains the *T. reesei* cbhI 5' flanking sequence, *T. reesei* Cel7A cellobiohydrolase I gene promoter, *Aspergillus fumigatus* Cel7A cellobiohydrolase I coding sequence, *T. reesei* Cel7A cellobiohydrolase I gene terminator, *T. reesei* Cel6A cellobiohydrolase II gene promoter, *Aspergillus fumigatus* Cel6A cellobiohydrolase II coding sequence, *T. reesei* Cel6A cellobiohydrolase II gene terminator, *T. reesei* Cel7A cellobiohydrolase I gene terminator repeat, Herpes simplex virus thymidine kinase (tk) gene, *E. coli* hygromycin phosphotransferase (hpt/hygR) selection marker, *T. reesei* cbhI 3' flanking sequence, and ampicillin resistance marker gene.

The *Aspergillus fumigatus* cellobiohydrolase II expression cassette was amplified from pJfyS144 (Example 10) using the gene-specific forward and reverse primers shown below. The region in italics represents sequence homology to the site of insertion for an IN-FUSION® reaction and the underlined portion is an introduced Bam HI site and Nhe I site, respectively.

Forward primer:

(SEQ ID NO: 67)
5'-tcaagcttggtaccgagctcggatCCAAGTATCCAGAGGTGTATGGAAAT-3'

Reverse primer:

(SEQ ID NO: 68)
5'-ctggcggccgttactagtgctagcACTCGGAGTTGTTATACGCTAC-3'

The amplification reaction was composed of 164 ng of pJfyS144, 1 μM primers, 1× ACCUPRIME™ Pfx Reaction Buffer (Invitrogen, Carlsbad, Calif., USA), and 2.5 units of ACCUPRIME™ Pfx DNA Polymerase (Invitrogen, Carlsbad, Calif., USA) in a final volume of 50 μl. The amplification reaction was incubated in an EPPENDORF® MASTERCYCLER® 5333 epgradient S programmed for 1 cycle at 95° C. for 2 minutes; and 35 cycles each at 95° C. for 15 seconds, 58° C. for 30 seconds, and 68° C. for 5 minutes. The PCR products were separated by 1% agarose gel electrophoresis using TAE buffer where an approximately 3.5 kb fragment was excised from the gel and extracted using a QIAQUICK® Gel Extraction Kit according to the manufacturer's protocol.

Figure 10:
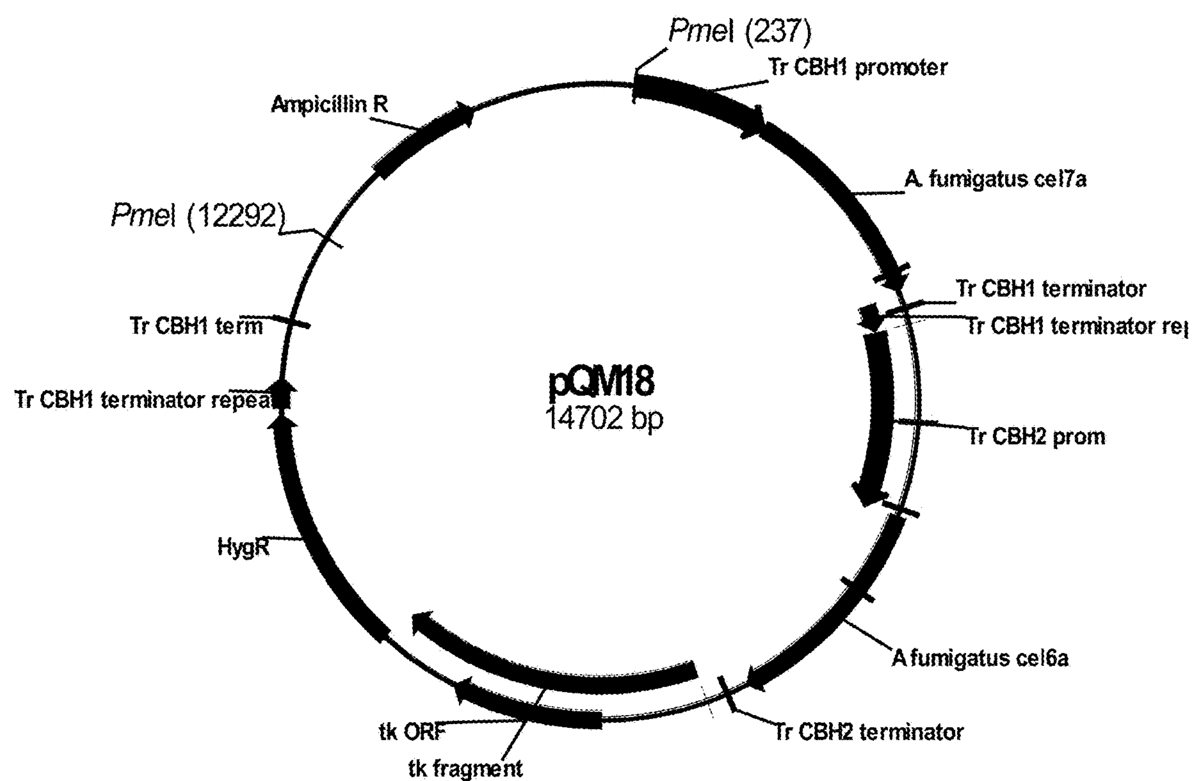
FIG. 10 shows a restriction map of plasmid pQM18.

The 3.5 kb PCR product was inserted into Bam HI digested pJfyS139 (Example 11) using an IN-FUSION™ Advantage PCR Cloning Kit according to the manufacturer's suggested protocol. The IN-FUSION™ reaction was composed of 1× IN-FUSION™ Reaction Buffer, 103 ng of Bam HI digested pJfyS139, 62 ng of the 3.5 kb PCR product, and 1 μl of IN-FUSION™ Enzyme in a 10 μl reaction volume. The reaction was incubated for 15 minutes at 37° C. followed by 15 minutes at 50° C. After the incubation period 15 μl of TE were added to the reaction. A 2 μl aliquot was used to transform SOLOPACK® Gold Supercompetent cells according to the manufacturer's protocol. The *E. coli* transformation reactions were spread onto 2XYT plus ampicillin plates. The transformants were screened by sequencing and one clone containing the insert with no PCR errors was identified and designated pQM18 (FIG. 10). Plasmid pQM18 was used to insert a homologous repeat fragment from the *T. reesei* 3' cbhI gene flanking region after the tandem expression cassette and to modify the *T. reesei* 3' cbhII gene flanking region.

The homologous repeat fragment from the *T. reesei* 3' cbhI gene flanking region was amplified from pJfyS139 using the forward and reverse primers below. The region in italics represents sequence homology to the site of insertion for an IN-FUSION® reaction and the underlined portion represents introduced Nhe I site and Xba I sites for cloning.

Forward Primer:

(SEQ ID NO: 69)
5'-gagtagcgtataacaactccgagtgctagcTTTAAGATAACGGAATAGAAGAAAG-3'

Reverse Primer:

(SEQ ID NO: 70)
5'-ctggcggccgttactagtctagaCGCGCCACTACCGCGTTCG-3'

The *T. reesei* 3' cbhI gene flanking sequence was amplified from pJfyS139 using the forward and reverse primers below. The region in italics represents vector homology to the site of insertion for an IN-FUSION® reaction and the underlined portion represents an introduced Not I site for cloning.

Forward Primer:

(SEQ ID NO: 71)
5'-tctgcagatatccatcacactggcggccgcTTTAAGATAACGGAATAGAAGAAAG-3'

Reverse Primer:

(SEQ ID NO: 72)
5'-aaactctaggatgcatgctcgagcggccgcACGGCACGGTTAAGCAGGGT-3'

The amplification reaction was composed of 350 ng of pJfyS139, 1 μM primers, 1× ACCUPRIME™ Pfx Reaction Buffer, and 2.5 units of ACCUPRIME™ Pfx DNA Polymerase in a final volume of 50 μl. The amplification reaction was incubated in an EPPENDORF® MASTERCYCLER® 5333 epgradient S programmed for 1 cycle at 95° C. for 2 minutes; and 35 cycles each at 95° C. for 15 seconds, 58° C. for 30 seconds, and 68° C. for 5 minutes. The PCR products were purified by 1% agarose gel electrophoresis using TAE buffer where an approximately 1.1 kb fragment and an approximately 260 bp fragment were excised from the gel and extracted using a QIAQUICK® Gel Extraction Kit according to the manufacturer's protocol.

A DNA fragment containing the tk gene and hpt (hygromycin phosphotransferase) selection marker was liberated from pQM18 by digesting the plasmid with Nhe I and Not I. The digestion was analyzed by 1% agarose gel electrophoresis using TAE buffer where an approximately 4.4 kb band was excised from the gel and extracted using a QIAQUICK® Gel Extraction Kit according to the manufacturer's protocol.

An approximately 9 kb DNA fragment from Nhe I and Not I digested pQM18 was separated by 1% agarose gel electrophoresis using TAE buffer. The 9 kb fragment was excised from the gel and extracted using a QIAQUICK® Gel Extraction Kit according to the manufacturer's protocol.

Figure 11:
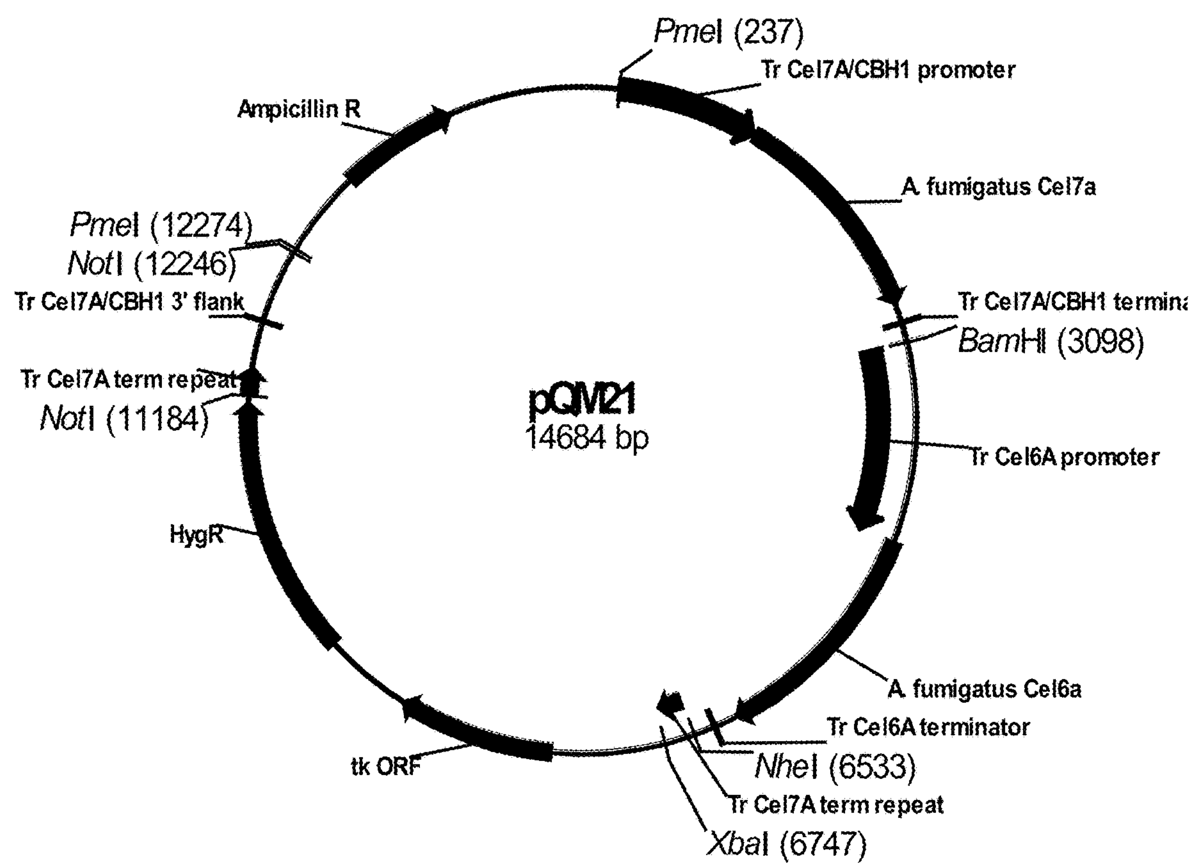
FIG. 11 shows a restriction map of plasmid pQM21.

An IN-FUSION™ reaction was composed of 1× IN-FUSION™ Reaction Buffer, 158 ng of the 9 kb Nhe I and Not I digested pQM18, 13 ng of the 260 bp homologous repeat fragment from *T. reesei* cbhI 3' flanking region, 39 ng of the 1.1 kb 3' cbhI flank, 56 ng of the 4.4 kb tk-hpt fragment, and 1 μl IN-FUSION™ Enzyme in a 10 μl reaction volume. The reaction was incubated for 15 minutes at 37° C. and 15 minutes at 50° C. After the incubation period 40 μl of TE were added to the reaction. A 2.5 μl aliquot was used to transform SOLOPACK® Gold Supercompetent cells according to the manufacturer's protocol. The *E. coli* transformation reactions were spread onto 2XYT plus ampicillin plates and incubated overnight at 37° C. Transformants were screened by sequencing and one clone containing the insert with no PCR errors was identified and designated pQM21 (FIG. 11). Plasmid pQM21 was used as the vector to replace the cbhI gene.

Example 13: Replacement of Native *Trichoderma reesei* cbhI Gene with the *Aspergillus Fumigatus* Cellobiohydrolase I and *Aspergillus fumigatus* Cellobiohydrolase II Tandem Expression Cassette Protoplast preparation and transformation of *Trichoderma reesei* strain AgJg115-104-7B1 were performed as described in Example 4.

In order to replace the native cbhI gene with the *Aspergillus fumigatus* cbhI-cbhII tandem expression cassette, approximately 137 μg of pQM21 (Example 12) was digested with Pme I. The digestion reaction was purified by 1% agarose gel electrophoresis using TAE buffer where an approximately 12 kb DNA band containing the *Aspergillus fumigatus* CBHI-CBHII tandem expression cassette for targeting to the *T. reesei* cbhI locus was excised from the gel and extracted using a NUCLEOSPIN® Extract II Purification Kit. Approximately 1-3 μg of the resulting purified 12 kb DNA was added to 100 μl of the *Trichoderma reesei* ku70-strain AgJg115-104-7B1 protoplast solution and mixed gently. PEG buffer (250 μl) was added, mixed, and incubated at 34° C. for 30 minutes. STC (3 ml) was then added, mixed, and spread onto each PDA plate supplemented with 1 M sucrose. After incubation at 28° C. for 16 hours, 20 ml of an overlay PDA medium supplemented with 35 μg of hygromycin B per ml were added to each plate. The plates were incubated at 28° C. for 4-7 days.

Seven transformants were obtained and each one was picked and transferred to a PDA plate and incubated for 7 days at 28° C. A fungal spore PCR method using the protocol described below was used to screen for transformants bearing replacement using the forward primer shown below annealing to a region upstream of the cbhI 5' flanking region of integration, and the reverse primer shown below annealing to a region in the tk region.

```
Forward Primer:
                                    (SEQ ID NO: 73)
5'-CAAGCAAAGCGTTCCGTCGCAGTAGCAGGC-3'

Reverse Primer:
                                    (SEQ ID NO: 74)
5'-CAGTGGCGCTTATTACTCAG-3'
```

An approximately 7 kb PCR product would be generated only upon the occurrence of a precise gene replacement at the cbhII locus. If the cassette had integrated elsewhere in the genome, no amplification would result.

A small amount of spores from each transformant was suspended in 25 μl of TE buffer and heated on high in a microwave oven for 1 minute. Each microwaved spore suspension was used as a template in the PCR reaction. The reaction was composed of 2 μl of the microwaved spore suspension, 200 μM dNTP's, 1 μM primers, 1× LONGAMP® Taq Reaction Buffer (New England Biolabs, Inc, Ipswich, Mass., USA), and 2 units of LONGAMP® Taq DNA Polymerase (New England Biolabs, Inc, Ipswich, Mass., USA) in a final volume of 20 μl. The reaction was incubated in an EPPENDORF® MASTERCYCLER® 5333 epgradient S programmed for 1 cycle at 95° C. for 4 minutes; 35 cycles each at 95° C. for 15 seconds, 50° C. for 30 seconds, and 68° C. for 7 minutes; and 1 cycle at 68° C. for 15 minutes. The PCR reactions were analyzed by 1% agarose gel electrophoresis using TAE buffer. The spore PCR indicated that five of the seven transformants contained the replacement cassette at the cbhI locus.

Genomic DNA was isolated from four of the positive transformants according to the procedure described in Example 9 and submitted to Southern analysis to confirm the replacement cassette was in a single copy.

For Southern analysis, 2 μg of genomic DNA was digested with 10 units of Bam HI in a 20 μl reaction volume and subjected to 0.7% agarose electrophoresis using TAE buffer. The DNA in the gel was depurinated in 0.25 N HCl for 15 minutes, denatured in Denaturing Solution twice for 15 minutes each time, neutralized in Neutralization Solution for 10 to 30 minutes, and transferred to a NYTRAN® Supercharge membrane (Whatman, Inc., Florham Park, N.J., USA) using a TURBOBLOTTER™ System (Whatman, Inc., Florham Park, N.J., USA) according to the manufacturer's protocol. The DNA was UV crosslinked to the membrane using a STRATALINKER™ UV Crosslinker (Stratagene, La Jolla, Calif., USA) and prehybridized for 1 hour at 42° C. in 20 ml of DIG Easy Hyb (Roche Diagnostics Corporation, Indianapolis, Ind., USA).

A probe hybridizing to the 3' flanking region of the cbhI gene was generated using a PCR Dig Probe Synthesis Kit (Roche Diagnostics Corporation, Indianapolis, Ind., USA) according to the manufacturer's instructions with the forward and reverse primers shown below. The PCR reaction was composed of 1× EXPAND® High Fidelity PCR Buffer with $MgCl_2$ (Roche Diagnostics Corporation, Indianapolis, Ind., USA), 1×PCR DIG Probe Synthesis Mix (Roche Diagnostics Corporation, Indianapolis, Ind., USA), 1 μM of each primer, 100 μg of the 1.1 kb 3' cbhI flanking region, and 2.625 units of EXPAND® High Fidelity Enzyme Mix (Roche Diagnostics Corporation, Indianapolis, Ind., USA). The PCR was performed in an EPPENDORF® MASTERCYCLER® 5333 epgradient S programmed for 1 cycle at 95° C. for 2 minutes; 10 cycles each at 95° C. for 30 seconds, 60° C. for 30 seconds, and 72° C. for 40 seconds; 20 cycles each at 95° C. for 30 seconds, 60° C. for 30 seconds, and 72° C. for 40 seconds with an additional 20 seconds for each successive cycle; and 1 cycle at 72° C. for 7 minutes.

```
Forward primer:
                                    (SEQ ID NO: 75)
5'-GAGAACACAGTGAGACCATAGC-3'

Reverse primer:
                                    (SEQ ID NO: 76)
5'-TCTCAACCCAATCAGCAACATG-3'
```

The probe was purified by 1% agarose gel electrophoresis using TAE buffer where a 720 bp band corresponding to the probe was excised from the gel and extracted using a NUCLEOSPIN® Extract II Purification Kit. The probe was boiled for 5 minutes, chilled on ice for 2 minutes, and added to 10 ml of DIG Easy Hyb to produce the hybridization solution. Hybridization was performed at 42° C. for 15-17 hours. The membrane was then washed under low stringency conditions in 2×SSC plus 0.1% SDS for 5 minutes at room temperature followed by two high stringency washes in 0.5×SSC plus 0.1% SDS for 15 minutes each at 65° C. The probe-target hybrids were detected by chemiluminescent assay (Roche Diagnostics, Indianapolis, Ind., USA) according to the manufacturer's instructions. Southern analysis indicated that one transformant designated *T. reesei* QMJi029-A5 contained the replacement cassette at the cbhI locus and was chosen for curing of the tk and hpt markers.

Spores of *T. reesei* QMJi029-A5 from a seven-day-old PDA plate grown at 28° C. were collected in 5 ml of 0.01% TWEEN® 20 using a sterile spreader. The concentration of spores was determined using a hemocytometer and $10^4$ and/or $10^5$ spores were spread onto 150 mm plates containing TrMM-G medium supplemented with 1 μM 5-fluoro-2'-deoxyuridine (FdU).

Ten FdU-resistant spore isolates were picked and genomic DNA was extracted from three of the spore isolates as described above. The isolates were submitted to Southern analysis as described above and the results indicated that all of the spore isolates had excised the hpt/tk region between the homologous repeats of the replacement cassette. One strain designated *T. reesei* QMJi030-A5.6 was selected for replacing the cbhII gene.

Spores of *T. reesei* QMJi029-A5 and *T. reesei* QMJi030-A5.6 from seven-day-old PDA plates grown at 28° C. were collected with a 10 μl inoculating loop and transferred to 25 ml of CIM medium in a 125 ml plastic shake flask. The shake flask cultures were incubated for 5 days at 28° C., 200 rpm. A 1 ml aliquot of each culture was centrifuged at 13,400×g in a microcentrifuge and culture supernatant was recovered. Five μl of each culture supernatant were analyzed by SDS-PAGE using a CRITERION® 8-16% Tris-HCl Gel according to the manufacturer's instructions. The resulting gel was stained with BIO-SAFE™ Coomassie. SDS-PAGE profiles of the cultures showed that the transformants produced two major protein bands between 50 and 70 kDa, corresponding to *Aspergillus fumigatus* cellobiohydrolase I and *Aspergillus fumigatus* cellobiohydrolase II, respectively. Expression of *Aspergillus fumigatus* cellobiohydrolase I and *Aspergillus fumigatus* cellobiohydrolase II were confirmed by mass spectroscopic analysis (Example 14).

Example 14: In-Gel Digestion of Polypeptides for Peptide Sequencing

A MULTIPROBE® II Liquid Handling Robot (PerkinElmer Life and Analytical Sciences, Boston, Mass., USA) was used to perform in-gel digestions. A section of the SDS-PAGE gel described in Example 13 was excised between the 50 and 70 kDa MW markers containing the proteins of interest. The gel piece was reduced with 50 μl of a 10 mM dithiothreitol (DTT) in 100 mM ammonium bicarbonate pH 8.0 for 30 minutes. Following reduction, the gel piece was alkylated with 50 μl of 55 mM iodoacetamide in 100 mM ammonium bicarbonate pH 8.0 for 20 minutes. The dried gel piece was allowed to swell in 25 μl of a trypsin digestion solution containing 6 ng of sequencing grade trypsin (Promega, Madison, Wis., USA) per μl of 50 mM ammonium bicarbonate pH 8 for 30 minutes at room temperature, followed by an 8 hour digestion at 40° C. Each of the reaction steps described above was followed by numerous washes and pre-washes with the appropriate solutions following the manufacturer's standard protocol. Fifty μl of acetonitrile was used to de-hydrate the gel piece between reactions and the gel piece was air dried between steps. Peptides were extracted twice with 1% formic acid/2% acetonitrile in HPLC grade water for 30 minutes. Peptide extraction solutions were transferred to a 96 well skirted PCR type plate (ABGene, Rochester, N.Y., USA) that had been cooled to 10-15° C. and covered with a 96-well plate lid (PerkinElmer Life and Analytical Sciences, Boston, Mass., USA) to prevent evaporation. Plates were further stored at 4° C. until mass spectrometry analysis could be performed.

Protein Identification.

For de novo peptide sequencing by tandem mass spectrometry, a SYNAPT™ MS (Waters Corp., Milford, Mass., USA), a hybrid orthogonal quadrupole time-of-flight mass spectrometer, was used for LC/MS/MS analysis. The SYNAPT™ MS is fully microprocessor controlled using MASSLYNX® software version 4.1 (Waters Corp., Milford, Mass., USA). The SYNAPT™ MS was fitted with a NANOACQUITY UPLC® (Waters Corp, Milford, Mass., USA) for concentrating and desalting samples. Samples were loaded onto a trapping column (180 μm ID×20 mm, 5 μm SYMMETRY® C18) (Waters Corp, Milford, Mass., USA) fitted in the injection loop and washed with 0.1% formic acid in water at 15 μl per minute for 1 minute using the binary solvent manager pump. Peptides were separated on a 100 μm ID×100 mm, C18, 1.7 μm, BEH130™ C18 nanoflow fused capillary column (Waters Corp, Milford, Mass., USA) at a flow rate of 400 nl/minute. A step elution gradient of 1% to 85% acetonitrile in 0.1% formic acid was applied over a 30 minute interval. The column eluent was monitored at 214 nm and introduced into the SYNAPT™ MS through an electrospray ion source fitted with the nanospray interface.

Data was acquired in survey scan mode from a mass range of m/z 250 to 1900 with switching criteria for MS to MS/MS to include an ion intensity of greater than 10.0 counts per second and charge states of +2, +3, and +4. Analysis spectra of up to 6 co-eluting species with a scan time of 2.0 seconds could be obtained. A cone voltage of 45 volts was typically used and the collision energy was programmed to vary according to the mass and charge state of the eluting peptide and in the range of 10-60 volts. The acquired spectra were combined, smoothed, and centered in an automated fashion and a peak list generated. The peak list was searched against selected databases using PROTEINLYNX GLOBAL SERVER® 2.4 software (Waters Corp, Milford, Mass., USA) and MASCOT® v. 2.2 (Matrix Sciences Ltd., London, UK) Results from the PROTEINLYNX GLOBAL SERVER® and MASCOT® searches were evaluated and peptide identifications were based on peptide mass fingerprint matches to the sequence of the expected protein.

Peptide mass fingerprinting confirmed that the SDS-PAGE samples of *T. reesei* QMJi029-A5 and *T. reesei* QMJ1030A5.6 contained *A. fumigatus* Cel7A cellobiohydrolase I, *A. fumigatus* Cel6A cellobiohydrolase II, *T. reesei* cellobiohydrolase II, and other minor *T. reesei* host background proteins.

Figure 12:
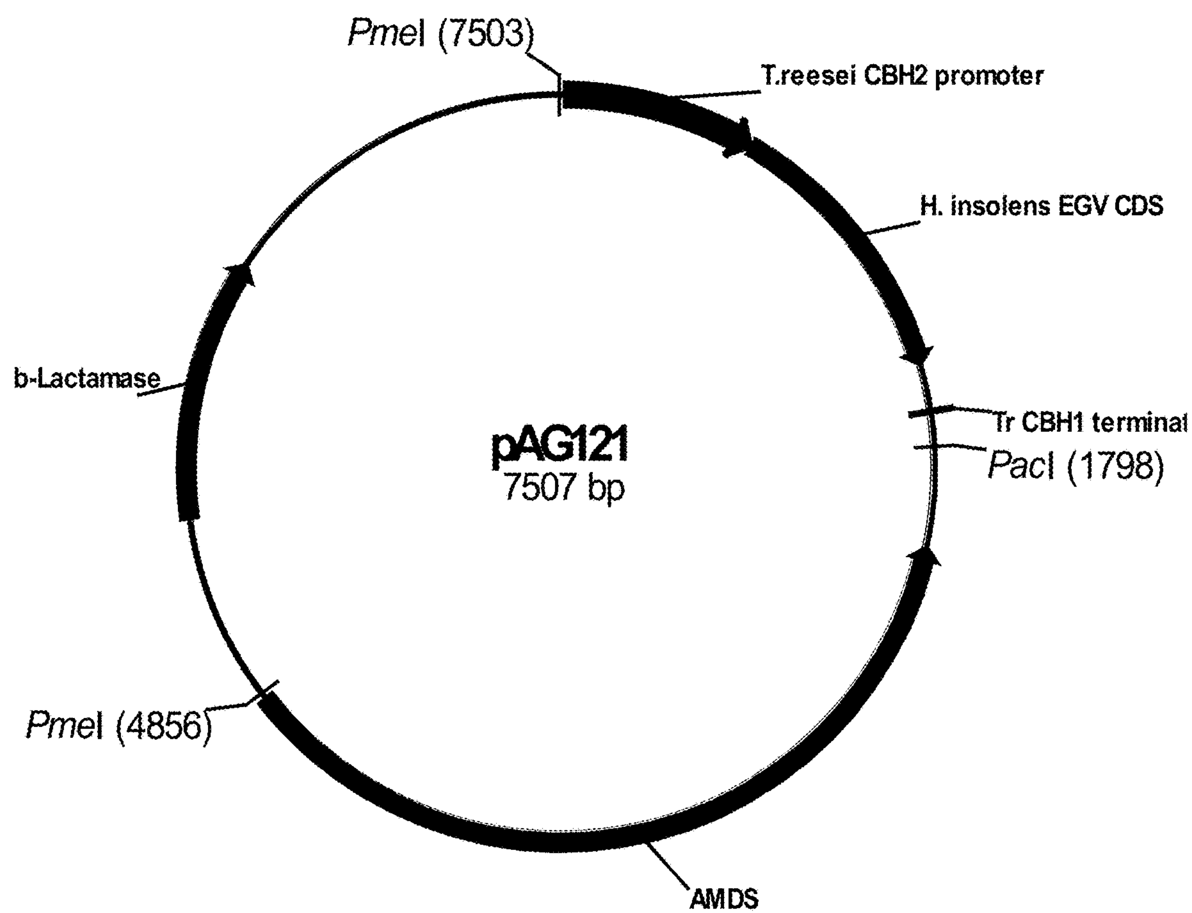
FIG. 12 shows a restriction map of plasmid pAG121.

Example 15: Generation of a Tandem Gene Expression Plasmid pRRAB01 Encoding *Penicillium emersonii* GH61A Polypeptide and *Aspergillus fumigatus* Cel3A Beta-Glucosidase The *Trichoderma reesei* cellobiohydrolase II (cbhII) gene promoter was amplified from plasmid pAG121 (FIG. 12; SEQ ID NO: 77; from nucleotide position 6 to nucleotide position 620, see restriction map and sequence for pAG121) using the gene-specific forward and reverse primers shown below. The region in italics in the forward primer represents sequence homology to the pDM286 vector backbone and the region in italics in the reverse primer represents sequence homology to the next insert, i.e., the *Aspergillus fumigatus* beta-glucosidase coding sequence for an IN-FUSION® reaction.

Forward primer:

(SEQ ID NO: 78)

5'-*cgaacgcggtagtgg*GAATTCTAGGCTAGGTATGC-3'

Reverse Primer:

(SEQ ID NO: 79)

5'-*ccaaccgaatctcat*GGTGCAATACACAGAGGGTG-3'

The amplification reaction was composed of 1 ng of pAG121 DNA, 100 μmoles of each of the primers listed above, 1 μl of a 10 mM blend of dATP, dTTP, dGTP, and dCTP, PHUSION™ High-Fidelity Hot Start DNA Polymerase Buffer, and 1 unit of PHUSION™ High-Fidelity Hot Start DNA Polymerase in a final volume of 50 μl. The amplification reaction was incubated in an EPPENDORF® MASTERCYCLER® 5333 epgradient S programmed for 1 cycle at 98° C. for 30 seconds; 35 cycles each at 98° C. for 10 second and 72° C. for 20 seconds; and 1 cycle at 72° C. for 10 minutes. The PCR products were separated by 1% agarose gel electrophoresis using TAE buffer where an approximately 640 bp fragment was excised from the gel and extracted using a QIAGEN® Gel Extraction Kit according to the manufacturer's protocol.

The *Aspergillus fumigatus* beta-glucosidase coding sequence was amplified from plasmid pDM290 using the gene-specific forward and reverse primers shown below. The region in italics in the forward primer represents sequence homology to the previous insert, i.e., the *Trichoderma reesei* cellobiohydrolase II coding sequence, and the region in italics in the reverse primer represents sequence homology to the next insert, i.e., the *Trichoderma reesei* cellobiohydrolase II gene terminator, for an IN-FUSION® reaction.

```
Forward primer:
                                        (SEQ ID NO: 80)
5'-tctgtgtattgcaccATGAGATTCGGTTGGCTCGA-3'

Reverse Primer:
                                        (SEQ ID NO: 81)
5'-ccggtcacgaaagccCTAGTAGACACGGGGCAGAG-3'
```

The amplification reaction was composed of 1 ng of pDM290 DNA, 100 μmoles of each of the primers listed above, 1 μl of a 10 mM blend of dATP, dTTP, dGTP, and dCTP, PHUSION™ High-Fidelity Hot Start DNA Polymerase Buffer, and 1 unit of PHUSION™ High-Fidelity Hot Start DNA Polymerase in a final volume of 50 μl. The amplification reaction was incubated in an EPPENDORF® MASTERCYCLER® 5333 epgradient S programmed for 1 cycle at 98° C. for 30 seconds; 35 cycles each at 98° C. for 10 seconds, 65° C. for 30 seconds, and 72° C. for 1:35 seconds; and 1 cycle at 72° C. for 10 minutes. The PCR products were separated by 1% agarose gel electrophoresis using TAE buffer where an approximately 3.1 kb fragment was excised from the gel and extracted using a QIAGEN® Gel Extraction Kit according to the manufacturer's protocol.

The *Trichoderma reesei* cellobiohydrolase II gene terminator was amplified from plasmid pJfyS144 using the gene-specific forward and reverse primers shown below. The region in italics in the forward primer represents sequence homology to the *Aspergillus fumigatus* beta-glucosidase coding sequence, and the region in italics in the reverse primer represents sequence homology to the pDM286 backbone for an IN-FUSION® reaction.

```
Forward primer:
                                        (SEQ ID NO: 82)
5'-ccccgtgtctactagGGCTTTCGTGACCGGGCTTC-3'

Reverse Primer:
                                        (SEQ ID NO: 83)
5'-gtcattaccaattggACTCGGAGTTGTTATACGCT-3'
```

The amplification reaction was composed of 1 ng of pJfyS144 DNA, 100 μmoles of each of the primers listed above, 1 μl of a 10 mM blend of dATP, dTTP, dGTP, and dCTP, PHUSION™ High-Fidelity Hot Start DNA Polymerase Buffer, and 1 unit of PHUSION™ High-Fidelity Hot Start DNA Polymerase in a final volume of 50 μl. The amplification reaction was incubated in an EPPENDORF® MASTERCYCLER® 5333 epgradient S programmed for 1 cycle at 98° C. for 30 seconds; 35 cycles each at 98° C. for 10 seconds and 72° C. for 10 seconds; and 1 cycle at 72° C. for 10 minutes. The PCR products were separated by 1% agarose gel electrophoresis using TAE buffer where a 330 bp fragment was excised from the gel and extracted using a QIAGEN® Gel Extraction Kit according to the manufacturer's protocol.

The *Trichoderma reesei* cellobiohydrolase II gene promoter, *Aspergillus fumigatus* beta-glucosidase coding sequence, and *Trichoderma reesei* cellobiohydrolase II gene terminator were combined in a splicing by overlap extension (SOE) PCR reaction using the gene-specific forward and reverse primers shown below. The regions in italics represent sequence homology to the site of insertion in pDM286 for an IN-FUSION® reaction.

```
Forward primer:
                                        (SEQ ID NO: 84)
5'-cgaacgcggtagtggGAATTCTAGGCTAGGTATGC-3'

Reverse Primer:
                                        (SEQ ID NO: 85)
5'-gtcattaccaattggACTCGGAGTTGTTATACGCT-3'
```

The SOE PCR reaction was composed of 48 ng of the 640 bp *T. reesei* cbhII promoter amplified from pAG121, 228 ng of the 3.1 kb *A. fumigatus* beta-glucosidase gene fragment amplified from pDM290, 24 ng of the 330 bp *T. reesei* cbhII terminator amplified from pJfyS144, 100 μmoles of each of the primers listed above, 1 μl of a 10 mM blend of dATP, dTTP, dGTP, and dCTP, 1× PHUSION™ High-Fidelity Hot Start DNA Polymerase Buffer, and 1 unit of PHUSION™ High-Fidelity Hot Start DNA Polymerase in a final volume of 50 μl. The amplification reaction was incubated in an EPPENDORF® MASTERCYCLER® 5333 epgradient S programmed for 1 cycle at 98° C. for 30 seconds; 35 cycles each at 98° C. for 10 seconds and 72° C. for 2 minutes and 5 seconds; and 1 cycle at 72° C. for 10 minutes. The PCR products were separated by 1% agarose gel electrophoresis using TAE buffer where an approximately 4.1 kb fragment was excised from the gel and extracted using a QIAGEN® Gel Extraction Kit according to the manufacturer's protocol.

Plasmid pDM286 was digested with Asc I and the Asc I-digested pDM286 was separated by 1% agarose gel electrophoresis using TAE buffer where an approximately 8 kb fragment was excised from the gel and extracted using a QIAGEN® Gel Extraction Kit according to the manufacturer's protocol.

Figure 13:
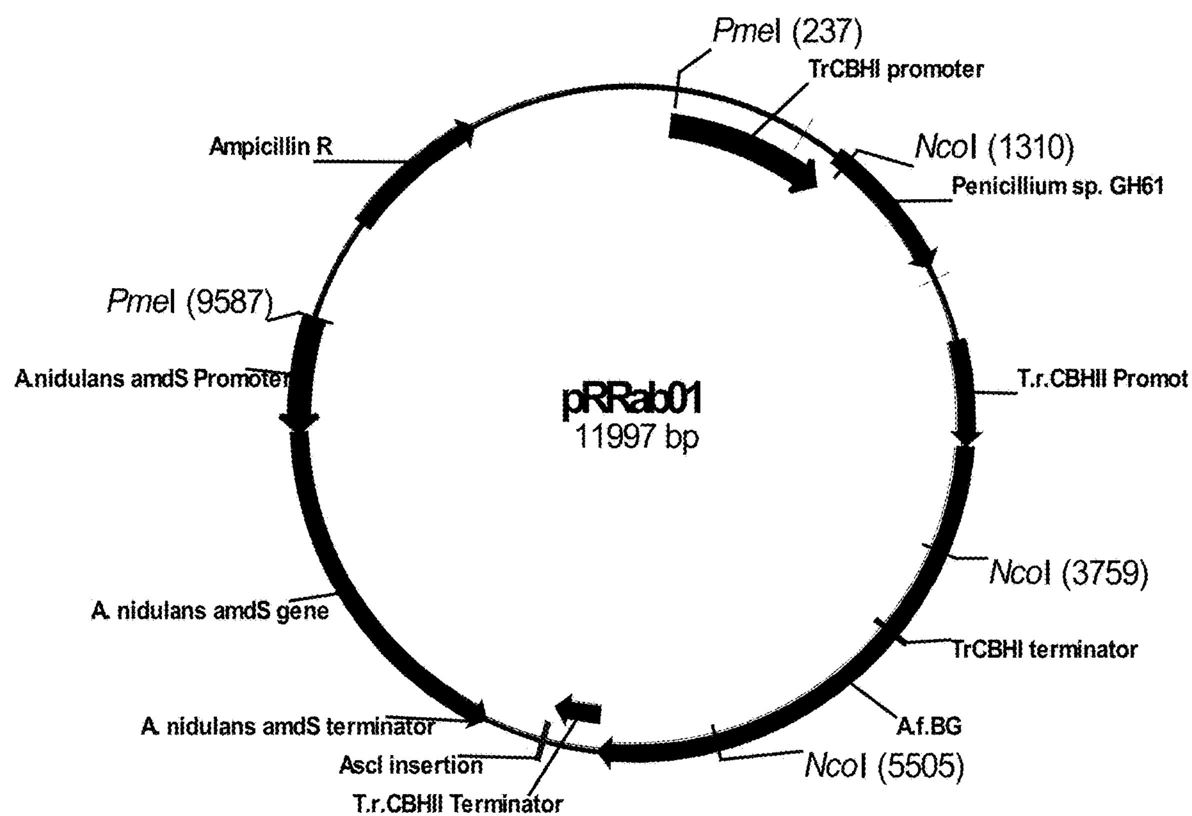
FIG. 13 shows a restriction map of plasmid pRRAB01.

The 4.1 kb PCR product was inserted into Asc I-digested pDM286 using an IN-FUSION™ Advantage PCR Cloning Kit according to the manufacturer's protocol. The IN-FUSION™ reaction was composed of 1× IN-FUSION™ Reaction Buffer, 200 ng of approximately 8 kb gel purified Asc I-digested pDM286, 203.1 ng of the 4.1 kb PCR product, and 1 μl of IN-FUSION™ Enzyme in a 10 μl reaction volume. The reaction was incubated for 15 minutes at 37° C. and 15 minutes at 50° C. After the incubation period 40 μl of TE were added to the reaction. A 2 μl aliquot was used to transform ONE SHOT® TOP10 competent cells according to the manufacturer's protocol. The *E. coli* transformation reactions were spread onto 2XYT plus ampicillin plates. The transformants were screened by sequencing and one clone containing the insert with no PCR errors was identified and designated pRRAB01 (FIG. 13).

Example 16: Generation of a *Trichoderma reesei* Expression Vector Encoding *Aspergillus fumigatus* Beta-Glucosidase (Cel3A) Mutant Gene A variant of the *Aspergillus fumigatus* Family 3A beta-glucosidase containing the substitutions G142S, Q183R, H266Q, and D703G was constructed by performing site-directed mutagenesis on pEJG97 (WO 2005/074647) using a QUIKCHANGE® Multi Site-Directed Mutagenesis Kit (Stratagene, La Jolla, Calif., USA). A summary of the oligos used for the site-directed mutagenesis are shown in Table 1.

The resulting variant plasmid pDFng128-6 was prepared using a BIOROBOT® 9600. The variant plasmid construct was sequenced using an Applied Biosystems 3130xl Genetic Analyzer (Applied Biosystems, Foster City, Calif., USA) to verify the changes.

TABLE 1

| Amino acid changes | Primer name | Sequences | Cloning Plasmid Name |
|---|---|---|---|
| F100D | AfBGmutF100DF | ccctttgggtatccgtGACtgtgagctatacccgcg (SEQ ID NO: 86) | pDFng128-6 |
| S283G | AfBGmutS283GF | cgtcatgagtgactggGGCgctcaccacagcggtg (SEQ ID NO: 87) | |
| N456E | AfBGmutN456EF | gggtagtggtactgccGAGttcccttaccttgtcac (SEQ ID NO: 88) | |
| F512Y | AfBGmutF512YF | gccgactctggagagggtTACatcagtgtcgacggcaac (SEQ ID NO: 89) | |

Two synthetic oligonucleotide primers shown below were designed to PCR amplify the *Aspergillus fumigatus* beta-glucosidase mutant coding sequence from plasmid pDFng128-6. An IN-FUSION™ Cloning Kit was used to clone the fragment directly into the expression vector pMJ09. Bold letters represent coding sequence. The remaining sequence is homologous to insertion sites of pMJ09.

Forward primer:

(SEQ ID NO: 90)
5'-CGGACTGCGCACCATGAGATTCGGTTGGCTCGA-3'

Reverse primer:

(SEQ ID NO: 91)
5'-TCGCCACGGAGCTTACTAGTAGACACGGGGCAGAG-3'

Fifty picomoles of each of the primers above were used in a PCR reaction composed of 50 ng of pDFng128-6, 1× EXPAND® High Fidelity PCR Buffer with $MgCl_2$, 0.25 mM each of dATP, dTTP, dGTP, and dCTP, and 2.6 units of EXPAND® High Fidelity Enzyme Mix in a final volume of 50 μl. The amplification was performed in an EPPENDORF® MASTERCYCLER® 5333 epgradient S programmed for 1 cycle at 94° C. for 2 minutes; 30 cycles each at 94° C. for 15 seconds, 65° C. for 30 seconds, and 68° C. for 1 minute; and a final elongation at 68° C. for 7 minutes. The heat block then went to a 4° C. soak cycle. The reaction products were isolated by 0.7% agarose gel electrophoresis using TBE buffer where an approximately 3.1 kb product band was excised from the gel and extracted using a QIAQUICK® Gel Extraction Kit according to the manufacturer's instructions.

Plasmid pMJ09 was digested with Nco I and Pac I, isolated by 1.0% agarose gel electrophoresis using TBE buffer, excised from the gel, and extracted using a QIAQUICK® Gel Extraction Kit according to the manufacturer's instructions.

Figure 14:
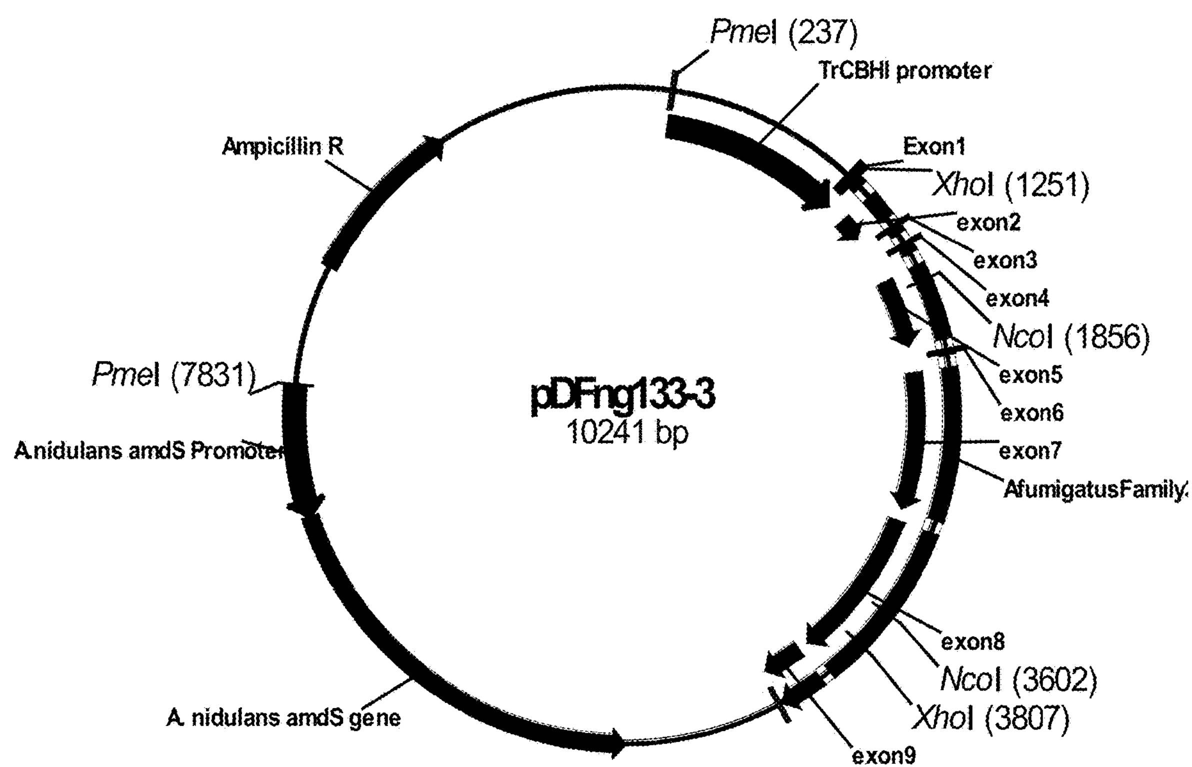
FIG. 14 shows a restriction map of plasmid pDFng113-3.

The 3.1 kb gene fragment and the digested vector were ligated together using an IN-FUSION™ Cloning Kit resulting in pDFng113-3 (FIG. 14) in which transcription of the beta-glucosidase mutant coding sequence was under the control of a promoter from the *Trichoderma reesei* cbhI gene. The ligation reaction (20 μl) was composed of 1× IN-FUSION™ Reaction Buffer, 1×BSA, 1 μl of IN-FUSION™ Enzyme (diluted 1:10), 200 ng of the gel-purified Nco I/Pac I digested pMJ09, and 172.2 ng of the purified 3.1 kb PCR product. The reaction was incubated at 37° C. for 15 minutes followed by 50° C. for 15 minutes. Two μl of the reaction were used to transform *E. coli* XL10 SOLOPACK® Gold Supercompetent cells. The *E. coli* transformation reactions were spread onto 2XYT plus ampicillin plates. An *E. coli* transformant containing pDFng133-3 was prepared using a BIOROBOT® 9600. The *Aspergillus fumigatus* beta-glucosidase mutant insert in pDFng133-3 was confirmed by DNA sequencing.

Example 17: Construction of a Tandem Expression Vector pAmFs074 Encoding *Penicillium emersonii* GH61A Polypeptide and *Aspergillus fumigatus* Cel3A Beta-Glucosidase Variant A tandem expression vector, pAmFs074, was generated by combining restriction enzyme fragments from pRRAB01 and pDFNG133-3 to generate a single vector for the expression of the *Penicillium emersonii* GH61A polypeptide and *Aspergillus fumigatus* Cel3A beta-glucosidase variant.

One microgram of plasmid pRRAB01 (Example 15) purified using a Plasmid Midi Kit (QIAGEN Inc., Valencia, Calif., USA) was combined with 20 units of XhoI (New England Biolabs Inc, Ipswich, Mass., USA), 1×NEB Buffer 4 (New England Biolabs Inc, Ipswich, Mass., USA), and 1×BSA in a final volume of 20 μl. The reaction was incubated at 37° C. for 3 hours and then combined with 4 μl of 5×DNA loading dye (QIAGEN Inc., Valencia, Calif., USA). The restriction digestion reaction products were separated by 1% agarose gel electrophoresis using TBE buffer where an approximately 9.4 kb fragment was excised from the gel and extracted using a NUCLEOSPIN® Extract II Kit according to the manufacturer's protocol. The 9.4 kb fragment contains the *T. reesei* Cel7A cellobiohydrolase I gene promoter, *P. emersonii* GH61A polypeptide coding sequence, *T. reesei* Cel7A cellobiohydrolase I gene terminator, *T. reesei* Cel6A cellobiohydrolase II gene promoter, a 487 bp portion of the 3' end and a 16 bp portion of the 5' end of the *A. fumigatus* beta-glucosidase Cel3A beta-glucosidase coding sequence, *T. reesei* Cel6A cellobiohydrolase II gene terminator, *Aspergillus nidulans* acetamidase (amdS) gene, and ampicillin resistance marker gene.

One microgram of plasmid pDFNG133-3 (Example 16) purified using a Plasmid Midi Kit was combined with 20 units of restriction enzyme Xho I, 1×NEB Buffer 4, and 1×BSA in a final volume of 20 μl. The reaction was incubated at 37° C. for 3 hours and then combined with 4 μl of 5×DNA loading dye. The restriction digestion reaction products were separated by 1% agarose gel electrophoresis using TBE buffer where an approximately 2.6 kb fragment was excised from the gel and extracted using a NUCLEO- SPIN® Extract II Kit according to the manufacturer's protocol. The 2.6 kb fragment contains a 1940 bp portion of the *A. fumigatus* beta-glucosidase Cel3A beta-glucosidase mutant gene.

Figure 15:
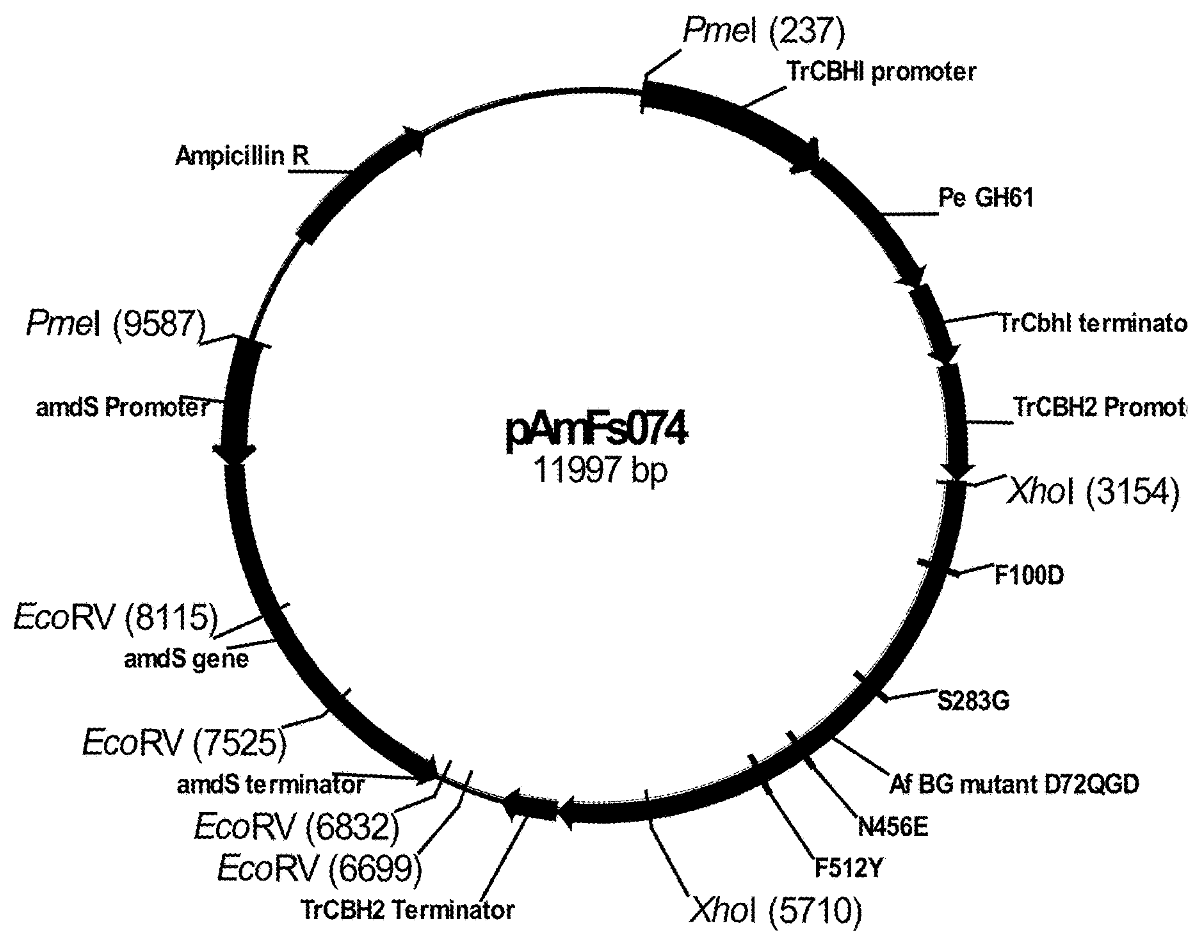
FIG. 15 shows a restriction map of plasmid pAmFs074.

The purified 9.4 kb pRRAB01 Xho I restriction fragment and the purified 2.6 kb pDFNG133-3 Xho I restriction fragment were ligated together using a QUICK LIGATION™ Kit according to the manufacturer's protocol. A 50 ng aliquot of the 9.4 kb pRRAB01 fragment and a 50 ng aliquot of the 2.6 kb pDFNG133-3 fragment were combined and the volume adjusted to 10 μl using sterile water. Then 10 μl of 2× QUICK LIGATION™ Buffer and 1 μl of QUICK LIGASE™ were added and mixed thoroughly. The reaction was carried out at 25° C. for 5 minutes and then placed on ice. A 2 μl aliquot of the ligation reaction was used to transform ONE SHOT® TOP10 competent cells according to the manufacturer's protocol. The *E. coli* transformation reactions were spread onto 2XYT plus ampicillin plates. Transformants were screened by restriction mapping and sequencing. One clone containing the insert in the correct orientation with no sequence errors was identified and designated pAmFs074 (FIG. 15).

Plasmid pAmFs074 can be digested with Pme I to generate an approximately 9.35 kb fragment for *T. reesei* transformation. The 9.35 kb fragment contains an expression cassette composed of (1) the *T. reesei* Cel7A cellobiohydrolase I gene promoter, *P. emersonii* GH61A polypeptide coding sequence, and *T. reesei* Cel7A cellobiohydrolase I gene terminator, and (2) *T. reesei* Cel6A cellobiohydrolase II gene promoter, *A. fumigatus* beta-glucosidase Cel3A beta-glucosidase mutant coding sequence, and *T. reesei* Cel6A cellobiohydrolase II gene terminator. The 9.35 kb fragment also contains the *Aspergillus nidulans* acetamidase (amdS) gene.

Example 18: Generation of a *Penicillium emersonii* GH61A Polypeptide and *Aspergillus Fumigatus* Cel3A Variant Beta-Glucosidase Tandem Expression Vector for Replacement of the *T. reesei* cbhII The tandem replacement vector pQM22 was constructed for replacing the *T. reesei* cbhII gene in *Trichoderma reesei* with a tandem expression cassette for expressing two recombinant proteins in addition to a fungal selection marker. Vector pQM22 contains a *T. reesei* cbhII 5' flanking region, *T. reesei* Cel7A cellobiohydrolase I promoter, *P. emersonii* GH61A polypeptide coding sequence, *T. reesei* Cel7A cellobiohydrolase I gene terminator, *T. reesei* Cel6A cellobiohydrolase II gene promoter, *A. fumigatus* beta-glucosidase Cel3A beta-glucosidase mutant coding sequence, *T. reesei* Cel6A cellobiohydrolase II gene terminator, Herpes simplex virus thymidine kinase (tk) gene, *E. coli* hygromycin phosphotransferase (hpt/hygR) selection marker, *T. reesei* cbhII 3' flanking region, and ampicillin resistance marker gene.

Vector pQM22 was made by inserting an approximately 6.4 kb tandem expression cassette liberated from pAmFs074 and an approximately 1.5 kb *T. reesei* cbhII 5' flanking region amplified from *T. reesei* strain AgJg115-104-7B1 genomic DNA (isolated according to Example 9) into an approximately 8.7 kb vector fragment from pJfyS142 (Example 9) digested with Sap I and Pac I.

The 6.4 kb tandem expression cassette for the *P. emersonii* GH61A polypeptide and *A. fumigatus* beta-glucosidase variant was liberated from pAmFs074 by digesting the plasmid with Pme I and Eco RV. The digestion was subjected to 1% agarose gel electrophoresis using TAE buffer where an approximately 6.4 kb band was excised from the gel and extracted using a NUCLEOSPIN® Extract II Purification Kit according to the manufacturer's protocol.

The 5' *T. reesei* cbhII flanking sequence was amplified from *Trichoderma reesei* strain QMJi030-A5.6 genomic DNA using the forward and reverse primers below. The region in italics represents sequence homology to the site of insertion for an IN-FUSION® reaction and the underlined portion represents introduced Pac I and Psi I sites for cloning.

```
Forward Primer:
                                        (SEQ ID NO: 92)
5'-gcgagtcagtgagcgaggaagcggaagagcttaattaaTCTTGAGT
GGATGTGTGATCTAG-3'

Reverse Primer:
                                        (SEQ ID NO: 93)
5'-gttcggataacaatcctacattcggtcgacttataaGGATGTATCA
ATGGGTTATACG-3'
```

The amplification reaction was composed of approximately 150 ng of *Trichoderma reesei* QMJi030-A5.6 (Example 13) genomic DNA, 1 μM primers, 200 μM GeneAmp® dNTP (Appiled Biosystems, Foster City, USA), 1× PHUSION™ High-Fidelity Hot Start DNA Polymerase Buffer, and 1 unit of PHUSION™ High-Fidelity Hot Start DNA Polymerase in a final volume of 50 μl. The amplification reaction was incubated in an EPPENDORF® MASTERCYCLER® 5333 epgradient S programmed for 1 cycle at 98° C. for 2 minutes; 35 cycles each at 98° C. for 15 seconds, 60° C. for 30 seconds, and 72° C. for 1 minute; and 1 cycle at 72° C. for 10 minutes. The PCR products were separated by 1% agarose gel electrophoresis using TAE buffer where an approximately 1.5 kb band was excised from the gel and extracted using a NUCLEOSPIN® Extract II Purification Kit according to the manufacturer's protocol.

Approximately 36 μg of pJfyS142 were digested with Sap I and Pac I. The digestion reaction was separated by 1% agarose gel electrophoresis using TAE buffer where an approximately 8.7 kb band was excised from the gel and extracted using a NUCLEOSPIN® Extract II Purification Kit according to the manufacturer's protocol.

Figure 16:
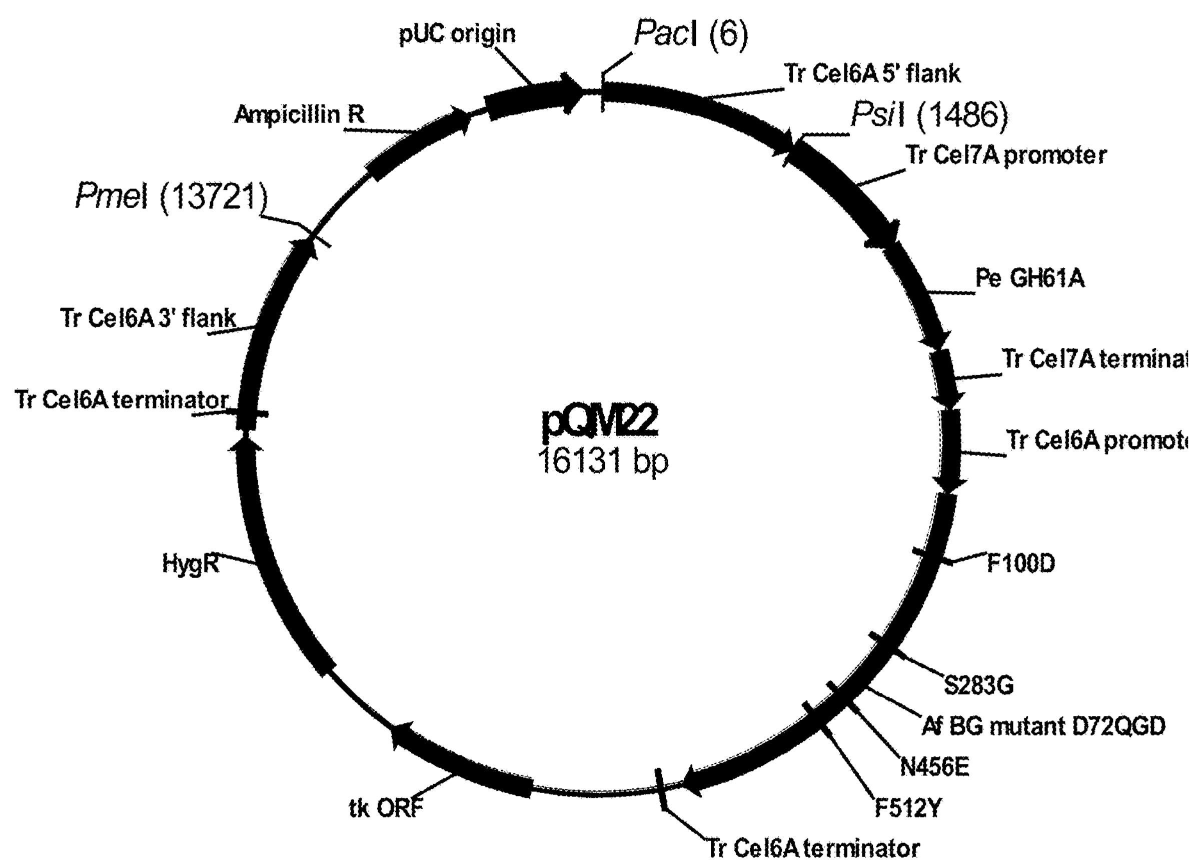
FIG. 16 shows a restriction map of plasmid pQM22.

An IN-FUSION™ reaction was composed of 1× IN-FUSION™ Reaction Buffer, 138 ng of the 8.7 kb pJfyS142 fragment digested with Sap I and Pac I, 205 ng of the 6.4 kb fragment from pAmFs074, 49 ng of the 1.5 kb fragment of the *T. reesei* cbhII 5' flanking region, and 1 μl of IN-FUSION™ Enzyme in a 10 μl reaction volume. The reaction was incubated for 15 minutes at 37° C. and 15 minutes at 50° C. After the incubation period 40 μl of TE were added to the reaction. A 2.5 μl aliquot was used to transform ONE SHOT® TOP10 competent cells according to manufacturer's protocol. The *E. coli* transformation reactions were spread onto 2XYT plus ampicillin plates. Transformants were screened by sequencing and one clone containing the insert with no PCR errors was identified and designated pQM22 (FIG. 16). Plasmid pQM22 was used as the vector to replace the *T. reesei* cbhII gene.

Example 19: Replacement of the Native *Trichoderma reesei* cbhII Gene with *Penicillium Emersonii* GH61A Polypeptide and *Aspergillus fumigatus* Beta-Glucosidase Mutant Tandem Expression Cassette To replace the native *T. reesei* cbhII gene with the *P. emersonii* GH61 polypeptide-*Aspergillus fumigatus* beta-glucosidase mutant tandem expression cassette, *Trichoderma reesei* QMJi030-A5.6 (Example 13) was transformed with 6.3 μg of Pme I-linearized pQM22 (Example 18). Thirty-one transformants were obtained and each one was picked and transferred to a PDA plate and incubated for 7 days at 28° C. After screening out transformants containing an intact cbhII gene locus using the fungal spore PCR method described in Example 13 with primer set A shown below, genomic DNA was isolated from eight transformants according to the procedure of Example 9 and analyzed by PCR using primer set B shown below, a forward primer annealing to a region upstream of the cbhII 5' flanking region of integration, a reverse primer-1 in the tk region after the *A. fumigatus* beta-glucosidase mutant region, and another reverse primer-2 downstream of the *T. reesei* cbhII 3' flanking region.

```
Primer set A Forward primer:
                                   (SEQ ID NO: 94)
5'-TCAACCAGCTTCTTTATTGG-3'

Primer set A Reverse primer:
                                   (SEQ ID NO: 95)
5'-GATCGCCATAGGCTCATGCTCCGCA-3'

Primer set B Forward primer:
                                   (SEQ ID NO: 96)
5'-GCGGCATCAAACACGAACCTG-3'

Primer set B Reverse-1 primer:
                                   (SEQ ID NO: 97)
5'-CAGTGGCGCTTATTACTCAG-3'

Primer set B Reverse-2 primer:
                                   (SEQ ID NO: 98)
5'-GATCGCCATAGGCTCATGCTCCGCA-3'
```

The reaction was composed of 2 μl of the spore suspension, 200 μM dNTP's, 1 μM primers, 1× LONGAMP® Taq Reaction Buffer, and 2 units of LONGAMP® Taq DNA Polymerase in a final volume of 20 μl. The reaction was incubated in an EPPENDORF® MASTERCYCLER® 5333 epgradient S programmed for 1 cycle at 95° C. for 4 minutes; 35 cycles each at 95° C. for 15 seconds, 55° C. for 30 seconds, 68° C. for 11 minutes; and 1 cycle at 68° C. for 15 minutes. The PCR reactions were analyzed by 1% agarose gel electrophoresis using TAE buffer. The PCR results indicated one transformant contained the replacement cassette at the targeted cbhII locus. Southern analysis was performed as described below to confirm the replacement cassette as a single copy for both the *P. emersonii* GH61A polypeptide sequence and the *A. fumigatus* beta-glucosidase mutant coding sequence.

Genomic DNA was isolated from the transformants according to the procedure described In Example 9 and each transformant submitted to Southern analysis. For Southern analysis, 6 μg of genomic DNA was digested with 10 units of Cla I and/or a restriction enzyme mixture containing 5 units of Stu I and 5 units of Sex AI in a 70 μl reaction volume. The digested DNA reaction was mixed with 14 μl of 5×DNA loading dye and 25 μl of each mixture was subjected to 1% agarose electrophoresis using TAE buffer. The DNA in the gel was depurinated in 0.25 N HCl for 15 minutes, denatured in Denaturing Solution twice for 15 minutes each time, neutralized in Neutralization Solution for 10 to 30 minutes, and transferred to a NYTRAN® Supercharge membrane. The DNA was UV crosslinked to the membrane using a UV STRATALINKER™ UV crosslinker and prehybridized for 1 hour at 42° C. in 20 ml of DIG Easy Hyb.

Approximately 1 μg of pQM22 was digested with Stu I and Xba I. The digestion reaction was separated by 1% agarose gel electrophoresis using TAE buffer where an approximately 800 bp band from the *P. emersonii* GH61A polypeptide coding sequence was excised from the gel and extracted using a MINELUTE® Gel Extraction Kit according to the manufacturer's protocol.

Approximately 1 μg of pQM22 was digested with Xho I and Nru I. The digestion reaction was separated by 1% agarose gel electrophoresis using TAE buffer where an approximately 1 kb band from the *A. fumigatus* Cel3A beta-glucosidase mutant coding sequence was excised from the gel and extracted using a MINELUTE® Gel Extraction Kit according to the manufacturer's protocol.

Approximately 1 μg of pQM22 was digested with Not I and Pvu I. The digestion reaction was separated by 1% agarose gel electrophoresis using TAE buffer where an approximately 1.1 kb band from the hpt gene was excised from the gel and extracted using a MINELUTE® Gel Extraction Kit according to the manufacturer's protocol.

Amounts of 266 ng of the 800 bp fragment, 168 ng of the 1 kb fragment, and 240 ng of the 1.1 kb fragment were each combined in a final volume of 16 μl to generate a probe using a DIG-High Prime DNA Labeling Kit (Roche Diagnostics Corporation, Indianapolis, Ind., USA) according to the manufacturer's instructions. The DNA mixture was boiled for ten minutes and then quickly chilled on ice before adding 4 μl of a DIG-High Prime Mix (Roche Diagnostics Corporation, Indianapolis, Ind., USA). The reaction was incubated at 37° C. for approximately 20 hours before adding 2 μl of 0.2 M EDTA and then heating at 65° C. for 10 minutes to stop the reaction.

The probe was purified using a MINELUTE® Gel Extraction Kit according to the manufacturer's protocol. The probe was boiled for 5 minutes, chilled on ice for 2 minutes, and added to 10 ml of DIG Easy Hyb to produce the hybridization solution. Hybridization was performed at 42° C. for approximately 17 hours. The membrane was then washed under low stringency conditions in 2×SSC plus 0.1% SDS for 5 minutes at room temperature followed by two high stringency washes in 0.5×SSC plus 0.1% SDS for 15 minutes each at 65° C. The probe-target hybrids were detected by chemiluminescent assay (Roche Diagnostics, Indianapolis, Ind., USA) according to the manufacturer's instructions. Southern analysis indicated that the transformant contained a single copy of the *P. emersonii* GH61A polypeptide coding sequence and *A. fumigatus* beta-glucosidase (Cel3A) mutant coding sequence at the targeted cbhII locus. The transformant was designated *T. reesei* QMJi033.

Example 20: *Trichoderma reesei* Protoplast Generation and Transformation

Protoplast preparation and transformation were performed using a modified protocol by Penttila et al., 1987, *Gene* 61: 155-164. Briefly, *Trichoderma reesei* strain AgJg115-104-7B1 (PCT/US2010/061105; WO 2011/075677) was cultivated in 25 ml of YP medium supplemented with 2% (w/v) glucose and 10 mM uridine at 27° C. for 17 hours with gentle agitation at 90 rpm. Mycelia were collected by filtration using a Vacuum Driven Disposable Filtration System and washed twice with deionized water and twice with 1.2 M sorbitol. Protoplasts were generated by suspending the washed mycelia in 20 ml of 1.2 M sorbitol containing 15 mg of GLUCANEX® 200 G per ml and 0.36 units of chitinase per ml for 15-25 minutes at 34° C. with gentle shaking at 90 rpm. Protoplasts were collected by centrifuging for 7 minutes at 400×g and washed twice with cold 1.2 M sorbitol. The protoplasts were counted using a haemocytometer and re-suspended to a final concentration of $1\times10^8$ protoplasts per ml in STC. Excess protoplasts were stored in a Cryo 1° C. Freezing Container at −80° C.

Approximately 100 μg of a transforming plasmid described in the following examples were digested with Pme I. The digestion reaction was purified by 1% agarose gel electrophoresis using TAE buffer. A DNA band was excised from the gel and extracted using a QIAQUICK® Gel Extraction Kit. The resulting purified DNA was added to 100 μl of the protoplast solution and mixed gently. PEG buffer (250 μl) was added, mixed, and incubated at 34° C. for 30 minutes. STC (3 ml) was then added, mixed, and spread onto PDA plates supplemented with 1 M sucrose. After incubation at 28° C. for 16 hours, 20 ml of an overlay PDA medium supplemented with 35 μg of hygromycin B per ml was added to each plate. The plates were incubated at 28° C. for 4-7 days.

Example 21: Replacement of Native *Trichoderma reesei* cbhI Gene with the *Aspergillus fumigatus* cbhI Gene In order to replace the *Trichoderma reesei* native cbhI gene (SEQ ID NO: 1 [DNA sequence] and SEQ ID NO: 2 [deduced amino acid sequence]) with the *Aspergillus fumigatus* cbhI coding sequence (SEQ ID NO: 57 [DNA sequence] and SEQ ID NO: 58 [deduced amino acid sequence]), *Trichoderma reesei* ku70-strain AgJg115-104-7B1 (PCT/US2010/061105; WO 2011/075677) was transformed with 4×2 μg of Pme I-linearized pJfyS139 (Example 11) according to the procedure described in Example 20. Seven transformants were obtained and each one was picked and transferred to a PDA plate and incubated for 7 days at 28° C. Genomic DNA was isolated from the transformants according to the procedure described in Example 9 and each transformant submitted to Southern analysis.

For Southern analysis, 2 μg of genomic DNA was digested with 33 units of Bgl II in a 50 μl reaction volume and subjected to 1% agarose electrophoresis using TAE buffer. The DNA in the gel was depurinated with one 10 minute wash in 0.25 N HCl, denatured with two 15 minute washes in 0.5 N NaOH-1.5 M NaCl, neutralized with one 30 minute wash in 1 M Tris pH 8-1.5 M NaCl, and incubated in 20×SSC for 5 minutes. The DNA was transferred to a NYTRAN® Supercharge membrane using a TURBOBLOTTER™ System according to the manufacturer's protocol. The DNA was UV crosslinked to the membrane using a STRATALINKER™ UV Crosslinker and prehybridized for 1 hour at 42° C. in 20 ml of DIG Easy Hyb.

A probe hybridizing to the 3' cbhI gene flanking sequence was generated using a PCR Dig Probe Synthesis Kit according to the manufacturer's instructions with the forward and reverse primers shown below. The PCR reaction was composed of 1× HERCULASE® Reaction Buffer, 400 nM of each primer, 200 μM DIG-labeled dUTP-containing dNTPs, 20 ng of pJfyS139, and 1.5 units of HERCULASE® Hot Start High-Fidelity DNA Polymerase. The amplification reaction was incubated in an EPPENDORF® MASTERCYCLER® 5333 epgradient S programmed for 1 cycle at 95° C. for 2 minutes; 25 cycles each at 95° C. for 30 seconds, 55° C. for 30 seconds, and 72° C. for 40 seconds; and 1 cycle at 72° C. for 7 minutes.

```
Forward primer:
                                   (SEQ ID NO: 99)
5'-AAAAAACAAACATCCCGTTCATAAC-3'

Reverse primer:
                                  (SEQ ID NO: 100)
5'-AACAAGGTTTACCGGTTTCGAAAAG-3'
```

The probe was purified by 1% agarose gel electrophoresis using TAE buffer where a 0.5 kb band corresponding to the probe was excised from the gel and extracted using a MINELUTE® Gel Extraction Kit. The probe was boiled for 5 minutes, chilled on ice for 2 minutes, and added to 10 ml of DIG Easy Hyb to produce the hybridization solution. Hybridization was performed at 42° C. for 15-17 hours. The membrane was then washed under low stringency conditions in 2×SSC plus 0.1% SDS for 5 minutes at room temperature followed by two high stringency washes in 0.5×SSC plus 0.1% SDS for 15 minutes each at 65° C. The probe-target hybrids were detected by chemiluminescent assay (Roche Diagnostics, Indianapolis, Ind., USA) according to the manufacturer's instructions. Southern analysis indicated that 3 of the 7 transformants contained the replacement cassette at the cbhI locus and one transformant, *T. reesei* JfyS139-8, was chosen for curing the hpt and tk markers.

A fresh plate of spores was generated by transferring spores of a 7 day old PDA plate grown at 28° C. to a PDA plate and incubating for 7 days at 28° C. Spores were collected in 10 ml of 0.01% TWEEN® 20 using a sterile spreader. The concentration of spores was determined using a hemocytometer and $10^5$ spores were spread onto 150 mm plates containing TrMM-G medium supplemented with 1 μM 5-fluoro-2'-deoxyuridine (FdU).

Three hundred FdU-resistant spore isolates were obtained and DNA was extracted from 2 of the spore isolates as described above. The isolates were submitted to Southern analysis as described above and the results indicated that both spore isolates had excised the hpt/tk region between the homologous repeats of the replacement cassette. One strain designated *T. reesei* JfyS139-8A was chosen for replacing the cbhII gene.

Example 22: Replacement of the Native *Trichoderma reesei* cbhII Gene with the *Aspergillus fumigatus* cbhII Gene In order to replace the native *T. reesei* cbhII gene with the *Aspergillus fumigatus* cbhII coding sequence, *Trichoderma reesei* JfyS139-8A (Example 21) was transformed according to the procedure described in Example 20 with 2 μg of Pme I-linearized and gel purified pJfyS144 (Example 10). Seven transformants were obtained and each one was picked and transferred to a PDA plate and incubated for 7 days at 28° C. A fungal spore PCR method described below was used to screen for transformants bearing gene replacement using the forward primer shown below annealing to a region upstream of the 5' cbhII gene flanking sequence beyond the region of integration, and the reverse primer shown below for the *A. fumigatus* cbhII coding sequence.

```
Forward primer:
                                  (SEQ ID NO: 101)
5'-AGCCACATGCCGCATATTGACAAAG-3'

Reverse primer:
                                  (SEQ ID NO: 102)
5'-AGGGATTCAGTGTGCTACAGGCTGC-3'
```

A 1.8 kb PCR product would be generated only upon the occurrence of a precise gene replacement at the cbhII locus. If the cassette had integrated elsewhere in the genome, no amplification would result.

A small amount of spores from each transformant was suspended in 25 μl of TE buffer and heated on high in a microwave oven for 1 minute. Each microwaved spore suspension was used as a template in the PCR reaction. The reaction was composed of 1 μl of the microwaved spore suspension, 1 μl of a 10 mM dNTPs, 12.5 μl of 2× ADVANTAGE® GC-Melt LA Buffer (Clontech, Mountain View, Calif., USA), 25 pmol of forward primer, 25 pmol of reverse primer, 1.25 units of ADVANTAGE® GC Genomic LA Polymerase Mix (Clontech, Mountain View, Calif., USA), and 9.25 μl of water. The reaction was incubated in an EPPENDORF® MASTERCYCLER® 5333 epgradient S programmed for 1 cycle at 95° C. for 10 minutes; 35 cycles each at 95° C. for 30 seconds, 56° C. for 30 seconds, and 72° C. for 1 minute 40 seconds; 1 cycle at 72° C. for 7 minutes; and a 4° C. hold. The PCR reactions were subjected to 1% agarose gel electrophoresis using TAE buffer. The spore PCR indicated that four of the seven transformants contained the replacement cassette at the targeted locus and three of them were submitted to Southern analysis to confirm the replacement cassette was in a single copy.

Genomic DNA was isolated from the three transformants according to the procedure described in Example 9 and each transformant submitted to Southern analysis. For Southern analysis, 2 μg of genomic DNA was digested with 50 units of Dra I in a 50 μl reaction volume and subjected to 1% agarose electrophoresis using TAE buffer. The DNA in the gel was depurinated with one 10 minute wash in 0.25 N HCl, denatured with two 15 minute washes in 0.5 N NaOH-1.5 M NaCl, neutralized with one 30 minute wash in 1 M Tris pH 8-1.5 M NaCl, and incubated in 20×SSC for 5 minutes. The DNA was transferred to a NYTRAN® Supercharge membrane. The DNA was UV crosslinked to the membrane using a STRATALINKER™ UV crosslinker and prehybridized for 1 hour at 42° C. in 20 ml of DIG Easy Hyb.

A probe hybridizing to the 3' cbhII gene flanking sequence was generated using a PCR Dig Probe Synthesis Kit according to the manufacturer's instructions with the forward and reverse primers indicated below. The PCR reaction was composed of 1× HERCULASE® Reaction Buffer, 400 nM each primer, 200 μM DIG-labeled dUTP-containing dNTPs, 150 ng of *T. reesei* RutC30 genomic DNA, and 1.5 units of HERCULASE® Hot Start High-Fidelity DNA Polymerase. The reaction was incubated in an EPPENDORF® MASTERCYCLER® 5333 epgradient S programmed for 1 cycle at 95° C. for 2 minutes; 30 cycles each at 95° C. for 30 seconds, 51° C. for 30 seconds, and 72° C. for 40 seconds; and 1 cycle at 72° C. for 7 minutes.

```
Forward primer:
                                    (SEQ ID NO: 103)
5'-AAAAAACAAACATCCCGTTCATAAC-3'

Reverse primer:
                                    (SEQ ID NO: 104)
5'-AACAAGGTTTACCGGTTTCGAAAAG-3'
```

The probe was purified by 1% agarose gel electrophoresis using TAE buffer where a 0.5 kb band corresponding to the probe was excised from the gel and extracted using a QIAQUICK® Gel Extraction Kit. The probe was boiled for 5 minutes, chilled on ice for 2 minutes, and added to 10 ml of DIG Easy Hyb to produce the hybridization solution. Hybridization was performed at 42° C. for approximately 17 hours. The membrane was then washed under low stringency conditions in 2×SSC plus 0.1% SDS for 5 minutes at room temperature followed by two high stringency washes in 0.5×SSC plus 0.1% SDS for 15 minutes each at 65° C. The probe-target hybrids were detected by chemiluminescent assay (Roche Diagnostics, Indianapolis, Ind., USA) according to the manufacturer's instructions. Southern analysis indicated that the three transformants contained the replacement cassette at the cbhII locus and all three (designated JfyS139/144-5, -6, and -10) were chosen for curing the hpt and tk markers.

A fresh plate of spores was generated by transferring a plug of a 7 day old culture grown on a PDA plate at 28° C. to a new PDA plate and incubating for 7 days at 28° C. Spores were collected in 10 ml of 0.01% TWEEN® 20 using a sterile spreader. The concentration of spores was determined using a hemacytometer and $10^5$ and $10^4$ spores were spread onto 150 mm plates containing TrMM-G medium supplemented with 1 μM FdU.

Approximately 500 FdU-resistant spore isolates for each transformant were obtained from the plate containing $10^5$ spores and approximately 100 FdU-resistant spore isolates for each transformant from the plate containing $10^4$ spores. Eight spore isolates were picked for strains JfyS139/144-5 and -6 and four were picked for strain JfyS139/144-10. Each isolate 1 to 8 from primary transformant 5 was designated JfyS139/144-5A to -5H. Isolates 1 to 8 from primary transformant 6 were designated JfyS139/144-6A to 6H. Isolates from primary transformant 10 were designated JfyS139/144-10A to 10D for isolates 1 to 4. Spore PCR was conducted as described above, using the forward and reverse primers shown below, to confirm the hpt and tk markers had been correctly excised.

```
Forward primer:
                                    (SEQ ID NO: 105)
5'-GTTAAGCATACAATTGAACGAGAATGG-3'

Reverse primer:
                                    (SEQ ID NO: 106)
5'-GATGATATAATGGAGCAAATAAGGG-3'
```

The PCR reactions were performed as described above with the following cycling parameters: 1 cycle at 95° C. for 2 minutes; 30 cycles each at 95° C. for 30 seconds, 55° C. for 30 seconds, and 72° C. for 6 minutes seconds; and 1 cycle at 72° C. for 7 minutes.

The primers annealed to the 5' (forward) and 3' (reverse) flanking sequences used for the cbhII gene replacement. Strains from which the hpt/tk cassette had been correctly excised would display a 3.5 kb fragment while those with the markers intact would display an 8 kb fragment. The PCR screen indicated that all of the spore isolates had correctly excised the hpt/tk cassette.

DNA was extracted from the A and B spore isolates from each primary transformant and submitted to Southern analysis as described above. The Southern analysis confirmed that each spore isolate had correctly excised the hpt/tk cassette. Spore isolate *T. reesei* JfyS139/144-10B was chosen to represent the strain containing both the *T. reesei* cbhI and cbhII genes replaced with the respective homologs from *Aspergillus fumigatus.*

Example 23: Generation of *Trichoderma reesei* Ku70 Gene Repair Plasmid pTH239

Four DNA segments were combined using an IN-FUSION® Advantage PCR Cloning Kit to generate a construct to replace the disrupted *Trichoderma reesei* ku70 coding sequence with the native *Trichoderma reesei* ku70 coding sequence (SEQ ID NO: 107 [DNA sequence] and SEQ ID NO: 108 [deduced amino acid sequence]). The ampicillin resistance marker region including the prokaryotic origin of replication was amplified from pJfyS139-B (Example 11) using the sequence-specific forward and reverse primers shown below (SEQ ID NOs: 109 and 110). The *T. reesei* ku70 gene upstream sequence (consisting of 989 bp from upstream of the ku70 coding sequence and the first 1010 bp of the ku70 coding sequence) was amplified from *T. reesei* 981-O-8 genomic DNA using the sequence-specific forward and reverse primers shown below (SEQ ID NOs: 111 and 112). The *T. reesei* ku70 gene downstream sequence (consisting of a 500 bp segment repeated from the 3' end of the 1010 bp segment of the ku70 coding sequence amplified in the upstream PCR product, and a 1067 bp segment containing the remainder of the ku70 coding sequence, and 461 bp from downstream of the ku70 coding sequence) was amplified from *T. reesei* 981-O-8 genomic DNA using the sequence-specific forward and reverse primers shown below (SEQ ID NOs: 113 and 114). *T. reesei* 981-O-8 genomic DNA was prepared according to the procedure described in Example 9.

```
Forward primer:
                                        (SEQ ID NO: 109)
5'-GTGTGCGGCCGCTCGAGCATGCATGTTTAAACAGCTTGGCACTGGC

CGTCGTTTT-3'

Reverse primer:
                                        (SEQ ID NO: 110)
5'-ATCAGCCCCGAGACGGCGCCGCGTTTAAACAATTCGTAATCATGG

TCATAGCTGT-3'

Forward primer:
                                        (SEQ ID NO: 111)
5'-CATGATTACGAATTGTTTAAACGCGGCGCCGTCTCGGGGCTGATC

TTGTCGAGGA-3'

Reverse primer:
                                        (SEQ ID NO: 112)
5'-GGCGGCCGTTACTAGTGGATCCAGCCCTTGACAGTGATCTTGAG

TCCAGGTGCAA-3'

Forward primer:
                                        (SEQ ID NO: 113)
5'-TGCAGATATCCATCACACTGGCGGCCGCAGTTTCCATGTCCAAC

GTGTTGTTTTGCGC-3'

Reverse primer:
                                        (SEQ ID NO: 114)
5'-GCCAGTGCCAAGCTGTTTAAACATGCATGCTCGAGCGGCCGCAC

ACGCCCTCTCCTCG-3'
```

For amplification of the ampicillin resistance marker and prokaryotic origin of replication region, the reaction was composed of 100 ng of *T. reesei* 981-O-8 genomic DNA, 200 μM dNTPs, 1 μM of each primer (SEQ ID NOs: 109 and 110), 1× PHUSION® High-Fidelity Hot Start DNA Polymerase Buffer, and 1.0 unit of PHUSION® High-Fidelity Hot Start DNA Polymerase in a final volume of 50 μl. The amplification reaction was incubated in an EPPENDORF® MASTERCYCLER® 5333 epgradient S programmed for 1 cycle at 98° C. for 30 seconds; 30 cycles each at 98° C. for 10 seconds, 55° C. for 30 seconds, and 72° C. for 1 minute 30 seconds; and 1 cycle at 72° C. for 7 minutes. The PCR product was separated by 1% agarose gel electrophoresis using TAE buffer where a 2.692 kb fragment was excised from the gel and extracted using a MINELUTE® Gel Extraction Kit.

For amplification of the ku70 gene upstream sequence and downstream sequence, the reactions were composed of 100 ng of pJfyS139-B, 200 μM dNTPs, 1 μM of each primer (SEQ ID NOs: 111 and 112 or 113 and 114), 1× PHUSION® High-Fidelity Hot Start DNA Polymerase Buffer, and 1.0 unit of PHUSION® High-Fidelity Hot Start DNA Polymerase in a final volume of 50 μl. The amplification reactions were incubated in an EPPENDORF® MASTERCYCLER® 5333 epgradient S programmed for 1 cycle at 98° C. for 30 seconds; 30 cycles each at 98° C. for 10 seconds, 55° C. for 30 seconds, and 72° C. for 1 minute 30 seconds; and 1 cycle at 72° C. for 7 minutes. The PCR products were separated by 1% agarose gel electrophoresis using TAE buffer where 1.999 kb and 2.028 kb fragments were separately excised from the gels and extracted using a MINELUTE® Gel Extraction Kit.

The fourth DNA segment was generated from a restriction enzyme digestion of pJfyS139-B with Not I and Bam HI. The reaction was composed of 5 μg of pJfyS139-B, 10 units of Not I, 20 units of Bam HI, and 20 μl of Restriction Enzyme Buffer 2 (New England Biolabs, Inc., Ipswich, Mass., USA) in a total volume of 50 μl. The reaction was incubated for 1 hour at 37° C. and then separated by 1% agarose gel electrophoresis using TAE buffer where a 4.400 kb fragment was excised from the gel and extracted using a MINELUTE® Gel Extraction Kit.

The three PCR products of 2,028 bp, 1,999 bp, and 2,692 bp were inserted into Not I and Bam HI-digested pJfyS139-B using an IN-FUSION® Advantage PCR Cloning Kit according to the manufacturer's protocol. The IN-FUSION® reaction was composed of 1× IN-FUSION® Reaction Buffer, 50 ng of the Not I/Bam HI-digested pJfyS139-B, 50 ng of the 1.999 kb ku70 gene upstream PCR product, 50 ng of the 2.028 kb ku70 gene downstream PCR product, 50 ng of the 2.692 kb ampicillin resistance marker and prokaryotic origin of replication PCR product, and 1 μl of IN-FUSION® Enzyme in a 10 μl reaction volume. The reaction was incubated for 15 minutes at 37° C. followed by 15 minutes at 50° C. After the incubation period 40 μl of TE were added to the reaction. A 3 μl aliquot was used to transform *E. coli* XL10 GOLD® competent cells (Stratagene, La Jolla, Calif., USA) according to the manufacturer's protocol. The cells were heat shocked at 42° C. for 30 seconds and then 500 μl of NZY+ medium, pre-heated to 42° C., were added. The tubes were incubated at 37° C. with shaking at 200 rpm for 40 minutes and then plated onto 150 mm diameter 2XYT plus ampicillin plates and incubated at 37° C. overnight. The resulting transformants were screened by restriction digestion analysis with Hind III and Xba I and positive clones sequenced to ensure the absence of PCR errors. One clone containing the insert with no PCR errors was identified and designated pTH239.

Example 24: Repair of the Ku70 Gene in the *A. fumigatus* cbh1 and cbh2 Replacement Strain JfyS139/144-10B The native *Trichoderma reesei* ku70 gene was repaired in strain *T. reesei* JfyS139/144-10B (Example 22) in order to facilitate strain manipulation steps requiring the function of the ku70 gene in non-homologous end-joining. *T. reesei* JfyS129/144-10B was transformed with 23×2 μg of Pme I-linearized pTH239 (Example 23) according to the procedure described in Example 4. Nineteen transformants were obtained and each one was separately transferred to a PDA plate and incubated for 7 days at 28° C.

All nineteen transformants were screened by PCR to confirm homologous integration of the pTH239 Pme I fragment at the disrupted ku70 gene locus. For each of the transformants a sterile inoculation loop was used to collect spores from a 7 day old PDA plate. The spores were transferred to a tube containing 25 μl of 1 mM EDTA-10 mM Tris buffer and microwaved on high for 1 minute. A 1 μl aliquot of the microwaved spore mixture was added directly to the PCR reaction as template DNA. A set of PCR primers shown below were designed to amplify across the disrupted region of the ku70 coding sequence to distinguish between the host genome with the disruption in the ku70 coding sequence (848 bp) and the pTH239 targeted strain of interest (606 bp). The PCR reaction was composed of 1× ADVANTAGE® Genomic LA Polymerase Reaction Buffer (Clontech, Mountain View, Calif., USA), 400 nM of each primer, 200 μM dNTPs, 1 μl of microwaved TE-spore mixture (described above), and 1.0 unit of ADVANTAGE® Genomic LA Polymerase (Clontech, Mountain View, Calif., USA). The amplification reaction was incubated in an EPPENDORF® MASTERCYCLER® 5333 epgradient S programmed for 1 cycle at 95° C. for 10 minutes; 30 cycles each at 95° C. for 30 seconds, 55° C. for 30 seconds, and 72° C. for 60 seconds; and 1 cycle at 72° C. for 7 minutes.

```
Forward primer:
                              (SEQ ID NO: 115)
5'-CAATGACGATCCGCACGCGT-3'

Reverse primer:
                              (SEQ ID NO: 116)
5'-CAATGACGATCCGCACGCGT-3'
```

Only one of the nineteen transformants (#19) was positive for the 606 bp PCR product and negative for the 848 bp PCR product indicative of a strain containing the pTH239 PmeI fragment homologously integrated at the ku70 locus.

Spores from the 7 day old PDA plate of transformant #19 were collected in 10 ml of 0.01% TWEEN® 20 using a sterile spreader. The concentration of spores was determined using a hemocytometer and $10^6$ spores were spread onto 150 mm plates containing TrMM-G medium supplemented with 1 μM 5-fluoro-2'-deoxyuridine (FdU) and cultured for 5 days at 28° C. Twenty-two FdU-resistant spore isolates were obtained and transferred to PDA plates and cultivated at 28° C. for five days.

All twenty-two spore isolates (#19A-V) were screened by PCR for excision of the hpt/tk marker region present between the homologous repeats of the ku70 coding sequence within the repair cassette. For each of the spore isolates a sterile inoculating loop was used to collect spores from a 7 day old PDA plate. The spores were transferred to a tube containing 25 μl of 1 mM EDTA-10 mM Tris buffer and microwaved on high for 1 minute. A 1 μl aliquot of the spore mixture was added directly to the PCR reaction as template genomic DNA. A set of PCR primers shown below were designed to amplify across the hpt/tk region to distinguish between the presence (6 kb) or absence (1.1 kb) of the hpt/tk region. The PCR reaction was composed of 1× ADVANTAGE® Genomic LA Polymerase Reaction Buffer, 400 nM of each primer (below), 200 μM dNTPs, 1 μl of microwaved TE-spore mixture (described above), and 1.0 unit of ADVANTAGE® Genomic LA Polymerase. The amplification reaction was incubated in an EPPENDORF® MASTERCYCLER® 5333 epgradient S programmed for 1 cycle at 95° C. for 10 minutes; 30 cycles each at 95° C. for 30 seconds, 50° C. for 30 seconds, and 72° C. for 6 minutes; and 1 cycle at 72° C. for 7 minutes.

```
Forward primer:
                              (SEQ ID NO: 117)
5'-GACACTCTTTTCTCCCATCT-3'

Reverse primer:
                              (SEQ ID NO: 118)
5'-GAGGAGCAGAAGAAGCTCCG-3'
```

All twenty-two spore isolates were negative for the 6 kb PCR product corresponding to the hpt/tk marker region.

Spores from the 7 day old PDA plates of isolates #19A and #19L were collected in 10 ml of 0.01% TWEEN® 20 using a sterile spreader. The concentration of spores was determined using a hemocytometer and $10^3$, $10^2$, and $10^1$ spores were spread onto 150 mm PDA plates containing 1 M sucrose and cultured for 3 days at 28° C. Ten spore isolates were selected from the PDA plates for both strains #19A and #19L and transferred to fresh PDA plates and placed at 28° C.

Genomic DNA was extracted from 6 spore isolates of both #19L and #19A, according to the procedure described in Example 9 and submitted to Southern analysis.

For Southern analysis, 2 μg of genomic DNA was digested with (1) 5 units and 10 units, respectively, of Asc I and Xho I or (2) 5 units and 25 units, respectively, of Asc I and Apa I in a 50 μl reaction volume and subjected to 1% agarose electrophoresis using TAE buffer. The DNA in the gel was depurinated with one 10 minute wash in 0.25 N HCl, denatured with two 15 minute washes in 0.5 N NaOH-1.5 M NaCl, neutralized with one 30 minute wash in 1 M Tris pH 8-1.5 M NaCl, and incubated in 20×SSC for 5 minutes. The DNA was transferred to a NYTRAN® Supercharge membrane using a TURBOBLOTTER™ System according to the manufacturer's protocol. The DNA was UV crosslinked to the membrane using a STRATALINKER™ UV Crosslinker and prehybridized for 1 hour at 42° C. in 20 ml of DIG Easy Hyb.

A probe hybridizing to the 3' end of the ku70 coding sequence was generated using a PCR Dig Probe Synthesis Kit according to the manufacturer's instructions with the forward and reverse primers shown below. In order to generate a pure template for the probe PCR reaction, the 3' end of the ku70 coding sequence was amplified from *T. reesei* 981-O-8 genomic DNA. The PCR reaction was composed of 1× PHUSION® High-Fidelity Hot Start DNA Polymerase Buffer, 1 μM of each primer, 200 μM dNTPs, 165 ng of *T. reesei* 981-O-8 genomic DNA, and 1.0 unit of PHUSION® High-Fidelity Hot Start DNA Polymerase. The amplification reaction was incubated in an EPPENDORF® MASTERCYCLER® 5333 epgradient S programmed for 1 cycle at 98° C. for 30 seconds; 35 cycles each at 98° C. for 10 seconds, 60° C. for 30 seconds, and 72° C. for 15 seconds; and 1 cycle at 72° C. for 10 minutes.

```
Forward primer:
                              (SEQ ID NO: 119)
5'-gcatatataacccactcaagta-3'

Reverse primer:
                              (SEQ ID NO: 120)
5'-attatcttggaccggccgcagg-3'
```

The 0.5 kb probe template was purified by 1% agarose gel electrophoresis using TAE buffer and excised from the gel and extracted using a MINELUTE® Gel Extraction Kit. The purified PCR product was used to generate a DIG-labeled probe as specified by the manufacturer's instructions using the primers and amplification conditions specified above. The 0.5 kb DIG-labeled probe was purified by 1% agarose gel electrophoreseis using TAE buffer and excised from the gel and extracted using a MINELUTE® Gel Extraction Kit. The probe was boiled for 5 minutes, chilled on ice for 2 minutes, and added to 10 ml of DIG Easy Hyb to produce a hybridization solution. Hybridization was performed at 42° C. for 15-17 hours. The membrane was then washed under low stringency conditions in 2×SSC plus 0.1% SDS for 5 minutes at room temperature followed by two high stringency washes in 0.5×SSC plus 0.1% SDS for 15 minutes each at 65° C. The probe-target hybrids were detected by chemiluminescent assay (Roche Diagnostics, Indianapolis, Ind., USA) according to the manufacturer's instructions. Southern analysis indicated that all spore isolates contained the repair/replacement cassette at the ku70 locus and were cured of the hpt and tk markers. One strain designated *T. reesei* 981-O-8.5#10B+Ku70#19L3 was chosen for further transformations.

Example 25: *Trichoderma reesei* 981-O-8.5#10B+Ku70#19L3 Protoplast Generation and Transformation Protoplast preparation and transformation were performed using a modified protocol by Penttila et al., 1987, *Gene* 61: 155-164. Briefly, *Trichoderma reesei* strain 981-O-8.5#10B+Ku70#19L3 was cultivated in 25 ml of YP medium supplemented with 2% (w/v) glucose and 10 mM uridine at 27° C. for 17 hours with gentle agitation at 90 rpm. Mycelia were collected by filtration using a Vacuum Driven Disposable Filtration System and washed twice with deionized water and twice with 1.2 M sorbitol. Protoplasts were generated by suspending the washed mycelia in 20 ml of 1.2 M sorbitol containing 15 mg of GLUCANEX® 200 G per ml and 0.36 units of chitinase per ml for 15-25 minutes at 34° C. with gentle shaking at 90 rpm. Protoplasts were collected by centrifuging for 7 minutes at 400×g and washed twice with cold 1.2 M sorbitol. The protoplasts were counted using a haemocytometer and resuspended to a final concentration of $1\times10^8$ protoplasts per ml in STC. Excess protoplasts were stored in a Cryo 1° C. Freezing Container at −80° C.

Approximately 100 μg of plasmid pAmFs074 were digested with Pme I. The digestion reaction was purified by 0.8% agarose gel electrophoresis using TAE buffer. An approximately 9.4 kb DNA band containing the tandem expression cassette comprising the *Penicillium emersonii* GH61A polypeptide coding sequence, *Aspergillus fumigatus* beta-glucosidase mutant coding sequence, and amdS marker was excised from the gel and extracted using a QIAQUICK® Gel Extraction Kit according to the manufacturer's suggested protocol.

The resulting 9.4 kb fragment (5×2 μg or 2×3.5 μg of the 9.4 kb Pme I digested pAmFs074) was added to 100 μl of the protoplast solution and mixed gently. PEG buffer (250 μl) was added, and the reaction was mixed and incubated at 34° C. for 30 minutes. STC (3 ml) was then added, and the reaction was mixed and then spread onto COVE plates for amdS selection. The plates were incubated at 28° C. for 6-11 days.

Example 26: Evaluation of *Trichoderma reesei* Transformants in Shake Flasks for Expression of *Penicillium emersonii* GH61A Polypeptide and *Aspergillus fumigatus* Beta-Glucosidase Variant One hundred and twelve *Trichoderma reesei* 981-O-8.5#10B+Ku70#19L3 transformants were transferred from COVE transformation plates to COVE2 plates supplemented with 10 mM uridine using an inoculation loop and incubated 5-7 days at 28° C. Spores were collected with an inoculating loop and transferred to 25 ml of CIM medium in 125 ml plastic shake flasks. The shake flask cultures were incubated for 5 days at 28° C., 200 rpm. Approximately 14-15 ml of each of the cultures were poured into 15 ml tubes. The tubes were centrifuged at 863×g for 20 minutes. The supernatants were decanted into fresh tubes. The supernatants were assayed for beta-glucosidase activity using a BIOMEK® 3000, a BIOMEK® NX, and an ORCA® robotic arm (Beckman Coulter, Inc, Fullerton, Calif., USA). The supernatants were diluted appropriately in 0.1 M succinate, 0.01% TRITON® X-100 (4-(1,1,3,3-tetramethylbutyl)phenyl-polyethylene glycol) buffer pH 5.0 (sample buffer) followed by a series of dilutions from 0-fold to ⅓-fold to ⅑-fold of the diluted sample. A total of 20 μl of each dilution was transferred to a 96-well flat bottom plate. Two hundred microliters of a 1 mg/ml p-nitrophenyl-beta-D-glucopyranoside substrate in 0.1 M succinate pH 5.0 buffer were added to each well and then incubated at ambient temperature for 45 minutes. Upon completion of the incubation period 50 μl of quenching buffer (1 M Tris pH 9) was added to each well. An endpoint was measured at an optical density of 405 nm for the 96-well plate. Thirty-three samples showing activity greater than 16,000 μM/min/ml were analyzed by SDS-PAGE to determine expression of the GH61A polypeptide.

Ten μl of each culture supernatant were analyzed by SDS-PAGE using a CRITERION® 8-16% Tris-HCl Gel according to the manufacturer's instructions. The resulting gel was stained with BIO-SAFE™ Coomassie. SDS-PAGE profiles of the cultures showed that the transformants produced major protein bands of approximately 130 kDa corresponding to the *Aspergillus fumigatus* beta-glucosidase variant and approximately 27 kDa corresponding to the *Penicillium emersonii* GH61A polypeptide. Based on expression of the GH61A polypeptide on SDS-PAGE profiles, twenty-one transformants were selected for further spore purification and analysis.

Spore purification was performed by touching a plate of spores with a 1 μl inoculating loop before dipping the loop in 1 ml of 0.01% TWEEN® 20 followed by vortexing. One microliter and ten microliters of this spore mixture were mixed with 100 μl of 0.01% TWEEN® 20 and plated onto a large COVE plate. Plates were incubated at 28° C. until single spore isolates appeared on the plates.

Single spore isolates for all twenty-one candidates were transferred to COVE2+10 mM uridine plates and incubated at 28° C. for about a week before inoculating 125 ml plastic shake flasks containing 25 ml of CIM medium. The resulting shake flask cultures were analyzed by SDS-PAGE as described above and compared with the shake flask culture of primary transformants. Six spore purified transformants, namely 597A, 676D, 679C, 680A, 683A and 686C, were chosen for 2 liter fermentations to determine yield.

Example 27: Fermentation

The top six spore purified *T. reesei* 981-O-8.5#10B+Ku70#19L3 transformants (597A, 676D, 679C, 680A, 683A and 686C) and *T. reesei* QMJi033 were cultivated on PDA plates at 28° C. for about a week.

Shake flask medium was composed of 20 g of dextrose, 10 g of corn steep solids, 1.45 g of $(NH_4)_2SO_4$, 2.08 g of $KH_2PO_4$, 0.36 g of $CaCl_2$, 0.42 g of $MgSO_4.7H_2O$, and 0.42 ml of trace metals solution. The trace metals solution was composed of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, 336 g of citric acid, and deionized water to 1 liter.

One hundred ml of shake flask medium were added to a 500 ml shake flask. The shake flask was inoculated with two plugs from a solid plate culture and incubated at 28° C. on an orbital shaker at 200 rpm for 48 hours. Fifty ml of the shake flask broth were used to inoculate a 2 liter fermentation vessel.

Fermentation batch medium was composed per liter of 30 g of cellulose, 4 g of dextrose, 10 g of corn steep solids, 3.8 g of $(NH_4)_250_4$, 2.8 g of $KH_2PO_4$, 2.64 g of $CaCl_2$, 1.63 g of $MgSO_4.7H_2O$, 1.8 ml of anti-foam, and 0.66 ml of trace metals solution. The trace metals solution was composed per liter of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, and 336 g of citric acid. Fermentation feed medium was composed of dextrose.

A total of 1.8 liters of the fermentation batch medium was added to an APPLIKON® three liter glass jacketed fermentor (Applikon Biotechnology Inc., Foster City Calif. USA). Fermentation feed medium was dosed at a rate of 0 to 4 g/l/hr for a period of 185 hours. The fermentation vessel was maintained at a temperature of 28° C. and pH was controlled using an APPLIKON® 1030 control system (Applikon Biotechnology Inc., Foster City Calif. USA) to a set-point of 4.5+/−0.1. Air was added to the vessel at a rate of 1 vvm and the broth was agitated by Rushton impeller rotating at 1100 to 1300 rpm. At the end of the fermentation, whole broth was harvested from the vessel and centrifuged at 3000×g to remove the biomass. The supernatant was sterile filtered and stored at 5 to 10° C.

Example 28: Evaluation of *Trichoderma reesei* Transformants in 2 Liter Fermentation Broth for Expression of *Penicillium emersonii* GH61A Polypeptide and *Aspergillus fumigatus* Beta-Glucosidase Variant in 2 Liter Fermentation Broth Fermentation broth of the top six spore purified *T. reesei* 981-O-8.5#10B+Ku70#19L3 transformants (597A, 676D, 679C, 680A, 683A and 686C) and *T. reesei* QMJi033 were analyzed by SDS-PAGE to evaluate the expression level for the *Penicillium emersonii* GH61A polypeptide and *Aspergillus fumigatus* beta-glucosidase variant. A 0.5 μl volume of fermentation broth supernatant of each strain was mixed with 25 μl of deionized water and 25 μl of Laemmli dye (Bio-Rad Laboratories, Hercules, Calif., USA) containing 5% 2-mercaptoethanol. The mixture was heated at 95° C. for 5 minutes and 10 μl (equivalent to 0.1 μl fermentation broth) were loaded onto a stain-free CRITERION® 8-16% Tris-HCl Gel (Bio-Rad Laboratories, Hercules, Calif., USA) according to the manufacturer's instructions. The gel was run at 200 volts for about 55 minutes and then analyzed by a Gel Doc™ EZ Imager (Bio-Rad Laboratories, Hercules, Calif., USA). SDS-PAGE profiles of the fermentation broth supernatants showed that expression of the *Penicillium emersonii* GH61A polypeptide and *Aspergillus fumigatus* beta-glucosidase variant in *T. reesei* QMJi033 were comparable to the top six *T. reesei* 981-O-8.5#10B+Ku70#19L3 transformants (597A, 676D, 679C, 680A, 683A and 686C).

The present invention is further described by the following numbered paragraphs:

[1] A method for constructing a filamentous fungal strain for production of multiple recombinant polypeptides having biological activity, comprising: (a) replacing an endogenous first gene by targeted integration by introducing into the filamentous fungal strain a first tandem construct comprising (i) a homologous 5' region of the first gene, a homologous flanking region thereof, or a combination thereof, (ii) one or more first selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the first gene, a homologous flanking region thereof, or a combination thereof; (b) replacing an endogenous second gene by targeted integration by introducing into the filamentous fungal strain a second tandem construct comprising (i) a homologous 5' region of the second gene, a homologous flanking region thereof, or a combination thereof, (ii) one or more second selectable markers, (iii) a third polynucleotide encoding a third polypeptide having biological activity operably linked to a third promoter and a third terminator, (iv) a fourth polynucleotide encoding a fourth polypeptide having biological activity operably linked to a fourth promoter and a fourth terminator, and (v) a homologous 3' region of the second gene, a homologous flanking region thereof, or a combination thereof; or (c) a combination of (a) and (b).

[2] The method of paragraph 1, wherein the first gene is a cellobiohydrolase I gene.

[3] The method of paragraph 2, wherein the cellobiohydrolase I gene encodes a cellobiohydrolase I selected from the group consisting of: (i) a cellobiohydrolase I comprising the mature polypeptide of SEQ ID NO: 2; (ii) a cellobiohydrolase I comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 2; (iii) a cellobiohydrolase I encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 1; and (iv) a cellobiohydrolase I encoded by a polynucleotide that hybridizes under at least high stringency conditions, e.g., very high stringency conditions, with the mature polypeptide coding sequence of SEQ ID NO: 1 or the full-length complement thereof.

[4] The method of paragraph 1, wherein the second gene is a cellobiohydrolase II gene.

[5] The method of paragraph 4, wherein the cellobiohydrolase II gene encodes a cellobiohydrolase II selected from the group consisting of: (i) a cellobiohydrolase II comprising the mature polypeptide of SEQ ID NO: 4; (ii) a cellobiohydrolase II comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 4; (iii) a cellobiohydrolase II encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 3; and (iv) a cellobiohydrolase II encoded by a polynucleotide that hybridizes under at least high stringency conditions, e.g., very high stringency conditions, with the mature polypeptide coding sequence of SEQ ID NO: 3 or the full-length complement thereof.

[6] The method of any of paragraphs 1-5, wherein each of the tandem constructs integrates by homologous recombination into the chromosome of the filamentous fungal strain.

[7] The method of any of paragraphs 1-6, wherein the homologous 5' region of the first gene, the homologous flanking region thereof, or the combination thereof is at least 50 bp, e.g., at least 100 bp, at least 200 bp, at least 400 bp, at least 800 bp, at least 1000 bp, at least 1500 bp, or at least 2000 bp.

[8] The method of any of paragraphs 1-7, wherein the homologous 3' region of the first gene, the homologous flanking region thereof, or the combination thereof is at least 50 bp, e.g., at least 100 bp, at least 200 bp, at least 400 bp, at least 800 bp, at least 1000 bp, at least 1500 bp, or at least 2000 bp.

[9] The method of any of paragraphs 1-8, wherein the homologous 5' region of the second gene, the homologous flanking region thereof, or the combination thereof is at least 50 bp, e.g., at least 100 bp, at least 200 bp, at least 400 bp, at least 800 bp, at least 1000 bp, at least 1500 bp, or at least 2000 bp.

[10] The method of any of paragraphs 1-9, wherein the homologous 3' region of the second gene, the homologous flanking region thereof, or the combination thereof is at least 50 bp, e.g., at least 100 bp, at least 200 bp, at least 400 bp, at least 800 bp, at least 1000 bp, at least 1500 bp, or at least 2000 bp.

[11] The method of any of paragraphs 1-10, which further comprises replacing one or more additional endogenous genes each by targeted integration by introducing into the filamentous fungal strain a corresponding tandem construct for each gene comprising (i) a homologous 5' region of the gene, a homologous flanking region thereof, or a combination thereof, (ii) one or more selectable markers, (iii) a polynucleotide encoding a polypeptide having biological activity operably linked to a promoter and a terminator, (iv) another polynucleotide encoding another polypeptide having biological activity operably linked to another promoter and another terminator, and (v) a homologous 3' region of the gene, a homologous flanking region thereof, or a combination thereof.

[12] The method of any of paragraphs 1-11, wherein one or more of the tandem constructs further comprise a first homologous repeat flanking 5' of the one or more selectable markers and a second homologous repeat flanking 3' of the one or more selectable markers, wherein the first homologous repeat and the second homologous repeat undergo homologous recombination to excise the one or more selectable markers.

[13] The method of paragraph 12, wherein the first and second homologous repeats are identical or have a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to each other.

[14] The method of paragraph 12 or 13, wherein the first and second homologous repeats are each at least 50 bp, e.g., at least 100 bp, at least 200 bp, at least 400 bp, at least 800 bp, at least 1000 bp, at least 1500 bp, or at least 2000 bp.

[15] The method of any of paragraphs 12-14, wherein upon the excision of the one or more selectable markers, the one or more selectable markers can be reused for replacing the one or more additional endogenous genes each by targeted integration with the corresponding tandem construct for each gene.

[16] The method of any of paragraphs 1-15, further comprising transforming the filamentous fungal host cell with a tandem construct comprising (i) one or more selectable markers, (ii) a fifth polynucleotide encoding a fifth polypeptide having biological activity operably linked to a fifth promoter and a fifth terminator, and (iii) a sixth polynucleotide encoding a sixth polypeptide having biological activity operably linked to a sixth promoter and a sixth terminator, wherein the tandem construct integrates by ectopic integration.

[17] The method of any of paragraphs 1-16, wherein the polypeptides having biological activity are different polypeptides.

[18] The method of any of paragraphs 1-16, wherein two or more of the polypeptides having biological activity are the same polypeptide.

[19] The method of any of paragraphs 1-18, wherein the promoters are different promoters.

[20] The method of any of paragraphs 1-18, wherein two or more of the promoters are the same promoter.

[21] The method of any of paragraphs 1-20, wherein the terminators are different terminators.

[22] The method of any of paragraphs 1-20, wherein two or more of the terminators are the same terminator.

[23] The method of any of paragraphs 1-22, wherein one or more of the tandem constructs are contained in an expression vector.

[24] The method of any of paragraphs 1-23, wherein the filamentous fungal strain is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes*, or *Trichoderma* strain.

[25] The method of paragraph 24, wherein the *Trichoderma* strain is selected from the group consisting of *Trichoderma harzianum, Trichoderma koningii, Trichoderma longibrachiatum, Trichoderma reesei*, and *Trichoderma viride*.

[26] The method of paragraph 24, wherein the *Trichoderma* strain is *Trichoderma reesei*.

[27] A filamentous fungal strain obtained according to the methods of any of paragraphs 1-26.

[28] A filamentous fungal strain, comprising: (a) an endogenous first gene replaced by targeted integration with a first tandem construct comprising (i) a homologous 5' region of the first gene, a homologous flanking region thereof, or a combination thereof, (ii) one or more selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the first gene, a homologous flanking region thereof, or a combination thereof; (b) an endogenous second gene replaced by targeted integration with a second tandem construct comprising (i) a homologous 5' region of the second gene, a homologous flanking region thereof, or a combination thereof, (ii) one or more selectable markers, (iii) a third polynucleotide encoding a third polypeptide having biological activity operably linked to a third promoter and a third terminator, (iv) a fourth polynucleotide encoding a fourth polypeptide having biological activity operably linked to a fourth promoter and a fourth terminator, and (v) a homologous 3' region of the second gene, a homologous flanking region thereof, or a combination thereof; or (c) a combination of (a) and (b).

[29] The filamentous fungal strain of paragraph 28, wherein the first gene is a cellobiohydrolase I gene.

[30] The filamentous fungal strain of paragraph 29, wherein the cellobiohydrolase I gene encodes a cellobiohydrolase I selected from the group consisting of: (i) a cellobiohydrolase I comprising the mature polypeptide of SEQ ID NO: 2; (ii) a cellobiohydrolase I comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 2; (iii) a cellobiohydrolase I encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 1; and (iv) a cellobiohydrolase I encoded by a polynucleotide that hybridizes under at least high stringency conditions, e.g., very high stringency conditions, with the mature polypeptide coding sequence of SEQ ID NO: 1 or the full-length complement thereof.

[31] The filamentous fungal strain of paragraph 28, wherein the second gene is a cellobiohydrolase II gene.

[32] The filamentous fungal strain of paragraph 31, wherein the cellobiohydrolase II gene encodes a cellobiohydrolase II selected from the group consisting of: (i) a cellobiohydrolase II comprising the mature polypeptide of SEQ ID NO: 4; (ii) a cellobiohydrolase II comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 4; (iii) a cellobiohydrolase II encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 3; and (iv) a cellobiohydrolase II encoded by a polynucleotide that hybridizes under at least high stringency conditions, e.g., very high stringency conditions, with the mature polypeptide coding sequence of SEQ ID NO: 3 or the full-length complement thereof.

[33] The filamentous fungal strain of any of paragraphs 28-32, wherein each of the tandem constructs integrated by homologous recombination into the chromosome of the filamentous fungal strain.

[34] The filamentous fungal strain of any of paragraphs 28-33, wherein the homologous 5' region of the first gene, the homologous flanking region thereof, or the combination thereof of the first tandem construct is at least 50 bp, e.g., at least 100 bp, at least 200 bp, at least 400 bp, at least 800 bp, at least 1000 bp, at least 1500 bp, or at least 2000 bp.

[35] The filamentous fungal strain of any of paragraphs 28-34, wherein the homologous 3' region of the first gene, the homologous flanking region thereof, or the combination thereof of the first tandem construct is at least 50 bp, e.g., at least 100 bp, at least 200 bp, at least 400 bp, at least 800 bp, at least 1000 bp, at least 1500 bp, or at least 2000 bp.

[36] The filamentous fungal strain of any of paragraphs 28-35, wherein the homologous 5' region of the second gene, the homologous flanking region thereof, or the combination thereof of the second tandem construct is at least 50 bp, e.g., at least 100 bp, at least 200 bp, at least 400 bp, at least 800 bp, at least 1000 bp, at least 1500 bp, or at least 2000 bp.

[37] The filamentous fungal strain of any of paragraphs 28-36, wherein the homologous 3' region of the second gene, the homologous flanking region thereof, or the combination thereof of the second tandem construct is at least 50 bp, e.g., at least 100 bp, at least 200 bp, at least 400 bp, at least 800 bp, at least 1000 bp, at least 1500 bp, or at least 2000 bp.

[38] The filamentous fungal strain of any of paragraphs 28-37, which further comprises one or more additional endogenous genes each replaced by targeted integration with a corresponding tandem construct for each gene comprising (i) a homologous 5' region of the gene, a homologous flanking region thereof, or a combination thereof, (ii) one or more selectable markers, (iii) a polynucleotide encoding a polypeptide having biological activity operably linked to a promoter and a terminator, (iv) another polynucleotide encoding another polypeptide having biological activity operably linked to another promoter and another terminator, and (v) a homologous 3' region of the gene, a homologous flanking region thereof, or a combination thereof.

[39] The filamentous fungal strain of any of paragraphs 28-38, wherein one or more of the tandem constructs further comprise a first homologous repeat flanking 5' of the one or more selectable markers and a second homologous repeat flanking 3' of the one or more selectable markers, wherein the first homologous repeat and the second homologous repeat undergo homologous recombination to excise the one or more selectable markers.

[40] The filamentous fungal strain of paragraph 39, wherein the first and second homologous repeats are identical or have a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to each other.

[41] The filamentous fungal strain of paragraph 39 or 40, wherein the first and second homologous repeats are each at least 50 bp, e.g., at least 100 bp, at least 200 bp, at least 400 bp, at least 800 bp, at least 1000 bp, at least 1500 bp, or at least 2000 bp.

[42] The filamentous fungal strain of any of paragraphs 39-41, wherein upon the excision of the one or more selectable markers, the one or more selectable markers can be reused for replacing the one or more additional endogenous genes each by targeted integration with a corresponding tandem construct for each gene.

[43] The filamentous fungal strain of any of paragraphs 28-42, further comprising a tandem construct comprising (i) one or more selectable markers, (ii) a fifth polynucleotide encoding a fifth polypeptide having biological activity operably linked to a fifth promoter and a fifth terminator, and (iii) a sixth polynucleotide encoding a sixth polypeptide having biological activity operably linked to a sixth promoter and a sixth terminator, wherein the tandem construct integrates by ectopic integration.

[44] The filamentous fungal strain of any of paragraphs 28-43, wherein the polypeptides having biological activity are different polypeptides.

[45] The filamentous fungal strain of any of paragraphs 28-43, wherein two or more of the polypeptides having biological activity are the same polypeptide.

[46] The filamentous fungal strain of any of paragraphs 28-45, wherein the promoters are different promoters.

[47] The filamentous fungal strain of any of paragraphs 28-45, wherein two or more of the promoters are the same promoter.

[48] The filamentous fungal strain of any of paragraphs 28-47, wherein the terminators are different terminators.

[49] The filamentous fungal strain of any of paragraphs 28-47, wherein two or more of the terminators are the same terminator.

[50] The filamentous fungal strain of any of paragraphs 28-49, wherein one or more of the tandem constructs are contained in an expression vector.

[51] The filamentous fungal strain of any of paragraphs 28-50, wherein the filamentous fungal strain is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes*, or *Trichoderma* strain.

[52] The filamentous fungal strain of paragraph 51, wherein the *Trichoderma* strain is selected from the group consisting of *Trichoderma harzianum, Trichoderma koningii, Trichoderma longibrachiatum, Trichoderma reesei*, and *Trichoderma viride.*

[53] The filamentous fungal strain of paragraph 51, wherein the *Trichoderma* strain is *Trichoderma reesei.*

[54] A method for producing multiple recombinant polypeptides having biological activity in a filamentous fungal strain, comprising: cultivating a filamentous fungal host cell under conditions conducive for production of the polypeptides, wherein the filamentous fungal host cell comprises (a) an endogenous first gene replaced by targeted integration with a first tandem construct comprising (i) a homologous 5' region of the first gene, a homologous flanking region thereof, or a combination thereof, (ii) one or more selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the first gene, a homologous flanking region thereof, or a combination thereof; (b) an endogenous second gene replaced by targeted integration with a second tandem construct comprising (i) a homologous 5' region of the second gene, a homologous flanking region thereof, or a combination thereof, (ii) one or more selectable markers, (iii) a third polynucleotide encoding a third polypeptide having biological activity operably linked to a third promoter and a third terminator, (iv) a fourth polynucleotide encoding a fourth polypeptide having biological activity operably linked to a fourth promoter and a fourth terminator, and (v) a homologous 3' region of the second gene, a homologous flanking region thereof, or a combination thereof; or (c) a combination of (a) and (b).

[55] The method of claim 54, further comprising recovering the multiple recombinant polypeptides.

[56] The method of paragraph 54 or 55, wherein the first gene is a cellobiohydrolase I gene.

[57] The method of paragraph 56, wherein the cellobiohydrolase I gene encodes a cellobiohydrolase I selected from the group consisting of: (i) a cellobiohydrolase I comprising the mature polypeptide of SEQ ID NO: 2; (ii) a cellobiohydrolase I comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 2; (iii) a cellobiohydrolase I encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 1; and (iv) a cellobiohydrolase I encoded by a polynucleotide that hybridizes under at least high stringency conditions, e.g., very high stringency conditions, with the mature polypeptide coding sequence of SEQ ID NO: 1 or the full-length complement thereof.

[58] The method of paragraph 54 or 55, wherein the second gene is a cellobiohydrolase II gene.

[59] The method of paragraph 58, wherein the cellobiohydrolase II gene encodes a cellobiohydrolase II selected from the group consisting of: (i) a cellobiohydrolase II comprising the mature polypeptide of SEQ ID NO: 4; (ii) a cellobiohydrolase II comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 4; (iii) a cellobiohydrolase II encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 3; and (iv) a cellobiohydrolase II encoded by a polynucleotide that hybridizes under at least high stringency conditions, e.g., very high stringency conditions, with the mature polypeptide coding sequence of SEQ ID NO: 3 or the full-length complement thereof.

[60] The method of any of paragraphs 54-59, wherein the homologous 5' region of the first gene, the homologous flanking region thereof, or the combination thereof of the first tandem construct is at least 50 bp, e.g., at least 100 bp, at least 200 bp, at least 400 bp, at least 800 bp, at least 1000 bp, at least 1500 bp, or at least 2000 bp.

[61] The method of any of paragraphs 54-60, wherein the homologous 3' region of the first gene, the homologous flanking region thereof, or the combination thereof of the first tandem construct is at least 50 bp, e.g., at least 100 bp, at least 200 bp, at least 400 bp, at least 800 bp, at least 1000 bp, at least 1500 bp, or at least 2000 bp.

[62] The method of any of paragraphs 54-61, wherein the homologous 5' region of the second gene, the homologous flanking region thereof, or the combination thereof of the second tandem construct is at least 50 bp, e.g., at least 100 bp, at least 200 bp, at least 400 bp, at least 800 bp, at least 1000 bp, at least 1500 bp, or at least 2000 bp.

[63] The method of any of paragraphs 54-62, wherein the homologous 3' region of the second gene, the homologous flanking region thereof, or the combination thereof of the second tandem construct is at least 50 bp, e.g., at least 100 bp, at least 200 bp, at least 400 bp, at least 800 bp, at least 1000 bp, at least 1500 bp, or at least 2000 bp.

[64] The method of any of paragraphs 54-63, wherein the filamentous fungal host cell further comprises one or more additional endogenous genes each replaced by targeted integration with a corresponding tandem construct for each gene comprising (i) a homologous 5' region of the gene, a homologous flanking region thereof, or a combination thereof, (ii) one or more selectable markers, (iii) a polynucleotide encoding a polypeptide having biological activity operably linked to a promoter and a terminator, (iv) another polynucleotide encoding another polypeptide having biological activity operably linked to another promoter and another terminator, and (v) a homologous 3' region of the gene, a homologous flanking region thereof, or a combination thereof.

[65] The method of any of paragraphs 54-64, wherein one or more of the tandem constructs further comprise a first homologous repeat flanking 5' of the one or more selectable markers and a second homologous repeat flanking 3' of the one or more selectable markers, wherein the first homologous repeat and the second homologous repeat undergo homologous recombination to excise the one or more selectable markers.

[66] The method of paragraph 65, wherein the first and second homologous repeats are identical or have a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to each other.

[67] The method of paragraph 65 or 66, wherein the first and second homologous repeats are each at least 50 bp, e.g., at least 100 bp, at least 200 bp, at least 400 bp, at least 800 bp, at least 1000 bp, at least 1500 bp, or at least 2000 bp.

[68] The method of any of paragraphs 65-67, wherein upon the excision of the one or more selectable markers, the one or more selectable markers can be reused for replacing the one or more additional endogenous genes each by targeted integration with the corresponding tandem construct for each gene.

[69] The method of any of paragraphs 54-68, wherein the filamentous fungal host cell further comprises a tandem construct comprising (i) one or more selectable markers, (ii) a fifth polynucleotide encoding a fifth polypeptide having biological activity operably linked to a fifth promoter and a fifth terminator, and (iii) a sixth polynucleotide encoding a sixth polypeptide having biological activity operably linked to a sixth promoter and a sixth terminator, wherein the tandem construct integrates by ectopic integration.

[70] The method of any of paragraphs 54-69, wherein the polypeptides having biological activity are different polypeptides.

[71] The method of any of paragraphs 54-69, wherein two or more of the polypeptides having biological activity are the same polypeptide.

[72] The method of any of paragraphs 54-71, wherein the promoters are different promoters.

[73] The method of any of paragraphs 54-71, wherein two or more of the promoters are the same promoter.

[74] The method of any of paragraphs 54-73, wherein the terminators are different terminators.

[75] The method of any of paragraphs 54-73, wherein two or more of the terminators are the same terminator.

[76] The method of any of paragraphs 54-75, wherein one or more of the tandem constructs are contained in an expression vector.

[77] The method of any of paragraphs 54-76, wherein the filamentous fungal strain is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes*, or *Trichoderma* strain.

[78] The method of paragraph 77, wherein the *Trichoderma* strain is selected from the group consisting of *Trichoderma harzianum, Trichoderma koningii, Trichoderma longibrachiatum, Trichoderma reesei*, and *Trichoderma viride.*

[79] The method of paragraph 77, wherein the *Trichoderma* strain is *Trichoderma reesei.*

[80] A tandem construct comprising (i) a homologous 5' region of a gene, a homologous flanking region thereof, or a combination thereof, (ii) one or more first selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the gene, a homologous flanking region thereof, or a combination thereof.

[81] The tandem construct of paragraph 80, wherein the gene is a cellobiohydrolase I gene.

[82] The tandem construct of paragraph 81, wherein the cellobiohydrolase I gene encodes a cellobiohydrolase I selected from the group consisting of: (i) a cellobiohydrolase I comprising the mature polypeptide of SEQ ID NO: 2; (ii) a cellobiohydrolase I comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 2; (iii) a cellobiohydrolase I encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 1; and (iv) a cellobiohydrolase I encoded by a polynucleotide that hybridizes under at least high stringency conditions, e.g., very high stringency conditions, with the mature polypeptide coding sequence of SEQ ID NO: 1 or the full-length complement thereof.

[83] The tandem construct of paragraph 80, wherein the gene is a cellobiohydrolase II gene.

[84] The tandem construct of paragraph 83, wherein the cellobiohydrolase II gene encodes a cellobiohydrolase II selected from the group consisting of: (i) a cellobiohydrolase II comprising the mature polypeptide of SEQ ID NO: 4; (ii) a cellobiohydrolase II comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 4; (iii) a cellobiohydrolase II encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 3; and (iv) a cellobiohydrolase II encoded by a polynucleotide that hybridizes under at least high stringency conditions, e.g., very high stringency conditions, with the mature polypeptide coding sequence of SEQ ID NO: 3 or the full-length complement thereof.

[85] The tandem construct of any of paragraphs 80-84, wherein the homologous 5' region of the gene, the homologous flanking region thereof, or the combination thereof is at least 50 bp, e.g., at least 100 bp, at least 200 bp, at least 400 bp, at least 800 bp, at least 1000 bp, at least 1500 bp, or at least 2000 bp.

[86] The tandem construct of any of paragraphs 80-85, wherein the homologous 3' region of the gene, the homologous flanking region thereof, or the combination thereof is at least 50 bp, e.g., at least 100 bp, at least 200 bp, at least 400 bp, at least 800 bp, at least 1000 bp, at least 1500 bp, or at least 2000 bp.

[87] The tandem construct of any of paragraphs 80-86, wherein the polypeptides having biological activity are different polypeptides.

[88] The tandem construct of any of paragraphs 80-86, wherein two or more of the polypeptides having biological activity are the same polypeptide.

[89] The tandem construct of any of paragraphs 80-88, wherein the promoters are different promoters.

[90] The tandem construct of any of paragraphs 80-88, wherein two or more of the promoters are the same promoter.

[91] The tandem construct of any of paragraphs 80-90, wherein the terminators are different terminators.

[92] The tandem construct of any of paragraphs 80-90, wherein two or more of the terminators are the same terminator.

[93] An expression vector comprising the tandem construct of any of paragraphs 80-92.

[94] A method for constructing a filamentous fungal strain for production of multiple recombinant polypeptides having biological activity, comprising: (a) inserting into an endogenous first locus by targeted integration a first tandem construct comprising (i) a homologous 5' region of the first locus, a homologous flanking region thereof, or a combination thereof, (ii) one or more first selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the first locus, a homologous flanking region thereof, or a combination thereof; (b) inserting into an endogenous second locus by targeted integration a second tandem construct comprising (i) a homologous 5' region of the second locus, a homologous flanking region thereof, or a combination thereof, (ii) one or more second selectable markers, (iii) a third polynucleotide encoding a third polypeptide having biological activity operably linked to a third promoter and a third terminator, (iv) a fourth polynucleotide encoding a fourth polypeptide having biological activity operably linked to a fourth promoter and a fourth terminator, and (v) a homologous 3' region of the second locus, a homologous flanking region thereof, or a combination thereof; or (c) a combination of (a) and (b).

[95] The method of paragraph 94, wherein the first locus is a cellobiohydrolase I gene.

[96] The method of paragraph 95, wherein the cellobiohydrolase I gene encodes a cellobiohydrolase I selected from the group consisting of: (i) a cellobiohydrolase I comprising the mature polypeptide of SEQ ID NO: 2; (ii) a cellobiohydrolase I comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 2; (iii) a cellobiohydrolase I encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 1; and (iv) a cellobiohydrolase I encoded by a polynucleotide that hybridizes under at least high stringency conditions, e.g., very high stringency conditions, with the mature polypeptide coding sequence of SEQ ID NO: 1 or the full-length complement thereof.

[97] The method of paragraph 94, wherein the second locus is a cellobiohydrolase II gene.

[98] The method of paragraph 97, wherein the cellobiohydrolase II gene encodes a cellobiohydrolase II selected from the group consisting of: (i) a cellobiohydrolase II comprising the mature polypeptide of SEQ ID NO: 4; (ii) a cellobiohydrolase II comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 4; (iii) a cellobiohydrolase II encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 3; and (iv) a cellobiohydrolase II encoded by a polynucleotide that hybridizes under at least high stringency conditions, e.g., very high stringency conditions, with the mature polypeptide coding sequence of SEQ ID NO: 3 or the full-length complement thereof.

[99] The method of any of paragraphs 94-98, wherein each of the tandem constructs integrates by homologous recombination into the chromosome of the filamentous fungal strain.

[100] The method of any of paragraphs 94-99, wherein the homologous 5' region of the first locus, the homologous flanking region thereof, or a combination thereof is at least 50 bp, e.g., at least 100 bp, at least 200 bp, at least 400 bp, at least 800 bp, at least 1000 bp, at least 1500 bp, or at least 2000 bp.

[101] The method of any of paragraphs 94-100, wherein the homologous 3' region of the first locus, the homologous flanking region thereof, or a combination thereof is at least 50 bp, e.g., at least 100 bp, at least 200 bp, at least 400 bp, at least 800 bp, at least 1000 bp, at least 1500 bp, or at least 2000 bp.

[102] The method of any of paragraphs 94-101, wherein the homologous 5' region of the second locus, the homologous flanking region thereof, or a combination thereof is at least 50 bp, e.g., at least 100 bp, at least 200 bp, at least 400 bp, at least 800 bp, at least 1000 bp, at least 1500 bp, or at least 2000 bp.

[103] The method of any of paragraphs 94-102, wherein the homologous 3' region of the second locus, the homologous flanking region thereof, or a combination thereof is at least 50 bp, e.g., at least 100 bp, at least 200 bp, at least 400 bp, at least 800 bp, at least 1000 bp, at least 1500 bp, or at least 2000 bp.

[104] The method of any of paragraphs 94-103, which further comprises inserting into one or more additional endogenous loci each by targeted integration a corresponding tandem construct for each locus comprising (i) a homologous 5' region of the locus, a homologous flanking region thereof, or a combination thereof, (ii) one or more selectable markers, (iii) a polynucleotide encoding a polypeptide having biological activity operably linked to a promoter and a terminator, (iv) another polynucleotide encoding another polypeptide having biological activity operably linked to another promoter and another terminator, and (v) a homologous 3' region of the locus, a homologous flanking region thereof, or a combination thereof.

[105] The method of any of paragraphs 94-104, wherein one or more of the tandem constructs further comprise a first homologous repeat flanking 5' of the one or more selectable markers and a second homologous repeat flanking 3' of the one or more selectable markers, wherein the first homologous repeat and the second homologous repeat undergo homologous recombination to excise the one or more selectable markers.

[106] The method of paragraph 105, wherein the first and second homologous repeats are identical or have a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to each other.

[107] The method of paragraph 105 or 106, wherein the first and second homologous repeats are each at least 50 bp, e.g., at least 100 bp, at least 200 bp, at least 400 bp, at least 800 bp, at least 1000 bp, at least 1500 bp, or at least 2000 bp.

[108] The method of any of paragraphs 105-107, wherein upon the excision of the one or more selectable markers, the one or more selectable markers can be reused for modifying by insertion the one or more additional endogenous loci each by targeted integration with the corresponding tandem construct for each locus.

[109] The method of any of paragraphs 94-108, further comprising transforming the filamentous fungal host cell with a tandem construct comprising (i) one or more selectable markers, (ii) a fifth polynucleotide encoding a fifth polypeptide having biological activity operably linked to a fifth promoter and a fifth terminator, and (iii) a sixth polynucleotide encoding a sixth polypeptide having biological activity operably linked to a sixth promoter and a sixth terminator, wherein the tandem construct integrates by ectopic integration.

[110] The method of any of paragraphs 94-109, wherein the polypeptides having biological activity are different polypeptides.

[111] The method of any of paragraphs 94-109, wherein two or more of the polypeptides having biological activity are the same polypeptide.

[112] The method of any of paragraphs 94-111, wherein the promoters are different promoters.

[113] The method of any of paragraphs 94-111, wherein two or more of the promoters are the same promoter.

[114] The method of any of paragraphs 94-113, wherein the terminators are different terminators.

[115] The method of any of paragraphs 94-113, wherein two or more of the terminators are the same terminator.

[116] The method of any of paragraphs 94-115, wherein one or more of the tandem constructs are contained in an expression vector.

[117] The method of any of paragraphs 94-116, wherein the filamentous fungal strain is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes*, or *Trichoderma* strain.

[118] The method of paragraph 117, wherein the *Trichoderma* strain is selected from the group consisting of *Trichoderma harzianum, Trichoderma koningii, Trichoderma longibrachiatum, Trichoderma reesei*, and *Trichoderma viride.*

[119] The method of paragraph 117, wherein the *Trichoderma* strain is *Trichoderma reesei.*

[120] A filamentous fungal strain obtained according to the methods of any of paragraphs 94-119.

[121] A filamentous fungal strain, comprising: (a) an endogenous first locus modified by insertion by targeted integration with a first tandem construct comprising (i) a homologous 5' region of the first locus, a homologous flanking region thereof, or a combination thereof, (ii) one or more selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the first locus, a homologous flanking region thereof, or a combination thereof; (b) an endogenous second locus modified by insertion by targeted integration with a second tandem construct comprising (i) a homologous 5' region of the second locus, a homologous flanking region thereof, or a combination thereof, (ii) one or more selectable markers, (iii) a third polynucleotide encoding a third polypeptide having biological activity operably linked to a third promoter and a third terminator, (iv) a fourth polynucleotide encoding a fourth polypeptide having biological activity operably linked to a fourth promoter and a fourth terminator, and (v) a homologous 3' region of the second locus, a homologous flanking region thereof, or a combination thereof; or (c) a combination of (a) and (b).

[122] The filamentous fungal strain of paragraph 121, wherein the first locus is a cellobiohydrolase I gene.

[123] The filamentous fungal strain of paragraph 122, wherein the cellobiohydrolase I gene encodes a cellobiohydrolase I selected from the group consisting of: (i) a cellobiohydrolase I comprising the mature polypeptide of SEQ ID NO: 2; (ii) a cellobiohydrolase I comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 2; (iii) a cellobiohydrolase I encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 1; and (iv) a cellobiohydrolase I encoded by a polynucleotide that hybridizes under at least high stringency conditions, e.g., very high stringency conditions, with the mature polypeptide coding sequence of SEQ ID NO: 1 or the full-length complement thereof.

[124] The filamentous fungal strain of paragraph 121, wherein the second locus is a cellobiohydrolase II gene.

[125] The filamentous fungal strain of paragraph 124, wherein the cellobiohydrolase II gene encodes a cellobiohydrolase II selected from the group consisting of: (i) a cellobiohydrolase II comprising the mature polypeptide of SEQ ID NO: 4; (ii) a cellobiohydrolase II comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 4; (iii) a cellobiohydrolase II encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 3; and (iv) a cellobiohydrolase II encoded by a polynucleotide that hybridizes under at least high stringency conditions, e.g., very high stringency conditions, with the mature polypeptide coding sequence of SEQ ID NO: 3 or the full-length complement thereof.

[126] The filamentous fungal strain of any of paragraphs 121-125, wherein each of the tandem constructs integrated by homologous recombination into the chromosome of the filamentous fungal strain.

[127] The filamentous fungal strain of any of paragraphs 121-126, wherein the homologous 5' region of the first locus, the homologous flanking region thereof, or a combination thereof of the first tandem construct is at least 50 bp, e.g., at least 100 bp, at least 200 bp, at least 400 bp, at least 800 bp, at least 1000 bp, at least 1500 bp, or at least 2000 bp.

[128] The filamentous fungal strain of any of paragraphs 121-127, wherein the homologous 3' region of the first locus, the homologous flanking region thereof, or a combination thereof of the first tandem construct is at least 50 bp, e.g., at least 100 bp, at least 200 bp, at least 400 bp, at least 800 bp, at least 1000 bp, at least 1500 bp, or at least 2000 bp.

[129] The filamentous fungal strain of any of paragraphs 121-128, wherein the homologous 5' region of the second locus, the homologous flanking region thereof, or a combination thereof of the second tandem construct is at least 50 bp, e.g., at least 100 bp, at least 200 bp, at least 400 bp, at least 800 bp, at least 1000 bp, at least 1500 bp, or at least 2000 bp.

[130] The filamentous fungal strain of any of paragraphs 121-129, wherein the homologous 3' region of the second locus, the homologous flanking region thereof, or a combination thereof of the second tandem construct is at least 50 bp, e.g., at least 100 bp, at least 200 bp, at least 400 bp, at least 800 bp, at least 1000 bp, at least 1500 bp, or at least 2000 bp.

[131] The filamentous fungal strain of any of paragraphs 121-130, which further comprises one or more additional endogenous loci each modified by insertion by targeted integration with a corresponding tandem construct for each locus comprising (i) a homologous 5' region of the locus, a homologous flanking region thereof, or a combination thereof, (ii) one or more selectable markers, (iii) a polynucleotide encoding a polypeptide having biological activity operably linked to a promoter and a terminator, (iv) another polynucleotide encoding another polypeptide having biological activity operably linked to another promoter and another terminator, and (v) a homologous 3' region of the locus, a homologous flanking region thereof, or a combination thereof.

[132] The filamentous fungal strain of any of paragraphs 121-131, wherein one or more of the tandem constructs further comprise a first homologous repeat flanking 5' of the one or more selectable markers and a second homologous repeat flanking 3' of the one or more selectable markers, wherein the first homologous repeat and the second homologous repeat undergo homologous recombination to excise the one or more selectable markers.

[133] The filamentous fungal strain of paragraph 132, wherein the first and second homologous repeats are identical or have a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to each other.

[134] The filamentous fungal strain of paragraph 132 or 133, wherein the first and second homologous repeats are each at least 50 bp, e.g., at least 100 bp, at least 200 bp, at least 400 bp, at least 800 bp, at least 1000 bp, at least 1500 bp, or at least 2000 bp.

[135] The filamentous fungal strain of any of paragraphs 132-134, wherein upon the excision of the one or more selectable markers, the one or more selectable markers can be reused for inserting into the one or more additional endogenous loci each by targeted integration a corresponding tandem construct for each locus.

[136] The filamentous fungal strain of any of paragraphs 121-135, further comprising a tandem construct comprising (i) one or more selectable markers, (ii) a fifth polynucleotide encoding a fifth polypeptide having biological activity operably linked to a fifth promoter and a fifth terminator, and (iii) a sixth polynucleotide encoding a sixth polypeptide having biological activity operably linked to a sixth promoter and a sixth terminator, wherein the tandem construct integrates by ectopic integration.

[137] The filamentous fungal strain of any of paragraphs 121-136, wherein the polypeptides having biological activity are different polypeptides.

[138] The filamentous fungal strain of any of paragraphs 121-136, wherein two or more of the polypeptides having biological activity are the same polypeptide.

[139] The filamentous fungal strain of any of paragraphs 121-138, wherein the promoters are different promoters.

[140] The filamentous fungal strain of any of paragraphs 121-138, wherein two or more of the promoters are the same promoter.

[141] The filamentous fungal strain of any of paragraphs 121-140, wherein the the terminators are different terminators.

[142] The filamentous fungal strain of any of paragraphs 121-140, wherein two or more of the terminators are the same terminator.

[143] The filamentous fungal strain of any of paragraphs 121-142, wherein one or more of the tandem constructs are contained in an expression vector.

[144] The filamentous fungal strain of any of paragraphs 121-143, wherein the filamentous fungal strain is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes*, or *Trichoderma* strain.

[145] The filamentous fungal strain of paragraph 144, wherein the *Trichoderma* strain is selected from the group consisting of *Trichoderma harzianum, Trichoderma koningii, Trichoderma longibrachiatum, Trichoderma reesei*, and *Trichoderma viride.*

[146] The filamentous fungal strain of paragraph 144, wherein the *Trichoderma* strain is *Trichoderma reesei.*

[147] A method for producing multiple recombinant polypeptides having biological activity in a filamentous fungal strain, comprising: cultivating a filamentous fungal host cell under conditions conducive for production of the polypeptides, wherein the filamentous fungal host cell comprises (a) an endogenous first locus modified by insertion by targeted integration with a first tandem construct comprising (i) a homologous 5' region of the first locus, a homologous flanking region thereof, or a combination thereof, (ii) one or more selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the first locus, a homologous flanking region thereof, or a combination thereof; (b) an endogenous second locus modified by insertion by targeted integration with a second tandem construct comprising (i) a homologous 5' region of the second locus, a homologous flanking region thereof, or a combination thereof, (ii) one or more selectable markers, (iii) a third polynucleotide encoding a third polypeptide having biological activity operably linked to a third promoter and a third terminator, (iv) a fourth polynucleotide encoding a fourth polypeptide having biological activity operably linked to a fourth promoter and a fourth terminator, and (v) a homologous 3' region of the second locus, a homologous flanking region thereof, or a combination thereof; or (c) a combination of (a) and (b).

[148] The method of claim 147, further comprising recovering the multiple recombinant polypeptides.

[149] The method of paragraph 147 or 148, wherein the first locus is a cellobiohydrolase I gene.

[150] The method of paragraph 149, wherein the cellobiohydrolase I gene encodes a cellobiohydrolase I selected from the group consisting of: (i) a cellobiohydrolase I comprising the mature polypeptide of SEQ ID NO: 2; (ii) a cellobiohydrolase I comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 2; (iii) a cellobiohydrolase I encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 1; and (iv) a cellobiohydrolase I encoded by a polynucleotide that hybridizes under at least high stringency conditions, e.g., very high stringency conditions, with the mature polypeptide coding sequence of SEQ ID NO: 1 or the full-length complement thereof.

[151] The method of paragraph 147 or 148, wherein the second locus is a cellobiohydrolase II gene.

[152] The method of paragraph 151, wherein the cellobiohydrolase II gene encodes a cellobiohydrolase II selected from the group consisting of: (i) a cellobiohydrolase II comprising the mature polypeptide of SEQ ID NO: 4; (ii) a cellobiohydrolase II comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 4; (iii) a cellobiohydrolase II encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 3; and (iv) a cellobiohydrolase II encoded by a polynucleotide that hybridizes under at least high stringency conditions, e.g., very high stringency conditions, with the mature polypeptide coding sequence of SEQ ID NO: 3 or the full-length complement thereof.

[153] The method of any of paragraphs 147-152, wherein the homologous 5' region of the first locus, the homologous flanking region thereof, or a combination thereof of the first tandem construct is at least 50 bp, e.g., at least 100 bp, at least 200 bp, at least 400 bp, at least 800 bp, at least 1000 bp, at least 1500 bp, or at least 2000 bp.

[154] The method of any of paragraphs 147-153, wherein the homologous 3' region of the first locus, the homologous flanking region thereof, or a combination thereof of the first tandem construct is at least 50 bp, e.g., at least 100 bp, at least 200 bp, at least 400 bp, at least 800 bp, at least 1000 bp, at least 1500 bp, or at least 2000 bp.

[155] The method of any of paragraphs 147-154, wherein the homologous 5' region of the second locus, the homologous flanking region thereof, or a combination thereof of the second tandem construct is at least 50 bp, e.g., at least 100 bp, at least 200 bp, at least 400 bp, at least 800 bp, at least 1000 bp, at least 1500 bp, or at least 2000 bp.

[156] The method of any of paragraphs 147-155, wherein the homologous 3' region of the second locus, the homologous flanking region thereof, or a combination thereof of the second tandem construct is at least 50 bp, e.g., at least 100 bp, at least 200 bp, at least 400 bp, at least 800 bp, at least 1000 bp, at least 1500 bp, or at least 2000 bp.

[157] The method of any of paragraphs 147-156, wherein the filamentous fungal host cell further comprises one or more additional endogenous loci each modified by insertion by targeted integration with a corresponding tandem construct for each locus comprising (i) a homologous 5' region of the locus, a homologous flanking region thereof, or a combination thereof, (ii) one or more selectable markers, (iii) a polynucleotide encoding a polypeptide having biological activity operably linked to a promoter and a terminator, (iv) another polynucleotide encoding another polypeptide having biological activity operably linked to another promoter and another terminator, and (v) a homologous 3' region of the locus, a homologous flanking region thereof, or a combination thereof.

[158] The method of any of paragraphs 147-157, wherein one or more of the tandem constructs further comprise a first homologous repeat flanking 5' of the one or more selectable markers and a second homologous repeat flanking 3' of the one or more selectable markers, wherein the first homologous repeat and the second homologous repeat undergo homologous recombination to excise the one or more selectable markers.

[159] The method of paragraph 158, wherein the first and second homologous repeats are identical or have a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to each other.

[160] The method of paragraph 158 or 159, wherein the first and second homologous repeats are each at least 50 bp, e.g., at least 100 bp, at least 200 bp, at least 400 bp, at least 800 bp, at least 1000 bp, at least 1500 bp, or at least 2000 bp.

[161] The method of any of paragraphs 158-160, wherein upon the excision of the one or more selectable markers, the one or more selectable markers can be reused for modifying by insertion the one or more additional endogenous loci each by targeted integration with the corresponding tandem construct for each locus.

[162] The method of any of paragraphs 147-161, wherein the filamentous fungal host cell further comprises a tandem construct comprising (i) one or more selectable markers, (ii) a fifth polynucleotide encoding a fifth polypeptide having biological activity operably linked to a fifth promoter and a fifth terminator, and (iii) a sixth polynucleotide encoding a sixth polypeptide having biological activity operably linked to a sixth promoter and a sixth terminator, wherein the tandem construct integrates by ectopic integration.

[163] The method of any of paragraphs 147-162, wherein the polypeptides having biological activity are different polypeptides.

[164] The method of any of paragraphs 147-162, wherein two or more of the polypeptides having biological activity are the same polypeptide.

[165] The method of any of paragraphs 147-164, wherein the promoters are different promoters.

[166] The method of any of paragraphs 147-164, wherein two or more of the promoters are the same promoter.

[167] The method of any of paragraphs 147-166, wherein the terminators are different terminators.

[168] The method of any of paragraphs 147-166, wherein two or more of the terminators are the same terminator.

[169] The method of any of paragraphs 147-168, wherein one or more of the tandem constructs are contained in an expression vector.

[170] The method of any of paragraphs 147-169, wherein the filamentous fungal strain is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* strain.

[171] The method of paragraph 170, wherein the *Trichoderma* strain is selected from the group consisting of *Trichoderma harzianum, Trichoderma koningii, Trichoderma longibrachiatum, Trichoderma reesei*, and *Trichoderma viride*.

[172] The method of paragraph 170, wherein the *Trichoderma* strain is *Trichoderma reesei*.

[173] A tandem construct comprising (i) a homologous 5' region of a locus, a homologous flanking region thereof, or a combination thereof, (ii) one or more first selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the locus, a homologous flanking region thereof, or a combination thereof.

[174] The tandem construct of paragraph 173, wherein the locus is a cellobiohydrolase I gene.

[175] The tandem construct of paragraph 174, wherein the cellobiohydrolase I gene encodes a cellobiohydrolase I selected from the group consisting of: (i) a cellobiohydrolase I comprising the mature polypeptide of SEQ ID NO: 2; (ii) a cellobiohydrolase I comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 2; (iii) a cellobiohydrolase I encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 1; and (iv) a cellobiohydrolase I encoded by a polynucleotide that hybridizes under at least high stringency conditions, e.g., very high stringency conditions, with the mature polypeptide coding sequence of SEQ ID NO: 1 or the full-length complement thereof.

[176] The tandem construct of paragraph 173, wherein the locus is a cellobiohydrolase II gene.

[177] The tandem construct of paragraph 176, wherein the cellobiohydrolase II gene encodes a cellobiohydrolase II selected from the group consisting of: (i) a cellobiohydrolase II comprising the mature polypeptide of SEQ ID NO: 4; (ii) a cellobiohydrolase II comprising an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 4; (iii) a cellobiohydrolase II encoded by a polynucleotide comprising a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 3; and (iv) a cellobiohydrolase II encoded by a polynucleotide that hybridizes under at least high stringency conditions, e.g., very high stringency conditions, with the mature polypeptide coding sequence of SEQ ID NO: 3 or the full-length complement thereof.

[178] The tandem construct of any of paragraphs 173-177, wherein the homologous 5' region of the locus, the homologous flanking region thereof, or a combination thereof is at least 50 bp, e.g., at least 100 bp, at least 200 bp, at least 400 bp, at least 800 bp, at least 1000 bp, at least 1500 bp, or at least 2000 bp.

[179] The tandem construct of any of paragraphs 173-178, wherein the homologous 3' region of the locus, the homologous flanking region thereof, or a combination thereof is at least 50 bp, e.g., at least 100 bp, at least 200 bp, at least 400 bp, at least 800 bp, at least 1000 bp, at least 1500 bp, or at least 2000 bp.

[180] The tandem construct of any of paragraphs 173-179, wherein the polypeptides having biological activity are different polypeptides.

[181] The tandem construct of any of paragraphs 173-179, wherein two or more of the polypeptides having biological activity are the same polypeptide.

[182] The tandem construct of any of paragraphs 173-181, wherein the promoters are different promoters.

[183] The tandem construct of any of paragraphs 173-181, wherein two or more of the promoters are the same promoter.

[184] The tandem construct of any of paragraphs 173-183, wherein the terminators are different terminators.

[185] The tandem construct of any of paragraphs 173-183, wherein two or more of the terminators are the same terminator.

[186] An expression vector comprising the tandem construct of any of paragraphs 173-185.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A method for constructing a filamentous fungal strain for production of multiple recombinant polypeptides having biological activity, comprising:

(a) inserting into an endogenous first locus by targeted integration by homologous recombination a first tandem construct comprising (i) a homologous 5' region of the first locus, a homologous flanking region thereof, or a combination thereof, (ii) one or more first selectable markers, (iii) a first polynucleotide encoding a first polypeptide having biological activity operably linked to a first promoter and a first terminator, (iv) a second polynucleotide encoding a second polypeptide having biological activity operably linked to a second promoter and a second terminator, and (v) a homologous 3' region of the first locus, a homologous flanking region thereof, or a combination thereof; and (b) inserting into an endogenous second locus by targeted integration by homologous recombination a second tandem construct comprising (i) a homologous 5' region of the second locus, a homologous flanking region thereof, or a combination thereof, (ii) one or more second selectable markers, (iii) a third polynucleotide encoding a third polypeptide having biological activity operably linked to a third promoter and a third terminator, (iv) a fourth polynucleotide encoding a fourth polypeptide having biological activity operably linked to a fourth promoter and a fourth terminator, and (v) a homologous 3' region of the second locus, a homologous flanking region thereof, or a combination thereof.

2. The method of claim 1, wherein one or more of the tandem constructs further comprise a first homologous repeat flanking 5' of the one or more selectable markers and a second homologous repeat flanking 3' of the one or more selectable markers, wherein the first homologous repeat and the second homologous repeat undergo homologous recombination to excise the one or more selectable markers, and wherein upon the excision of the one or more selectable markers, the one or more selectable markers can be reused for modifying by insertion one or more additional endogenous loci each by targeted integration with a corresponding tandem construct for each locus.

3. The method of claim 2, wherein the first and second homologous repeats are identical or have a sequence identity of at least 70% to each other.

4. The method of claim 2, wherein the first and second homologous repeats are each at least 50 bp.

5. The method of claim 1, wherein the first locus is a cellobiohydrolase I gene.

6. The method of claim 5, wherein the cellobiohydrolase I gene encodes a cellobiohydrolase I selected from the group consisting of: (i) a cellobiohydrolase I comprising the mature polypeptide of SEQ ID NO: 2; (ii) a cellobiohydrolase I comprising an amino acid sequence having at least 70% sequence identity to the mature polypeptide of SEQ ID NO: 2; (iii) a cellobiohydrolase I encoded by a polynucleotide comprising a nucleotide sequence having at least 70% sequence identity to the mature polypeptide coding sequence of SEQ ID NO: 1; and (iv) a cellobiohydrolase I encoded by a polynucleotide that hybridizes under high stringency conditions with the mature polypeptide coding sequence of SEQ ID NO: 1 or the full-length complement thereof, wherein high stringency conditions are defined as prehybridization and hybridization at 42° C. in 5×SSPE, 0.3% SDS, 200 micrograms/ml sheared and denatured salmon sperm DNA, and 50% formamide for 12 to 24 hours and washing three times each for 15 minutes using 2×SSC, 0.2% SDS at 65° C.

7. The method of claim 1, wherein the second locus is a cellobiohydrolase II gene.

8. The method of claim 7, wherein the cellobiohydrolase II gene encodes a cellobiohydrolase II selected from the group consisting of: (i) a cellobiohydrolase II comprising the mature polypeptide of SEQ ID NO: 4; (ii) a cellobiohydrolase II comprising an amino acid sequence having at least 70% sequence identity to the mature polypeptide of SEQ ID NO: 4; (iii) a cellobiohydrolase II encoded by a polynucleotide comprising a nucleotide sequence having at least 70% sequence identity to the mature polypeptide coding sequence of SEQ ID NO: 3; and (iv) a cellobiohydrolase II encoded by a polynucleotide that hybridizes under high stringency conditions with the mature polypeptide coding sequence of SEQ ID NO: 3 or the full-length complement thereof, wherein high stringency conditions are defined as prehybridization and hybridization at 42° C. in 5×SSPE, 0.3% SDS, 200 micrograms/ml sheared and denatured salmon sperm DNA, and 50% formamide for 12 to 24 hours and washing three times each for 15 minutes using 2×SSC, 0.2% SDS at 65° C.

9. The method of claim 1, wherein the homologous 5' region of the first locus, the homologous flanking region thereof, or a combination thereof is at least 50 bp.

10. The method of claim 1, wherein the homologous 3' region of the first locus, the homologous flanking region thereof, or a combination thereof is at least 50 bp.

11. The method of claim 1, wherein the homologous 5' region of the second locus, the homologous flanking region thereof, or a combination thereof is at least 50 bp.

12. The method of claim 1, wherein the homologous 3' region of the second locus, the homologous flanking region thereof, or a combination thereof is at least 50 bp.

13. The method of claim 1, which further comprises inserting into one or more additional endogenous loci each by targeted integration by introducing into the filamentous fungal strain a corresponding tandem construct for each locus comprising (i) a homologous 5' region of the locus, a homologous flanking region thereof, or a combination thereof, (ii) one or more selectable markers, (iii) a polynucleotide encoding a polypeptide having biological activity operably linked to a promoter and a terminator, (iv) another polynucleotide encoding another polypeptide having biological activity operably linked to another promoter and another terminator, and (v) a homologous 3' region of the locus, a homologous flanking region thereof, or a combination thereof.

14. The method of claim 1, further comprising transforming the filamentous fungal host cell with a tandem construct comprising (i) one or more selectable markers, (ii) a fifth polynucleotide encoding a fifth polypeptide having biological activity operably linked to a fifth promoter and a fifth terminator, and (iii) a sixth polynucleotide encoding a sixth polypeptide having biological activity operably linked to a sixth promoter and a sixth terminator, wherein the tandem construct integrates by ectopic integration.

15. The method of claim 1, wherein the polypeptides having biological activity are different polypeptides.

16. The method of claim 1, wherein two or more of the polypeptides having biological activity are the same polypeptide.

17. The method of claim 1, wherein the promoters are different promoters.

18. The method of claim 1, wherein two or more of the promoters are the same promoter.

19. The method of claim 1, wherein the terminators are different terminators.

20. The method of claim 1, wherein two or more of the terminators are the same terminator.

21. The method of claim 1, wherein the filamentous fungal strain is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* strain.

22. The method of claim 21, wherein the *Trichoderma* strain is selected from the group consisting of *Trichoderma harzianum, Trichoderma koningii, Trichoderma longibrachiatum, Trichoderma reesei*, and *Trichoderma viride.*

23. The method of claim 21, wherein the *Trichoderma* strain is *Trichoderma reesei*.

24. A filamentous fungal strain obtained by the method of claim 1.

* * * * *

SEQUENCE LISTING

```
<160> NUMBER OF SEQ ID NOS: 120

<210> SEQ ID NO 1
<211> LENGTH: 1545
<212> TYPE: DNA
<213> ORGANISM: Trichoderma reesei

<400> SEQUENCE: 1

atgtatcgga agttggccgt catctcggcc ttcttggcca cagctcgtgc tcagtcggcc      60

tgcactctcc aatcggagac tcacccgcct ctgacatggc agaaatgctc gtctggtggc     120

acgtgcactc aacagacagg ctccgtggtc atcgacgcca actggcgctg gactcacgct     180

acgaacagca gcacgaactg ctacgatggc aacacttgga gctcgaccct atgtcctgac     240

aacgagacct gcgcgaagaa ctgctgtctg gacggtgccg cctacgcgtc cacgtacgga     300

gttaccacga gcggtaacag cctctccatt ggctttgtca cccagtctgc gcagaagaac     360

gttggcgctc gcctttacct tatggcgagc gacacgacct accaggaatt caccctgctt     420

ggcaacgagt tctctttcga tgttgatgtt tcgcagctgc cgtgcggctt gaacggagct     480

ctctacttcg tgtccatgga cgcggatggt ggcgtgagca agtatcccac caacaccgct     540
```

```
ggcgccaagt acggcacggg gtactgtgac agccagtgtc cccgcgatct gaagttcatc    600

aatggccagg ccaacgttga gggctgggag ccgtcatcca acaacgcgaa cacgggcatt    660

ggaggacacg gaagctgctg ctctgagatg gatatctggg aggccaactc catctccgag    720

gctcttaccc cccacccttg cacgactgtc ggccaggaga tctgcgaggg tgatgggtgc    780

ggcggaactt actccgataa cagatatggc ggcacttgcg atcccgatgg ctgcgactgg    840

aacccatacc gcctgggcaa caccagcttc tacggccctg gctcaagctt taccctcgat    900

accaccaaga aattgaccgt tgtcacccag ttcgagacgt cgggtgccat caaccgatac    960

tatgtccaga atggcgtcac tttccagcag cccaacgccg agcttggtag ttactctggc   1020

aacgagctca acgatgatta ctgcacagct gaggaggcag aattcggcgg atcctctttc   1080

tcagacaagg gcggcctgac tcagttcaag aaggctacct ctggcggcat ggttctggtc   1140

atgagtctgt gggatgatta ctacgccaac atgctgtggc tggactccac ctacccgaca   1200

aacgagacct cctccacacc cggtgccgtg cgcggaagct gctccaccag ctccggtgtc   1260

cctgctcagg tcgaatctca gtctcccaac gccaaggtca ccttctccaa catcaagttc   1320

ggacccattg gcagcaccgg caaccctagc ggcggcaacc ctcccggcgg aaacccgcct   1380

ggcaccacca ccacccgccg cccagccact accactggaa gctctcccgg acctacccag   1440

tctcactacg gccagtgcgg cggtattggc tacagcggcc ccacggtctg cgccagcggc   1500

acaacttgcc aggtcctgaa cccttactac tctcagtgcc tgtaa                   1545
```

```
<210> SEQ ID NO 2
<211> LENGTH: 514
<212> TYPE: PRT
<213> ORGANISM: Trichoderma reesei

<400> SEQUENCE: 2

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190
```

```
Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
        435                 440                 445

Pro Ser Gly Gly Asn Pro Pro Gly Gly Asn Pro Pro Gly Thr Thr Thr
    450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
                485                 490                 495

Cys Ala Ser Gly Thr Thr Cys Gln Val Leu Asn Pro Tyr Tyr Ser Gln
            500                 505                 510

Cys Leu
```

<210> SEQ ID NO 3
<211> LENGTH: 1611
<212> TYPE: DNA
<213> ORGANISM: Trichoderma reesei

<400> SEQUENCE: 3

```
atgattgtcg gcattctcac cacgctggct acgctggcca cactcgcagc tagtgtgcct      60

ctagaggagc ggcaagcttg ctcaagcgtc tggtaattat gtgaaccctc tcaagagacc     120

caaatactga gatatgtcaa ggggccaatg tggtggccag aattggtcgg gtccgacttg     180

ctgtgcttcc ggaagcacat gcgtctactc caacgactat tactcccagt gtcttcccgg     240

cgctgcaagc tcaagctcgt ccacgcgcgc cgcgtcgacg acttctcgag tatccccccac    300
```

```
aacatcccgg tcgagctccg cgacgcctcc acctggttct actactacca gagtacctcc    360

agtcggatcg ggaaccgcta cgtattcagg caaccctttt gttggggtca ctccttgggc    420

caatgcatat tacgcctctg aagttagcag cctcgctatt cctagcttga ctggagccat    480

ggccactgct gcagcagctg tcgcaaaggt tccctctttt atgtggctgt aggtcctccc    540

ggaaccaagg caatctgtta ctgaaggctc atcattcact gcagagatac tcttgacaag    600

acccctctca tggagcaaac cttggccgac atccgcaccg ccaacaagaa tggcggtaac    660

tatgccggac agtttgtggt gtatgacttg ccggatcgcg attgcgctgc ccttgcctcg    720

aatggcgaat actctattgc cgatggtggc gtcgccaaat ataagaacta tatcgacacc    780

attcgtcaaa ttgtcgtgga atattccgat atccggaccc tcctggttat tggtatgagt    840

ttaaacacct gcctcccccc cccttccct tcctttcccg ccggcatctt gtcgttgtgc    900

taactattgt tccctcttcc agagcctgac tctcttgcca acctggtgac caacctcggt    960

actccaaagt gtgccaatgc tcagtcagcc taccttgagt gcatcaacta cgccgtcaca   1020

cagctgaacc ttccaaatgt tgcgatgtat ttggacgctg gccatgcagg atggcttggc   1080

tggccggcaa accaagaccc ggccgctcag ctatttgcaa atgtttacaa gaatgcatcg   1140

tctccgagag ctcttcgcgg attggcaacc aatgtcgcca actacaacgg gtggaacatt   1200

accagccccc catcgtacac gcaaggcaac gctgtctaca acgagaagct gtacatccac   1260

gctattggac gtcttcttgc caatcacggc tggtccaacg ccttcttcat cactgatcaa   1320

ggtcgatcgg gaaagcagcc taccggacag caacagtggg gagactggtg caatgtgatc   1380

ggcaccggat ttggtattcg cccatccgca aacactgggg actcgttgct ggattcgttt   1440

gtctgggtca agccaggcgg cgagtgtgac ggcaccagcg acagcagtgc gccacgattt   1500

gactcccact gtgcgctccc agatgccttg caaccggcgc ctcaagctgg tgcttggttc   1560

caagcctact ttgtgcagct tctcacaaac gcaaacccat cgttcctgta a            1611
```

```
<210> SEQ ID NO 4
<211> LENGTH: 471
<212> TYPE: PRT
<213> ORGANISM: Trichoderma reesei

<400> SEQUENCE: 4

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Ser Thr Arg Ala Ala Ser Thr Thr Ser Arg
65                  70                  75                  80

Val Ser Pro Thr Thr Ser Arg Ser Ser Ser Ala Thr Pro Pro Pro Gly
                85                  90                  95

Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140
```

```
Ala Thr Ala Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
        275                 280                 285

Gly His Ala Gly Trp Leu Gly Trp Pro Ala Asn Gln Asp Pro Ala Ala
    290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Arg Leu Leu Ala Asn His Gly Trp Ser Asn
        355                 360                 365

Ala Phe Phe Ile Thr Asp Gln Gly Arg Ser Gly Lys Gln Pro Thr Gly
    370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
            420                 425                 430

Pro Arg Phe Asp Ser His Cys Ala Leu Pro Asp Ala Leu Gln Pro Ala
        435                 440                 445

Pro Gln Ala Gly Ala Trp Phe Gln Ala Tyr Phe Val Gln Leu Leu Thr
    450                 455                 460

Asn Ala Asn Pro Ser Phe Leu
465                 470
```

<210> SEQ ID NO 5
<211> LENGTH: 1377
<212> TYPE: DNA
<213> ORGANISM: Trichoderma reesei

<400> SEQUENCE: 5

```
atggcgccct cagttacact gccgttgacc acggccatcc tggccattgc ccggctcgtc      60

gccgcccagc aaccgggtac cagcaccccc gaggtccatc ccaagttgac aacctacaag     120

tgtacaaagt ccgggggggtg cgtggcccag gacacctcgg tggtccttga ctggaactac     180

cgctggatgc acgacgcaaa ctacaactcg tgcaccgtca acggcggcgt caacaccacg     240
```

```
ctctgccctg acgaggcgac ctgtggcaag aactgcttca tcgagggcgt cgactacgcc    300

gcctcgggcg tcacgacctc gggcagcagc ctcaccatga accagtacat gcccagcagc    360

tctggcggct acagcagcgt ctctcctcgg ctgtatctcc tggactctga cggtgagtac    420

gtgatgctga agctcaacgg ccaggagctg agcttcgacg tcgacctctc tgctctgccg    480

tgtggagaga acggctcgct ctacctgtct cagatggacg agaacggggg cgccaaccag    540

tataacacgg ccggtgccaa ctacgggagc ggctactgcg atgctcagtg ccccgtccag    600

acatggagga acggcaccct caacactagc caccagggct tctgctgcaa cgagatggat    660

atcctggagg gcaactcgag ggcgaatgcc ttgacccctc actcttgcac ggccacggcc    720

tgcgactctg ccggttgcgg cttcaacccc tatggcagcg gctacaaaag ctactacggc    780

cccggagata ccgttgacac ctccaagacc ttcaccatca tcacccagtt caacacggac    840

aacggctcgc cctcgggcaa ccttgtgagc atcacccgca agtaccagca aaacggcgtc    900

gacatcccca gcgcccagcc cggcggcgac accatctcgt cctgcccgtc cgcctcagcc    960

tacggcggcc tcgccaccat gggcaaggcc ctgagcagcg gcatggtgct cgtgttcagc   1020

atttggaacg acaacagcca gtacatgaac tggctcgaca gcggcaacgc cggcccctgc   1080

agcagcaccg agggcaaccc atccaacatc ctggccaaca accccaacac gcacgtcgtc   1140

ttctccaaca tccgctgggg agacattggg tctactacga actcgactgc gcccccgccc   1200

ccgcctgcgt ccagcacgac gttttcgact acacggagga gctcgacgac ttcgagcagc   1260

ccgagctgca cgcagactca ctgggggcag tgcggtggca ttgggtacag cgggtgcaag   1320

acgtgcacgt cgggcactac gtgccagtat agcaacgact actactcgca atgcctt      1377
```

<210> SEQ ID NO 6
<211> LENGTH: 459
<212> TYPE: PRT
<213> ORGANISM: Trichoderma reesei

<400> SEQUENCE: 6

```
Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
            20                  25                  30

His Pro Lys Leu Thr Thr Tyr Lys Cys Thr Lys Ser Gly Gly Cys Val
        35                  40                  45

Ala Gln Asp Thr Ser Val Val Leu Asp Trp Asn Tyr Arg Trp Met His
    50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
                85                  90                  95

Val Asp Tyr Ala Ala Ser Gly Val Thr Thr Ser Gly Ser Ser Leu Thr
            100                 105                 110

Met Asn Gln Tyr Met Pro Ser Ser Ser Gly Gly Tyr Ser Ser Val Ser
        115                 120                 125

Pro Arg Leu Tyr Leu Leu Asp Ser Asp Gly Glu Tyr Val Met Leu Lys
    130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175
```

```
Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
        195                 200                 205

Thr Ser His Gln Gly Phe Cys Cys Asn Glu Met Asp Ile Leu Glu Gly
    210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
        275                 280                 285

Val Ser Ile Thr Arg Lys Tyr Gln Gln Asn Gly Val Asp Ile Pro Ser
    290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
            340                 345                 350

Asp Ser Gly Asn Ala Gly Pro Cys Ser Ser Thr Glu Gly Asn Pro Ser
        355                 360                 365

Asn Ile Leu Ala Asn Asn Pro Asn Thr His Val Val Phe Ser Asn Ile
    370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
                405                 410                 415

Thr Ser Ser Ser Pro Ser Cys Thr Gln Thr His Trp Gly Gln Cys Gly
            420                 425                 430

Gly Ile Gly Tyr Ser Gly Cys Lys Thr Cys Thr Ser Gly Thr Thr Cys
        435                 440                 445

Gln Tyr Ser Asn Asp Tyr Tyr Ser Gln Cys Leu
    450                 455
```

<210> SEQ ID NO 7
<211> LENGTH: 1254
<212> TYPE: DNA
<213> ORGANISM: Trichoderma reesei

<400> SEQUENCE: 7

```
atgaacaagt ccgtggctcc attgctgctt gcagcgtcca tactatatgg cggcgccgtc     60

gcacagcaga ctgtctgggg ccagtgtgga ggtattggtt ggagcggacc tacgaattgt    120

gctcctggct cagcttgttc gaccctcaat ccttattatg cgcaatgtat tccgggagcc    180

actactatca ccacttcgac ccggccacca tccggtccaa ccaccaccac cagggctacc    240

tcaacaagct catcaactcc acccacgagc tctggggtcc gatttgccgg cgttaacatc    300

gcgggttttg actttggctg taccacagat ggcacttgcg ttacctcgaa ggtttatcct    360

ccgttgaaga acttcaccgg ctcaaacaac taccccgatg gcatcggcca gatgcagcac    420

ttcgtcaacg aggacgggat gactattttc cgcttacctg tcggatggca gtacctcgtc    480
```

```
aacaacaatt tgggcggcaa tcttgattcc acgagcattt ccaagtatga tcagcttgtt    540

caggggtgcc tgtctctggg cgcatactgc atcgtcgaca tccacaatta tgctcgatgg    600

aacggtggga tcattggtca gggcggccct actaatgctc aattcacgag cctttggtcg    660

cagttggcat caaagtacgc atctcagtcg agggtgtggt tcggcatcat gaatgagccc    720

cacgacgtga acatcaacac ctgggctgcc acggtccaag aggttgtaac cgcaatccgc    780

aacgctggtg ctacgtcgca attcatctct ttgcctggaa atgattggca atctgctggg    840

gctttcatat ccgatggcag tgcagccgcc ctgtctcaag tcacgaaccc ggatgggtca    900

acaacgaatc tgatttttga cgtgcacaaa tacttggact cagacaactc cggtactcac    960

gccgaatgta ctacaaataa cattgacggc gccttttctc cgcttgccac ttggctccga   1020

cagaacaatc gccaggctat cctgacagaa accggtggtg gcaacgttca gtcctgcata   1080

caagacatgt gccagcaaat ccaatatctc aaccagaact cagatgtcta tcttggctat   1140

gttggttggg gtgccggatc atttgatagc acgtatgtcc tgacggaaac accgactagc   1200

agtggtaact catggacgga cacatccttg gtcagctcgt gtctcgcaag aaag          1254


<210> SEQ ID NO 8
<211> LENGTH: 418
<212> TYPE: PRT
<213> ORGANISM: Trichoderma reesei

<400> SEQUENCE: 8

Met Asn Lys Ser Val Ala Pro Leu Leu Leu Ala Ala Ser Ile Leu Tyr
1               5                   10                  15

Gly Gly Ala Val Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Glu
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240
```

```
His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
                325                 330                 335

Thr Trp Leu Arg Gln Asn Asn Arg Gln Ala Ile Leu Thr Glu Thr Gly
            340                 345                 350

Gly Gly Asn Val Gln Ser Cys Ile Gln Asp Met Cys Gln Gln Ile Gln
        355                 360                 365

Tyr Leu Asn Gln Asn Ser Asp Val Tyr Leu Gly Tyr Val Gly Trp Gly
    370                 375                 380

Ala Gly Ser Phe Asp Ser Thr Tyr Val Leu Thr Glu Thr Pro Thr Ser
385                 390                 395                 400

Ser Gly Asn Ser Trp Thr Asp Thr Ser Leu Val Ser Ser Cys Leu Ala
                405                 410                 415

Arg Lys


<210> SEQ ID NO 9
<211> LENGTH: 2615
<212> TYPE: DNA
<213> ORGANISM: Trichoderma reesei

<400> SEQUENCE: 9

atgggatttg gccgcaatgc tgccgagccc gagtgtttct gcaacgttat ccaggagatt      60

tgcgcttgcc caagagggag ttgacgggga gagtcccaac tggttccttc agtaacgcca     120

ccctggcaga ctatataact tgtggacaag actctgcttt gttgagttct tcctaccagt     180

cttgaccaag accattctgt tgagcccaat cagaaatgcg ttaccgaaca gcagctgcgc     240

tggcacttgc cactgggccc tttgctaggg cagacagtca gtatagctgg tccatactgg     300

gatgtatatg tatcctggag acaccatgct gactcttgaa tcaaggtagc tcaacatcgg     360

gggcctcggc tgaggcagtt gtacctcctg cagggactcc atggggaacc gcgtacgaca     420

aggcgaaggc cgcattggca aagctcaatc tccaagataa ggtcggcatc gtgagcggtg     480

tcggctggaa cggcggtcct tgcgttggaa acacatctcc ggcctccaag atcagctatc     540

catcgctatg ccttcaagac ggacccctcg gtgttcgata ctcgacaggc agcacagcct     600

ttacgccggg cgttcaagcg gcctcgacgt gggatgtcaa tttgatccgc gaacgtggac     660

agttcatcgg tgaggaggtg aaggcctcgg ggattcatgt catacttggt cctgtggctg     720

ggccgctggg aaagactccg cagggcggtc gcaactggga gggcttcggt gtcgatccat     780

atctcacggg cattgccatg ggtcaaacca tcaacggcat ccagtcggta ggcgtgcagg     840

cgacagcgaa gcactatatc ctcaacgagc aggagctcaa tcgagaaacc atttcgagca     900

acccagatga ccgaactctc catgagctgt atacttggcc atttgccgac gcggttcagg     960

ccaatgtcgc ttctgtcatg tgctcgtaca acaaggtcaa taccacctgg gcctgcgagg    1020

atcagtacac gctgcagact gtgctgaaag accagctggg gttcccaggc tatgtcatga    1080
```

```
cggactggaa cgcacagcac acgactgtcc aaagcgcgaa ttctgggctt gacatgtcaa   1140
tgcctggcac agacttcaac ggtaacaatc ggctctgggg tccagctctc accaatgcgg   1200
taaatagcaa tcaggtcccc acgagcagag tcgacgatat ggtgactcgt atcctcgccg   1260
catggtactt gacaggccag gaccaggcag gctatccgtc gttcaacatc agcagaaatg   1320
ttcaaggaaa ccacaagacc aatgtcaggg caattgccag ggacggcatc gttctgctca   1380
agaatgacgc caacatcctg ccgctcaaga agcccgctag cattgccgtc gttggatctg   1440
ccgcaatcat tggtaaccac gccagaaact cgccctcgtg caacgacaaa ggctgcgacg   1500
acggggcctt gggcatgggt tggggttccg gcgccgtcaa ctatccgtac ttcgtcgcgc   1560
cctacgatgc catcaatacc agagcgtctt cgcagggcac ccaggttacc ttgagcaaca   1620
ccgacaacac gtcctcaggc gcatctgcag caagaggaaa ggacgtcgcc atcgtcttca   1680
tcaccgccga ctcgggtgaa ggctacatca ccgtggaggg caacgcgggc gatcgcaaca   1740
acctggatcc gtggcacaac ggcaatgccc tggtccaggc ggtggccggt gccaacagca   1800
acgtcattgt tgttgtccac tccgttggcg ccatcattct ggagcagatt cttgctcttc   1860
cgcaggtcaa ggccgttgtc tgggcgggtc ttccttctca ggagagcggc aatgcgctcg   1920
tcgacgtgct gtggggagat gtcagccctt ctggcaagct ggtgtacacc attgcgaaga   1980
gccccaatga ctataacact cgcatcgttt ccggcggcag tgacagcttc agcgagggac   2040
tgttcatcga ctataagcac ttcgacgacg ccaatatcac gccgcggtac gagttcggct   2100
atggactgtg taagtttgct aacctgaaca atctattaga caggttgact gacggatgac   2160
tgtggaatga tagcttacac caagttcaac tactcacgcc tctccgtctt gtcgaccgcc   2220
aagtctggtc ctgcgactgg ggccgttgtg ccgggaggcc cgagtgatct gttccagaat   2280
gtcgcgacag tcaccgttga catcgcaaac tctggccaag tgactggtgc cgaggtagcc   2340
cagctgtaca tcacctaccc atcttcagca cccaggaccc ctccgaagca gctgcgaggc   2400
tttgccaagc tgaacctcac gcctggtcag agcggaacag caacgttcaa catccgacga   2460
cgagatctca gctactggga cacggcttcg cagaaatggg tggtgccgtc ggggtcgttt   2520
ggcatcagcg tgggagcgag cagccgggat atcaggctga cgagcactct gtcggtagcg   2580
tagcgcgagg agggtgaagg cggttgacct gtgac                              2615
```

```
<210> SEQ ID NO 10
<211> LENGTH: 744
<212> TYPE: PRT
<213> ORGANISM: Trichoderma reesei

<400> SEQUENCE: 10

Met Arg Tyr Arg Thr Ala Ala Ala Leu Ala Leu Ala Thr Gly Pro Phe
1               5                   10                  15

Ala Arg Ala Asp Ser His Ser Thr Ser Gly Ala Ser Ala Glu Ala Val
            20                  25                  30

Val Pro Pro Ala Gly Thr Pro Trp Gly Thr Ala Tyr Asp Lys Ala Lys
        35                  40                  45

Ala Ala Leu Ala Lys Leu Asn Leu Gln Asp Lys Val Gly Ile Val Ser
    50                  55                  60

Gly Val Gly Trp Asn Gly Gly Pro Cys Val Gly Asn Thr Ser Pro Ala
65                  70                  75                  80

Ser Lys Ile Ser Tyr Pro Ser Leu Cys Leu Gln Asp Gly Pro Leu Gly
                85                  90                  95

Val Arg Tyr Ser Thr Gly Ser Thr Ala Phe Thr Pro Gly Val Gln Ala
```

```
            100                 105                 110

Ala Ser Thr Trp Asp Val Asn Leu Ile Arg Glu Arg Gly Gln Phe Ile
        115                 120                 125

Gly Glu Glu Val Lys Ala Ser Gly Ile His Val Ile Leu Gly Pro Val
    130                 135                 140

Ala Gly Pro Leu Gly Lys Thr Pro Gln Gly Gly Arg Asn Trp Glu Gly
145                 150                 155                 160

Phe Gly Val Asp Pro Tyr Leu Thr Gly Ile Ala Met Gly Gln Thr Ile
                165                 170                 175

Asn Gly Ile Gln Ser Val Gly Val Gln Ala Thr Ala Lys His Tyr Ile
            180                 185                 190

Leu Asn Glu Gln Glu Leu Asn Arg Glu Thr Ile Ser Ser Asn Pro Asp
        195                 200                 205

Asp Arg Thr Leu His Glu Leu Tyr Thr Trp Pro Phe Ala Asp Ala Val
    210                 215                 220

Gln Ala Asn Val Ala Ser Val Met Cys Ser Tyr Asn Lys Val Asn Thr
225                 230                 235                 240

Thr Trp Ala Cys Glu Asp Gln Tyr Thr Leu Gln Thr Val Leu Lys Asp
                245                 250                 255

Gln Leu Gly Phe Pro Gly Tyr Val Met Thr Asp Trp Asn Ala Gln His
            260                 265                 270

Thr Thr Val Gln Ser Ala Asn Ser Gly Leu Asp Met Ser Met Pro Gly
        275                 280                 285

Thr Asp Phe Asn Gly Asn Asn Arg Leu Trp Gly Pro Ala Leu Thr Asn
    290                 295                 300

Ala Val Asn Ser Asn Gln Val Pro Thr Ser Arg Val Asp Asp Met Val
305                 310                 315                 320

Thr Arg Ile Leu Ala Ala Trp Tyr Leu Thr Gly Gln Asp Gln Ala Gly
                325                 330                 335

Tyr Pro Ser Phe Asn Ile Ser Arg Asn Val Gln Gly Asn His Lys Thr
            340                 345                 350

Asn Val Arg Ala Ile Ala Arg Asp Gly Ile Val Leu Leu Lys Asn Asp
        355                 360                 365

Ala Asn Ile Leu Pro Leu Lys Lys Pro Ala Ser Ile Ala Val Val Gly
    370                 375                 380

Ser Ala Ala Ile Ile Gly Asn His Ala Arg Asn Ser Pro Ser Cys Asn
385                 390                 395                 400

Asp Lys Gly Cys Asp Asp Gly Ala Leu Gly Met Gly Trp Gly Ser Gly
                405                 410                 415

Ala Val Asn Tyr Pro Tyr Phe Val Ala Pro Tyr Asp Ala Ile Asn Thr
            420                 425                 430

Arg Ala Ser Ser Gln Gly Thr Gln Val Thr Leu Ser Asn Thr Asp Asn
        435                 440                 445

Thr Ser Ser Gly Ala Ser Ala Ala Arg Gly Lys Asp Val Ala Ile Val
    450                 455                 460

Phe Ile Thr Ala Asp Ser Gly Glu Gly Tyr Ile Thr Val Glu Gly Asn
465                 470                 475                 480

Ala Gly Asp Arg Asn Asn Leu Asp Pro Trp His Asn Gly Asn Ala Leu
                485                 490                 495

Val Gln Ala Val Ala Gly Ala Asn Ser Asn Val Ile Val Val Val His
            500                 505                 510

Ser Val Gly Ala Ile Ile Leu Glu Gln Ile Leu Ala Leu Pro Gln Val
        515                 520                 525
```

```
Lys Ala Val Val Trp Ala Gly Leu Pro Ser Gln Glu Ser Gly Asn Ala
    530                 535                 540

Leu Val Asp Val Leu Trp Gly Asp Val Ser Pro Ser Gly Lys Leu Val
545                 550                 555                 560

Tyr Thr Ile Ala Lys Ser Pro Asn Asp Tyr Asn Thr Arg Ile Val Ser
                565                 570                 575

Gly Gly Ser Asp Ser Phe Ser Glu Gly Leu Phe Ile Asp Tyr Lys His
            580                 585                 590

Phe Asp Asp Ala Asn Ile Thr Pro Arg Tyr Glu Phe Gly Tyr Gly Leu
        595                 600                 605

Ser Tyr Thr Lys Phe Asn Tyr Ser Arg Leu Ser Val Leu Ser Thr Ala
    610                 615                 620

Lys Ser Gly Pro Ala Thr Gly Ala Val Val Pro Gly Gly Pro Ser Asp
625                 630                 635                 640

Leu Phe Gln Asn Val Ala Thr Val Thr Val Asp Ile Ala Asn Ser Gly
                645                 650                 655

Gln Val Thr Gly Ala Glu Val Ala Gln Leu Tyr Ile Thr Tyr Pro Ser
            660                 665                 670

Ser Ala Pro Arg Thr Pro Pro Lys Gln Leu Arg Gly Phe Ala Lys Leu
        675                 680                 685

Asn Leu Thr Pro Gly Gln Ser Gly Thr Ala Thr Phe Asn Ile Arg Arg
    690                 695                 700

Arg Asp Leu Ser Tyr Trp Asp Thr Ala Ser Gln Lys Trp Val Val Pro
705                 710                 715                 720

Ser Gly Ser Phe Gly Ile Ser Val Gly Ala Ser Ser Arg Asp Ile Arg
                725                 730                 735

Leu Thr Ser Thr Leu Ser Val Ala
            740
```

<210> SEQ ID NO 11
<211> LENGTH: 752
<212> TYPE: DNA
<213> ORGANISM: Trichoderma reesei

<400> SEQUENCE: 11

```
atggttgcct tttccagcct catctgcgct ctcaccagca tcgccagtac tctggcgatg      60

cccacaggcc tcgagcctga gagcagtgtc aacgtcacag agcgtggcat gtacgacttt     120

gttcttggag ctcacaatga tcatcgccgt cgtgctagca tcaactacga ccaaaactac     180

caaactggcg gacaagtcag ctattcgcct tccaacactg gcttctcagt gaactggaac     240

actcaagatg actttgttgt gggcgttggt tggacgactg gatcttctgc gtaggaggac     300

tcctcatcat tctgcacttt gaaagcatct tctgaccaaa agcttctctt agtcccatca     360

actttggcgg ctcttttagt gtcaacagcg gaactggcct gctttccgtc tatggctgga     420

gcaccaaccc actggttgag tactacatca tggaggacaa ccacaactac ccagcacagg     480

gtaccgtcaa gggaaccgtc accagcgacg gagccactta caccatctgg gagaataccc     540

gtgtcaacga gccttccatc cagggcacag cgaccttcaa ccagtacatt tccgtgcgga     600

actcgcccag gaccagcgga actgttactg tgcagaacca cttcaatgct tgggcctcgc     660

ttggcctgca ccttgggcag atgaactacc aggttgtcgc tgtcgaaggc tggggtggta     720

gtggttctgc ctcacagagt gtcagcaact ag                                   752
```

<210> SEQ ID NO 12

```
<211> LENGTH: 229
<212> TYPE: PRT
<213> ORGANISM: Trichoderma reesei

<400> SEQUENCE: 12

Met Val Ala Phe Ser Ser Leu Ile Cys Ala Leu Thr Ser Ile Ala Ser
1               5                   10                  15

Thr Leu Ala Met Pro Thr Gly Leu Glu Pro Glu Ser Ser Val Asn Val
            20                  25                  30

Thr Glu Arg Gly Met Tyr Asp Phe Val Leu Gly Ala His Asn Asp His
        35                  40                  45

Arg Arg Arg Ala Ser Ile Asn Tyr Asp Gln Asn Tyr Gln Thr Gly Gly
    50                  55                  60

Gln Val Ser Tyr Ser Pro Ser Asn Thr Gly Phe Ser Val Asn Trp Asn
65                  70                  75                  80

Thr Gln Asp Asp Phe Val Val Gly Val Gly Trp Thr Thr Gly Ser Ser
                85                  90                  95

Ala Pro Ile Asn Phe Gly Gly Ser Phe Ser Val Asn Ser Gly Thr Gly
            100                 105                 110

Leu Leu Ser Val Tyr Gly Trp Ser Thr Asn Pro Leu Val Glu Tyr Tyr
        115                 120                 125

Ile Met Glu Asp Asn His Asn Tyr Pro Ala Gln Gly Thr Val Lys Gly
    130                 135                 140

Thr Val Thr Ser Asp Gly Ala Thr Tyr Thr Ile Trp Glu Asn Thr Arg
145                 150                 155                 160

Val Asn Glu Pro Ser Ile Gln Gly Thr Ala Thr Phe Asn Gln Tyr Ile
                165                 170                 175

Ser Val Arg Asn Ser Pro Arg Thr Ser Gly Thr Val Thr Val Gln Asn
            180                 185                 190

His Phe Asn Ala Trp Ala Ser Leu Gly Leu His Leu Gly Gln Met Asn
        195                 200                 205

Tyr Gln Val Val Ala Val Glu Gly Trp Gly Gly Ser Gly Ser Ala Ser
    210                 215                 220

Gln Ser Val Ser Asn
225


<210> SEQ ID NO 13
<211> LENGTH: 796
<212> TYPE: DNA
<213> ORGANISM: Trichoderma reesei

<400> SEQUENCE: 13

caagaagaca tcaacatggt ctccttcacc tccctcctcg ccggcgtcgc cgccatctcg      60

ggcgtcttgg ccgctcccgc cgccgaggtc gaatccgtgg ctgtggagaa gcgccagacg     120

attcagcccg gcacgggcta caacaacggc tacttctact cgtactggaa cgatggccac     180

ggcggcgtga cgtacaccaa tggtcccggc gggcagttct ccgtcaactg gtccaactcg     240

ggcaactttg tcggcggcaa gggatggcag cccggcacca agaacaagta agactaccta     300

ctcttacccc ctttgaccaa cacagcacaa cacaatacaa cacatgtgac taccaatcat     360

ggaatcggat ctaacagctg tgttttcaaa aaaaagggtc atcaacttct cgggcagcta     420

caaccccaac ggcaacagct acctctccgt gtacggctgg tcccgcaacc ccctgatcga     480

gtactacatc gtcgagaact ttggcaccta caacccgtcc acgggcgcca ccaagctggg     540

cgaggtcacc tccgacggca gcgtctacga catttaccgc acgcagcgcg tcaaccagcc     600
```

gtccatcatc ggcaccgcca ccttttacca gtactggtcc gtccgccgca accaccgctc 660
gagcggctcc gtcaacacgg cgaaccactt caacgcgtgg gctcagcaag gcctgacgct 720
cgggacgatg gattaccaga ttgttgccgt ggagggttac tttagctctg gctctgcttc 780
catcaccgtc agctaa 796

<210> SEQ ID NO 14
<211> LENGTH: 223
<212> TYPE: PRT
<213> ORGANISM: Trichoderma reesei

<400> SEQUENCE: 14

Met Val Ser Phe Thr Ser Leu Leu Ala Gly Val Ala Ala Ile Ser Gly
1 5 10 15

Val Leu Ala Ala Pro Ala Ala Glu Val Glu Ser Val Ala Val Glu Lys
20 25 30

Arg Gln Thr Ile Gln Pro Gly Thr Gly Tyr Asn Asn Gly Tyr Phe Tyr
35 40 45

Ser Tyr Trp Asn Asp Gly His Gly Gly Val Thr Tyr Thr Asn Gly Pro
50 55 60

Gly Gly Gln Phe Ser Val Asn Trp Ser Asn Ser Gly Asn Phe Val Gly
65 70 75 80

Gly Lys Gly Trp Gln Pro Gly Thr Lys Asn Lys Val Ile Asn Phe Ser
85 90 95

Gly Ser Tyr Asn Pro Asn Gly Asn Ser Tyr Leu Ser Val Tyr Gly Trp
100 105 110

Ser Arg Asn Pro Leu Ile Glu Tyr Tyr Ile Val Glu Asn Phe Gly Thr
115 120 125

Tyr Asn Pro Ser Thr Gly Ala Thr Lys Leu Gly Glu Val Thr Ser Asp
130 135 140

Gly Ser Val Tyr Asp Ile Tyr Arg Thr Gln Arg Val Asn Gln Pro Ser
145 150 155 160

Ile Ile Gly Thr Ala Thr Phe Tyr Gln Tyr Trp Ser Val Arg Arg Asn
165 170 175

His Arg Ser Ser Gly Ser Val Asn Thr Ala Asn His Phe Asn Ala Trp
180 185 190

Ala Gln Gln Gly Leu Thr Leu Gly Thr Met Asp Tyr Gln Ile Val Ala
195 200 205

Val Glu Gly Tyr Phe Ser Ser Gly Ser Ala Ser Ile Thr Val Ser
210 215 220

<210> SEQ ID NO 15
<211> LENGTH: 1352
<212> TYPE: DNA
<213> ORGANISM: Trichoderma reesei

<400> SEQUENCE: 15
atgaaagcaa acgtcatctt gtgcctcctg gcccccctgg tcgccgctct ccccaccgaa 60
accatccacc tcgaccccga gctcgccgct ctccgcgcca acctcaccga gcgaacagcc 120
gacctctggg accgccaagc ctctcaaagc atcgaccagc tcatcaagag aaaaggcaag 180
ctctactttg gcaccgccac cgaccgcggc ctcctccaac gggaaaagaa cgcggccatc 240
atccaggcag acctcggcca ggtgacgccg gagaacagca tgaagtggca gtcgctcgag 300
aacaaccaag gccagctgaa ctggggagac gccgactatc tcgtcaactt tgcccagcaa 360
aacggcaagt cgatacgcgg ccacactctg atctggcact cgcagctgcc tgcgtgggtg 420

```
aacaatatca acaacgcgga tactctgcgg caagtcatcc gcacccatgt ctctactgtg    480

gttgggcggt acaagggcaa gattcgtgct tgggtgagtt ttgaacacca catgcccctt    540

ttcttagtcc gctcctcctc ctcttggaac ttctcacagt tatagccgta tacaacattc    600

gacaggaaat ttaggatgac aactactgac tgacttgtgt gtgtgatggc gataggacgt    660

ggtcaatgaa atcttcaacg aggatggaac gctgcgctct tcagtctttt ccaggctcct    720

cggcgaggag tttgtctcga ttgcctttcg tgctgctcga gatgctgacc cttctgcccg    780

tctttacatc aacgactaca atctcgaccg cgccaactat ggcaaggtca acgggttgaa    840

gacttacgtc tccaagtgga tctctcaagg agttcccatt gacggtattg gtgagccacg    900

accccctaaat gtcccccatt agagtctctt tctagagcca aggcttgaag ccattcaggg    960

actgacacga gagccttctc tacaggaagc cagtcccatc tcagcggcgg cggaggctct   1020

ggtacgctgg gtgcgctcca gcagctggca acggtacccg tcaccgagct ggccattacc   1080

gagctggaca ttcagggggc accgacgacg gattacaccc aagttgttca agcatgcctg   1140

agcgtctcca agtgcgtcgg catcaccgtg tggggcatca gtgacaaggt aagttgcttc   1200

ccctgtctgt gcttatcaac tgtaagcagc aacaactgat gctgtctgtc tttacctagg   1260

actcgtggcg tgccagcacc aaccctcttc tgtttgacgc aaacttcaac cccaagccgg   1320

catataacag cattgttggc atcttacaat ag                                  1352

<210> SEQ ID NO 16
<211> LENGTH: 347
<212> TYPE: PRT
<213> ORGANISM: Trichoderma reesei

<400> SEQUENCE: 16

Met Lys Ala Asn Val Ile Leu Cys Leu Leu Ala Pro Leu Val Ala Ala
1               5                   10                  15

Leu Pro Thr Glu Thr Ile His Leu Asp Pro Glu Leu Ala Ala Leu Arg
            20                  25                  30

Ala Asn Leu Thr Glu Arg Thr Ala Asp Leu Trp Asp Arg Gln Ala Ser
        35                  40                  45

Gln Ser Ile Asp Gln Leu Ile Lys Arg Lys Gly Lys Leu Tyr Phe Gly
    50                  55                  60

Thr Ala Thr Asp Arg Gly Leu Leu Gln Arg Glu Lys Asn Ala Ala Ile
65                  70                  75                  80

Ile Gln Ala Asp Leu Gly Gln Val Thr Pro Glu Asn Ser Met Lys Trp
                85                  90                  95

Gln Ser Leu Glu Asn Asn Gln Gly Gln Leu Asn Trp Gly Asp Ala Asp
            100                 105                 110

Tyr Leu Val Asn Phe Ala Gln Gln Asn Gly Lys Ser Ile Arg Gly His
        115                 120                 125

Thr Leu Ile Trp His Ser Gln Leu Pro Ala Trp Val Asn Asn Ile Asn
    130                 135                 140

Asn Ala Asp Thr Leu Arg Gln Val Ile Arg Thr His Val Ser Thr Val
145                 150                 155                 160

Val Gly Arg Tyr Lys Gly Lys Ile Arg Ala Trp Asp Val Val Asn Glu
                165                 170                 175

Ile Phe Asn Glu Asp Gly Thr Leu Arg Ser Ser Val Phe Ser Arg Leu
            180                 185                 190

Leu Gly Glu Glu Phe Val Ser Ile Ala Phe Arg Ala Ala Arg Asp Ala
        195                 200                 205
```

```
Asp Pro Ser Ala Arg Leu Tyr Ile Asn Asp Tyr Asn Leu Asp Arg Ala
    210                 215                 220

Asn Tyr Gly Lys Val Asn Gly Leu Lys Thr Tyr Val Ser Lys Trp Ile
225                 230                 235                 240

Ser Gln Gly Val Pro Ile Asp Gly Ile Gly Ser Gln Ser His Leu Ser
                245                 250                 255

Gly Gly Gly Gly Ser Gly Thr Leu Gly Ala Leu Gln Gln Leu Ala Thr
            260                 265                 270

Val Pro Val Thr Glu Leu Ala Ile Thr Glu Leu Asp Ile Gln Gly Ala
        275                 280                 285

Pro Thr Thr Asp Tyr Thr Gln Val Val Gln Ala Cys Leu Ser Val Ser
    290                 295                 300

Lys Cys Val Gly Ile Thr Val Trp Gly Ile Ser Asp Lys Asp Ser Trp
305                 310                 315                 320

Arg Ala Ser Thr Asn Pro Leu Leu Phe Asp Ala Asn Phe Asn Pro Lys
                325                 330                 335

Pro Ala Tyr Asn Ser Ile Val Gly Ile Leu Gln
            340                 345


<210> SEQ ID NO 17
<211> LENGTH: 2564
<212> TYPE: DNA
<213> ORGANISM: Trichoderma reesei

<400> SEQUENCE: 17

ggacagccgg acgcaatggt gaataacgca gctcttctcg ccgccctgtc ggctctcctg     60

cccacggccc tggcgcagaa caatcaaaca tacgccaact actctgctca gggccagcct    120

gatctctacc ccgagacact tgccacgctc acactctcgt tccccgactg cgaacatggc    180

cccctcaaga acaatctcgt ctgtgactca tcggccggct atgtagagcg agcccaggcc    240

ctcatctcgc tcttcaccct cgaggagctc attctcaaca cgcaaaactc gggccccggc    300

gtgcctcgcc tgggtcttcc gaactaccaa gtctggaatg aggctctgca cggcttggac    360

cgcgccaact tcgccaccaa gggcggccag ttcgaatggg cgacctcgtt ccccatgccc    420

atcctcacta cggcggccct caaccgcaca ttgatccacc agattgccga catcatctcg    480

acccaagctc gagcattcag caacagcggc cgttacggtc tcgacgtcta tgcgccaaac    540

gtcaatggct tccgaagccc cctctggggc cgtggccagg agacgcccgg cgaagacgcc    600

tttttcctca gctccgccta tacttacgag tacatcacgg gcatccaggg tggcgtcgac    660

cctgagcacc tcaaggttgc cgccacggtg aagcactttg ccggatacga cctcgagaac    720

tggaacaacc agtcccgtct cggtttcgac gccatcataa ctcagcagga cctctccgaa    780

tactacactc cccagttcct cgctgcggcc cgttatgcaa agtcacgcag cttgatgtgc    840

gcatacaact ccgtcaacgg cgtgcccagc tgtgccaaca gcttcttcct gcagacgctt    900

ttgcgcgaga gctggggctt ccccgaatgg ggatacgtct cgtccgattg cgatgccgtc    960

tacaacgttt tcaaccctca tgactacgcc agcaaccagt cgtcagccgc cgccagctca   1020

ctgcgagccg gcaccgatat cgactgcggt cagacttacc cgtggcacct caacgagtcc   1080

tttgtggccg gcgaagtctc ccgcggcgag atcgagcggt ccgtcacccg tctgtacgcc   1140

aacctcgtcc gtctcggata cttcgacaag aagaaccagt accgctcgct cggttggaag   1200

gatgtcgtca agactgatgc ctggaacatc tcgtacgagg ctgctgttga gggcatcgtc   1260

ctgctcaaga acgatggcac tctccctctg tccaagaagg tgcgcagcat tgctctgatc   1320
```

```
ggaccatggg ccaatgccac aacccaaatg caaggcaact actatggccc tgccccatac   1380

ctcatcagcc ctctggaagc tgctaagaag gccggctatc acgtcaactt tgaactcggc   1440

acagagatcg ccggcaacag caccactggc tttgccaagg ccattgctgc cgccaagaag   1500

tcggatgcca tcatctacct cggtggaatt gacaacacca ttgaacagga gggcgctgac   1560

cgcacggaca ttgcttggcc cggtaatcag ctggatctca tcaagcagct cagcgaggtc   1620

ggcaaacccc ttgtcgtcct gcaaatgggc ggtggtcagg tagactcatc ctcgctcaag   1680

agcaacaaga aggtcaactc cctcgtctgg ggcggatatc ccggccagtc gggaggcgtt   1740

gccctcttcg acattctctc tggcaagcgt gctcctgccg gccgactggt caccactcag   1800

tacccggctg agtatgttca ccaattcccc cagaatgaca tgaacctccg acccgatgga   1860

aagtcaaacc ctggacagac ttacatctgg tacaccggca aacccgtcta cgagtttggc   1920

agtggtctct tctacaccac cttcaaggag actctcgcca gccaccccaa gagcctcaag   1980

ttcaacacct catcgatcct ctctgctcct caccccggat acacttacag cgagcagatt   2040

cccgtcttca ccttcgaggc caacatcaag aactcgggca agacggagtc cccatatacg   2100

gccatgctgt ttgttcgcac aagcaacgct ggcccagccc cgtacccgaa caagtggctc   2160

gtcggattcg accgacttgc cgacatcaag cctggtcact cttccaagct cagcatcccc   2220

atccctgtca gtgctctcgc ccgtgttgat tctcacggaa accggattgt ataccccggc   2280

aagtatgagc tagccttgaa caccgacgag tctgtgaagc ttgagtttga gttggtggga   2340

gaagaggtaa cgattgagaa ctggccgttg gaggagcaac agatcaagga tgctacacct   2400

gacgcataag ggttttaatg atgttgttat gacaaacggg tagagtagtt aatgatggaa   2460

taggaagagg ccatagtttt ctgtttgcaa accatttttg ccattgcgaa aaaaaaaaaa   2520

aaaaaaaaaa aaaaaaaaaa aaaaaaaaaa aaaaaaaaaa aaaa                    2564
```

```
<210> SEQ ID NO 18
<211> LENGTH: 780
<212> TYPE: PRT
<213> ORGANISM: Trichoderma reesei

<400> SEQUENCE: 18

Met Val Asn Asn Ala Ala Leu Leu Ala Ala Leu Ser Ala Leu Leu Pro
1               5                   10                  15

Thr Ala Leu Ala Gln Asn Asn Gln Thr Tyr Ala Asn Tyr Ser Ala Gln
            20                  25                  30

Gly Gln Pro Asp Leu Tyr Pro Glu Thr Leu Ala Thr Leu Thr Leu Ser
        35                  40                  45

Phe Pro Asp Cys Glu His Gly Pro Leu Lys Asn Asn Leu Val Cys Asp
    50                  55                  60

Ser Ser Ala Gly Tyr Val Glu Arg Ala Gln Ala Leu Ile Ser Leu Phe
65                  70                  75                  80

Thr Leu Glu Glu Leu Ile Leu Asn Thr Gln Asn Ser Gly Pro Gly Val
                85                  90                  95

Pro Arg Leu Gly Leu Pro Asn Tyr Gln Val Trp Asn Glu Ala Leu His
            100                 105                 110

Gly Leu Asp Arg Ala Asn Phe Ala Thr Lys Gly Gly Gln Phe Glu Trp
        115                 120                 125

Ala Thr Ser Phe Pro Met Pro Ile Leu Thr Thr Ala Ala Leu Asn Arg
    130                 135                 140

Thr Leu Ile His Gln Ile Ala Asp Ile Ile Ser Thr Gln Ala Arg Ala
```

```
145                 150                 155                 160

Phe Ser Asn Ser Gly Arg Tyr Gly Leu Asp Val Tyr Ala Pro Asn Val
                165                 170                 175

Asn Gly Phe Arg Ser Pro Leu Trp Gly Arg Gly Gln Glu Thr Pro Gly
            180                 185                 190

Glu Asp Ala Phe Phe Leu Ser Ser Ala Tyr Thr Tyr Glu Tyr Ile Thr
        195                 200                 205

Gly Ile Gln Gly Gly Val Asp Pro Glu His Leu Lys Val Ala Ala Thr
    210                 215                 220

Val Lys His Phe Ala Gly Tyr Asp Leu Glu Asn Trp Asn Asn Gln Ser
225                 230                 235                 240

Arg Leu Gly Phe Asp Ala Ile Ile Thr Gln Gln Asp Leu Ser Glu Tyr
                245                 250                 255

Tyr Thr Pro Gln Phe Leu Ala Ala Ala Arg Tyr Ala Lys Ser Arg Ser
            260                 265                 270

Leu Met Cys Ala Tyr Asn Ser Val Asn Gly Val Pro Ser Cys Ala Asn
        275                 280                 285

Ser Phe Phe Leu Gln Thr Leu Leu Arg Glu Ser Trp Gly Phe Pro Glu
    290                 295                 300

Trp Gly Tyr Val Ser Ser Asp Cys Asp Ala Val Tyr Asn Val Phe Asn
305                 310                 315                 320

Pro His Asp Tyr Ala Ser Asn Gln Ser Ser Ala Ala Ala Ser Ser Leu
                325                 330                 335

Arg Ala Gly Thr Asp Ile Asp Cys Gly Gln Thr Tyr Pro Trp His Leu
            340                 345                 350

Asn Glu Ser Phe Val Ala Gly Glu Val Ser Arg Gly Glu Ile Glu Arg
        355                 360                 365

Ser Val Thr Arg Leu Tyr Ala Asn Leu Val Arg Leu Gly Tyr Phe Asp
    370                 375                 380

Lys Lys Asn Gln Tyr Arg Ser Leu Gly Trp Lys Asp Val Val Lys Thr
385                 390                 395                 400

Asp Ala Trp Asn Ile Ser Tyr Glu Ala Ala Val Glu Gly Ile Val Leu
                405                 410                 415

Leu Lys Asn Asp Gly Thr Leu Pro Leu Ser Lys Lys Val Arg Ser Ile
            420                 425                 430

Ala Leu Ile Gly Pro Trp Ala Asn Ala Thr Thr Gln Met Gln Gly Asn
        435                 440                 445

Tyr Tyr Gly Pro Ala Pro Tyr Leu Ile Ser Pro Leu Glu Ala Ala Lys
    450                 455                 460

Lys Ala Gly Tyr His Val Asn Phe Glu Leu Gly Thr Glu Ile Ala Gly
465                 470                 475                 480

Asn Ser Thr Thr Gly Phe Ala Lys Ala Ile Ala Ala Ala Lys Lys Ser
                485                 490                 495

Asp Ala Ile Ile Tyr Leu Gly Gly Ile Asp Asn Thr Ile Glu Gln Glu
            500                 505                 510

Gly Ala Asp Arg Thr Asp Ile Ala Trp Pro Gly Asn Gln Leu Asp Leu
        515                 520                 525

Ile Lys Gln Leu Ser Glu Val Gly Lys Pro Leu Val Val Leu Gln Met
    530                 535                 540

Gly Gly Gly Gln Val Asp Ser Ser Ser Leu Lys Ser Asn Lys Lys Val
545                 550                 555                 560

Asn Ser Leu Val Trp Gly Gly Tyr Pro Gly Gln Ser Gly Gly Val Ala
                565                 570                 575
```

```
Leu Phe Asp Ile Leu Ser Gly Lys Arg Ala Pro Ala Gly Arg Leu Val
            580                 585                 590

Thr Thr Gln Tyr Pro Ala Glu Tyr Val His Gln Phe Pro Gln Asn Asp
        595                 600                 605

Met Asn Leu Arg Pro Asp Gly Lys Ser Asn Pro Gly Gln Thr Tyr Ile
    610                 615                 620

Trp Tyr Thr Gly Lys Pro Val Tyr Glu Phe Gly Ser Gly Leu Phe Tyr
625                 630                 635                 640

Thr Thr Phe Lys Glu Thr Leu Ala Ser His Pro Lys Ser Leu Lys Phe
                645                 650                 655

Asn Thr Ser Ser Ile Leu Ser Ala Pro His Pro Gly Tyr Thr Tyr Ser
            660                 665                 670

Glu Gln Ile Pro Val Phe Thr Phe Glu Ala Asn Ile Lys Asn Ser Gly
        675                 680                 685

Lys Thr Glu Ser Pro Tyr Thr Ala Met Leu Phe Val Arg Thr Ser Asn
    690                 695                 700

Ala Gly Pro Ala Pro Tyr Pro Asn Lys Trp Leu Val Gly Phe Asp Arg
705                 710                 715                 720

Leu Ala Asp Ile Lys Pro Gly His Ser Ser Lys Leu Ser Ile Pro Ile
                725                 730                 735

Pro Val Ser Ala Leu Ala Arg Val Asp Ser His Gly Asn Arg Ile Val
            740                 745                 750

Tyr Pro Gly Lys Tyr Glu Leu Ala Leu Asn Thr Asp Glu Ser Val Lys
        755                 760                 765

Leu Glu Phe Glu Leu Val Gly Glu Glu Val Thr Ile
    770                 775                 780
```

<210> SEQ ID NO 19
<211> LENGTH: 2779
<212> TYPE: DNA
<213> ORGANISM: Trichoderma reesei

<400> SEQUENCE: 19

```
atgtccgcgt ctagtgattt atatgtagaa tgatcacaat tcatgtaact gcgttttcgc      60

acatgcaaaa agccctaacg tgagactgag ccacttccta gttttcgtat catgtcagtt     120

gcaaggttac accacaatgc agctcaacga gacaacgctg ccagcccata ataatggata     180

gctggttgta gagagattaa gaagagaatg ctgtttcaga aggaagacta tatcatagca     240

gctgctacat ttccctcttt ccctctttcc atcccttaat agatacgtac ccttgcaatt     300

ggccgtttcg gaagagcttt tctgcttatc ctaaccacct acgccagaat accggtggaa     360

taatcagtgc tcaataggga aacccccaac tgcagcatat aagcctatta acaagacgtc     420

ccaacatgca ttttccttca gtccgcagca ggctatagag agtaggcaat ttacacacca     480

cttttagcct ctgcacatat ctcaccacat ttgcattacg gcatccacta ttacaaccac     540

ttggcacctg atggctttgc tctacccata tcggttttta cgttccgctg tgttcagtcg     600

ttaaatccgt ggtggagcag aacgaccagc ttctcgtatc gggaactccg cttatccgat     660

accctcagtc gaacccttcg tgatactcag cctaaataac atcgcatcgt agcagacaac     720

ttcagtaatt tttgtggggt aatggtcaga tcgctcctct tatatataaa gcagaggtta     780

gtgggctaag gaaattcgtg gttcgcttat agtagagctg tcagttgccc ttcccgaact     840

gttagacggg atggctggta agcttatcct cgtggctcta gcaagccttg tatcactctc     900

tattcagcag aattgcgcag cattattgta agagtgttga gcgtgttgag taccatctgt     960
```

```
atcgttgcta acgtaggctt ttagtggcca atgtggaggc atagggtggt ccggcaccac   1020

atgttgcgtt gctggcgccc agtgcagttt tgtcaatgac tggtactccc agtgccttgc   1080

gtcaaccgta tgagctccga tccgggccgt caatatcttc taactccaga ctgtacaggg   1140

cggaaacccc ccaaacggaa caacttcctc tagcttggtt tcacggacgt cgtcagcatc   1200

ctcatccgtc ggctcgtctt cacccggcgg caactcacca actggcagtg cttccaccta   1260

cacaaccaca gatacagcta ccgtggctcc tcattcgcag tctccttacc ccagcattgc   1320

cgcatccagt tgcggatcgt ggaccctcgt ggataatgtt tgctgcccat catattgtgc   1380

taatgatgac acatccgagt catgctcagg ctgcggtacc tgcactacgc cgccctcggc   1440

ggactgcaaa tccggaacca tgtatccaga ggtccatcac gtatccagca acgagagctg   1500

gcactacagt gtaagatgac caacgctggg gtatctaatc ctttgtcttc ctcggcgtgc   1560

tgaccttgga gcatttagag atcaacccac tttggcctaa cgagcggcgg ggcctgtggc   1620

tttggcctgt acggtctctg cacaaagggc agtgttacag ccagctggac ggatcccatg   1680

cttggcgcga cgtgtgacgc tttttgtaca gcgtatcccc tgctttgcaa agaccctacc   1740

ggcactaccc ttcgtggcaa cttcgcagct ccaaacggcg attactacac ccaagttggg   1800

gaccccgaga ggcaatcatt ttctggtgta gtattcactg acagtgcgat agttctggtc   1860

ctcgttgcca ggagccctcg ataactacct gtcctgcggc gagtgcattg agctgataca   1920

aacaaagccc gatgggaccg attatgctgt cggagaagcc ggctacacgg atccaattac   1980

tctcgagatt gtggacagct gcccgtgcag cgcgaactcc aagtggtgct gtcagagagc   2040

cccgtccatc ccgtccattg tactacatgc gccaaccgaa tggccctggc taacatctcg   2100

caggtggtcc gggcgccgat cattgcggag agatcgactt caaatacggc tgtcctcttc   2160

ctgctgacag cattcatctc gacctgtcag acattgccat gggccgtttg cagggcaatg   2220

gatcactaac caatggcgtc atcccgactc gatatagaag agtccaatgc cccaaagttg   2280

ggaacgccta catttggctt cgaaatggcg gagggcctta ctattttgct ctcacggcag   2340

tcaacaccaa cggaccgggc tcagtcacca aaatcgagat caagggcgca gacaccgaca   2400

actgggttgc cttggtccat gacccaaact atacgagtag ccgcccacaa gaacgctatg   2460

gcagttgggt aatcccacag ggatcagggc cctttaactt gcctgttgga attcgtctga   2520

ctagcccaac gggggaacag attgtgaatg aacaggccat caagacattc actcctccgg   2580

ccacaggtga ccccaatttt tactacattg acattggtgt gcagtttagc cagaattgat   2640

ggcaagcatt gggcaatggg cttcttgctg tgggacaatg atgtaggcta gattctcaat   2700

gcttcaagta tgtggtgtac gtcttcgtgt gtatagatag gtatgctgtt cacttaaata   2760

cacatccttt ggtacgttg                                                 2779
```

```
<210> SEQ ID NO 20
<211> LENGTH: 493
<212> TYPE: PRT
<213> ORGANISM: Trichoderma reesei

<400> SEQUENCE: 20

Met Ala Gly Lys Leu Ile Leu Val Ala Leu Ala Ser Leu Val Ser Leu
1               5                   10                  15

Ser Ile Gln Gln Asn Cys Ala Ala Leu Phe Gly Gln Cys Gly Gly Ile
            20                  25                  30

Gly Trp Ser Gly Thr Thr Cys Cys Val Ala Gly Ala Gln Cys Ser Phe
        35                  40                  45
```

```
Val Asn Asp Trp Tyr Ser Gln Cys Leu Ala Ser Thr Gly Gly Asn Pro
    50                  55                  60

Pro Asn Gly Thr Thr Ser Ser Ser Leu Val Ser Arg Thr Ser Ser Ala
65                  70                  75                  80

Ser Ser Ser Val Gly Ser Ser Ser Pro Gly Gly Asn Ser Pro Thr Gly
                85                  90                  95

Ser Ala Ser Thr Tyr Thr Thr Thr Asp Thr Ala Thr Val Ala Pro His
            100                 105                 110

Ser Gln Ser Pro Tyr Pro Ser Ile Ala Ala Ser Ser Cys Gly Ser Trp
        115                 120                 125

Thr Leu Val Asp Asn Val Cys Cys Pro Ser Tyr Cys Ala Asn Asp Asp
    130                 135                 140

Thr Ser Glu Ser Cys Ser Gly Cys Gly Thr Cys Thr Thr Pro Pro Ser
145                 150                 155                 160

Ala Asp Cys Lys Ser Gly Thr Met Tyr Pro Glu Val His His Val Ser
                165                 170                 175

Ser Asn Glu Ser Trp His Tyr Ser Arg Ser Thr His Phe Gly Leu Thr
            180                 185                 190

Ser Gly Gly Ala Cys Gly Phe Gly Leu Tyr Gly Leu Cys Thr Lys Gly
        195                 200                 205

Ser Val Thr Ala Ser Trp Thr Asp Pro Met Leu Gly Ala Thr Cys Asp
    210                 215                 220

Ala Phe Cys Thr Ala Tyr Pro Leu Leu Cys Lys Asp Pro Thr Gly Thr
225                 230                 235                 240

Thr Leu Arg Gly Asn Phe Ala Ala Pro Asn Gly Asp Tyr Tyr Thr Gln
                245                 250                 255

Phe Trp Ser Ser Leu Pro Gly Ala Leu Asp Asn Tyr Leu Ser Cys Gly
            260                 265                 270

Glu Cys Ile Glu Leu Ile Gln Thr Lys Pro Asp Gly Thr Asp Tyr Ala
        275                 280                 285

Val Gly Glu Ala Gly Tyr Thr Asp Pro Ile Thr Leu Glu Ile Val Asp
    290                 295                 300

Ser Cys Pro Cys Ser Ala Asn Ser Lys Trp Cys Cys Gly Pro Gly Ala
305                 310                 315                 320

Asp His Cys Gly Glu Ile Asp Phe Lys Tyr Gly Cys Pro Leu Pro Ala
                325                 330                 335

Asp Ser Ile His Leu Asp Leu Ser Asp Ile Ala Met Gly Arg Leu Gln
            340                 345                 350

Gly Asn Gly Ser Leu Thr Asn Gly Val Ile Pro Thr Arg Tyr Arg Arg
        355                 360                 365

Val Gln Cys Pro Lys Val Gly Asn Ala Tyr Ile Trp Leu Arg Asn Gly
    370                 375                 380

Gly Gly Pro Tyr Tyr Phe Ala Leu Thr Ala Val Asn Thr Asn Gly Pro
385                 390                 395                 400

Gly Ser Val Thr Lys Ile Glu Ile Lys Gly Ala Asp Thr Asp Asn Trp
                405                 410                 415

Val Ala Leu Val His Asp Pro Asn Tyr Thr Ser Ser Arg Pro Gln Glu
            420                 425                 430

Arg Tyr Gly Ser Trp Val Ile Pro Gln Gly Ser Gly Pro Phe Asn Leu
        435                 440                 445

Pro Val Gly Ile Arg Leu Thr Ser Pro Thr Gly Glu Gln Ile Val Asn
    450                 455                 460
```

```
Glu Gln Ala Ile Lys Thr Phe Thr Pro Pro Ala Thr Gly Asp Pro Asn
465                 470                 475                 480

Phe Tyr Tyr Ile Asp Ile Gly Val Gln Phe Ser Gln Asn
                485                 490


<210> SEQ ID NO 21
<211> LENGTH: 2777
<212> TYPE: DNA
<213> ORGANISM: Trichoderma reesei

<400> SEQUENCE: 21

atggtgcgct ccgccctatt cgtgtcgctg ctcgcgacct tctccggagt cattgcccgt      60

gtctccgggc atgggtcaaa gatcgttccc ggcgcgtaca tcttcgaatt cgaggattca     120

caggtgagtc tcgctcggcc gttggcaccg gatgacatgc ctccagctgt ggcaatgctg     180

acgggactcc atccaggaca cggccgattt ctacaagaag ctcaacggcg agggctcaac     240

gcgcctgaag ttcgactaca agctgttcaa gggcgtctcc gtccagctca aggacctaga     300

caaccatgag gcaaaggccc agcagatggc ccagctgcct gctgtcaaga acgtgtggcc     360

cgtcaccctc atcgacgccc ccaaccccaa ggtcgagtgg gttgccggca gcacggcgcc     420

tactctggag agcagggcga tcaagaagcc accgatcccg aacgactcga gcgacttccc     480

cacgcaccag atgacccaaa tcgacaagct gcgagccaag ggctacacgg gcaagggcgt     540

cagggttgcc gtcattgata caggcgtgag tacaagccca ctgtcccaag caagtcgtgt     600

agacgctcac atacggccag attgactaca cccaccctgc tctcggcggc tgctttggta     660

ggggctgtct ggtctccttt ggcaccgatt tggtcggtga cgactacacc ggctttaaca     720

cgcctgtccc cgatgatgac cccgtcgact gcgccggcca cggttctcac gttgctggta     780

tcattgctgc gcaggagaat ccgtacggct tcactggcgg cgctcccgat gtcaccctcg     840

gcgcttatcg agtctttggc tgcgacggcc aggccggtaa cgatgtcctg atttccgctt     900

acaaccaggc ctttgaggac ggtgcccaga tcatcactgc ctccattggc ggtccctctg     960

gctgggctga ggagccgtgg gccgttgccg tcacccgcat cgttgaggca ggtgttccct    1020

gcacggtctc tgccggcaac gagggcgact ctggtctctt ctttgccagc acggcagcca    1080

atggcaagaa agtcattgct gtcgcctccg tcgacaacga gaacatccct tcagtgctgt    1140

ccgtggcctc ttacaaaatt gacagcggcg ctgcccagga ctttggctac gtctcctcct    1200

ccaaggcgtg ggacggcgtg agcaagcccc tgtatgctgt gtcgttcgac actactattc    1260

ccgacgatgg ctgctcgcct ctccctgaca gcactcccga cctctctgac tacattgtcc    1320

ttgtccgccg tggcacctgc acctttgtcc agaaagccca aaatgtcgct gcaaagggcg    1380

ccaagtacct gctctattat aacaacattc ccggtgcgct ggccgtcgat gtcagcgccg    1440

tccccgagat tgaggctgtc ggcatggtcg atgacaagac gggtgctacc tggattgccg    1500

ccctcaagga tggaaagacc gtcaccctga cactgactga cccgatcgag agcgagaagc    1560

aaattcagtt cagcgacaac ccgacaactg gcggtgctct gagcggctac acaacctggg    1620

gccctacctg ggagctggac gtcaagcctc agatcagctc tcccggcggc aacattctct    1680

ccacgtaccc cgtggctctc ggaggatatg ccaccctgtc cggtacctcc atggcctgcc    1740

ccctgacggc ggctgctgtt gctctgattg gacaagctcg tggcaccttt gaccctgcct    1800

tgatcgacaa cttgttggca acgactgcga acccccagct gttcaacgac ggcgagaagt    1860

tctacgactt cctcgccccc gttccccaac agggcggtgg cctcatccag gcctacgatg    1920

ccgcctttgc gaccactctc ctgtcaccgt ccagcctgtc gttcaacgac actgaccact    1980
```

```
tcatcaagaa gaagcagatc accctcaaga acaccagcaa gcagagggtc acctacaagc   2040

tcaaccacgt ccccaccaac accttttaca ctctggcacc cggtaacggc tatccagctc   2100

cctttcctaa cgacgccgtt gccgctcacg ccaatctcaa gtttaatctg cagcaagtga   2160

ccctgcccgc cggcaggtcc atcactgtcg acgtcttccc tactccccccc agggacgtcg   2220

acgccaagcg cctggcgctt tggtcgggct acatcacggt caacggcacg gatggcacca   2280

gtctgtctgt cccgtaccag ggcctcaccg gctccctgca caagcagaag gtgctctatc   2340

cggaggactc ctggatcgcc gattccaccg atgaaagcct ggcccctgtt gagaacggca   2400

ccgtcttcac cattcccgcg ccgggcaacg ctggccccga tgacaagctc ccatcgctcg   2460

tcgtcagccc tgcccttggc tctcgttatg tccgcgttga tctcgtcctc ctgtccgcgc   2520

ctcctcatgg caccaagctc aagacggtca agttcctcga caccacctcc atcggccagc   2580

ctgccggatc accgctcctc tggatcagcc gtggcgccaa ccctattgct tggaccggcg   2640

agctgtctga caacaagttt gctccccctg gaacgtacaa ggccgtgttc catgctctgc   2700

gtattttcgg caacgagaag aagaaggagg actgggatgt gagcgaatct cctgccttca   2760

ccatcaagta tgcgtag                                                  2777

<210> SEQ ID NO 22
<211> LENGTH: 882
<212> TYPE: PRT
<213> ORGANISM: Trichoderma reesei

<400> SEQUENCE: 22

Met Val Arg Ser Ala Leu Phe Val Ser Leu Leu Ala Thr Phe Ser Gly
1               5                   10                  15

Val Ile Ala Arg Val Ser Gly His Gly Ser Lys Ile Val Pro Gly Ala
            20                  25                  30

Tyr Ile Phe Glu Phe Glu Asp Ser Gln Asp Thr Ala Asp Phe Tyr Lys
        35                  40                  45

Lys Leu Asn Gly Glu Gly Ser Thr Arg Leu Lys Phe Asp Tyr Lys Leu
    50                  55                  60

Phe Lys Gly Val Ser Val Gln Leu Lys Asp Leu Asp Asn His Glu Ala
65                  70                  75                  80

Lys Ala Gln Gln Met Ala Gln Leu Pro Ala Val Lys Asn Val Trp Pro
                85                  90                  95

Val Thr Leu Ile Asp Ala Pro Asn Pro Lys Val Glu Trp Val Ala Gly
            100                 105                 110

Ser Thr Ala Pro Thr Leu Glu Ser Arg Ala Ile Lys Lys Pro Pro Ile
        115                 120                 125

Pro Asn Asp Ser Ser Asp Phe Pro Thr His Gln Met Thr Gln Ile Asp
    130                 135                 140

Lys Leu Arg Ala Lys Gly Tyr Thr Gly Lys Gly Val Arg Val Ala Val
145                 150                 155                 160

Ile Asp Thr Gly Ile Asp Tyr Thr His Pro Ala Leu Gly Gly Cys Phe
                165                 170                 175

Gly Arg Gly Cys Leu Val Ser Phe Gly Thr Asp Leu Val Gly Asp Asp
            180                 185                 190

Tyr Thr Gly Phe Asn Thr Pro Val Pro Asp Asp Asp Pro Val Asp Cys
        195                 200                 205

Ala Gly His Gly Ser His Val Ala Gly Ile Ile Ala Ala Gln Glu Asn
    210                 215                 220
```

-continued

```
Pro Tyr Gly Phe Thr Gly Gly Ala Pro Asp Val Thr Leu Gly Ala Tyr
225                 230                 235                 240

Arg Val Phe Gly Cys Asp Gly Gln Ala Gly Asn Asp Val Leu Ile Ser
                245                 250                 255

Ala Tyr Asn Gln Ala Phe Glu Asp Gly Ala Gln Ile Ile Thr Ala Ser
            260                 265                 270

Ile Gly Gly Pro Ser Gly Trp Ala Glu Glu Pro Trp Ala Val Ala Val
        275                 280                 285

Thr Arg Ile Val Glu Ala Gly Val Pro Cys Thr Val Ser Ala Gly Asn
    290                 295                 300

Glu Gly Asp Ser Gly Leu Phe Phe Ala Ser Thr Ala Ala Asn Gly Lys
305                 310                 315                 320

Lys Val Ile Ala Val Ala Ser Val Asp Asn Glu Asn Ile Pro Ser Val
                325                 330                 335

Leu Ser Val Ala Ser Tyr Lys Ile Asp Ser Gly Ala Ala Gln Asp Phe
            340                 345                 350

Gly Tyr Val Ser Ser Ser Lys Ala Trp Asp Gly Val Ser Lys Pro Leu
        355                 360                 365

Tyr Ala Val Ser Phe Asp Thr Thr Ile Pro Asp Asp Gly Cys Ser Pro
    370                 375                 380

Leu Pro Asp Ser Thr Pro Asp Leu Ser Asp Tyr Ile Val Leu Val Arg
385                 390                 395                 400

Arg Gly Thr Cys Thr Phe Val Gln Lys Ala Gln Asn Val Ala Ala Lys
                405                 410                 415

Gly Ala Lys Tyr Leu Leu Tyr Tyr Asn Asn Ile Pro Gly Ala Leu Ala
            420                 425                 430

Val Asp Val Ser Ala Val Pro Glu Ile Glu Ala Val Gly Met Val Asp
        435                 440                 445

Asp Lys Thr Gly Ala Thr Trp Ile Ala Ala Leu Lys Asp Gly Lys Thr
    450                 455                 460

Val Thr Leu Thr Leu Thr Asp Pro Ile Glu Ser Glu Lys Gln Ile Gln
465                 470                 475                 480

Phe Ser Asp Asn Pro Thr Thr Gly Gly Ala Leu Ser Gly Tyr Thr Thr
                485                 490                 495

Trp Gly Pro Thr Trp Glu Leu Asp Val Lys Pro Gln Ile Ser Ser Pro
            500                 505                 510

Gly Gly Asn Ile Leu Ser Thr Tyr Pro Val Ala Leu Gly Gly Tyr Ala
        515                 520                 525

Thr Leu Ser Gly Thr Ser Met Ala Cys Pro Leu Thr Ala Ala Ala Val
    530                 535                 540

Ala Leu Ile Gly Gln Ala Arg Gly Thr Phe Asp Pro Ala Leu Ile Asp
545                 550                 555                 560

Asn Leu Leu Ala Thr Thr Ala Asn Pro Gln Leu Phe Asn Asp Gly Glu
                565                 570                 575

Lys Phe Tyr Asp Phe Leu Ala Pro Val Pro Gln Gln Gly Gly Gly Leu
            580                 585                 590

Ile Gln Ala Tyr Asp Ala Ala Phe Ala Thr Thr Leu Leu Ser Pro Ser
        595                 600                 605

Ser Leu Ser Phe Asn Asp Thr Asp His Phe Ile Lys Lys Lys Gln Ile
    610                 615                 620

Thr Leu Lys Asn Thr Ser Lys Gln Arg Val Thr Tyr Lys Leu Asn His
625                 630                 635                 640

Val Pro Thr Asn Thr Phe Tyr Thr Leu Ala Pro Gly Asn Gly Tyr Pro
```

```
                645                 650                 655

Ala Pro Phe Pro Asn Asp Ala Val Ala Ala His Ala Asn Leu Lys Phe
            660                 665                 670

Asn Leu Gln Gln Val Thr Leu Pro Ala Gly Arg Ser Ile Thr Val Asp
        675                 680                 685

Val Phe Pro Thr Pro Pro Arg Asp Val Asp Ala Lys Arg Leu Ala Leu
    690                 695                 700

Trp Ser Gly Tyr Ile Thr Val Asn Gly Thr Asp Gly Thr Ser Leu Ser
705                 710                 715                 720

Val Pro Tyr Gln Gly Leu Thr Gly Ser Leu His Lys Gln Lys Val Leu
                725                 730                 735

Tyr Pro Glu Asp Ser Trp Ile Ala Asp Ser Thr Asp Glu Ser Leu Ala
            740                 745                 750

Pro Val Glu Asn Gly Thr Val Phe Thr Ile Pro Ala Pro Gly Asn Ala
        755                 760                 765

Gly Pro Asp Asp Lys Leu Pro Ser Leu Val Val Ser Pro Ala Leu Gly
    770                 775                 780

Ser Arg Tyr Val Arg Val Asp Leu Val Leu Leu Ser Ala Pro Pro His
785                 790                 795                 800

Gly Thr Lys Leu Lys Thr Val Lys Phe Leu Asp Thr Thr Ser Ile Gly
                805                 810                 815

Gln Pro Ala Gly Ser Pro Leu Leu Trp Ile Ser Arg Gly Ala Asn Pro
            820                 825                 830

Ile Ala Trp Thr Gly Glu Leu Ser Asp Asn Lys Phe Ala Pro Pro Gly
        835                 840                 845

Thr Tyr Lys Ala Val Phe His Ala Leu Arg Ile Phe Gly Asn Glu Lys
    850                 855                 860

Lys Lys Glu Asp Trp Asp Val Ser Glu Ser Pro Ala Phe Thr Ile Lys
865                 870                 875                 880

Tyr Ala


<210> SEQ ID NO 23
<211> LENGTH: 1302
<212> TYPE: DNA
<213> ORGANISM: Trichoderma reesei

<400> SEQUENCE: 23

atgcagacct ttggagcttt tctcgtttcc ttcctcgccg ccagcggcct ggccgcggcc     60

ctccccaccg agggtcagaa gacggcttcc gtcgaggtcc agtacaacaa gaactacgtc    120

ccccacggcc ctactgctct cttcaaggcc aagagaaagt atggcgctcc catcagcgac    180

aacctgaagt ctctcgtggc tgccaggcag gccaagcagg ctctcgccaa gcgccagacc    240

ggctcggcgc ccaaccaccc cagtgacagc gccgattcgg agtacatcac ctccgtctcc    300

atcggcactc cggctcaggt cctcccccctg gactttgaca ccggctcctc cgacctgtgg    360

gtctttagct ccgagacgcc caagtcttcg gccaccggcc acgccatcta cacgccctcc    420

aagtcgtcca cctccaagaa ggtgtctggc gccagctggt ccatcagcta cggcgacggc    480

agcagctcca gcggcgatgt ctacaccgac aaggtcacca tcggaggctt cagcgtcaac    540

acccagggcg tcgagtctgc caccccgcgtg tccaccgagt tcgtccagga cacggtcatc    600

tctggcctcg tcggccttgc ctttgacagc ggcaaccagg tcaggccgca cccgcagaag    660

acgtggttct ccaacgccgc cagcagcctg gctgagcccc ttttcactgc cgacctgagg    720

cacggacaga gtaagtagac actcactgga attcgttcct ttcccgatca tcatgaaagc    780
```

```
aagtagactg actgaaccaa acaactagac ggcagctaca actttggcta catcgacacc    840

agcgtcgcca agggccccgt tgcctacacc cccgttgaca acagccaggg cttctgggag    900

ttcactgcct cgggctactc tgtcggcggc ggcaagctca accgcaactc catcgacggc    960

attgccgaca ccggcaccac cctgctcctc ctcgacgaca acgtcgtcga tgcctactac   1020

gccaacgtcc agtcggccca gtacgacaac cagcaggagg gtgtcgtctt cgactgcgac   1080

gaggacctcc cttcgttcag cttcggtgtt ggaagctcca ccatcaccat ccctggcgat   1140

ctgctgaacc tgactcccct cgaggagggc agctccacct gcttcggtgg cctccagagc   1200

agctccggca ttggcatcaa catctttggt gacgttgccc tcaaggctgc cctggttgtc   1260

tttgacctcg gcaacgagcg cctgggctgg gctcagaaat aa                      1302
```

```
<210> SEQ ID NO 24
<211> LENGTH: 407
<212> TYPE: PRT
<213> ORGANISM: Trichoderma reesei

<400> SEQUENCE: 24

Met Gln Thr Phe Gly Ala Phe Leu Val Ser Phe Leu Ala Ala Ser Gly
1               5                   10                  15

Leu Ala Ala Ala Leu Pro Thr Glu Gly Gln Lys Thr Ala Ser Val Glu
            20                  25                  30

Val Gln Tyr Asn Lys Asn Tyr Val Pro His Gly Pro Thr Ala Leu Phe
        35                  40                  45

Lys Ala Lys Arg Lys Tyr Gly Ala Pro Ile Ser Asp Asn Leu Lys Ser
    50                  55                  60

Leu Val Ala Ala Arg Gln Ala Lys Gln Ala Leu Ala Lys Arg Gln Thr
65                  70                  75                  80

Gly Ser Ala Pro Asn His Pro Ser Asp Ser Ala Asp Ser Glu Tyr Ile
                85                  90                  95

Thr Ser Val Ser Ile Gly Thr Pro Ala Gln Val Leu Pro Leu Asp Phe
            100                 105                 110

Asp Thr Gly Ser Ser Asp Leu Trp Val Phe Ser Ser Glu Thr Pro Lys
        115                 120                 125

Ser Ser Ala Thr Gly His Ala Ile Tyr Thr Pro Ser Lys Ser Ser Thr
    130                 135                 140

Ser Lys Lys Val Ser Gly Ala Ser Trp Ser Ile Ser Tyr Gly Asp Gly
145                 150                 155                 160

Ser Ser Ser Ser Gly Asp Val Tyr Thr Asp Lys Val Thr Ile Gly Gly
                165                 170                 175

Phe Ser Val Asn Thr Gln Gly Val Glu Ser Ala Thr Arg Val Ser Thr
            180                 185                 190

Glu Phe Val Gln Asp Thr Val Ile Ser Gly Leu Val Gly Leu Ala Phe
        195                 200                 205

Asp Ser Gly Asn Gln Val Arg Pro His Pro Gln Lys Thr Trp Phe Ser
    210                 215                 220

Asn Ala Ala Ser Ser Leu Ala Glu Pro Leu Phe Thr Ala Asp Leu Arg
225                 230                 235                 240

His Gly Gln Asn Gly Ser Tyr Asn Phe Gly Tyr Ile Asp Thr Ser Val
                245                 250                 255

Ala Lys Gly Pro Val Ala Tyr Thr Pro Val Asp Asn Ser Gln Gly Phe
            260                 265                 270

Trp Glu Phe Thr Ala Ser Gly Tyr Ser Val Gly Gly Gly Lys Leu Asn
```

```
        275                 280                 285

Arg Asn Ser Ile Asp Gly Ile Ala Asp Thr Gly Thr Thr Leu Leu Leu
    290                 295                 300

Leu Asp Asp Asn Val Val Asp Ala Tyr Tyr Ala Asn Val Gln Ser Ala
305                 310                 315                 320

Gln Tyr Asp Asn Gln Gln Glu Gly Val Val Phe Asp Cys Asp Glu Asp
                325                 330                 335

Leu Pro Ser Phe Ser Phe Gly Val Gly Ser Ser Thr Ile Thr Ile Pro
            340                 345                 350

Gly Asp Leu Leu Asn Leu Thr Pro Leu Glu Glu Gly Ser Ser Thr Cys
        355                 360                 365

Phe Gly Gly Leu Gln Ser Ser Ser Gly Ile Gly Ile Asn Ile Phe Gly
    370                 375                 380

Asp Val Ala Leu Lys Ala Ala Leu Val Val Phe Asp Leu Gly Asn Glu
385                 390                 395                 400

Arg Leu Gly Trp Ala Gln Lys
                405


<210> SEQ ID NO 25
<211> LENGTH: 933
<212> TYPE: DNA
<213> ORGANISM: Trichoderma reesei

<400> SEQUENCE: 25

atggctcccg cttcccaagt cgtctcagct ctcatgctgc ccgctctcgc cttgggagcc      60

gccatccagc cccgtggcgc tgacatcgtg ggaggaaccg ccgcctcgct cggcgagttc     120

ccctacattg tcagtctgca gaaccccaac cagggcggcc acttctgcgg tggtgtcttg     180

gtcaacgcca acaccgtcgt taccgccgct cactgctccg ttgtctaccc tgcctcgcag     240

atccgcgtcc gcgccggtac tcttgtaagt ttgcttgttt cgagtcctcg aaaagacatg     300

aacctgcgat ggctaaccaa agcacctcct ctctgataga cctggaactc tggcggtacc     360

ctggtcggcg tctcccagat catcgtgaac ccgtcctaca acgaccgcac caccgacttt     420

gacgttgccg tctggcacct gtccagccct atccgcgaga gctccaccat tggctacgcc     480

actcttcccg cccagggctc cgaccccgtg gccggctcga ccgtcaccac cgctggctgg     540

taagcatcat catcattgat agccgggaca tgctggcgtc aaatccgagt ttgctaacca     600

ttcttccaaa aaaacagggg caccaccagc gagaactcca actccatccc ctcccgcctg     660

aacaaggtct ccgtccccgt cgtcgcccgc tccacctgcc aggccgacta ccgcagccag     720

gggctcagtg tcaccaacaa catgttctgc gccggcctca cccagggcgg caaggactct     780

tgctctggcg actctggcgg ccccatcgtt gacgccaacg gtgtcctcca gggtgtcgtt     840

tcttggggta tcggctgtgc tgaggccggt ttccctggtg tctacaccag aatcggcaac     900

tttgtcaact acatcaacca gaacctcgca taa                                  933


<210> SEQ ID NO 26
<211> LENGTH: 259
<212> TYPE: PRT
<213> ORGANISM: Trichoderma reesei

<400> SEQUENCE: 26

Met Ala Pro Ala Ser Gln Val Val Ser Ala Leu Met Leu Pro Ala Leu
1               5                   10                  15

Ala Leu Gly Ala Ala Ile Gln Pro Arg Gly Ala Asp Ile Val Gly Gly
            20                  25                  30
```

```
Thr Ala Ala Ser Leu Gly Glu Phe Pro Tyr Ile Val Ser Leu Gln Asn
        35                  40                  45

Pro Asn Gln Gly Gly His Phe Cys Gly Gly Val Leu Val Asn Ala Asn
    50                  55                  60

Thr Val Val Thr Ala Ala His Cys Ser Val Val Tyr Pro Ala Ser Gln
65                  70                  75                  80

Ile Arg Val Arg Ala Gly Thr Leu Thr Trp Asn Ser Gly Gly Thr Leu
                85                  90                  95

Val Gly Val Ser Gln Ile Ile Val Asn Pro Ser Tyr Asn Asp Arg Thr
            100                 105                 110

Thr Asp Phe Asp Val Ala Val Trp His Leu Ser Ser Pro Ile Arg Glu
        115                 120                 125

Ser Ser Thr Ile Gly Tyr Ala Thr Leu Pro Ala Gln Gly Ser Asp Pro
    130                 135                 140

Val Ala Gly Ser Thr Val Thr Thr Ala Gly Trp Gly Thr Thr Ser Glu
145                 150                 155                 160

Asn Ser Asn Ser Ile Pro Ser Arg Leu Asn Lys Val Ser Val Pro Val
                165                 170                 175

Val Ala Arg Ser Thr Cys Gln Ala Asp Tyr Arg Ser Gln Gly Leu Ser
            180                 185                 190

Val Thr Asn Asn Met Phe Cys Ala Gly Leu Thr Gln Gly Gly Lys Asp
        195                 200                 205

Ser Cys Ser Gly Asp Ser Gly Gly Pro Ile Val Asp Ala Asn Gly Val
    210                 215                 220

Leu Gln Gly Val Val Ser Trp Gly Ile Gly Cys Ala Glu Ala Gly Phe
225                 230                 235                 240

Pro Gly Val Tyr Thr Arg Ile Gly Asn Phe Val Asn Tyr Ile Asn Gln
                245                 250                 255

Asn Leu Ala
```

```
<210> SEQ ID NO 27
<211> LENGTH: 1684
<212> TYPE: DNA
<213> ORGANISM: Trichoderma reesei

<400> SEQUENCE: 27

atgcggtccg ttgtcgccct ctccatggcg gccgttgccc aggccagcac attccagatt      60

ggcaccatcc acgagaagtc ggcccccgtg ctgagcaacg tcgaggccaa cgccatcccc     120

gatgcctaca tcatcaagtt caaggaccac gtgggtgagg atgatgcctc caagcaccac     180

gactggatcc agagcatcca cacaaacgtt gagcaggagc gccttgagct ccgcaagcga     240

agcaacgtct ttggcgccga cgacgtcttt gacggtctga agcacacttt caagattggc     300

gacggcttca agggctacgc cggtcacttc cacgagtctg tcattgagca ggtccggaac     360

caccctgacg taagttttgc acagccgccc tcccttttgg ctccccaaca aagctaaccc     420

ctcccaggtt gagtacatcg agcgcgacag cattgtgcac accatgcttc ccctcgagtc     480

caaggacagc atcatcgttg aggactcgtg caacggcgag acggagaagc aggctccctg     540

ggtcttgccc cgtatctctc accgagagac gctcaacttt ggctccttca acaagtacct     600

ctacaccgct gatggtggtg agggtgttga tgcctatgtc attgacaccg gcaccaacat     660

cgagcacgtc gactttgagg gtcgtgccaa gtggggcaag accatccctg ccggcgatga     720

ggacgaggac ggcaacggcc acggcactca ctgctctggt accgttgctg gtaagaagta     780
```

```
cggtgttgcc aagaaggccc acgtctacgc cgtcaaggtg ctccgatcca acggatccgg    840

caccatgtct gacgtcgtca agggcgtcga gtacgctgct ctctcccaca ttgagcaggt    900

gaagaaggcc aagaagggca agcggaaggg cttcaagggc tccgtcgcca acatgtccct    960

cggtggtggc aagacccagg ctcttgacgc tgccgtcaac gccgccgtcc gcgccggtgt   1020

ccactttgcc gttgctgccg gcaacgacaa cgctgatgct tgcaactact cccccgctgc   1080

cgccactgag cccctcaccg tcggtgcttc tgctctcgat gacagccgtg cttacttctc   1140

caactacggc aagtgcactg acatcttcgc ccctggtctg agcatccagt ccacctggat   1200

tggctccaag tatgccgtca acaccatctc tggtacctcc atggcctctc ctcacatctg   1260

cggtctcctg gcctactacc tgtctctcca gcccgctggt gactctgagt tcgctgttgc   1320

ccccatcacc cccaagaagc tcaaggagag cgtcatctct gtcgccacca agaacgccct   1380

ctctgacctg cccgactctg acacccccaa cctgctcgcc tggaacggcg gtggctgcag   1440

caacttctcc cagattgtcg aggccggcag ctacactgtc aagcccaagc agaacaagca   1500

ggccaagctc cccagcacca ttgaggagct cgaggaggcc atcgagggtg actttgaggt   1560

cgtctctggc gagatcgtca agggtgccaa gagctttggc tccaaggcgg agaagtttgc   1620

caagaagatc cacgatctcg tcgaggagga gattgaggag ttcatctctg agctctccga   1680

gtaa                                                                1684
```

<210> SEQ ID NO 28
<211> LENGTH: 540
<212> TYPE: PRT
<213> ORGANISM: Trichoderma reesei

<400> SEQUENCE: 28

```
Met Arg Ser Val Val Ala Leu Ser Met Ala Ala Val Ala Gln Ala Ser
1               5                   10                  15

Thr Phe Gln Ile Gly Thr Ile His Glu Lys Ser Ala Pro Val Leu Ser
            20                  25                  30

Asn Val Glu Ala Asn Ala Ile Pro Asp Ala Tyr Ile Ile Lys Phe Lys
        35                  40                  45

Asp His Val Gly Glu Asp Asp Ala Ser Lys His His Asp Trp Ile Gln
    50                  55                  60

Ser Ile His Thr Asn Val Glu Gln Glu Arg Leu Glu Leu Arg Lys Arg
65                  70                  75                  80

Ser Asn Val Phe Gly Ala Asp Asp Val Phe Asp Gly Leu Lys His Thr
                85                  90                  95

Phe Lys Ile Gly Asp Gly Phe Lys Gly Tyr Ala Gly His Phe His Glu
            100                 105                 110

Ser Val Ile Glu Gln Val Arg Asn His Pro Val Glu Tyr Ile Glu Arg
        115                 120                 125

Asp Ser Ile Val His Thr Met Leu Pro Leu Glu Ser Lys Asp Ser Ile
    130                 135                 140

Ile Val Glu Asp Ser Cys Asn Gly Glu Thr Glu Lys Gln Ala Pro Trp
145                 150                 155                 160

Gly Leu Ala Arg Ile Ser His Arg Glu Thr Leu Asn Phe Gly Ser Phe
                165                 170                 175

Asn Lys Tyr Leu Tyr Thr Ala Asp Gly Gly Glu Gly Val Asp Ala Tyr
            180                 185                 190

Val Ile Asp Thr Gly Thr Asn Ile Glu His Val Asp Phe Glu Gly Arg
        195                 200                 205
```

```
Ala Lys Trp Gly Lys Thr Ile Pro Ala Gly Asp Glu Asp Glu Asp Gly
    210                 215                 220

Asn Gly His Gly Thr His Cys Ser Gly Thr Val Ala Gly Lys Lys Tyr
225                 230                 235                 240

Gly Val Ala Lys Lys Ala His Val Tyr Ala Val Lys Val Leu Arg Ser
                245                 250                 255

Asn Gly Ser Gly Thr Met Ser Asp Val Val Lys Gly Val Glu Tyr Ala
            260                 265                 270

Ala Leu Ser His Ile Glu Gln Val Lys Lys Ala Lys Lys Gly Lys Arg
        275                 280                 285

Lys Gly Phe Lys Gly Ser Val Ala Asn Met Ser Leu Gly Gly Gly Lys
    290                 295                 300

Thr Gln Ala Leu Asp Ala Ala Val Asn Ala Ala Val Arg Ala Gly Val
305                 310                 315                 320

His Phe Ala Val Ala Ala Gly Asn Asp Asn Ala Asp Ala Cys Asn Tyr
                325                 330                 335

Ser Pro Ala Ala Ala Thr Glu Pro Leu Thr Val Gly Ala Ser Ala Leu
            340                 345                 350

Asp Asp Ser Arg Ala Tyr Phe Ser Asn Tyr Gly Lys Cys Thr Asp Ile
        355                 360                 365

Phe Ala Pro Gly Leu Ser Ile Gln Ser Thr Trp Ile Gly Ser Lys Tyr
    370                 375                 380

Ala Val Asn Thr Ile Ser Gly Thr Ser Met Ala Ser Pro His Ile Cys
385                 390                 395                 400

Gly Leu Leu Ala Tyr Tyr Leu Ser Leu Gln Pro Ala Gly Asp Ser Glu
                405                 410                 415

Phe Ala Val Ala Pro Ile Thr Pro Lys Lys Leu Lys Glu Ser Val Ile
            420                 425                 430

Ser Val Ala Thr Lys Asn Ala Leu Ser Asp Leu Pro Asp Ser Asp Thr
        435                 440                 445

Pro Asn Leu Leu Ala Trp Asn Gly Gly Gly Cys Ser Asn Phe Ser Gln
    450                 455                 460

Ile Val Glu Ala Gly Ser Tyr Thr Val Lys Pro Lys Gln Asn Lys Gln
465                 470                 475                 480

Ala Lys Leu Pro Ser Thr Ile Glu Glu Leu Glu Glu Ala Ile Glu Gly
                485                 490                 495

Asp Phe Glu Val Val Ser Gly Glu Ile Val Lys Gly Ala Lys Ser Phe
            500                 505                 510

Gly Ser Lys Ala Glu Lys Phe Ala Lys Lys Ile His Asp Leu Val Glu
        515                 520                 525

Glu Glu Ile Glu Glu Phe Ile Ser Glu Leu Ser Glu
    530                 535                 540
```

<210> SEQ ID NO 29
<211> LENGTH: 1341
<212> TYPE: DNA
<213> ORGANISM: Trichoderma reesei

<400> SEQUENCE: 29

```
atgaagagcg cgttacttgc cgccgcggcg cttgtcggct ccgcccaagc cggcattcac      60

aagatgaagc tgcagaaggt ctccctggag cagcagctgg taagacgaca ccctcatcca     120

cggcctcgta ctctagccaa gcgcaatcac tgacacgccg cctctctcat ctaggagggt     180

tcgagcatcg aggcccacgt ccagcagctc ggccagaagt acatgggcgt ccgccctact     240
```

```
agccgtgccg aggtcatgtt caacgacaag ccgcccaagg tccagggcgg gcacccggtt    300

cccgtcacca acttcatgaa tgcccaatgt aagtcgtgat gcgcagcaca gcacgagagt    360

cccgctccca ggtagcgagc acatgcttac taacttgctc ggacagactt ctctgagatt    420

accatcggca cccccctca gtcgttcaag gttgtcctcg acacgggaag ctctaacctc    480

tgggttccct ctcagtcgtg caacagcatc gcctgcttcc tgcactccac gtacgattcg    540

tcttcatcgt cgacgtacaa gcccaacggc tccgattttg agatccacta cggatcaggt    600

agcttgactg gcttcatctc caacgatgtc gtgacgattg gcgacctcaa gatcaagggg    660

caggactttg ccgaggcaac cagcgagccc ggccttgcct ttgctttcgg ccgcttcgac    720

ggcattcttg gccttggcta cgataccatc tcggtcaatg gcattgtccc cccttttac    780

cagatggtca accagaagct gatcgacgag cccgtctttg ctttctacct gggaagcagc    840

gacgagggtt ccgaggctgt ctttggcggc gtcgacgatg ctcactacga gggcaagatt    900

gagtacattc ccctgcgccg caaggcctac tgggaggtgg accttgactc cattgccttc    960

ggtgacgagg tcgccgagct cgagaacact ggcgccatcc ttgacaccgg cacctctctc   1020

aacgtcctcc cctcgggcct cgccgagctc ctgaacgctg agattggcgc caagaagggc   1080

tttggcggtc agtacactgt tgactgctcc aagcgtgatt ccctccccga catcaccttc   1140

agcctggccg gctccaagta cagccttccc gccagcgact acatcattga gatgtctggc   1200

aactgcattt cgtccttcca gggcatggac ttccccgagc ccgtgggccc cctggtcatt   1260

ctgggtgatg ctttcttgcg ccgctactac tccgtctacg accttggcag ggacgccgtt   1320

ggtcttgcca aggccaaata a                                               1341


<210> SEQ ID NO 30
<211> LENGTH: 395
<212> TYPE: PRT
<213> ORGANISM: Trichoderma reesei

<400> SEQUENCE: 30

Met Lys Ser Ala Leu Leu Ala Ala Ala Ala Leu Val Gly Ser Ala Gln
1               5                   10                  15

Ala Gly Ile His Lys Met Lys Leu Gln Lys Val Ser Leu Glu Gln Gln
            20                  25                  30

Leu Glu Gly Ser Ser Ile Glu Ala His Val Gln Gln Leu Gly Gln Lys
        35                  40                  45

Tyr Met Gly Val Arg Pro Thr Ser Arg Ala Glu Val Met Phe Asn Asp
    50                  55                  60

Lys Pro Pro Lys Val Gln Gly Gly His Pro Val Pro Val Thr Asn Phe
65                  70                  75                  80

Met Asn Ala Gln Tyr Phe Ser Glu Ile Thr Ile Gly Thr Pro Pro Gln
                85                  90                  95

Ser Phe Lys Val Val Leu Asp Thr Gly Ser Ser Asn Leu Trp Val Pro
            100                 105                 110

Ser Gln Ser Cys Asn Ser Ile Ala Cys Phe Leu His Ser Thr Tyr Asp
        115                 120                 125

Ser Ser Ser Ser Ser Thr Tyr Lys Pro Asn Gly Ser Asp Phe Glu Ile
    130                 135                 140

His Tyr Gly Ser Gly Ser Leu Thr Gly Phe Ile Ser Asn Asp Val Val
145                 150                 155                 160

Thr Ile Gly Asp Leu Lys Ile Lys Gly Gln Asp Phe Ala Glu Ala Thr
                165                 170                 175
```

```
Ser Glu Pro Gly Leu Ala Phe Ala Phe Gly Arg Phe Asp Gly Ile Leu
            180                 185                 190

Gly Leu Gly Tyr Asp Thr Ile Ser Val Asn Gly Ile Val Pro Pro Phe
        195                 200                 205

Tyr Gln Met Val Asn Gln Lys Leu Ile Asp Glu Pro Val Phe Ala Phe
    210                 215                 220

Tyr Leu Gly Ser Ser Asp Glu Gly Ser Glu Ala Val Phe Gly Gly Val
225                 230                 235                 240

Asp Asp Ala His Tyr Glu Gly Lys Ile Glu Tyr Ile Pro Leu Arg Arg
                245                 250                 255

Lys Ala Tyr Trp Glu Val Asp Leu Asp Ser Ile Ala Phe Gly Asp Glu
            260                 265                 270

Val Ala Glu Leu Glu Asn Thr Gly Ala Ile Leu Asp Thr Gly Thr Ser
        275                 280                 285

Leu Asn Val Leu Pro Ser Gly Leu Ala Glu Leu Leu Asn Ala Glu Ile
    290                 295                 300

Gly Ala Lys Lys Gly Phe Gly Gly Gln Tyr Thr Val Asp Cys Ser Lys
305                 310                 315                 320

Arg Asp Ser Leu Pro Asp Ile Thr Phe Ser Leu Ala Gly Ser Lys Tyr
                325                 330                 335

Ser Leu Pro Ala Ser Asp Tyr Ile Ile Glu Met Ser Gly Asn Cys Ile
            340                 345                 350

Ser Ser Phe Gln Gly Met Asp Phe Pro Glu Pro Val Gly Pro Leu Val
        355                 360                 365

Ile Leu Gly Asp Ala Phe Leu Arg Arg Tyr Tyr Ser Val Tyr Asp Leu
    370                 375                 380

Gly Arg Asp Ala Val Gly Leu Ala Lys Ala Lys
385                 390                 395


<210> SEQ ID NO 31
<211> LENGTH: 37
<212> TYPE: DNA
<213> ORGANISM: Aspergillus fumigatus

<400> SEQUENCE: 31

actggattta ccatgacttt gtccaagatc acttcca                              37


<210> SEQ ID NO 32
<211> LENGTH: 40
<212> TYPE: DNA
<213> ORGANISM: Aspergillus fumigatus

<400> SEQUENCE: 32

tcacctctag ttaattaagc gttgaacagt gcaggaccag                           40


<210> SEQ ID NO 33
<211> LENGTH: 17
<212> TYPE: DNA
<213> ORGANISM: Aspergillus fumigatus

<400> SEQUENCE: 33

tgtcccttgt cgatgcg                                                    17


<210> SEQ ID NO 34
<211> LENGTH: 17
<212> TYPE: DNA
<213> ORGANISM: Aspergillus fumigatus

<400> SEQUENCE: 34
```

cacatgactt ggcttcc 17

<210> SEQ ID NO 35
<211> LENGTH: 862
<212> TYPE: DNA
<213> ORGANISM: Aspergillus fumigatus

<400> SEQUENCE: 35
atgactttgt ccaagatcac ttccattgct ggccttctgg cctcagcgtc tctcgtggct 60
ggccacggct ttgtttctgg cattgttgct gatgggaaat agtatgtgct tgaaccacac 120
aaatgacagc tgcaacagct aacttctatt ccagttacgg agggtacctt gttaaccaat 180
acccctacat gagcaaccct cccgacacca ttgcctggtc caccaccgcc accgacctcg 240
gctttgtgga cggcaccggc taccagtctc cggatattat ctgccacaga gacgcaaaga 300
atggcaagtt gaccgcaacc gttgcagccg gttcacagat cgaattccag tggacgacgt 360
ggccagagtc tcaccatgga ccggtacgac gccgaagaga agagaacata ttgtgaccag 420
ataggctaac atagcatagt tgattactta cctcgctcca tgcaacggcg actgtgccac 480
cgtggacaag accaccctga agtttgtcaa gatcgccgct caaggcttga tcgacggctc 540
caacccacct ggtgtttggg ctgatgatga aatgatcgcc aacaacaaca cggccacagt 600
gaccattcct gcctcctatg cccccggaaa ctacgtcctt cgccacgaga tcatcgccct 660
tcactctgcg ggtaacctga acggcgcgca gaactacccc cagtgtttca acatccaaat 720
caccggtggc ggcagtgctc agggatctgg caccgctggc acgtccctgt acaagaatac 780
tgatcctggc atcaagtttg acatctactc ggatctgagc ggtggatacc ctattcctgg 840
tcctgcactg ttcaacgctt aa 862

<210> SEQ ID NO 36
<211> LENGTH: 250
<212> TYPE: PRT
<213> ORGANISM: Aspergillus fumigatus

<400> SEQUENCE: 36

Met Thr Leu Ser Lys Ile Thr Ser Ile Ala Gly Leu Leu Ala Ser Ala
1 5 10 15

Ser Leu Val Ala Gly His Gly Phe Val Ser Gly Ile Val Ala Asp Gly
20 25 30

Lys Tyr Tyr Gly Gly Tyr Leu Val Asn Gln Tyr Pro Tyr Met Ser Asn
35 40 45

Pro Pro Asp Thr Ile Ala Trp Ser Thr Thr Ala Thr Asp Leu Gly Phe
50 55 60

Val Asp Gly Thr Gly Tyr Gln Ser Pro Asp Ile Ile Cys His Arg Asp
65 70 75 80

Ala Lys Asn Gly Lys Leu Thr Ala Thr Val Ala Ala Gly Ser Gln Ile
85 90 95

Glu Phe Gln Trp Thr Thr Trp Pro Glu Ser His His Gly Pro Leu Ile
100 105 110

Thr Tyr Leu Ala Pro Cys Asn Gly Asp Cys Ala Thr Val Asp Lys Thr
115 120 125

Thr Leu Lys Phe Val Lys Ile Ala Ala Gln Gly Leu Ile Asp Gly Ser
130 135 140

Asn Pro Pro Gly Val Trp Ala Asp Asp Glu Met Ile Ala Asn Asn Asn
145 150 155 160

```
Thr Ala Thr Val Thr Ile Pro Ala Ser Tyr Ala Pro Gly Asn Tyr Val
                165                 170                 175

Leu Arg His Glu Ile Ile Ala Leu His Ser Ala Gly Asn Leu Asn Gly
            180                 185                 190

Ala Gln Asn Tyr Pro Gln Cys Phe Asn Ile Gln Ile Thr Gly Gly Gly
        195                 200                 205

Ser Ala Gln Gly Ser Gly Thr Ala Gly Thr Ser Leu Tyr Lys Asn Thr
    210                 215                 220

Asp Pro Gly Ile Lys Phe Asp Ile Tyr Ser Asp Leu Ser Gly Gly Tyr
225                 230                 235                 240

Pro Ile Pro Gly Pro Ala Leu Phe Asn Ala
                245                 250


<210> SEQ ID NO 37
<211> LENGTH: 37
<212> TYPE: DNA
<213> ORGANISM: Aspergillus fumigatus

<400> SEQUENCE: 37

ggactgcgca ccatgacttt gtccaagatc acttcca                               37


<210> SEQ ID NO 38
<211> LENGTH: 38
<212> TYPE: DNA
<213> ORGANISM: Aspergillus fumigatus

<400> SEQUENCE: 38

gccacggagc ttaattaatt aagcgttgaa cagtgcag                              38


<210> SEQ ID NO 39
<211> LENGTH: 37
<212> TYPE: DNA
<213> ORGANISM: Aspergillus fumigatus

<400> SEQUENCE: 39

cgcggtagtg gcgcggtcga ccgaatgtag gattgtt                               37


<210> SEQ ID NO 40
<211> LENGTH: 36
<212> TYPE: DNA
<213> ORGANISM: Aspergillus fumigatus

<400> SEQUENCE: 40

ttaccaattg gcgcgccact accgcgttcg agaaga                                36


<210> SEQ ID NO 41
<211> LENGTH: 3060
<212> TYPE: DNA
<213> ORGANISM: Aspergillus fumigatus

<400> SEQUENCE: 41

atgagattcg gttggctcga ggtggccgct ctgacggccg cttctgtagc caatgcccag      60

gtttgtgatg ctttcccgtc attgtttcgg atatagttga caatagtcat ggaaataatc     120

aggaattggc tttctctcca ccattctacc cttcgccttg ggctgatggc cagggagagt     180

gggcagatgc ccatcgacgc gccgtcgaga tcgtttctca gatgacactg gcggagaagg     240

ttaaccttac aacgggtact gggtgggttg cgactttttt gttgacagtg agctttcttc     300

actgaccatc tacacagatg ggaaatggac cgatgcgtcg gtcaaaccgg cagcgttccc     360

aggtaagctt gcaattctgc aacaacgtgc aagtgtagtt gctaaaacgc ggtggtgcag     420
```

```
acttggtatc aactggggtc tttgtggcca ggattcccct ttgggtatcc gtttctgtga    480
gctatacccg cggagtcttt cagtccttgt attatgtgct gatgattgtc tctgtatagc    540
tgacctcaac tccgccttcc ctgctggtac taatgtcgcc gcgacatggg acaagacact    600
cgcctacctt cgtggcaagg ccatgggtga ggaattcaac gacaagggcg tggacatttt    660
gctggggcct gctgctggtc ctctcggcaa atacccggac ggcggcagaa tctgggaagg    720
cttctctcct gatccggttc tcactggtgt acttttcgcc gaaactatca agggtatcca    780
agacgcgggt gtgattgcta ctgccaagca ttacattctg aatgaacagg agcatttccg    840
acaggttggc gaggcccagg gatatggtta caacatcacg gagacgatca gctccaacgt    900
ggatgacaag accatgcacg agttgtacct ttggtgagta gttgacactg caaatgagga    960
ccttgattga tttgactgac ctggaatgca ggccctttgc agatgctgtg cgcggtaaga   1020
ttttccgtag acttgacctc gcgacgaaga aatcgctgac gaaccatcgt agctggcgtt   1080
ggcgctgtca tgtgttccta caatcaaatc aacaacagct acggttgtca aaacagtcaa   1140
actctcaaca agctcctcaa ggctgagctg ggcttccaag gcttcgtcat gagtgactgg   1200
agcgctcacc acagcggtgt cggcgctgcc ctcgctgggt tggatatgtc gatgcctgga   1260
gacatttcct tcgacgacgg actctccttc tggggcacga acctaactgt cagtgttctt   1320
aacggcaccg ttccagcctg gcgtgtcgat gacatggctg ttcgtatcat gaccgcgtac   1380
tacaaggttg gtcgtgaccg tcttcgtatt ccccctaact tcagctcctg gacccgggat   1440
gagtacggct gggagcattc tgctgtctcc gagggagcct ggaccaaggt gaacgacttc   1500
gtcaatgtgc agcgcagtca ctctcagatc atccgtgaga ttggtgccgc tagtacagtg   1560
ctcttgaaga acacgggtgc tcttcctttg accggcaagg aggttaaagt gggtgttctc   1620
ggtgaagacg ctggttccaa cccgtggggt gctaacggct gccccgaccg cggctgtgat   1680
aacggcactc ttgctatggc ctggggtagt ggtactgcca acttccctta ccttgtcacc   1740
cccgagcagg ctatccagcg agaggtcatc agcaacggcg gcaatgtctt tgctgtgact   1800
gataacgggg ctctcagcca gatggcagat gttgcatctc aatccaggtg agtgcgggct   1860
cttagaaaaa gaacgttctc tgaatgaagt tttttaacca ttgcgaacag cgtgtctttg   1920
gtgtttgtca acgccgactc tggagagggt ttcatcagtg tcgacggcaa cgagggtgac   1980
cgcaaaaatc tcactctgtg gaagaacggc gaggccgtca ttgacactgt tgtcagccac   2040
tgcaacaaca cgattgtggt tattcacagt gttgggcccg tcttgatcga ccggtggtat   2100
gataacccca acgtcactgc catcatctgg gccggcttgc ccggtcagga gagtggcaac   2160
tccctggtcg acgtgctcta tggccgcgtc aaccccagcg ccaagacccc gttcacctgg   2220
ggcaagactc gggagtctta cggggctccc ttgctcaccg agcctaacaa tggcaatggt   2280
gctccccagg atgatttcaa cgagggcgtc ttcattgact accgtcactt tgacaagcgc   2340
aatgagaccc ccatttatga gtttggccat ggcttgagct acaccacctt tggttactct   2400
caccttcggg ttcaggccct caatagttcg agttcggcat atgtcccgac tagcggagag   2460
accaagcctg cgccaaccta tggtgagatc ggtagtgccg ccgactacct gtatcccgag   2520
ggtctcaaaa gaattaccaa gtttatttac ccttggctca actcgaccga cctcgaggat   2580
tcttctgacg acccgaacta cggctgggag gactcggagt acattcccga aggcgctagg   2640
gatgggtctc ctcaacccct cctgaaggct ggcggcgctc ctggtggtaa ccctaccctt   2700
tatcaggatc ttgttagggt gtcggccacc ataaccaaca ctggtaacgt cgccggttat   2760
```

```
gaagtccctc aattggtgag tgacccgcat gttccttgcg ttgcaatttg gctaactcgc   2820

ttctagtatg tttcactggg cggaccgaac gagcctcggg tcgttctgcg caagttcgac   2880

cgaatcttcc tggctcctgg ggagcaaaag gtttggacca cgactcttaa ccgtcgtgat   2940

ctcgccaatt gggatgtgga ggctcaggac tgggtcatca caaagtaccc caagaaagtg   3000

cacgtcggca gctcctcgcg taagctgcct ctgagagcgc ctctgccccg tgtctactag   3060


<210> SEQ ID NO 42
<211> LENGTH: 863
<212> TYPE: PRT
<213> ORGANISM: Aspergillus fumigatus

<400> SEQUENCE: 42

Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
    130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Leu Asn Glu Gln Glu His Phe Arg Gln Val Gly Glu Ala Gln Gly
        195                 200                 205

Tyr Gly Tyr Asn Ile Thr Glu Thr Ile Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
            260                 265                 270

Gly Phe Gln Gly Phe Val Met Ser Asp Trp Ser Ala His His Ser Gly
        275                 280                 285

Val Gly Ala Ala Leu Ala Gly Leu Asp Met Ser Met Pro Gly Asp Ile
    290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
```

```
                325                 330                 335

Arg Ile Met Thr Ala Tyr Tyr Lys Val Gly Arg Asp Arg Leu Arg Ile
            340                 345                 350

Pro Pro Asn Phe Ser Ser Trp Thr Arg Asp Glu Tyr Gly Trp Glu His
        355                 360                 365

Ser Ala Val Ser Glu Gly Ala Trp Thr Lys Val Asn Asp Phe Val Asn
    370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
            420                 425                 430

Ala Asn Gly Cys Pro Asp Arg Gly Cys Asp Asn Gly Thr Leu Ala Met
        435                 440                 445

Ala Trp Gly Ser Gly Thr Ala Asn Phe Pro Tyr Leu Val Thr Pro Glu
    450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
                485                 490                 495

Ser Ser Val Ser Leu Val Phe Val Asn Ala Asp Ser Gly Glu Gly Phe
            500                 505                 510

Ile Ser Val Asp Gly Asn Glu Gly Asp Arg Lys Asn Leu Thr Leu Trp
        515                 520                 525

Lys Asn Gly Glu Ala Val Ile Asp Thr Val Val Ser His Cys Asn Asn
    530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
        595                 600                 605

Gly Ala Pro Leu Leu Thr Glu Pro Asn Asn Gly Asn Gly Ala Pro Gln
    610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
        675                 680                 685

Gly Glu Ile Gly Ser Ala Ala Asp Tyr Leu Tyr Pro Glu Gly Leu Lys
    690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
            740                 745                 750
```

```
Gly Ala Pro Gly Gly Asn Pro Thr Leu Tyr Gln Asp Leu Val Arg Val
        755                 760                 765

Ser Ala Thr Ile Thr Asn Thr Gly Asn Val Ala Gly Tyr Glu Val Pro
    770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
        835                 840                 845

Ser Ser Arg Lys Leu Pro Leu Arg Ala Pro Leu Pro Arg Val Tyr
    850                 855                 860
```

<210> SEQ ID NO 43
<211> LENGTH: 835
<212> TYPE: DNA
<213> ORGANISM: Penicillium sp.

<400> SEQUENCE: 43

```
atgctgtctt cgacgactcg caccctcgcc tttacaggcc ttgcgggcct tctgtccgct      60

cccctggtca aggcccatgg ctttgtccag ggcattgtca tcggtgacca attgtaagtc     120

cctctcttgc agttctgtcg attaactgct ggactgcttg cttgactccc tgctgactcc     180

caacagctac agcgggtaca tcgtcaactc gttcccctac gaatccaacc caccccccgt     240

catcggctgg gccacgaccg ccaccgacct gggcttcgtc gacggcacag gataccaagg     300

cccggacatc atctgccacc ggaatgcgac gcccgcgccg ctgacagccc ccgtggccgc     360

cggcggcacc gtcgagctgc agtggacgcc gtggccggac agccaccacg gacccgtcat     420

cacctacctg gcgccgtgca acggcaactg ctcgaccgtc gacaagacga cgctggagtt     480

cttcaagatc gaccagcagg gcctgatcga cgacacgagc ccgccgggca cctgggcgtc     540

ggacaacctc atcgccaaca acaatagctg gaccgtcacc attcccaaca gcgtcgcccc     600

cggcaactac gtcctgcgcc acgagatcat cgccctgcac tcggccaaca acaaggacgg     660

cgcccagaac tacccccagt gcatcaacat cgaggtcacg ggcggcggct ccgacgcgcc     720

tgagggtact ctgggcgagg atctctacca tgacaccgac ccgggcattc tggtcgacat     780

ttacgagccc attgcgacgt ataccattcc ggggccgcct gagccgacgt tctag          835
```

<210> SEQ ID NO 44
<211> LENGTH: 253
<212> TYPE: PRT
<213> ORGANISM: Penicillium sp.

<400> SEQUENCE: 44

```
Met Leu Ser Ser Thr Thr Arg Thr Leu Ala Phe Thr Gly Leu Ala Gly
1               5                   10                  15

Leu Leu Ser Ala Pro Leu Val Lys Ala His Gly Phe Val Gln Gly Ile
            20                  25                  30

Val Ile Gly Asp Gln Phe Tyr Ser Gly Tyr Ile Val Asn Ser Phe Pro
        35                  40                  45

Tyr Glu Ser Asn Pro Pro Pro Val Ile Gly Trp Ala Thr Thr Ala Thr
    50                  55                  60

Asp Leu Gly Phe Val Asp Gly Thr Gly Tyr Gln Gly Pro Asp Ile Ile
```

```
65                  70                  75                  80

Cys His Arg Asn Ala Thr Pro Ala Pro Leu Thr Ala Pro Val Ala Ala
                85                  90                  95

Gly Gly Thr Val Glu Leu Gln Trp Thr Pro Trp Pro Asp Ser His His
            100                 105                 110

Gly Pro Val Ile Thr Tyr Leu Ala Pro Cys Asn Gly Asn Cys Ser Thr
        115                 120                 125

Val Asp Lys Thr Thr Leu Glu Phe Phe Lys Ile Asp Gln Gln Gly Leu
    130                 135                 140

Ile Asp Asp Thr Ser Pro Pro Gly Thr Trp Ala Ser Asp Asn Leu Ile
145                 150                 155                 160

Ala Asn Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
        195                 200                 205

Thr Gly Gly Gly Ser Asp Ala Pro Glu Gly Thr Leu Gly Glu Asp Leu
    210                 215                 220

Tyr His Asp Thr Asp Pro Gly Ile Leu Val Asp Ile Tyr Glu Pro Ile
225                 230                 235                 240

Ala Thr Tyr Thr Ile Pro Gly Pro Pro Glu Pro Thr Phe
                245                 250


<210> SEQ ID NO 45
<211> LENGTH: 36
<212> TYPE: DNA
<213> ORGANISM: Penicillium sp.

<400> SEQUENCE: 45

cggactgcgc accatgctgt cttcgacgac tcgcac                               36


<210> SEQ ID NO 46
<211> LENGTH: 35
<212> TYPE: DNA
<213> ORGANISM: Penicillium sp.

<400> SEQUENCE: 46

tcgccacgga gcttatcgac ttcttctaga acgtc                                35


<210> SEQ ID NO 47
<211> LENGTH: 37
<212> TYPE: DNA
<213> ORGANISM: Aspergillus fumigatus

<400> SEQUENCE: 47

cgcggtagtg gcgcggtcga ccgaatgtag gattgtt                              37


<210> SEQ ID NO 48
<211> LENGTH: 36
<212> TYPE: DNA
<213> ORGANISM: Aspergillus fumigatus

<400> SEQUENCE: 48

ttaccaattg gcgcgccact accgcgttcg agaaga                               36


<210> SEQ ID NO 49
<211> LENGTH: 1713
<212> TYPE: DNA
```

<213> ORGANISM: Aspergillus fumigatus

<400> SEQUENCE: 49

```
atgaagcacc ttgcatcttc catcgcattg actctactgt tgcctgccgt gcaggcccag     60
cagaccgtat ggggccaatg tatgttctgg ctgtcactgg aataagactg tatcaactgc    120
tgatatgctt ctaggtggcg gccaaggctg gtctggcccg acgagctgtg ttgccggcgc    180
agcctgtagc acactgaatc cctgtatgtt agatatcgtc ctgagtggag acttatactg    240
acttccttag actacgctca gtgtatcccg ggagccaccg cgacgtccac caccctcacg    300
acgacgacgg cggcgacgac gacatcccag accaccacca aacctaccac gactggtcca    360
actacatccg cacccaccgt gaccgcatcc ggtaaccctt tcagcggcta ccagctgtat    420
gccaacccct actactcctc cgaggtccat actctggcca tgccttctct gcccagctcg    480
ctgcagccca aggctagtgc tgttgctgaa gtgccctcat ttgtttggct gtaagtggcc    540
ttatcccaat actgagacca actctctgac agtcgtagcg acgttgccgc caaggtgccc    600
actatgggaa cctacctggc cgacattcag gccaagaaca aggccggcgc caaccctcct    660
atcgctggta tcttcgtggt ctacgacttg ccggaccgtg actgcgccgc tctggccagt    720
aatggcgagt actcaattgc caacaacggt gtggccaact acaaggcgta cattgacgcc    780
atccgtgctc agctggtgaa gtactctgac gttcacacca tcctcgtcat cggtaggccg    840
tacacctccg ttgcgcgccg cctttctctg acatcttgca gaacccgaca gcttggccaa    900
cctggtgacc aacctcaacg tcgccaaatg cgccaatgcg cagagcgcct acctggagtg    960
tgtcgactat gctctgaagc agctcaacct gcccaacgtc gccatgtacc tcgacgcagg   1020
tatgcctcac ttcccgcatt ctgtatccct tccagacact aactcatcag gccatgcggg   1080
ctggctcgga tggcccgcca acttgggccc cgccgcaaca ctcttcgcca aagtctacac   1140
cgacgcgggt tcccccgcgg ctgttcgtgg cctggccacc aacgtcgcca actacaacgc   1200
ctggtcgctc agtacctgcc cctcctacac ccagggagac cccaactgcg acgagaagaa   1260
gtacatcaac gccatggcgc ctcttctcaa ggaagccggc ttcgatgccc acttcatcat   1320
ggatacctgt aagtgcttat tccaatcgcc gatgtgtgcc gactaatcaa tgtttcagcc   1380
cggaatggcg tccagcccac gaagcaaaac gcctggggtg actggtgcaa cgtcatcggc   1440
accggcttcg gtgttcgccc ctcgactaac accggcgatc cgctccagga tgcctttgtg   1500
tggatcaagc ccggtggaga gagtgatggc acgtccaact cgacttcccc ccggtatgac   1560
gcgcactgcg gatatagtga tgctctgcag cctgctcctg aggctggtac ttggttccag   1620
gtatgtcatc cattagccag atgagggata agtgactgac ggacctaggc ctactttgag   1680
cagcttctga ccaacgctaa cccgtccttt taa                                 1713
```

<210> SEQ ID NO 50
<211> LENGTH: 454
<212> TYPE: PRT
<213> ORGANISM: Aspergillus fumigatus

<400> SEQUENCE: 50

```
Met Lys His Leu Ala Ser Ser Ile Ala Leu Thr Leu Leu Leu Pro Ala
1               5                   10                  15

Val Gln Ala Gln Gln Thr Val Trp Gly Gln Cys Gly Gly Gln Gly Trp
            20                  25                  30

Ser Gly Pro Thr Ser Cys Val Ala Gly Ala Ala Cys Ser Thr Leu Asn
        35                  40                  45
```

```
Pro Tyr Tyr Ala Gln Cys Ile Pro Gly Ala Thr Ala Thr Ser Thr Thr
    50                  55                  60

Leu Thr Thr Thr Thr Ala Ala Thr Thr Thr Ser Gln Thr Thr Thr Lys
65                  70                  75                  80

Pro Thr Thr Thr Gly Pro Thr Thr Ser Ala Pro Thr Val Thr Ala Ser
                85                  90                  95

Gly Asn Pro Phe Ser Gly Tyr Gln Leu Tyr Ala Asn Pro Tyr Tyr Ser
            100                 105                 110

Ser Glu Val His Thr Leu Ala Met Pro Ser Leu Pro Ser Ser Leu Gln
        115                 120                 125

Pro Lys Ala Ser Ala Val Ala Glu Val Pro Ser Phe Val Trp Leu Asp
    130                 135                 140

Val Ala Ala Lys Val Pro Thr Met Gly Thr Tyr Leu Ala Asp Ile Gln
145                 150                 155                 160

Ala Lys Asn Lys Ala Gly Ala Asn Pro Pro Ile Ala Gly Ile Phe Val
                165                 170                 175

Val Tyr Asp Leu Pro Asp Arg Asp Cys Ala Ala Leu Ala Ser Asn Gly
            180                 185                 190

Glu Tyr Ser Ile Ala Asn Asn Gly Val Ala Asn Tyr Lys Ala Tyr Ile
        195                 200                 205

Asp Ala Ile Arg Ala Gln Leu Val Lys Tyr Ser Asp Val His Thr Ile
    210                 215                 220

Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
                245                 250                 255

Tyr Ala Leu Lys Gln Leu Asn Leu Pro Asn Val Ala Met Tyr Leu Asp
            260                 265                 270

Ala Gly His Ala Gly Trp Leu Gly Trp Pro Ala Asn Leu Gly Pro Ala
        275                 280                 285

Ala Thr Leu Phe Ala Lys Val Tyr Thr Asp Ala Gly Ser Pro Ala Ala
    290                 295                 300

Val Arg Gly Leu Ala Thr Asn Val Ala Asn Tyr Asn Ala Trp Ser Leu
305                 310                 315                 320

Ser Thr Cys Pro Ser Tyr Thr Gln Gly Asp Pro Asn Cys Asp Glu Lys
                325                 330                 335

Lys Tyr Ile Asn Ala Met Ala Pro Leu Leu Lys Glu Ala Gly Phe Asp
            340                 345                 350

Ala His Phe Ile Met Asp Thr Ser Arg Asn Gly Val Gln Pro Thr Lys
        355                 360                 365

Gln Asn Ala Trp Gly Asp Trp Cys Asn Val Ile Gly Thr Gly Phe Gly
    370                 375                 380

Val Arg Pro Ser Thr Asn Thr Gly Asp Pro Leu Gln Asp Ala Phe Val
385                 390                 395                 400

Trp Ile Lys Pro Gly Gly Glu Ser Asp Gly Thr Ser Asn Ser Thr Ser
                405                 410                 415

Pro Arg Tyr Asp Ala His Cys Gly Tyr Ser Asp Ala Leu Gln Pro Ala
            420                 425                 430

Pro Glu Ala Gly Thr Trp Phe Gln Ala Tyr Phe Glu Gln Leu Leu Thr
        435                 440                 445

Asn Ala Asn Pro Ser Phe
    450
```

<210> SEQ ID NO 51
<211> LENGTH: 54
<212> TYPE: DNA
<213> ORGANISM: Trichoderma reesei

<400> SEQUENCE: 51
acgaattgtt taaacgtcga cccaagtatc cagaggtgta tggaaatatc agat 54

<210> SEQ ID NO 52
<211> LENGTH: 44
<212> TYPE: DNA
<213> ORGANISM: Trichoderma reesei

<400> SEQUENCE: 52
cgcgtagatc tgcggccatg gtgcaataca cagagggtga tctt 44

<210> SEQ ID NO 53
<211> LENGTH: 48
<212> TYPE: DNA
<213> ORGANISM: Trichoderma reesei

<400> SEQUENCE: 53
atctacgcgt actagttaat taaggctttc gtgaccgggc ttcaaaca 48

<210> SEQ ID NO 54
<211> LENGTH: 46
<212> TYPE: DNA
<213> ORGANISM: Trichoderma reesei

<400> SEQUENCE: 54
gcggccgtta ctagtggatc cactcggagt tgttatacgc tactcg 46

<210> SEQ ID NO 55
<211> LENGTH: 46
<212> TYPE: DNA
<213> ORGANISM: Trichoderma reesei

<400> SEQUENCE: 55
atccatcaca ctggcggccg cgcttcaaac aatgatgtgc gatggt 46

<210> SEQ ID NO 56
<211> LENGTH: 46
<212> TYPE: DNA
<213> ORGANISM: Trichoderma reesei

<400> SEQUENCE: 56
gatgcatgct cgagcggccg cctaccttgg cagccctacg agagag 46

<210> SEQ ID NO 57
<211> LENGTH: 41
<212> TYPE: DNA
<213> ORGANISM: Aspergillus fumigatus

<400> SEQUENCE: 57
ctctgtgtat tgcaccatga agcaccttgc atcttccatc g 41

<210> SEQ ID NO 58
<211> LENGTH: 40
<212> TYPE: DNA
<213> ORGANISM: Aspergillus fumigatus

<400> SEQUENCE: 58
ccggtcacga aagccttaat taaaaggacg ggttagcgtt 40

<210> SEQ ID NO 59
<211> LENGTH: 1599
<212> TYPE: DNA
<213> ORGANISM: Aspergillus fumigatus

<400> SEQUENCE: 59

```
atgctggcct ccaccttctc ctaccgcatg tacaagaccg cgctcatcct ggccgccctt      60

ctgggctctg gccaggctca gcaggtcggt acttcccagg cggaagtgca tccgtccatg     120

acctggcaga gctgcacggc tggcggcagc tgcaccacca acaacggcaa ggtggtcatc     180

gacgcgaact ggcgttgggt gcacaaagtc ggcgactaca ccaactgcta caccggcaac     240

acctgggaca cgactatctg ccctgacgat gcgacctgcg catccaactg cgcccttgag     300

ggtgccaact acgaatccac ctatggtgtg accgccagcg gcaattccct ccgcctcaac     360

ttcgtcacca ccagccagca gaagaacatt ggctcgcgtc tgtacatgat gaaggacgac     420

tcgacctacg agatgtttaa gctgctgaac caggagttca ccttcgatgt cgatgtctcc     480

aacctcccct gcggtctcaa cggtgctctg tactttgtcg ccatggacgc cgacggtggc     540

atgtccaagt acccaaccaa caaggccggt gccaagtacg gtactggata ctgtgactcg     600

cagtgccctc gcgacctcaa gttcatcaac ggtcaggcca acgtcgaagg gtggcagccc     660

tcctccaacg atgccaatgc gggtaccggc aaccacgggt cctgctgcgc ggagatggat     720

atctgggagg ccaacagcat ctccacggcc ttcacccccc atccgtgcga cacgcccggc     780

caggtgatgt gcaccggtga tgcctgcggt ggcacctaca gctccgaccg ctacggcggc     840

acctgcgacc ccgacggatg tgatttcaac tccttccgcc agggcaacaa gaccttctac     900

ggccctggca tgaccgtcga caccaagagc aagtttaccg tcgtcaccca gttcatcacc     960

gacgacggca cctccagcgg caccctcaag gagatcaagc gcttctacgt gcagaacggc    1020

aaggtgatcc ccaactcgga gtcgacctgg accggcgtca gcggcaactc catcaccacc    1080

gagtactgca ccgcccagaa gagcctgttc caggaccaga acgtcttcga aaagcacggc    1140

ggcctcgagg gcatgggtgc tgccctcgcc cagggtatgg ttctcgtcat gtccctgtgg    1200

gatgatcact cggccaacat gctctggctc gacagcaact acccgaccac tgcctcttcc    1260

accactcccg gcgtcgcccg tggtacctgc gacatctcct ccggcgtccc tgcggatgtc    1320

gaggcgaacc accccgacgc ctacgtcgtc tactccaaca tcaaggtcgg ccccatcggc    1380

tcgaccttca acagcggtgg ctcgaacccc ggtggcggaa ccaccacgac aactaccacc    1440

cagcctacta ccaccacgac cacggctgga aaccctggcg gcaccggagt cgcacagcac    1500

tatggccagt gtggtggaat cggatggacc ggacccacaa cctgtgccag cccttatacc    1560

tgccagaagc tgaatgatta ttactctcag tgcctgtag                           1599
```

<210> SEQ ID NO 60
<211> LENGTH: 532
<212> TYPE: PRT
<213> ORGANISM: Aspergillus fumigatus

<400> SEQUENCE: 60

```
Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Gln Val Gly Thr Ser
            20                  25                  30

Gln Ala Glu Val His Pro Ser Met Thr Trp Gln Ser Cys Thr Ala Gly
        35                  40                  45
```

```
Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
65                  70                  75                  80

Thr Trp Asp Thr Thr Ile Cys Pro Asp Asp Ala Thr Cys Ala Ser Asn
                85                  90                  95

Cys Ala Leu Glu Gly Ala Asn Tyr Glu Ser Thr Tyr Gly Val Thr Ala
            100                 105                 110

Ser Gly Asn Ser Leu Arg Leu Asn Phe Val Thr Thr Ser Gln Gln Lys
        115                 120                 125

Asn Ile Gly Ser Arg Leu Tyr Met Met Lys Asp Asp Ser Thr Tyr Glu
    130                 135                 140

Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                165                 170                 175

Ala Asp Gly Gly Met Ser Lys Tyr Pro Thr Asn Lys Ala Gly Ala Lys
            180                 185                 190

Tyr Gly Thr Gly Tyr Cys Asp Ser Gln Cys Pro Arg Asp Leu Lys Phe
        195                 200                 205

Ile Asn Gly Gln Ala Asn Val Glu Gly Trp Gln Pro Ser Ser Asn Asp
    210                 215                 220

Ala Asn Ala Gly Thr Gly Asn His Gly Ser Cys Cys Ala Glu Met Asp
225                 230                 235                 240

Ile Trp Glu Ala Asn Ser Ile Ser Thr Ala Phe Thr Pro His Pro Cys
                245                 250                 255

Asp Thr Pro Gly Gln Val Met Cys Thr Gly Asp Ala Cys Gly Gly Thr
            260                 265                 270

Tyr Ser Ser Asp Arg Tyr Gly Gly Thr Cys Asp Pro Asp Gly Cys Asp
        275                 280                 285

Phe Asn Ser Phe Arg Gln Gly Asn Lys Thr Phe Tyr Gly Pro Gly Met
    290                 295                 300

Thr Val Asp Thr Lys Ser Lys Phe Thr Val Val Thr Gln Phe Ile Thr
305                 310                 315                 320

Asp Asp Gly Thr Ser Ser Gly Thr Leu Lys Glu Ile Lys Arg Phe Tyr
                325                 330                 335

Val Gln Asn Gly Lys Val Ile Pro Asn Ser Glu Ser Thr Trp Thr Gly
            340                 345                 350

Val Ser Gly Asn Ser Ile Thr Thr Glu Tyr Cys Thr Ala Gln Lys Ser
        355                 360                 365

Leu Phe Gln Asp Gln Asn Val Phe Glu Lys His Gly Gly Leu Glu Gly
    370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
                405                 410                 415

Thr Ala Ser Ser Thr Thr Pro Gly Val Ala Arg Gly Thr Cys Asp Ile
            420                 425                 430

Ser Ser Gly Val Pro Ala Asp Val Glu Ala Asn His Pro Asp Ala Tyr
        435                 440                 445

Val Val Tyr Ser Asn Ile Lys Val Gly Pro Ile Gly Ser Thr Phe Asn
    450                 455                 460

Ser Gly Gly Ser Asn Pro Gly Gly Gly Thr Thr Thr Thr Thr Thr Thr
```

```
465                 470                 475                 480

Gln Pro Thr Thr Thr Thr Thr Thr Ala Gly Asn Pro Gly Gly Thr Gly
                485                 490                 495

Val Ala Gln His Tyr Gly Gln Cys Gly Gly Ile Gly Trp Thr Gly Pro
            500                 505                 510

Thr Thr Cys Ala Ser Pro Tyr Thr Cys Gln Lys Leu Asn Asp Tyr Tyr
        515                 520                 525

Ser Gln Cys Leu
    530


<210> SEQ ID NO 61
<211> LENGTH: 40
<212> TYPE: DNA
<213> ORGANISM: Aspergillus fumigatus

<400> SEQUENCE: 61

cgcggactgc gcaccatgct ggcctccacc ttctcctacc                          40


<210> SEQ ID NO 62
<211> LENGTH: 48
<212> TYPE: DNA
<213> ORGANISM: Aspergillus fumigatus

<400> SEQUENCE: 62

ctttcgccac ggagcttaat taactacagg cactgagagt aataatca                 48


<210> SEQ ID NO 63
<211> LENGTH: 1131
<212> TYPE: DNA
<213> ORGANISM: Herpes simplex virus

<400> SEQUENCE: 63

atggcttcgt accccggcca tcaacacgcg tctgcgttcg accaggctgc gcgttctcgc     60

ggccatagca accgacgtac ggcgttgcgc cctcgccggc agcaagaagc cacggaagtc    120

cgcccggagc agaaaatgcc cacgctactg cgggtttata tagacggtcc ccacgggatg    180

gggaaaacca ccaccacgca actgctggtg gccctgggtt cgcgcgacga tatcgtctac    240

gtacccgagc cgatgactta ctggcgggtg ctgggggctt ccgagacaat cgcgaacatc    300

tacaccacac aacaccgcct cgaccagggt gagatatcgg ccggggacgc ggcggtggta    360

atgacaagcg cccagataac aatgggcatg ccttatgccg tgaccgacgc cgttctggct    420

cctcatatcg gggggaggc tgggagctca catgccccgc ccccggccct caccctcatc     480

ttcgaccgcc atcccatcgc cgccctcctg tgctacccgg ccgcgcggta ccttatgggc    540

agcatgaccc cccaggccgt gctggcgttc gtggccctca tcccgccgac cttgcccggc    600

accaacatcg tgcttggggc ccttccggag gacagacaca tcgaccgcct ggccaaacgc    660

cagcgccccg gcgagcggct ggacctggct atgctggctg cgattcgccg cgtttacggg    720

ctacttgcca atacggtgcg gtatctgcag tgcggcgggt cgtggcggga ggactgggga    780

cagctttcgg ggacggccgt gccgccccag ggtgccgagc cccagagcaa cgcgggccca    840

cgaccccata tcggggacac gttatttacc ctgtttcggg gccccgagtt gctggccccc    900

aacggcgacc tgtataacgt gtttgcctgg gccttggacg tcttggccaa acgcctccgt    960

tccatgcacg tctttatcct ggattacgac caatcgcccg ccggctgccg ggacgccctg   1020

ctgcaactta cctccgggat ggtccagacc cacgtcacca cccccggctc cataccgacg   1080

atatgcgacc tggcgcgcac gtttgcccgg gagatggggg aggctaactg a            1131
```

<210> SEQ ID NO 64
<211> LENGTH: 376
<212> TYPE: PRT
<213> ORGANISM: Herpes simplex virus

<400> SEQUENCE: 64

```
Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Pro Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Arg Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Gly Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
```

370 375

<210> SEQ ID NO 65
<211> LENGTH: 43
<212> TYPE: DNA
<213> ORGANISM: Trichoderma reesei

<400> SEQUENCE: 65
ttagactgcg gccgcgtggc gaaagcctga cgcaccggta gat 43

<210> SEQ ID NO 66
<211> LENGTH: 41
<212> TYPE: DNA
<213> ORGANISM: Trichoderma reesei

<400> SEQUENCE: 66
agtagttagc ggccgcacgg cacggttaag cagggtcttg c 41

<210> SEQ ID NO 67
<211> LENGTH: 50
<212> TYPE: DNA
<213> ORGANISM: Aspergillus fumigatus

<400> SEQUENCE: 67
tcaagcttgg taccgagctc ggatccaagt atccagaggt gtatggaaat 50

<210> SEQ ID NO 68
<211> LENGTH: 46
<212> TYPE: DNA
<213> ORGANISM: Aspergillus fumigatus

<400> SEQUENCE: 68
ctggcggccg ttactagtgc tagcactcgg agttgttata cgctac 46

<210> SEQ ID NO 69
<211> LENGTH: 55
<212> TYPE: DNA
<213> ORGANISM: Trichoderma reesei

<400> SEQUENCE: 69
gagtagcgta taacaactcc gagtgctagc tttaagataa cggaatagaa gaaag 55

<210> SEQ ID NO 70
<211> LENGTH: 42
<212> TYPE: DNA
<213> ORGANISM: Trichoderma reesei

<400> SEQUENCE: 70
ctggcggccg ttactagtct agacgcgcca ctaccgcgtt cg 42

<210> SEQ ID NO 71
<211> LENGTH: 55
<212> TYPE: DNA
<213> ORGANISM: Trichoderma reesei

<400> SEQUENCE: 71
tctgcagata tccatcacac tggcggccgc tttaagataa cggaatagaa gaaag 55

<210> SEQ ID NO 72
<211> LENGTH: 50
<212> TYPE: DNA
<213> ORGANISM: Trichoderma reesei

<400> SEQUENCE: 72
aaactctagg atgcatgctc gagcggccgc acggcacggt taagcagggt 50

<210> SEQ ID NO 73
<211> LENGTH: 30
<212> TYPE: DNA
<213> ORGANISM: Trichoderma reesei

<400> SEQUENCE: 73
caagcaaagc gttccgtcgc agtagcaggc 30

<210> SEQ ID NO 74
<211> LENGTH: 20
<212> TYPE: DNA
<213> ORGANISM: Trichoderma reesei

<400> SEQUENCE: 74
cagtggcgct tattactcag 20

<210> SEQ ID NO 75
<211> LENGTH: 22
<212> TYPE: DNA
<213> ORGANISM: Trichoderma reesei

<400> SEQUENCE: 75
gagaacacag tgagaccata gc 22

<210> SEQ ID NO 76
<211> LENGTH: 22
<212> TYPE: DNA
<213> ORGANISM: Trichoderma reesei

<400> SEQUENCE: 76
tctcaaccca atcagcaaca tg 22

<210> SEQ ID NO 77
<211> LENGTH: 15014
<212> TYPE: DNA
<213> ORGANISM: Trichoderma reesei

<400> SEQUENCE: 77
tcgacgaatt ctaggctagg tatgcgaggc acgcggatct agggcagact gggcattgca 60
agctgcttaa gatccgatcc atacgctccg tgcgcctaga tcccgtctga cccgtaacgt 120
tagctatggt gtagtagaac tcccgtcaac ggctattctc acctagactt tccccttcga 180
atcgatacca catcatcttg agggcagttg ccgataagag tggatctgaa aggggaagct 240
actgacaagt tgttatattg cctgtgtacc aagcgctaat gtggacagga ttaatgccag 300
tgactgttca acaatataac ggacacatgg ttcgcgatta cacctgtcct aattacggtc 360
agttcattag cctcaagtag agcctatttc ctcgccggaa agtcatctct cttattgcat 420
tcaagtaatc ggagttcatc tcggataaag gagcggcctt tcagtagaga gaataacgta 480
ttctgccctt cccactaact cagggtgcag cgcaacacta cacgcaacat atacacttta 540
aagacgggaa gggtgattga gtcccacgtc gcgttgtgat gtgcgttgta tatgtgaaat 600
ttagccgtgc aacaaggcta ttctacgaaa aatgctacac tccacatgtt aaaggcgcat 660
aatcggcacg ttgttccgat aagatgcttt ttacgatgtg aggtgtacaa tttccgcgta 720
tcaaccagct tctttattgg gtaatataca gccaggcggg gatgaagctc attagccgcc 780
agttggtcga agaaataacc cattatatgt cggtccgccc ctacttcgag taatcggcgg 840

```
actcaaggct atacaatgtt gccaactctc cgggctttat cctgtgctcc cgaataccac    900
tgagttccga tatgttacaa cggttgagag gcccgaaata ggacacgagg gcttatggtg    960
atcgtgatga tgcttcagcg cacggaagtc acagacaccg cctgtataaa agggggactg   1020
tagcactact acgaagtcgc gtgccttcag tgtctgtggc ggacatattt tccccctgac   1080
tgaccctgta tgaggcgcaa catggtctca cagcagctca cctgaagagg cttgtaagat   1140
actgggacat actccgcgtt gtaccagagt gtcgtcgagt ggacttctcc gaacattcta   1200
caccctctgt gtattgcacc atggcgttcc tccccctcc tccgctccgc cgttgtggcc   1260
gtgggagaca cataacgtgg taccgcaagg aggggggagg aggcgaggcg gcaacaccgg   1320
gccctgccgg tgttggccct tgccgctgat ggcaggtcca cccgctactg ggactgctgc   1380
cgggacggcc acaaccggga acggcgacta ccgtccaggt gggcgatgac cctgacgacg   1440
aagccttcgt gcggctgggc caagaaggct cccgtgaacc agcctgtctt ttcctgcaac   1500
ttcggaagca cgccgacccg gttcttccga gggcacttgg tcggacagaa aaggacgttg   1560
gccaacttcc agcgtatcac ggacttcgac gccaagtccg gctgcgagcc gggcggtgtc   1620
cggttgaagg tcgcatagtg cctgaagctg cggttcaggc cgacgctcgg cccgccacag   1680
gcctactcgt gcgccgacca gaccccatgg gctgtgaacg acgacttcgc gctcggtttt   1740
cggatgagca cgcggctggt ctggggtacc cgacacttgc tgctgaagcg cgagccaaaa   1800
gctgccacct ctattgccgg cagcaatgag gcgggctggt gctgcgcctg ctacgagctc   1860
cgacggtgga gataacggcc gtcgttactc cgcccgacca cgacgcggac gatgctcgag   1920
accttcacat ccggtcctgt tgctggcaag aagatggtcg tccagtccac cagcactggc   1980
tggaagtgta ggccaggaca acgaccgttc ttctaccagc aggtcaggtg gtcgtgaccg   2040
ggtgatcttg gcagcaacca cttcgatctc aacatccccg gcggcggcgt cggcatcttc   2100
ccactagaac cgtcgttggt gaagctagag ttgtaggggc cgccgccgca gccgtagaag   2160
gacggatgca ctccccagtt cggcggtctg cccggccagc gctacggcgg catctcgtcc   2220
ctgcctacgt gaggggtcaa gccgccagac gggccggtcg cgatgccgcc gtagagcagg   2280
cgcaacgagt gcgatcggtt ccccgacgcc ctcaagcccg gctgctactg gcgcttcgac   2340
gcgttgctca cgctagccaa ggggctgcgg gagttcgggc cgacgatgac cgcgaagctg   2400
tggttcaaga acgccgacaa tccgagcttc agcttccgtc aggtccagtg cccagccgag   2460
accaagttct tgcggctgtt aggctcgaag tcgaaggcag tccaggtcac gggtcggctc   2520
ctcgtcgctc gcaccggatg ccgccgcaac gacgacggca acttccctgc cgtccagatc   2580
gagcagcgag cgtggcctac ggcggcgttg ctgctgccgt tgaagggacg gcaggtctag   2640
ccctccagca gcaccagctc tccggtcaac cagcctacca gcaccagcac cacgtccacc   2700
gggaggtcgt cgtggtcgag aggccagttg gtcggatggt cgtggtcgtg gtgcaggtgg   2760
tccaccacct cgagcccgcc agtccagcct acgactccca gcggctgcac tgctgagagg   2820
aggtggtgga gctcgggcgg tcaggtcgga tgctgagggt cgccgacgtg acgactctcc   2880
tgggctcagt gcggcggcaa tggctggagc ggctgcacca cctgcgtcgc tggcagcact   2940
acccgagtca cgccgccgtt accgacctcg ccgacgtggt ggacgcagcg accgtcgtga   3000
tgcacgaaga ttaatgactg gtaccatcag tgcctgtaga attcgcggcc gcagatctac   3060
acgtgcttct aattactgac catggtagtc acggacatct taagcgccgg cgtctagatg   3120
gcgtactagt agctccgtgg cgaaagcctg acgcaccggt agattcttgg tgagcccgta   3180
cgcatgatca tcgaggcacc gctttcggac tgcgtggcca tctaagaacc actcgggcat   3240
```

```
tcatgacggc ggcgggagct acatggcccc gggtgattta tttttttgt atctacttct   3300
agtactgccg ccgccctcga tgtaccgggg cccactaaat aaaaaaaaca tagatgaaga   3360
gaccctttc aaatatacgg tcaactcatc tttcactgga gatgcggcct gcttggtatt   3420
ctgggaaaag tttatatgcc agttgagtag aaagtgacct ctacgccgga cgaaccataa   3480
gcgatgttgt cagcttggca aattgtggct ttcgaaaaca caaaacgatt ccttaattaa   3540
cgctacaaca gtcgaaccgt ttaacaccga aagcttttgt gttttgctaa ggaattaatt   3600
ctagaggtga ctgacacctg gcggtagaca atcaatccat ttcgctatag ttaaaggatg   3660
gatctccact gactgtggac cgccatctgt tagttaggta aagcgatatc aatttcctac   3720
gggatgaggg caattggtta tatgatcatg tatgtagtgg gtgtgcataa tagtagtgaa   3780
ccctactccc gttaaccaat atactagtac atacatcacc cacacgtatt atcatcactt   3840
atggaagcca agtcatgtga ttgtaatcga ccgacggaat tgaggatatc cggaaataca   3900
taccttcggt tcagtacact aacattagct ggctgcctta actcctatag gcctttatgt   3960
gacaccgtga aagccatgct ctttccttcg tgtagaagac cagacagaca gtccctgatt   4020
ctgtggcact ttcggtacga gaaaggaagc acatcttctg gtctgtctgt cagggactaa   4080
tacccttgca caaagcacta gaaaattagc attccatcct tctctgcttg ctctgctgat   4140
atgggaacgt gtttcgtgat cttttaatcg taaggtagga agagacgaac gagacgacta   4200
atcactgtca ttcaatgcat ctggaaacgc aaccctgaag ggattcttcc tttgagagat   4260
tagtgacagt aagttacgta gacctttgcg ttgggacttc cctaagaagg aaactctcta   4320
ggaagcgtgt catatctctt cggttctacg gcaggttttt ttctgctctt tcgtagcatg   4380
ccttcgcaca gtatagagaa gccaagatgc cgtccaaaaa aagacgagaa agcatcgtac   4440
gcatggtcac ttcagcgctt atttacagtt gctggtattg atttcttgtg caaattgcta   4500
cgtaccagtg aagtcgcgaa taaatgtcaa cgaccataac taaagaacac gtttaacgat   4560
tctgacactt attagctatg gagtcaccac atttcccagc aacttcccca cttcctctgc   4620
agactgtgaa taatcgatac ctcagtggtg taaagggtcg ttgaaggggt gaaggagacg   4680
aatcgccaac gtcctctctt cactgagtct ccgtccgata acctgcactg caaccggtgc   4740
ttagcggttg caggagagaa gtgactcaga ggcaggctat tggacgtgac gttggccacg   4800
cccatgatac gcctccggat catactcttc ctgcacgagg gcatcaagct cactaaccgc   4860
gggtactatg cggaggccta gtatgagaag gacgtgctcc cgtagttcga gtgattggcg   4920
cttgaaactc tcattcttct tatcgatgtt cttatccgca aaggtaaccg gaacaaccac   4980
gaactttgag agtaagaaga atagctacaa gaataggcgt ttccattggc cttgttggtg   5040
gctcgtgaaa tccagcaggt tgatcacaga ggcataccca tagtaccgga actggtcatg   5100
cgagcacttt aggtcgtcca actagtgtct ccgtatgggt atcatggcct tgaccagtac   5160
ccgtaccgca gcggtaggcg taatcggcgc gatgatggcg tccagttcct tcccggcctt   5220
ggcatggcgt cgccatccgc attagccgcg ctactaccgc aggtcaagga agggccggaa   5280
ttcttcagcc tcccgccatt tctcaaggta ctccatctgg taattccact tctggagatg   5340
aagaagtcgg agggcggtaa agagttccat gaggtagacc attaaggtga agacctctac   5400
cgtgtcccag agctcgttca tgttaacagc tttgatgttc gggttcagta ggtctttgat   5460
gcacagggtc tcgagcaagt acaattgtcg aaactacaag cccaagtcat ccagaaacta   5520
atttggagtc gccggctcgc cggatgcact gatatcgcgc attacgtcgg cgctgccgtc   5580
```

-continued

```
taaacctcag cggccgagcg gcctacgtga ctatagcgcg taatgcagcc gcgacggcag   5640
agccgcgtag atatgggaga tgagatcgtg gccgaaatcg tgcttgtatg gcgtccacgg   5700
tcggcgcatc tataccctct actctagcac cggctttagc acgaacatac cgcaggtgcc   5760
ggtcacggtg tgaccggctt tggcgagtgc ggcgacggtg gtttccacgc cgcgcaggat   5820
ccagtgccac actggccgaa accgctcacg ccgctgccac caaaggtgcg gcgcgtccta   5880
aggagggtgt ggaaggacat tgccgtcgaa gttgtagtag ccgatattga gcccgccgtt   5940
tcctcccaca ccttcctgta acggcagctt caacatcatc ggctataact cgggcggcaa   6000
cttgatcttg gaggcaataa tgtccgactc ggactggcgc cagggcatgg ggatgacctt   6060
gaactagaac ctccgttatt acaggctgag cctgaccgcg gtcccgtacc cctactggaa   6120
ggagtcgtat ttccaaggct cctgaccgag gacggatttg gtgaagaggc ggaggtctaa   6180
cctcagcata aaggttccga ggactggctc ctgcctaaac cacttctccg cctccagatt   6240
catacttcat cagtgactgc cggtctcgta tatagtataa aaagcaagaa aggaggacag   6300
gtatgaagta gtcactgacg gccagagcat atatcatatt tttcgttctt tcctcctgtc   6360
tggaggcctg gtatagagca ggaaaagaag gaagaggcga aggactcacc ctcaacagag   6420
acctccggac catatctcgt ccttttcttc cttctccgct tcctgagtgg gagttgtctc   6480
tgcgtaatcg gcccgacaac gctgtgcacc gtctcctgac cctccatgct gttcgccatc   6540
acgcattagc cgggctgttg cgacacgtgg cagaggactg ggaggtacga caagcggtag   6600
tttgcatacg gcagccgccc atgactcggc cttagaccgt acaggaagtt gaacgcggcc   6660
aaacgtatgc cgtcggcggg tactgagccg gaatctggca tgtccttcaa cttgcgccgg   6720
ggcactcgaa tcgagccacc gatatccgtt cctacaccga tgacgccacc acgaatccca   6780
ccgtgagctt agctcggtgg ctataggcaa ggatgtggct actgcggtgg tgcttagggt   6840
acgatcgcac cctcaccacc agaactgccg ccgcacgacc agttcttgtt gcgtgggttg   6900
tgctagcgtg ggagtggtgg tcttgacggc ggcgtgctgg tcaagaacaa cgcacccaac   6960
acggtgcgcc cgatgatgtt gttgactgtc tcgcagacca tcagggtctg cgggacagag   7020
tgccacgcgg gctactacaa caactgacag agcgtctggt agtcccagac gccctgtctc   7080
gtcttgacgt agaagacggc accggctttg cggagcatgg ttgtcagaac cgagtcccct   7140
cagaactgca tcttctgccg tggccgaaac gcctcgtacc aacagtcttg gctcagggga   7200
tcgtcgtact tgtttagcca tgagatgtag cccattgatg tttcgtagcc ctggtggcat   7260
agcagcatga acaaatcggt actctacatc gggtaactac aaagcatcgg gaccaccgta   7320
atgttagctg acaaaaaggg acatctaacg acttaggggc aacggtgtac cttgactcga   7380
tacaatcgac tgtttttccc tgtagattgc tgaatccccg ttgccacatg gaactgagct   7440
agctggtctt tgagagagat ggggaggcca tgaagtggac caacgggtct cttgtgcttt   7500
tcgaccagaa actctctcta cccctccggt acttcacctg gttgcccaga gaacacgaaa   7560
gcgtagtatt catcgagttc ccttgcctgc gcgagagcgg cgtcagggaa gaactcgtgg   7620
cgcatcataa gtagctcaag ggaacggacg cgctctcgcc gcagtccctt cttgagcacc   7680
gcgcagtttg tctgcacaga agccagcgtc agcttgatag tcccataagg tggcgttgtt   7740
cgcgtcaaac agacgtgtct tcggtcgcag tcgaactatc agggtattcc accgcaacaa   7800
acatctccct gagaggtaga ggggacccta ctaactgctg ggcgattgct gcccgtttac   7860
tgtagaggga ctctccatct cccctgggat gattgacgac ccgctaacga cgggcaaatg   7920
agaatgctag cgtaacttcc accgaggtca actctccggc cgccagcttg gacacaagat   7980
```

```
tcttacgatc gcattgaagg tggctccagt tgagaggccg gcggtcgaac ctgtgttcta   8040
ctgcagcgga ggcctctgtg atcttcagtt cggcctctga aaggatcccc gatttctttg   8100
gacgtcgcct ccggagacac tagaagtcaa gccggagact ttcctagggg ctaaagaaac   8160
ggaaatcaat aacgctgtct tccgcaggca gcgtctggac tttccattca tcagggatgg   8220
cctttagtta ttgcgacaga aggcgtccgt cgcagacctg aaaggtaagt agtccctacc   8280
tttttgcgag gcgggcgcgc ttatcagcgg ccagttcttc ccaggattga ggcattctgt   8340
aaaaacgctc cgcccgcgcg aatagtcgcc ggtcaagaag ggtcctaact ccgtaagaca   8400
gttagcttat agtcaggatg ttggctcgac gagtgtaaac tgggagttgg catgagggtt   8460
caatcgaata tcagtcctac aaccgagctg ctcacatttg accctcaacc gtactcccaa   8520
atgtaggctt ctttagcccc gcatccccct cattctcctc attgatcccg ggggagcgga   8580
tacatccgaa gaaatcgggg cgtagggggga gtaagaggag taactagggc cccctcgcct   8640
tggtgttgat aagagactaa ttataggttt tagctggtgc ctagctggtg attggctggc   8700
accacaacta ttctctgatt aatatcccaa atcgaccacg gatcgaccac taaccgaccg   8760
ttcgccgaat tttacgggcc aaggaaagct gcagaaccgc ggcactggta aacggtaatt   8820
aagcggctta aaatgcccgg ttcctttcga cgtcttggcg ccgtgaccat ttgccattaa   8880
aagctatcag ccccatgcta acgagtttaa attacgtgta ttgctgataa acaccaacag   8940
ttcgatagtc ggggtacgat tgctcaaatt taatgcacat aacgactatt tgtggttgtc   9000
agctttactg aaagatggga gtcacggtgt ggcttcccca ctgcgattat tgcacaagca   9060
tcgaaatgac tttctaccct cagtgccaca ccgaaggggt gacgctaata acgtgttcgt   9120
gcgagggcga acttgactgt cgtcgctgag cagcctgcag tcaaacatac atatatatca   9180
cgctcccgct tgaactgaca gcagcgactc gtcggacgtc agtttgtatg tatatatagt   9240
accgcgaaga cgtctggcct tgtagaacac gacgctccct agcaacacct gccgtgtcag   9300
tggcgcttct gcagaccgga acatcttgtg ctgcgaggga tcgttgtgga cggcacagtc   9360
cctctacggt tgttacttgc attcaggatg ctctccagcg ggcgagctat tcaaaatatt   9420
ggagatgcca acaatgaacg taagtcctac gagaggtcgc ccgctcgata agttttataa   9480
caaagcaggt atctcgtatt gccaggattc agctgaagca acaggtgcca aggaaatctg   9540
gtttcgtcca tagagcataa cggtcctaag tcgacttcgt tgtccacggt tcctttagac   9600
cgtcggttct catctgggct tgctcggtcc tggcgtagaa tgcatcctag agtttaaaca   9660
gcagccaaga gtagacccga acgagccagg accgcatctt acgtaggatc tcaaatttgt   9720
gcttggcact ggccgtcgtt ttacaacgtc gtgactggga aaaccctggc gttacccaac   9780
cgaaccgtga ccggcagcaa aatgttgcag cactgaccct tttgggaccg caatgggttg   9840
ttaatcgcct tgcagcacat ccccctttcg ccagctggcg taatagcgaa gaggcccgca   9900
aattagcgga acgtcgtgta gggggaaagc ggtcgaccgc attatcgctt ctccgggcgt   9960
ccgatcgccc ttcccaacag ttgcgcagcc tgaacggcga atggcgcctg atgcggtatt  10020
ggctagcggg aagggttgtc aacgcgtcgg acttgccgct taccgcggac tacgccataa  10080
ttctccttac gcatctgtgc ggtatttcac accgcatatg gtgcactctc agtacaatct  10140
aagaggaatg cgtagacacg ccataaagtg tggcgtatac cacgtgagag tcatgttaga  10200
gctctgatgc cgcatagtta agccagcccc gacacccgcc aacacccgct gacgcgccct  10260
cgagactacg gcgtatcaat tcggtcgggg ctgtgggcgg ttgtgggcga ctgcgcggga  10320
```

```
gacgggcttg tctgctcccg gcatccgctt acagacaagc tgtgaccgtc tccgggagct  10380
ctgcccgaac agacgagggc cgtaggcgaa tgtctgttcg acactggcag aggccctcga  10440
gcatgtgtca gaggttttca ccgtcatcac cgaaacgcgc gagacgaaag ggcctcgtga  10500
cgtacacagt ctccaaaagt ggcagtagtg gctttgcgcg ctctgctttc ccggagcact  10560
tacgcctatt tttataggtt aatgtcatga taataatggt ttcttagacg tcaggtggca  10620
atgcggataa aaatatccaa ttacagtact attattacca aagaatctgc agtccaccgt  10680
cttttcgggg aaatgtgcgc ggaaccccta tttgtttatt tttctaaata cattcaaata  10740
gaaaagcccc tttacacgcg ccttggggat aaacaaataa aaagatttat gtaagtttat  10800
tgtatccgct catgagacaa taaccctgat aaatgcttca ataatattga aaaaggaaga  10860
acataggcga gtactctgtt attgggacta tttacgaagt tattataact ttttccttct  10920
gtatgagtat tcaacatttc cgtgtcgccc ttattccctt ttttgcggca ttttgccttc  10980
catactcata agttgtaaag gcacagcggg aataagggaa aaaacgccgt aaaacggaag  11040
ctgtttttgc tcacccagaa acgctggtga aagtaaaaga tgctgaagat cagttgggtg  11100
gacaaaaacg agtgggtctt tgcgaccact ttcattttct acgacttcta gtcaacccac  11160
cacgagtggg ttacatcgaa ctggatctca acagcggtaa gatccttgag agttttcgcc  11220
gtgctcaccc aatgtagctt gacctagagt tgtcgccatt ctaggaactc tcaaaagcgg  11280
ccgaagaacg ttttccaatg atgagcactt ttaaagttct gctatgtggc gcggtattat  11340
ggcttcttgc aaaaggttac tactcgtgaa aatttcaaga cgatacaccg cgccataata  11400
cccgtattga cgccgggcaa gagcaactcg gtcgccgcat acactattct cagaatgact  11460
gggcataact gcggcccgtt ctcgttgagc cagcggcgta tgtgataaga gtcttactga  11520
tggttgagta ctcaccagtc acagaaaagc atcttacgga tggcatgaca gtaagagaat  11580
accaactcat gagtggtcag tgtcttttcg tagaatgcct accgtactgt cattctctta  11640
tatgcagtgc tgccataacc atgagtgata acactgcggc caacttactt ctgacaacga  11700
atacgtcacg acggtattgg tactcactat tgtgacgccg gttgaatgaa gactgttgct  11760
tcggaggacc gaaggagcta accgcttttt tgcacaacat gggggatcat gtaactcgcc  11820
agcctcctgg cttcctcgat tggcgaaaaa acgtgttgta cccccctagta cattgagcgg  11880
ttgatcgttg ggaaccggag ctgaatgaag ccataccaaa cgacgagcgt gacaccacga  11940
aactagcaac ccttggcctc gacttacttc ggtatggttt gctgctcgca ctgtggtgct  12000
tgcctgtagc aatggcaaca acgttgcgca aactattaac tggcgaacta cttactctag  12060
acggacatcg ttaccgttgt tgcaacgcgt ttgataattg accgcttgat gaatgagatc  12120
cttcccggca acaattaata gactggatgg aggcggataa agttgcagga ccacttctgc  12180
gaagggccgt tgttaattat ctgacctacc tccgcctatt tcaacgtcct ggtgaagacg  12240
gctcggccct tccggctggc tggtttattg ctgataaatc tggagccggt gagcgtgggt  12300
cgagccggga aggccgaccg accaaataac gactatttag acctcggcca ctcgcaccca  12360
ctcgcggtat cattgcagca ctggggccag atggtaagcc ctcccgtatc gtagttatct  12420
gagcgccata gtaacgtcgt gaccccggtc taccattcgg gagggcatag catcaataga  12480
acacgacggg gagtcaggca actatggatg aacgaaatag acagatcgct gagataggtg  12540
tgtgctgccc ctcagtccgt tgatacctac ttgctttatc tgtctagcga ctctatccac  12600
cctcactgat taagcattgg taactgtcag accaagttta ctcatatata ctttagattg  12660
ggagtgacta attcgtaacc attgacagtc tggttcaaat gagtatatat gaaatctaac  12720
```

```
atttaaaact tcatttttaa tttaaaagga tctaggtgaa gatccttttt gataatctca  12780
taaattttga agtaaaaatt aaattttcct agatccactt ctaggaaaaa ctattagagt  12840
tgaccaaaat cccttaacgt gagttttcgt tccactgagc gtcagacccc gtagaaaaga  12900
actggtttta gggaattgca ctcaaaagca aggtgactcg cagtctgggg catcttttct  12960
tcaaaggatc ttcttgagat ccttttttc tgcgcgtaat ctgctgcttg caaacaaaaa  13020
agtttcctag aagaactcta ggaaaaaaag acgcgcatta gacgacgaac gtttgttttt  13080
aaccaccgct accagcggtg gtttgtttgc cggatcaaga gctaccaact ctttttccga  13140
ttggtggcga tggtcgccac caaacaaacg gcctagttct cgatggttga gaaaaaggct  13200
aggtaactgg cttcagcaga gcgcagatac caaatactgt tcttctagtg tagccgtagt  13260
tccattgacc gaagtcgtct cgcgtctatg gtttatgaca agaagatcac atcggcatca  13320
taggccacca cttcaagaac tctgtagcac cgcctacata cctcgctctg ctaatcctgt  13380
atccggtggt gaagttcttg agacatcgtg gcggatgtat ggagcgagac gattaggaca  13440
taccagtggc tgctgccagt ggcgataagt cgtgtcttac cgggttggac tcaagacgat  13500
atggtcaccg acgacggtca ccgctattca gcacagaatg gcccaacctg agttctgcta  13560
agttaccgga taaggcgcag cggtcgggct gaacgggggg ttcgtgcaca cagcccagct  13620
tcaatggcct attccgcgtc gccagcccga cttgcccccc aagcacgtgt gtcgggtcga  13680
tggagcgaac gacctacacc gaactgagat acctacagcg tgagctatga gaaagcgcca  13740
acctcgcttg ctggatgtgg cttgactcta tggatgtcgc actcgatact ctttcgcggt  13800
cgcttcccga agggagaaag gcggacaggt atccggtaag cggcagggtc ggaacaggag  13860
gcgaagggct tccctctttc cgcctgtcca taggccattc gccgtcccag ccttgtcctc  13920
agcgcacgag ggagcttcca gggggaaacg cctggtatct ttatagtcct gtcgggtttc  13980
tcgcgtgctc cctcgaaggt cccccctttgc ggaccataga aatatcagga cagcccaaag  14040
gccacctctg acttgagcgt cgatttttgt gatgctcgtc aggggggcgg agcctatgga  14100
cggtggagac tgaactcgca gctaaaaaca ctacgagcag tcccccgcc tcggatacct  14160
aaaacgccag caacgcggcc tttttacggt tcctggcctt ttgctggcct tttgctcaca  14220
ttttgcggtc gttgcgccgg aaaaatgcca aggaccggaa aacgaccgga aaacgagtgt  14280
tgttctttcc tgcgttatcc cctgattctg tggataaccg tattaccgcc tttgagtgag  14340
acaagaaagg acgcaatagg ggactaagac acctattggc ataatggcgg aaactcactc  14400
ctgataccgc tcgccgcagc cgaacgaccg agcgcagcga gtcagtgagc gaggaagcgg  14460
gactatggcg agcggcgtcg gcttgctggc tcgcgtcgct cagtcactcg ctccttcgcc  14520
aagagcgccc aatacgcaaa ccgcctctcc ccgcgcgttg gccgattcat taatgcagct  14580
ttctcgcggg ttatgcgttt ggcggagagg ggcgcgcaac cggctaagta attacgtcga  14640
ggcacgacag gtttcccgac tggaaagcgg gcagtgagcg caacgcaatt aatgtgagtt  14700
ccgtgctgtc caaagggctg acctttcgcc cgtcactcgc gttgcgttaa ttacactcaa  14760
agctcactca ttaggcaccc caggctttac actttatgct tccggctcgt atgttgtgtg  14820
tcgagtgagt aatccgtggg gtccgaaatg tgaaatacga aggccgagca tacaacacac  14880
gaattgtgag cggataacaa tttcacacag gaaacagcta tgaccatgat tacgaattgt  14940
cttaacactc gcctattgtt aaagtgtgtc ctttgtcgat actggtacta atgcttaaca  15000
ttaaacgaat ttgc                                                    15014
```

<210> SEQ ID NO 78
<211> LENGTH: 35
<212> TYPE: DNA
<213> ORGANISM: Trichoderma reesei

<400> SEQUENCE: 78
cgaacgcggt agtgggaatt ctaggctagg tatgc 35

<210> SEQ ID NO 79
<211> LENGTH: 35
<212> TYPE: DNA
<213> ORGANISM: Trichoderma reesei

<400> SEQUENCE: 79
ccaaccgaat ctcatggtgc aatacacaga gggtg 35

<210> SEQ ID NO 80
<211> LENGTH: 35
<212> TYPE: DNA
<213> ORGANISM: Aspergillus fumigatus

<400> SEQUENCE: 80
tctgtgtatt gcaccatgag attcggttgg ctcga 35

<210> SEQ ID NO 81
<211> LENGTH: 35
<212> TYPE: DNA
<213> ORGANISM: Aspergillus fumigatus

<400> SEQUENCE: 81
ccggtcacga aagccctagt agacacgggg cagag 35

<210> SEQ ID NO 82
<211> LENGTH: 35
<212> TYPE: DNA
<213> ORGANISM: Trichoderma reesei

<400> SEQUENCE: 82
ccccgtgtct actagggctt tcgtgaccgg gcttc 35

<210> SEQ ID NO 83
<211> LENGTH: 35
<212> TYPE: DNA
<213> ORGANISM: Trichoderma reesei

<400> SEQUENCE: 83
gtcattacca attggactcg gagttgttat acgct 35

<210> SEQ ID NO 84
<211> LENGTH: 35
<212> TYPE: DNA
<213> ORGANISM: Trichoderma reesei

<400> SEQUENCE: 84
cgaacgcggt agtgggaatt ctaggctagg tatgc 35

<210> SEQ ID NO 85
<211> LENGTH: 35
<212> TYPE: DNA
<213> ORGANISM: Trichoderma reesei

<400> SEQUENCE: 85
gtcattacca attggactcg gagttgttat acgct 35

<210> SEQ ID NO 86
<211> LENGTH: 36
<212> TYPE: DNA
<213> ORGANISM: Aspergillus fumigatus

<400> SEQUENCE: 86
ccctttgggt atccgtgact gtgagctata cccgcg 36

<210> SEQ ID NO 87
<211> LENGTH: 35
<212> TYPE: DNA
<213> ORGANISM: Aspergillus fumigatus

<400> SEQUENCE: 87
cgtcatgagt gactggggcg ctcaccacag cggtg 35

<210> SEQ ID NO 88
<211> LENGTH: 36
<212> TYPE: DNA
<213> ORGANISM: Aspergillus fumigatus

<400> SEQUENCE: 88
gggtagtggt actgccgagt tcccttacct tgtcac 36

<210> SEQ ID NO 89
<211> LENGTH: 39
<212> TYPE: DNA
<213> ORGANISM: Aspergillus fumigatus

<400> SEQUENCE: 89
gccgactctg gagagggtta catcagtgtc gacggcaac 39

<210> SEQ ID NO 90
<211> LENGTH: 33
<212> TYPE: DNA
<213> ORGANISM: Aspergillus fumigatus

<400> SEQUENCE: 90
cggactgcgc accatgagat tcggttggct cga 33

<210> SEQ ID NO 91
<211> LENGTH: 35
<212> TYPE: DNA
<213> ORGANISM: Aspergillus fumigatus

<400> SEQUENCE: 91
tcgccacgga gcttactagt agacacgggg cagag 35

<210> SEQ ID NO 92
<211> LENGTH: 61
<212> TYPE: DNA
<213> ORGANISM: Trichoderma reesei

<400> SEQUENCE: 92
gcgagtcagt gagcgaggaa gcggaagagc ttaattaatc ttgagtggat gtctgatcta 60
g 61

<210> SEQ ID NO 93
<211> LENGTH: 58
<212> TYPE: DNA
<213> ORGANISM: Trichoderma reesei

<400> SEQUENCE: 93
gttcggataa caatcctaca ttcggtcgac ttataaggat gtatcaatgg gttatacg 58

<210> SEQ ID NO 94
<211> LENGTH: 20
<212> TYPE: DNA
<213> ORGANISM: Aspergillus fumigatus

<400> SEQUENCE: 94
tcaaccagct tctttattgg 20

<210> SEQ ID NO 95
<211> LENGTH: 25
<212> TYPE: DNA
<213> ORGANISM: Aspergillus fumigatus

<400> SEQUENCE: 95
gatcgccata ggctcatgct ccgca 25

<210> SEQ ID NO 96
<211> LENGTH: 21
<212> TYPE: DNA
<213> ORGANISM: Aspergillus fumigatus

<400> SEQUENCE: 96
gcggcatcaa acacgaacct g 21

<210> SEQ ID NO 97
<211> LENGTH: 20
<212> TYPE: DNA
<213> ORGANISM: Aspergillus fumigatus

<400> SEQUENCE: 97
cagtggcgct tattactcag 20

<210> SEQ ID NO 98
<211> LENGTH: 25
<212> TYPE: DNA
<213> ORGANISM: Aspergillus fumigatus

<400> SEQUENCE: 98
gatcgccata ggctcatgct ccgca 25

<210> SEQ ID NO 99
<211> LENGTH: 25
<212> TYPE: DNA
<213> ORGANISM: Trichoderma reesei

<400> SEQUENCE: 99
aaaaaacaaa catcccgttc ataac 25

<210> SEQ ID NO 100
<211> LENGTH: 25
<212> TYPE: DNA
<213> ORGANISM: Trichoderma reesei

<400> SEQUENCE: 100
aacaaggttt accggtttcg aaaag 25

<210> SEQ ID NO 101
<211> LENGTH: 25
<212> TYPE: DNA
<213> ORGANISM: Aspergillus fumigatus

<400> SEQUENCE: 101
agccacatgc cgcatattga caaag 25

<210> SEQ ID NO 102
<211> LENGTH: 25
<212> TYPE: DNA
<213> ORGANISM: Trichoderma reesei

<400> SEQUENCE: 102
agggattcag tgtgctacag gctgc 25

<210> SEQ ID NO 103
<211> LENGTH: 25
<212> TYPE: DNA
<213> ORGANISM: Trichoderma reesei

<400> SEQUENCE: 103
aaaaaacaaa catcccgttc ataac 25

<210> SEQ ID NO 104
<211> LENGTH: 25
<212> TYPE: DNA
<213> ORGANISM: Trichoderma reesei

<400> SEQUENCE: 104
aacaaggttt accggtttcg aaaag 25

<210> SEQ ID NO 105
<211> LENGTH: 27
<212> TYPE: DNA
<213> ORGANISM: Trichoderma reesei

<400> SEQUENCE: 105
gttaagcata caattgaacg agaatgg 27

<210> SEQ ID NO 106
<211> LENGTH: 25
<212> TYPE: DNA
<213> ORGANISM: Trichoderma reesei

<400> SEQUENCE: 106
gatgatataa tggagcaaat aaggg 25

<210> SEQ ID NO 107
<211> LENGTH: 2077
<212> TYPE: DNA
<213> ORGANISM: Trichoderma reesei

<400> SEQUENCE: 107
atgacggatg cacaaaagaa ttggaggaga gacgaaaacg acgaggacga tgaagcagag 60
caggagctcg atgaggctgt aagtcgccgc gagtcgcatc tggtctgaca agcgtcgtct 120
gacactcttt tctcccatct agagcctcaa ggcgcagaaa gatgcaattc ttctagccat 180
tgaagtcagt ccgtcgatgc ttgagcctcc gccagtctcc agctctagga aagctgatcg 240
ggacagcccc gttcaagctg cgctgaaatg cgcccgccac ctgatggagc agcgcatcat 300
ctccaacccc aaagacatga tgggaatcct cctctttggg acagaaaaga ccaagttccg 360
ggacgacaat ggccgcagtg ggctcgggta tccgaattgc tacctcttta tggacctcga 420
cattccggca gctgaagacg tcaaagcgtt gaaggcgctg accgaggacg aagacgaaga 480

```
cgaagtgctg aagcccgcca ccaccgacac agtttccatg tccaacgtgt tgttttgcgc    540

caaccagata ttcaccacaa aggcggccaa ctttggcagc cggcgacttt tcattgtgac    600

ggacaatgac gatccgcacg cgtcggacaa ggcggcgagg tctgctgccg ctgttcgggc    660

aaaggacttg tacgatctgg gcatcacgat cgacttgttt ccaatcacca caggagactc    720

caagtttgat ctcagcaaat tttacgatgt aagctatatt tcttcgtttc ttcgctctaa    780

aatcacccac cctccgtcgt gacatagact gacaaggaac taggatattg tctatcgcga    840

cccgaatgcc gaggccaatc gcaccgaagt gcgagcctca aaatcgggcg atggactgtc    900

tcttctcaac tcgctcattt caaacatcaa ttccaagcag acgcccaagc gagcattgtt    960

ccatctgcca tttgagattg cacctggact caagatcact gtcaagggct acaacattgt   1020

gcatcggcaa acgccggcga gaacgtgcta catctggctg gaaggggaga aggctcagat   1080

tgcaacaggc gaaacgacgc gagttgcaga ggattctgcc agaacagtcg aaaagcaaga   1140

gataaaaaag gcctacaagt ttggtggcga atacgtatac tttacgcccg aggagcagaa   1200

gaagctccgg gattttggcg cgcccacgat ccggatcatt ggattcaaga agcgcagcat   1260

gattcccgtc tgggccagcg tcaagaagtc gacctttatc tttcccagcg aagaggatta   1320

catcggatcg acacgcgtct tttcagccct atggcagaag cttctaaagg atgacaagat   1380

cggcctcgct tggtgcgtgc ttcgatctaa cgcgcagccc atgtttgccg ctctgattcc   1440

atcaagagag cagtccgaag acgacgcggg gacaccatat ctaccagctg gcctgtggct   1500

gtatcctctc cctacggctg acgacctgcg agatataaat gtcgaacgaa agctcgactg   1560

ctcggaggac ctaaaaacca aaatgagagt cattgtacaa cagctcaatc tccccaaggg   1620

catatataac ccactcaagt acccgaaccc ggctctgcaa tggcactaca agatcctcca   1680

gaccctcgcc ttggaggagg agatgccgga agaacccgaa gacttgacgg agcccaaaaa   1740

caaggcgata agcaaacgcg tcggaggtta cttggaggag tggtccgaga ctctgaaaga   1800

cgaggcggac agggccactc gatccaggtc cttgaagcga gagattgaag atgatgcccc   1860

ggagcgcccc gcaaagcaga gaaaggtagc tggagagcgg cccagcggat cgaatcttag   1920

catggcgcag cttagggatg ccattgagag cgggagcatc tcgaagatga cagtggcaca   1980

gctgaaggat gtcgctggcg ccagaggact cagcacgggt ggtaagaagg ctgatttgct   2040

ggagcggata gagcagtggg ttgaggagaa cagctga                            2077
```

<210> SEQ ID NO 108
<211> LENGTH: 649
<212> TYPE: PRT
<213> ORGANISM: Trichoderma reesei

<400> SEQUENCE: 108

```
Met Thr Asp Ala Gln Lys Asn Trp Arg Arg Asp Glu Asn Asp Glu Asp
1               5                   10                  15

Asp Glu Ala Glu Gln Glu Leu Asp Glu Ala Val Ser Arg Arg Asp Leu
            20                  25                  30

Lys Ala Gln Lys Asp Ala Ile Leu Leu Ala Ile Glu Val Ser Pro Ser
        35                  40                  45

Met Leu Glu Pro Pro Pro Val Ser Ser Ser Arg Lys Ala Asp Arg Asp
    50                  55                  60

Ser Pro Val Gln Ala Ala Leu Lys Cys Ala Arg His Leu Met Glu Gln
65                  70                  75                  80

Arg Ile Ile Ser Asn Pro Lys Asp Met Met Gly Ile Leu Leu Phe Gly
                85                  90                  95
```

```
Thr Glu Lys Thr Lys Phe Arg Asp Asp Asn Gly Arg Ser Gly Leu Gly
            100                 105                 110

Tyr Pro Asn Cys Tyr Leu Phe Met Asp Leu Asp Ile Pro Ala Ala Glu
        115                 120                 125

Asp Val Lys Ala Leu Lys Ala Leu Thr Glu Asp Glu Asp Glu Asp Glu
    130                 135                 140

Val Leu Lys Pro Ala Thr Thr Asp Thr Val Ser Met Ser Asn Val Leu
145                 150                 155                 160

Phe Cys Ala Asn Gln Ile Phe Thr Thr Lys Ala Ala Asn Phe Gly Ser
                165                 170                 175

Arg Arg Leu Phe Ile Val Thr Asp Asn Asp Asp Pro His Ala Ser Asp
            180                 185                 190

Lys Ala Ala Arg Ser Ala Ala Ala Val Arg Ala Lys Asp Leu Tyr Asp
        195                 200                 205

Leu Gly Ile Thr Ile Asp Leu Phe Pro Ile Thr Thr Gly Asp Ser Lys
    210                 215                 220

Phe Asp Leu Ser Lys Phe Tyr Asp Asp Ile Val Tyr Arg Asp Pro Asn
225                 230                 235                 240

Ala Glu Ala Asn Arg Thr Glu Val Arg Ala Ser Lys Ser Gly Asp Gly
                245                 250                 255

Leu Ser Leu Leu Asn Ser Leu Ile Ser Asn Ile Asn Ser Lys Gln Thr
            260                 265                 270

Pro Lys Arg Ala Leu Phe His Leu Pro Phe Glu Ile Ala Pro Gly Leu
        275                 280                 285

Lys Ile Thr Val Lys Gly Tyr Asn Ile Val His Arg Gln Thr Pro Ala
    290                 295                 300

Arg Thr Cys Tyr Ile Trp Leu Glu Gly Glu Lys Ala Gln Ile Ala Thr
305                 310                 315                 320

Gly Glu Thr Thr Arg Val Ala Glu Asp Ser Ala Arg Thr Val Glu Lys
                325                 330                 335

Gln Glu Ile Lys Lys Ala Tyr Lys Phe Gly Gly Glu Tyr Val Tyr Phe
            340                 345                 350

Thr Pro Glu Glu Gln Lys Lys Leu Arg Asp Phe Gly Ala Pro Thr Ile
        355                 360                 365

Arg Ile Ile Gly Phe Lys Lys Arg Ser Met Ile Pro Val Trp Ala Ser
    370                 375                 380

Val Lys Lys Ser Thr Phe Ile Phe Pro Ser Glu Glu Asp Tyr Ile Gly
385                 390                 395                 400

Ser Thr Arg Val Phe Ser Ala Leu Trp Gln Lys Leu Leu Lys Asp Asp
                405                 410                 415

Lys Ile Gly Leu Ala Trp Cys Val Leu Arg Ser Asn Ala Gln Pro Met
            420                 425                 430

Phe Ala Ala Leu Ile Pro Ser Arg Glu Gln Ser Glu Asp Asp Ala Gly
        435                 440                 445

Thr Pro Tyr Leu Pro Ala Gly Leu Trp Leu Tyr Pro Leu Pro Thr Ala
    450                 455                 460

Asp Asp Leu Arg Asp Ile Asn Val Glu Arg Lys Leu Asp Cys Ser Glu
465                 470                 475                 480

Asp Leu Lys Thr Lys Met Arg Val Ile Val Gln Gln Leu Asn Leu Pro
                485                 490                 495

Lys Gly Ile Tyr Asn Pro Leu Lys Tyr Pro Asn Pro Ala Leu Gln Trp
            500                 505                 510
```

```
His Tyr Lys Ile Leu Gln Thr Leu Ala Leu Glu Glu Glu Met Pro Glu
        515                 520                 525

Glu Pro Glu Asp Leu Thr Glu Pro Lys Asn Lys Ala Ile Ser Lys Arg
    530                 535                 540

Val Gly Gly Tyr Leu Glu Glu Trp Ser Glu Thr Leu Lys Asp Glu Ala
545                 550                 555                 560

Asp Arg Ala Thr Arg Ser Arg Ser Leu Lys Arg Glu Ile Glu Asp Asp
                565                 570                 575

Ala Pro Glu Arg Pro Ala Lys Gln Arg Lys Val Ala Gly Glu Arg Pro
            580                 585                 590

Ser Gly Ser Asn Leu Ser Met Ala Gln Leu Arg Asp Ala Ile Glu Ser
        595                 600                 605

Gly Ser Ile Ser Lys Met Thr Val Ala Gln Leu Lys Asp Val Ala Gly
    610                 615                 620

Ala Arg Gly Leu Ser Thr Gly Gly Lys Lys Ala Asp Leu Leu Glu Arg
625                 630                 635                 640

Ile Glu Gln Trp Val Glu Glu Asn Ser
                645
```

<210> SEQ ID NO 109
<211> LENGTH: 55
<212> TYPE: DNA
<213> ORGANISM: Trichoderma reesei

<400> SEQUENCE: 109
gtgtgcggcc gctcgagcat gcatgtttaa acagcttggc actggccgtc gtttt 55

<210> SEQ ID NO 110
<211> LENGTH: 55
<212> TYPE: DNA
<213> ORGANISM: Trichoderma reesei

<400> SEQUENCE: 110
atcagccccg agacggcgcc gcgtttaaac aattcgtaat catggtcata gctgt 55

<210> SEQ ID NO 111
<211> LENGTH: 55
<212> TYPE: DNA
<213> ORGANISM: Trichoderma reesei

<400> SEQUENCE: 111
catgattacg aattgtttaa acgcggcgcc gtctcggggc tgatcttgtc gagga 55

<210> SEQ ID NO 112
<211> LENGTH: 55
<212> TYPE: DNA
<213> ORGANISM: Trichoderma reesei

<400> SEQUENCE: 112
ggcggccgtt actagtggat ccagcccttg acagtgatct tgagtccagg tgcaa 55

<210> SEQ ID NO 113
<211> LENGTH: 58
<212> TYPE: DNA
<213> ORGANISM: Trichoderma reesei

<400> SEQUENCE: 113
tgcagatatc catcacactg gcggccgcag tttccatgtc caacgtgttg ttttgcgc 58

<210> SEQ ID NO 114

<211> LENGTH: 58
<212> TYPE: DNA
<213> ORGANISM: Trichoderma reesei

<400> SEQUENCE: 114
gccagtgcca agctgtttaa acatgcatgc tcgagcggcc gcacacgccc tctcctcg 58

<210> SEQ ID NO 115
<211> LENGTH: 20
<212> TYPE: DNA
<213> ORGANISM: Trichoderma reesei

<400> SEQUENCE: 115
caatgacgat ccgcacgcgt 20

<210> SEQ ID NO 116
<211> LENGTH: 20
<212> TYPE: DNA
<213> ORGANISM: Trichoderma reesei

<400> SEQUENCE: 116
caatgacgat ccgcacgcgt 20

<210> SEQ ID NO 117
<211> LENGTH: 20
<212> TYPE: DNA
<213> ORGANISM: Trichoderma reesei

<400> SEQUENCE: 117
gacactcttt tctcccatct 20

<210> SEQ ID NO 118
<211> LENGTH: 20
<212> TYPE: DNA
<213> ORGANISM: Trichoderma reesei

<400> SEQUENCE: 118
gaggagcaga agaagctccg 20

<210> SEQ ID NO 119
<211> LENGTH: 22
<212> TYPE: DNA
<213> ORGANISM: Trichoderma reesei

<400> SEQUENCE: 119
gcatatataa cccactcaag ta 22

<210> SEQ ID NO 120
<211> LENGTH: 22
<212> TYPE: DNA
<213> ORGANISM: Trichoderma reesei

<400> SEQUENCE: 120
attatcttgg accggccgca gg 22